(12) United States Patent
Parham et al.

(10) Patent No.: US 11,302,870 B2
(45) Date of Patent: Apr. 12, 2022

(54) MATERIALS FOR ELECTRONIC DEVICES

(71) Applicant: Merck Patent GmbH, Darmstadt (DE)

(72) Inventors: Amir Parham, Frankfurt am Main (DE); Dominik Joosten, Frankfurt am Main (DE); Aurélie Ludemann, Frankfurt am Main (DE); Tobias Grossmann, Darmstadt (DE); Jonas Kroeber, Frankfurt am Main (DE)

(73) Assignee: MERCK PATENT GMBH, Darmstadt (DE)

( * ) Notice: Subject to any disclaimer, the term of this patent is extended or adjusted under 35 U.S.C. 154(b) by 205 days.

(21) Appl. No.: 16/346,598

(22) PCT Filed: Oct. 30, 2017

(86) PCT No.: PCT/EP2017/077728
§ 371 (c)(1),
(2) Date: May 1, 2019

(87) PCT Pub. No.: WO2018/083053
PCT Pub. Date: May 11, 2018

(65) Prior Publication Data
US 2019/0288206 A1    Sep. 19, 2019

(30) Foreign Application Priority Data

Nov. 2, 2016 (EP) .................................... 16196934

(51) Int. Cl.
| | | |
|---|---|---|
| *H01L 51/00* | (2006.01) |
| *C07C 211/61* | (2006.01) |
| *C07C 209/74* | (2006.01) |
| *C09K 11/06* | (2006.01) |
| *C07C 211/57* | (2006.01) |
| *C07D 307/91* | (2006.01) |
| *C07D 333/76* | (2006.01) |
| *C07D 241/38* | (2006.01) |
| *C07D 405/12* | (2006.01) |
| *C07D 209/86* | (2006.01) |
| *C07D 471/06* | (2006.01) |
| *C07C 255/50* | (2006.01) |
| *C07D 239/70* | (2006.01) |
| *C07D 221/18* | (2006.01) |
| *C07C 255/51* | (2006.01) |
| *C07D 471/04* | (2006.01) |
| *C07D 495/04* | (2006.01) |
| *C07D 239/74* | (2006.01) |
| *C07D 491/048* | (2006.01) |
| *C07D 213/38* | (2006.01) |
| *H01L 51/50* | (2006.01) |

(52) U.S. Cl.
CPC .......... *H01L 51/006* (2013.01); *C07C 209/74* (2013.01); *C07C 211/57* (2013.01); *C07C 211/61* (2013.01); *C07C 255/50* (2013.01); *C07C 255/51* (2013.01); *C07D 209/86* (2013.01); *C07D 213/38* (2013.01); *C07D 221/18* (2013.01); *C07D 239/70* (2013.01); *C07D 239/74* (2013.01); *C07D 241/38* (2013.01); *C07D 307/91* (2013.01); *C07D 333/76* (2013.01); *C07D 405/12* (2013.01); *C07D 471/04* (2013.01); *C07D 471/06* (2013.01); *C07D 491/048* (2013.01); *C07D 495/04* (2013.01); *C09K 11/06* (2013.01); *H01L 51/0061* (2013.01); *C07C 2603/18* (2017.05); *C07C 2603/40* (2017.05); *C07C 2603/42* (2017.05); *C07C 2603/94* (2017.05); *C07C 2603/97* (2017.05); *C09K 2211/1007* (2013.01); *C09K 2211/1011* (2013.01); *C09K 2211/1014* (2013.01); *C09K 2211/1018* (2013.01); *H01L 51/0054* (2013.01); *H01L 51/0056* (2013.01); *H01L 51/0058* (2013.01); *H01L 51/0073* (2013.01); *H01L 51/0074* (2013.01); *H01L 51/5012* (2013.01); *H01L 51/5016* (2013.01); *H01L 51/5056* (2013.01); *H01L 51/5076* (2013.01); *H01L 51/5096* (2013.01)

(58) Field of Classification Search
None
See application file for complete search history.

(56) References Cited

U.S. PATENT DOCUMENTS

| | | | | |
|---|---|---|---|---|
| 2005/0142381 A1* | 6/2005 | Lyu | ..................... | H05B 33/14 428/690 |
| 2007/0149815 A1 | 6/2007 | Takada et al. | | |
| 2015/0322198 A1* | 11/2015 | Hayer | ..................... | C08L 65/02 252/500 |

FOREIGN PATENT DOCUMENTS

| | | | |
|---|---|---|---|
| CN | 102082232 A | | 6/2011 |
| CN | 103524399 A | * | 1/2014 |
| CN | 103524399 A | | 1/2014 |
| CN | 105175313 A | | 12/2015 |

(Continued)

OTHER PUBLICATIONS

Machine English translation of Jia et al. (CN 103524399 A). Apr. 21, 2021.*

(Continued)

*Primary Examiner* — Jay Yang
(74) *Attorney, Agent, or Firm* — Faegre Drinker Biddle & Reath LLP

(57) ABSTRACT

The present application relates to fluoranthenylamine compounds of a formula (I). These compounds are suitable for use in electronic devices, The present application further relates to processes for preparing the compounds mentioned, and to electronic devices comprising the compounds mentioned.

21 Claims, No Drawings

(56) References Cited

FOREIGN PATENT DOCUMENTS

| | | |
|---|---|---|
| CN | 105669467 A | 6/2016 |
| CN | 107056626 A | 8/2017 |
| EP | 2175005 A1 | 4/2010 |
| EP | 2907803 A1 | 8/2015 |
| JP | H03078757 A | 4/1991 |
| JP | 2004339064 A | 12/2004 |
| JP | 3801326 B2 | 7/2006 |
| JP | 3858951 B2 | 12/2006 |
| JP | 2010093181 A | 4/2010 |
| KR | 20110076271 A | 7/2011 |
| KR | 101290015 B1 | 7/2013 |
| KR | 20140142923 A | 12/2014 |
| KR | 20150004099 A | 1/2015 |
| KR | 20150007476 A | 1/2015 |
| WO | WO-2005044943 A1 | 5/2005 |
| WO | WO-2010050779 A1 | 5/2010 |
| WO | WO-2013081410 A1 | 6/2013 |
| WO | WO-2015041428 A1 | 3/2015 |
| WO | WO-2016013867 A1 | 1/2016 |

OTHER PUBLICATIONS

Machine English translation of Cho et al. (KR 10-2011-0076271). Apr. 21, 2021.*
International Search Report for PCT/EP2017/077728 dated Dec. 22, 2017.
Written Opinion of the International Searching Authority for PCT/EP2017/077728 dated Dec. 22, 2017.

* cited by examiner

MATERIALS FOR ELECTRONIC DEVICES

CROSS-REFERENCE TO RELATED APPLICATIONS

This application is a national stage application (under 35 U.S.C. § 371) of PCT/EP2017/077728, filed Oct. 30, 2017, which claims benefit of European Application No. 16196934.0, filed Nov. 2, 2016, both of which are incorporated herein by reference in their entirety.

The present application relates to fluoranthenylamine compounds of a formula (I) defined further down. These compounds are suitable for use in electronic devices. The present application further relates to processes for preparing the compounds mentioned, and to electronic devices comprising the compounds mentioned.

Electronic devices in the context of this application are understood to mean what are called organic electronic devices, which contain organic semiconductor materials as functional materials. More particularly, these are understood to mean OLEDs (organic electroluminescent devices). The term OLEDs is understood to mean electronic devices which have one or more layers comprising organic compounds and emit light on application of electrical voltage. The construction and general principle of function of OLEDs are known to those skilled in the art.

In electronic devices, especially OLEDs, there is great interest in improving the performance data, especially lifetime, efficiency and operating voltage. In these aspects, it has not yet been possible to find any entirely satisfactory solution.

A great influence on the performance data of electronic devices is possessed by emission layers and layers having a hole-transporting function. For use in these layers, there is still a search for new materials, especially materials having hole-transporting and electron-transporting properties. Of particular interest are materials that combine hole- and electron-transporting properties in one compound. Materials of this kind are referred to as bipolar materials. It is preferable here that the hole-transporting properties are localized in one part of the compound, and the electron-transporting properties in another part of the compound.

In the prior art, triarylamine compounds in particular are known as hole transport materials for electronic devices.

However, there is still a need for alternative compounds suitable for use in electronic devices.

There is also a need for improvement with regard to the performance data in use in electronic devices, especially with regard to lifetime and efficiency.

It has now been found that particular fluorantheneamine compounds are of excellent suitability for use in electronic devices, especially for use in OLEDs, even more especially for use therein as matrix materials for phosphorescent emitters.

The present application thus provides compounds of formula (I)

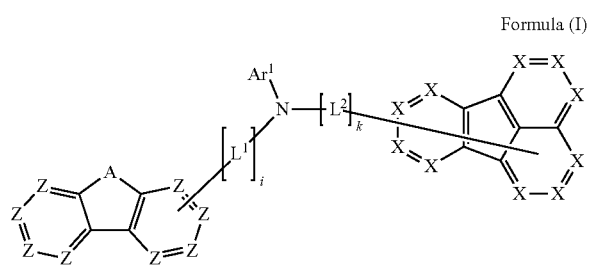

Formula (I)

where the variables that occur are as follows:
A is $C(R^1)_2$ or is

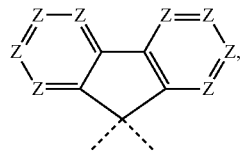

where the dotted lines represent the bonds to the six-membered aromatic rings;

Z is the same or different at each instance and is $CR^2$ or N or C, where a Z group is C in the specific case when the $[L^1]_l$ group is bonded to it;

X is the same or different at each instance and is $CR^3$ or N or C, where an X group is C in the specific case when the $[L^2]_k$ group is bonded to it;

$L^1$, $L^2$ is the same or different at each instance and is an aromatic ring system which has 6 to 24 aromatic ring atoms and may be substituted by one or more $R^4$ radicals, or a heteroaromatic ring system which has 5 to 24 aromatic ring atoms and may be substituted by one or more $R^4$ radicals;

$Ar^1$ is an aromatic ring system which has 6 to 24 aromatic ring atoms and may be substituted by one or more $R^5$ radicals, or a heteroaromatic ring system which has 5 to 24 aromatic ring atoms and may be substituted by one or more $R^5$ radicals, where $Ar^1$ does not comprise any nitrogen-containing heteroaryl group bonded directly to the amine nitrogen atom of the formula (I), and where $Ar^1$ and substituents bonded thereto do not contain any carbazole group;

$R^1$, $R^2$, $R^3$, $R^4$ are the same or different at each instance and are selected from H, D, F, $C(\!=\!O)R^6$, CN, $Si(R^6)_3$, $P(\!=\!O)(R^6)_2$, $OR^6$, $S(\!=\!O)R^6$, $S(\!=\!O)_2R^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$ or $R^2$ or $R^3$ or $R^4$ radicals may be joined to one another and may form a ring; where the alkyl, alkoxy, alkenyl and alkynyl groups mentioned and the aromatic ring systems and heteroaromatic ring systems mentioned may each be substituted by one or more $R^6$ radicals; and where one or more $CH_2$ groups in the alkyl, alkoxy, alkenyl and alkynyl groups mentioned may be replaced by $-\!R^6C\!=\!CR^6\!-\!$, $-\!C\!\equiv\!C\!-\!$, $Si(R^6)_2$, $C\!=\!O$, $C\!=\!NR^6$, $-\!C(\!=\!O)O\!-\!$, $-\!C(\!=\!O)NR^6\!-\!$, $NR^6$, $P(\!=\!O)(R^6)$, $-\!O\!-\!$, $-\!S\!-\!$, SO or $SO_2$;

$R^5$ is the same or different at each instance and is selected from H, D, $Si(R^6)_3$, $OR^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^5$ radicals may be joined to one another and may form a ring; where the alkyl, alkoxy, alkenyl and alkynyl groups mentioned and the aromatic ring systems and heteroaromatic ring systems mentioned may each be substituted by one or more $R^6$ radicals; and where one or more $CH_2$ groups in the alkyl, alkoxy, alkenyl and alkynyl groups mentioned may be replaced by —R⁶C=CR⁶—, —C≡C—, Si(R⁶)₂, NR⁶, O— or —S—;

R⁶ is the same or different at each instance and is selected from H, D, F, C(=O)R⁷, CN, Si(R⁷)₃, P(=O)(R⁷)₂, OR⁷, S(=O)R⁷, S(=O)₂R⁷, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R⁶ radicals may be joined to one another and may form a ring; where the alkyl, alkoxy, alkenyl and alkynyl groups mentioned and the aromatic ring systems and heteroaromatic ring systems mentioned may each be substituted by one or more R⁷ radicals; and where one or more CH₂ groups in the alkyl, alkoxy, alkenyl and alkynyl groups mentioned may be replaced by —R⁷C=CR⁷—, —C≡C—, Si(R⁷)₂, C=O, C=NR⁷, —C(=O)O—, —C(=O)NR⁷—, NR⁷, P(=O)(R⁷), —O—, —S—, SO or SO₂;

R⁷ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more R⁷ radicals may be joined to one another and may form a ring; and where the alkyl, alkoxy, alkenyl and alkynyl groups, aromatic ring systems and heteroaromatic ring systems mentioned may be substituted by F or CN;

i is 0, 1, 2 or 3; and k is 0, 1, 2 or 3.

The bond that passes through the fluoranthene group

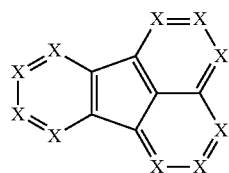

in formula (I) means that the fluoranthene group may be bonded to the rest of the structure of the formula (I) at any position.

The bond that passes through the six-membered ring in the unit

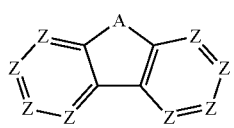

in formula (I) means that the unit in question may be bonded to the rest of the structure of the formula (I) at any position in the six-membered ring.

If i=0, the fluorenyl or spirobifluorenyl group is bonded directly to the amine nitrogen atom. If k=0, the fluoranthenyl group is bonded directly to the amine nitrogen atom.

An aryl group in the context of this invention contains 6 to 40 aromatic ring atoms of which none is a heteroatom. An aryl group in the context of this invention is understood to mean either a simple aromatic cycle, i.e. benzene, or a fused aromatic polycycle, for example naphthalene, phenanthrene or anthracene. A fused aromatic polycycle in the context of the present application consists of two or more simple aromatic cycles fused to one another. Fusion between cycles is understood here to mean that the cycles share at least one edge with one another.

A heteroaryl group in the context of this invention contains 5 to 40 aromatic ring atoms of which at least one is a heteroatom. The heteroatoms of the heteroaryl group are preferably selected from N, O and S. A heteroaryl group in the context of this invention is understood to mean either a simple heteroaromatic cycle, for example pyridine, pyrimidine or thiophene, or a fused heteroaromatic polycycle, for example quinoline or carbazole. A fused heteroaromatic polycycle in the context of the present application consists of two or more simple heteroaromatic cycles fused to one another. Fusion between cycles is understood here to mean that the cycles share at least one edge with one another.

An aryl or heteroaryl group, each of which may be substituted by the abovementioned radicals and which may be joined to the aromatic or heteroaromatic system via any desired positions, is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the context of this invention contains 6 to 40 carbon atoms in the ring system and does not include any heteroatoms as aromatic ring atoms. An aromatic ring system in the context of this invention therefore does not contain any heteroaryl groups. An aromatic ring system in the context of this invention shall be understood to mean a system which does not necessarily contain only aryl groups but in which it is also possible for a plurality of aryl groups to be bonded by a single bond or by a non-aromatic unit, for example one or more optionally substituted C, Si, N, O or S atoms. In this case, the nonaromatic unit comprises preferably less than 10% of the atoms other than H, based on the total number of atoms other than H in the system. For example, systems such as 9,9'-spirobifluorene, 9,9'-diarylfluorene, triarylamine, diaryl ethers and stilbene are also to be regarded as aromatic ring systems in the context of this invention, and likewise systems in which two or more aryl groups are joined, for example, by a linear or cyclic alkyl, alkenyl or alkynyl group or by a silyl group. In addition, systems in which two or more aryl groups are joined to one another via single bonds are also regarded as aromatic ring systems in the context of this invention, for example systems such as biphenyl and terphenyl.

A heteroaromatic ring system in the context of this invention contains 5 to 40 aromatic ring atoms, at least one of which is a heteroatom. The heteroatoms of the heteroaromatic ring system are preferably selected from N, O and/or S. A heteroaromatic ring system corresponds to the abovementioned definition of an aromatic ring system, but has at least one heteroatom as one of the aromatic ring atoms. In this way, it differs from an aromatic ring system in the sense of the definition of the present application, which, according to this definition, cannot contain any heteroatom as aromatic ring atom.

An aromatic ring system having 6 to 40 aromatic ring atoms or a heteroaromatic ring system having 5 to 40 aromatic ring atoms is especially understood to mean groups derived from the groups mentioned above under aryl groups and heteroaryl groups, and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, or from combinations of these groups.

In the context of the present invention, a straight-chain alkyl group having 1 to 20 carbon atoms and a branched or cyclic alkyl group having 3 to 20 carbon atoms and an alkenyl or alkynyl group having 2 to 40 carbon atoms in which individual hydrogen atoms or $CH_2$ groups may also be substituted by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals.

An alkoxy or thioalkyl group having 1 to 20 carbon atoms in which individual hydrogen atoms or $CH_2$ groups may also be replaced by the groups mentioned above in the definition of the radicals is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. In addition, however, the abovementioned wording shall also be understood to mean that, if one of the two radicals is hydrogen, the second radical binds to the position to which the hydrogen atom was bonded, forming a ring.

Preferably, in formula (I), the fluoranthene group is bonded in position 3 or 4, where the positions are numbered as follows:

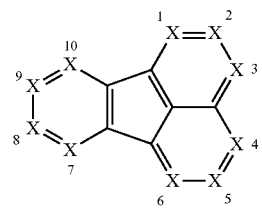

Preferably, in formula (I), the fluorenyl group or spirobifluorenyl group is bonded in one of positions 1, 3 and 4, more preferably in one of the two positions 1 and 4, most preferably in position 4. With the bond in the preferred positions in question, improved performance data of the compounds are obtained, especially in the case of use as a matrix material for phosphorescent emitters. The positions on the fluorenyl group or the spirobifluorenyl group are numbered as follows:

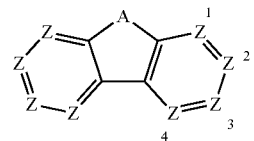

It is preferable that A is $C(R^1)_2$.

It is preferable that not more than two Z groups per aromatic six-membered ring are N; more preferably, only one Z group per aromatic six-membered ring is N.

Preferably, Z is $CR^2$ or C, where a Z group is C in the specific case when the $[L^1]_i$ group is bonded to it.

It is preferable that not more than two X groups in the fluoranthene group are N; more preferably, only one X group in the fluoranthene group is N. Most preferably, X is $CR^3$ or C, where an X group is C in the specific case when it is bonded to the $[L^2]_k$ group.

$L^1$, $L^2$ are preferably the same or different at each instance and are selected from a divalent group derived from benzene, biphenyl, terphenyl, fluorene, spirobifluorene, indenofluorene, carbazole, dibenzofuran or dibenzothiophene, each optionally substituted by $R^4$ radicals, or a combination of two or more of these groups. $L^1$, $L^2$ are more preferably the same or different at each instance and are selected from the following radicals that are optionally substituted by $R^4$ radicals: para-, meta- or ortho-phenylene, naphthylene, biphenylene, dibenzofuranylene and dibenzothiophenylene. Preferably, the groups mentioned are not substituted by $R^4$ radicals.

$L^1$, $L^2$ are preferably selected from groups of the following formulae:

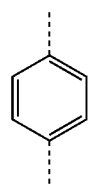

L-1

-continued
L-2
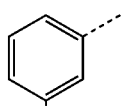
L-3
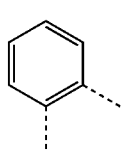
L-4
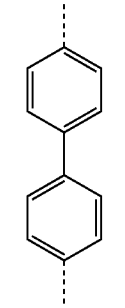
L-5
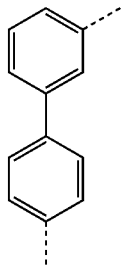
L-6
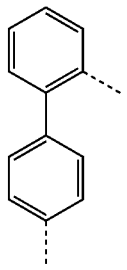
L-7
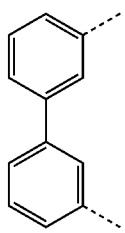
L-8
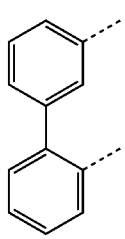
L-9
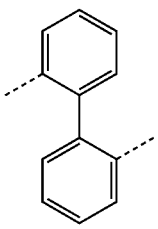
L-10
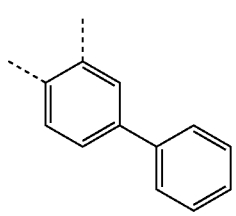
L-11
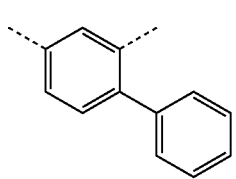
L-12
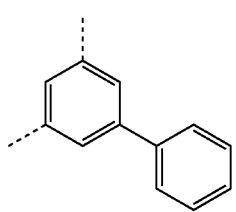
L-13
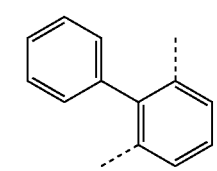
L-14
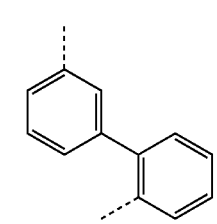
L-15
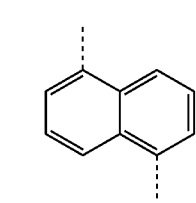
L-16
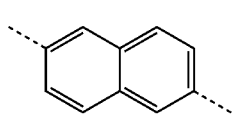

L-17 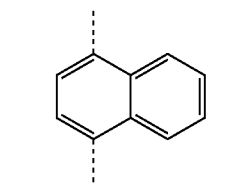
L-18 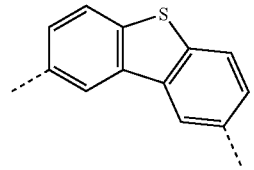
L-19 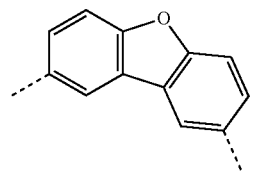
L-20 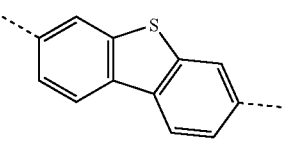
L-21 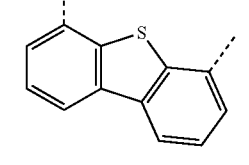
L-22 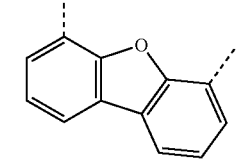
L-23 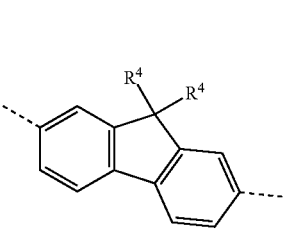
L-24 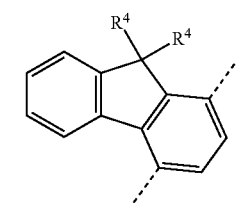
L-25 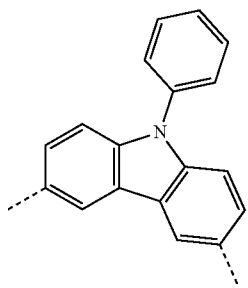
L-26 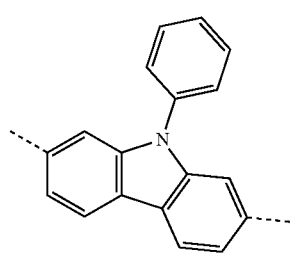
L-27 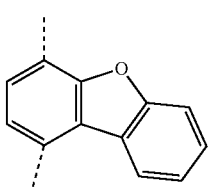
L-28 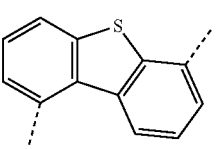
L-29 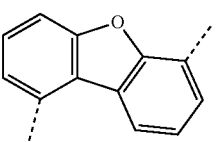
L-30 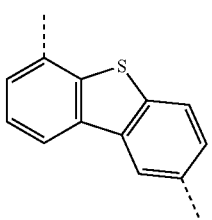
L-31 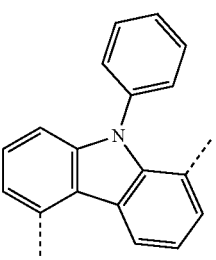

-continued

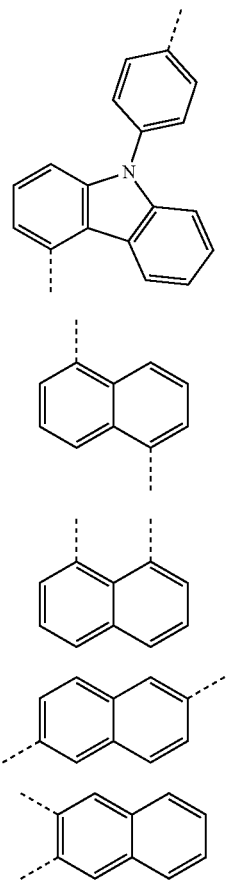

L-32

L-33

L-34

L-35

L-36 where the dotted bonds represent the bonds to the radical of the formula and the groups may be substituted at the free positions by one or more $R^4$ radicals, but are preferably unsubstituted at the free positions.

Preferably, $Ar^1$ is an aromatic ring system which has 6 to 24 aromatic ring atoms and may be substituted by one or more $R^5$ radicals, or a heteroaromatic ring system which has 5 to 24 aromatic ring atoms and may be substituted by one or more $R^5$ radicals, where $Ar^1$ does not comprise any nitrogen-containing heteroaryl group. More preferably, $Ar^1$ is selected from the following radicals that are optionally substituted by $R^5$ radicals: phenyl, biphenyl, branched terphenyl, unbranched terphenyl, branched quaterphenyl, unbranched quaterphenyl, fluorenyl, dibenzofuranyl, dibenzothiophenyl, fluorenylphenylene, dibenzofuranylphenylene, dibenzothiophenylphenylene, phenanthrenyl and triphenylyl.

Most preferably, $Ar^1$ is selected from the following groups:

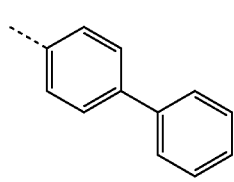

Ar-1

-continued

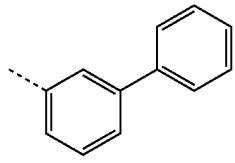

Ar-3

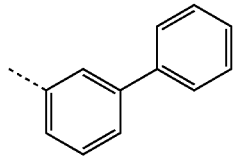

Ar-3

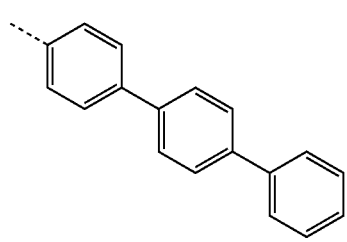

Ar-4

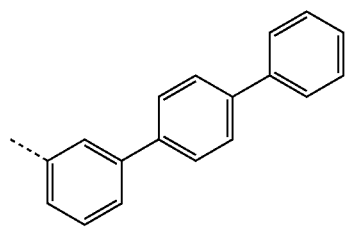

Ar-5

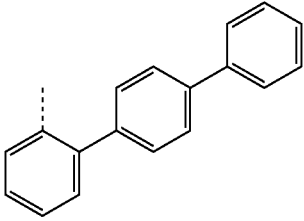

Ar-6

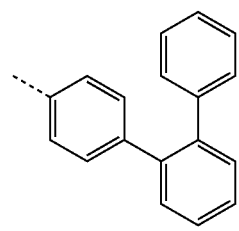

Ar-7

Ar-8

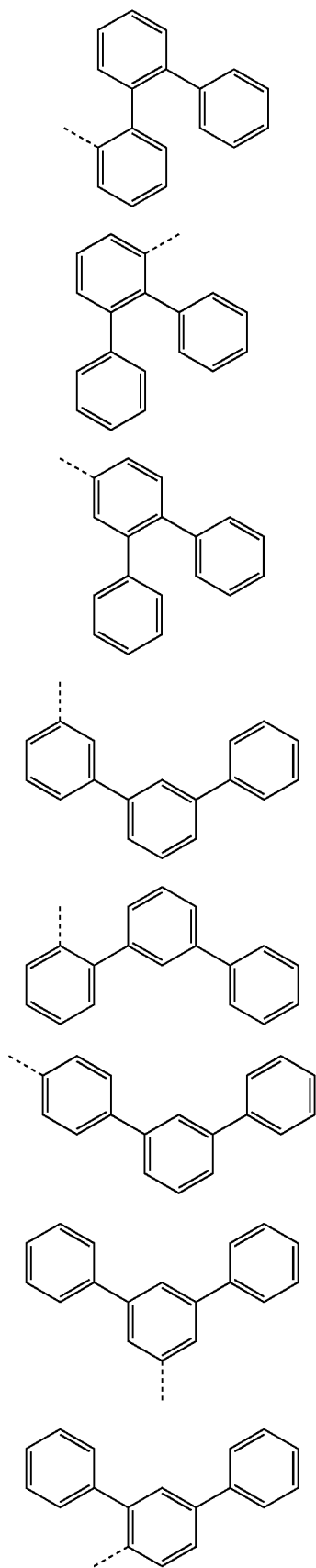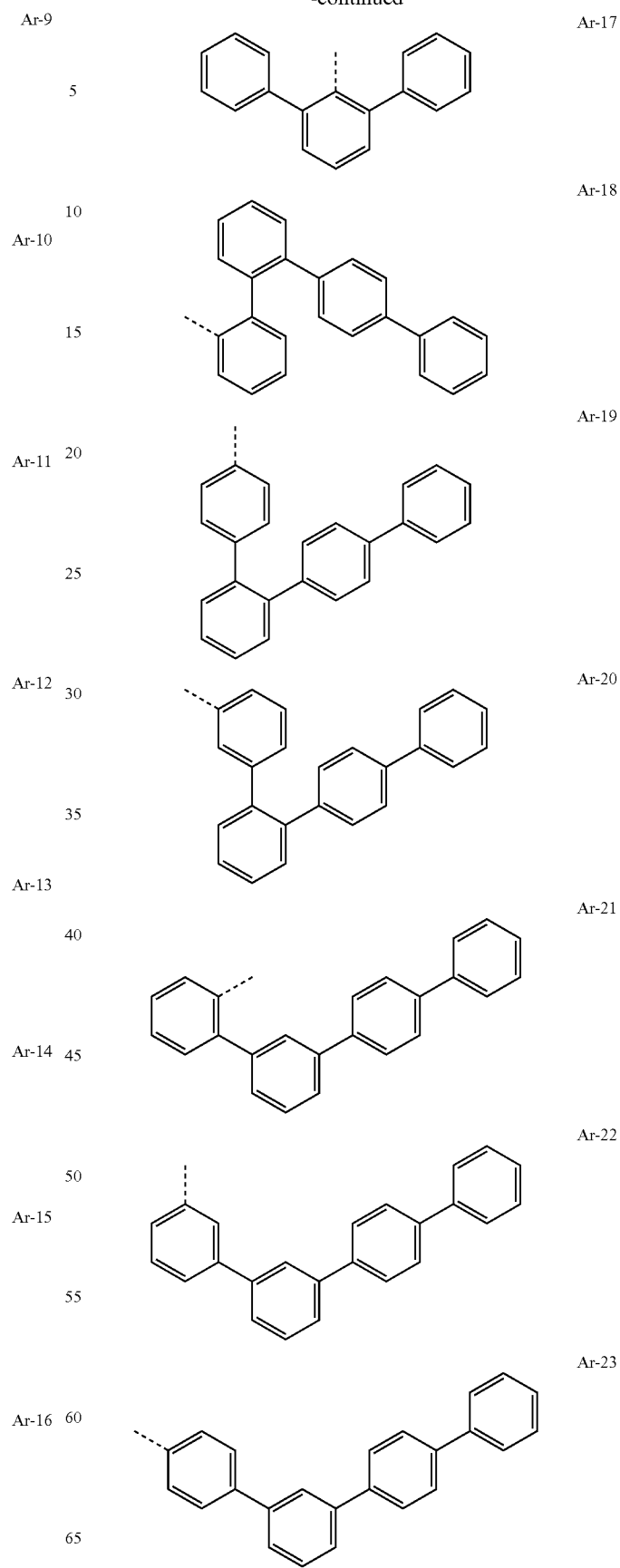

Ar-24
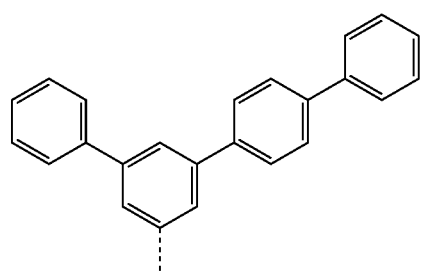
Ar-25
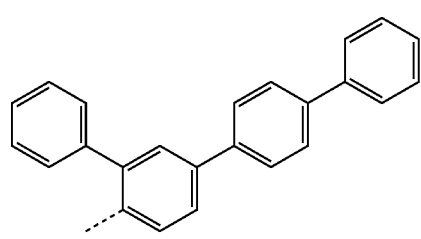
Ar-26
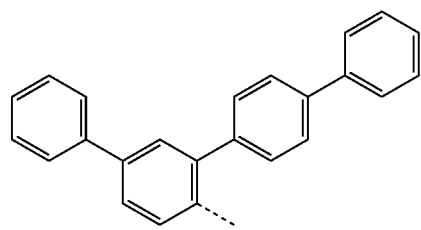
Ar-27
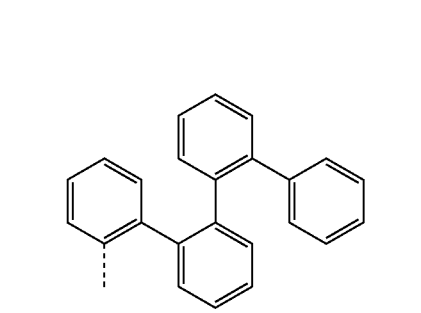
Ar-28
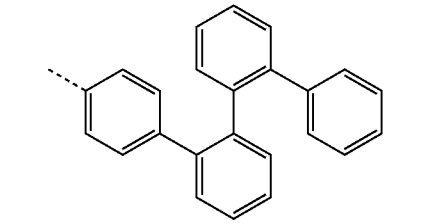
Ar-29
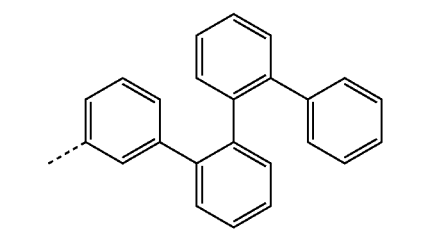
Ar-30
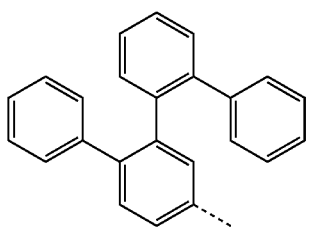
Ar-31
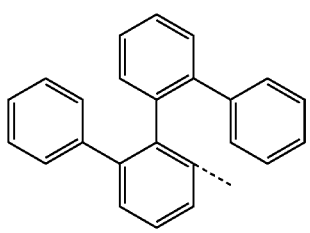
Ar-32
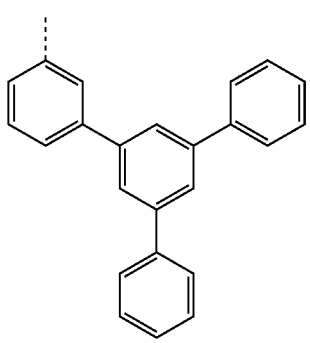
Ar-33
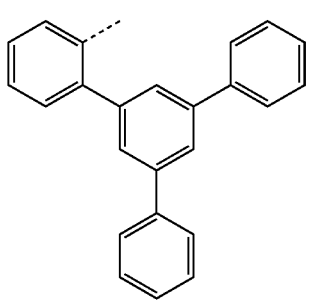
Ar-34
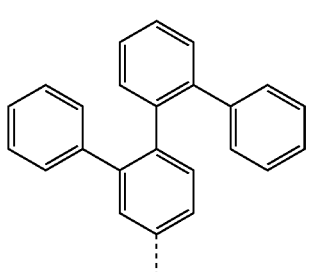
Ar-35
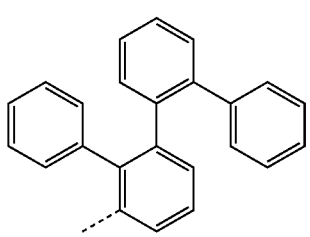

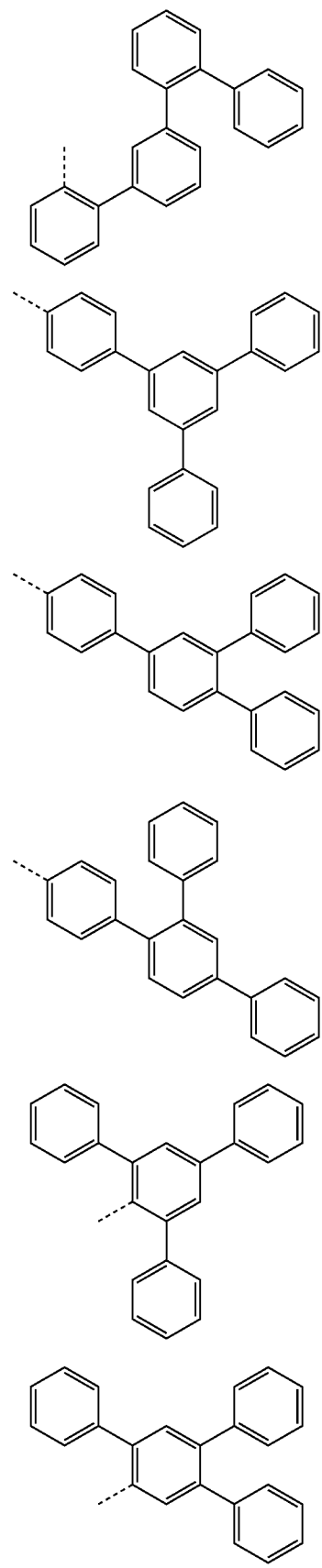
Ar-36
Ar-37
Ar-38
Ar-39
Ar-40
Ar-41
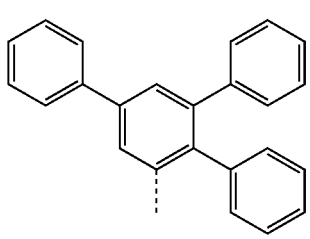
Ar-42
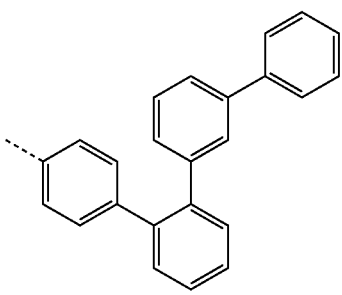
Ar-43
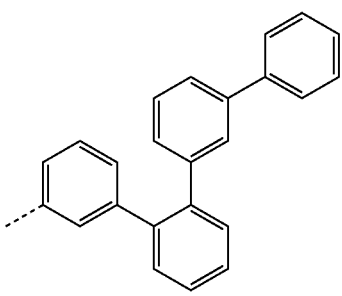
Ar-44
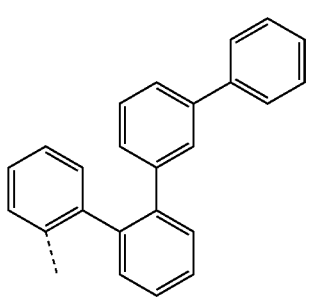
Ar-45
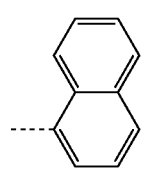
Ar-46
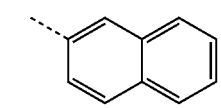
Ar-47
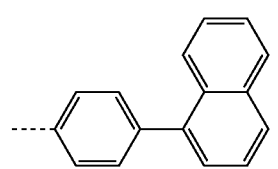
Ar-48

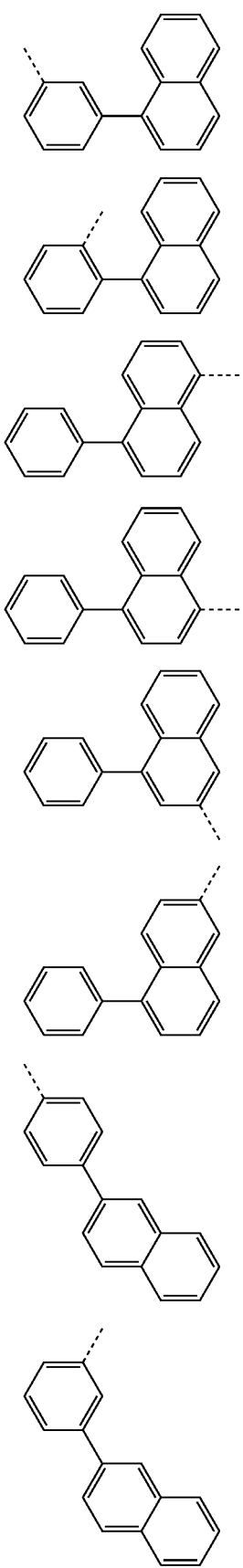
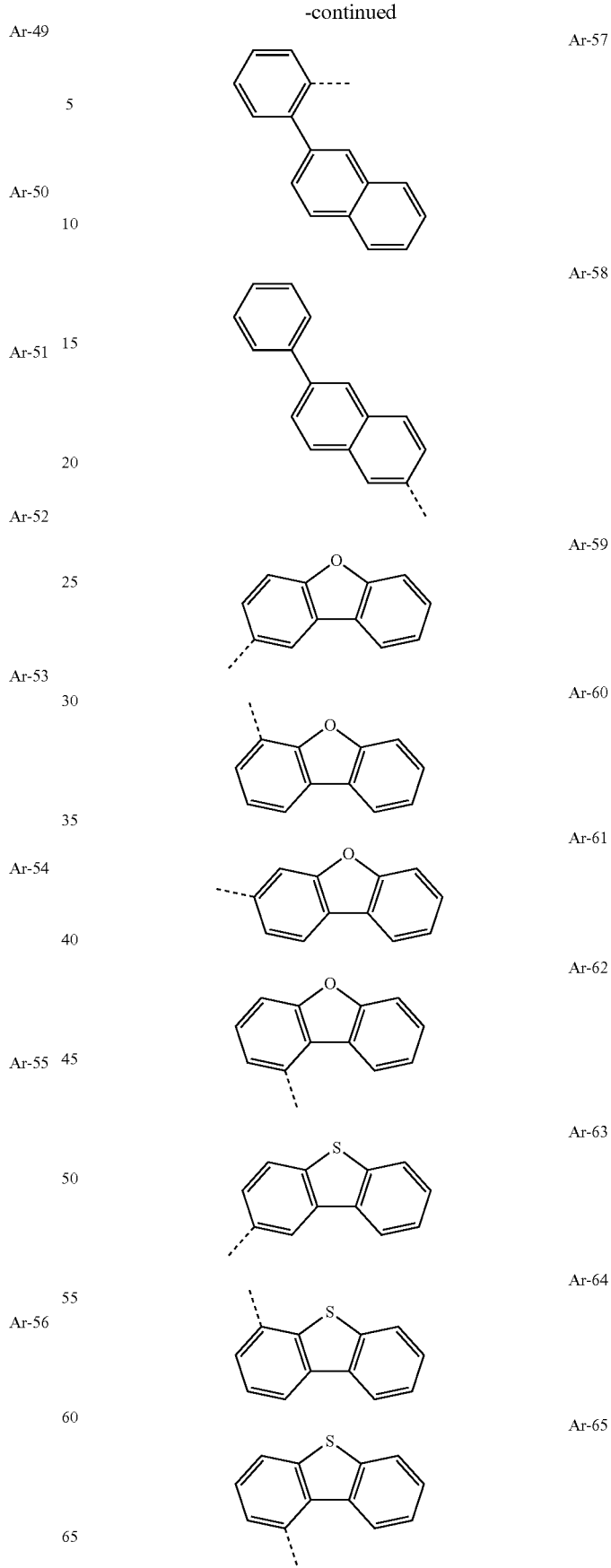

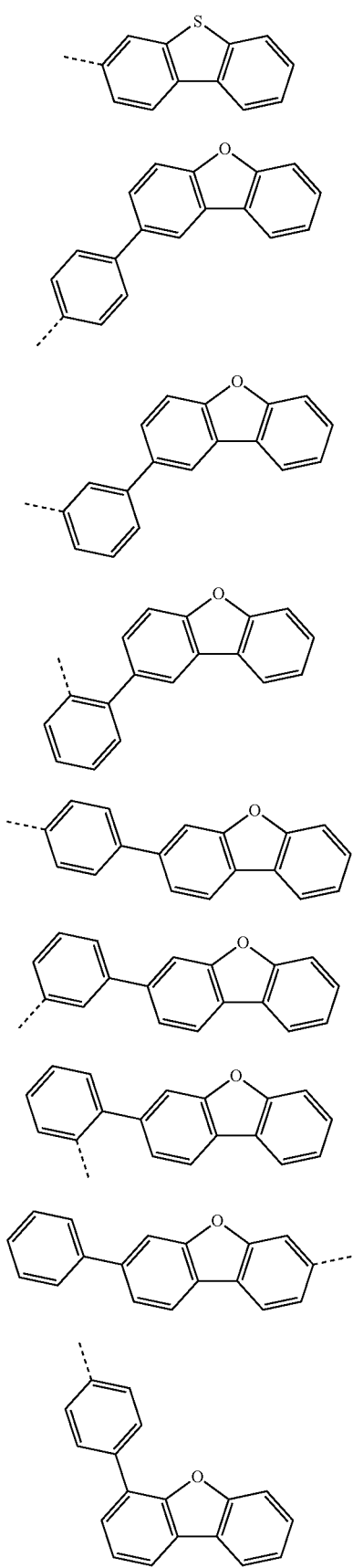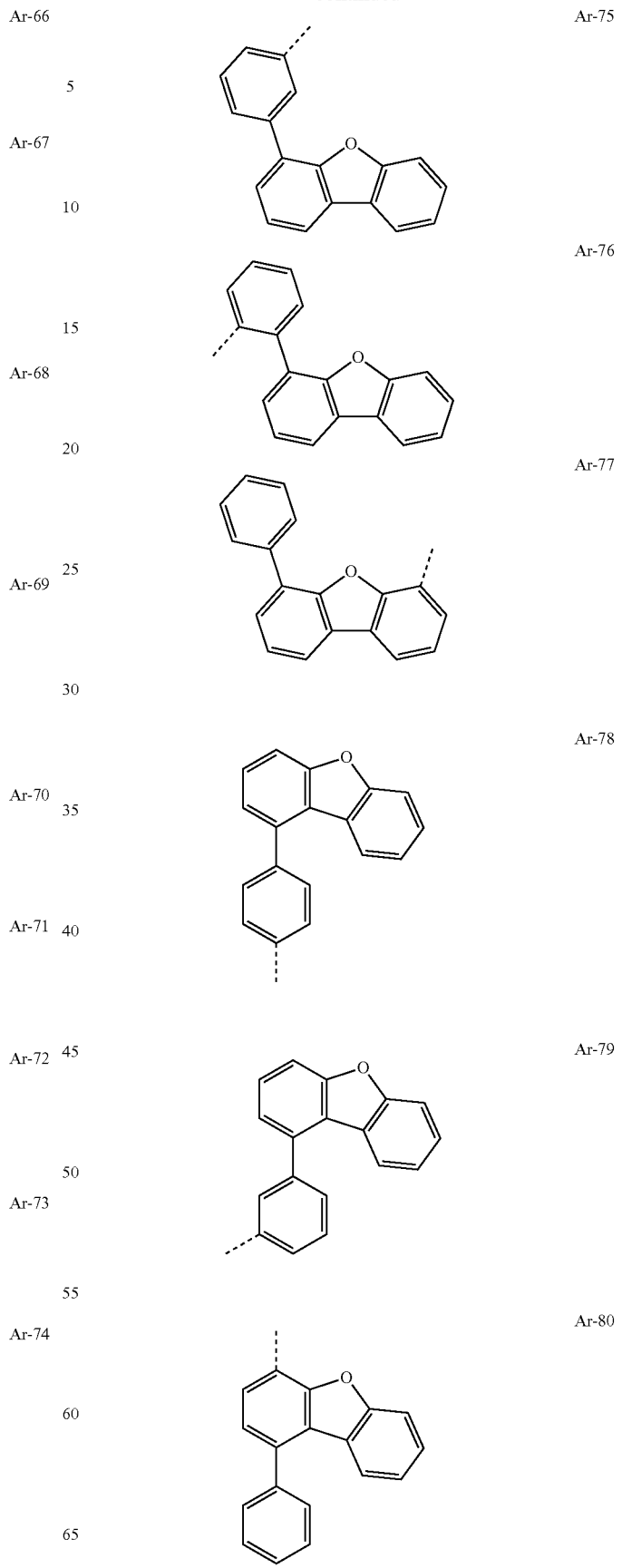

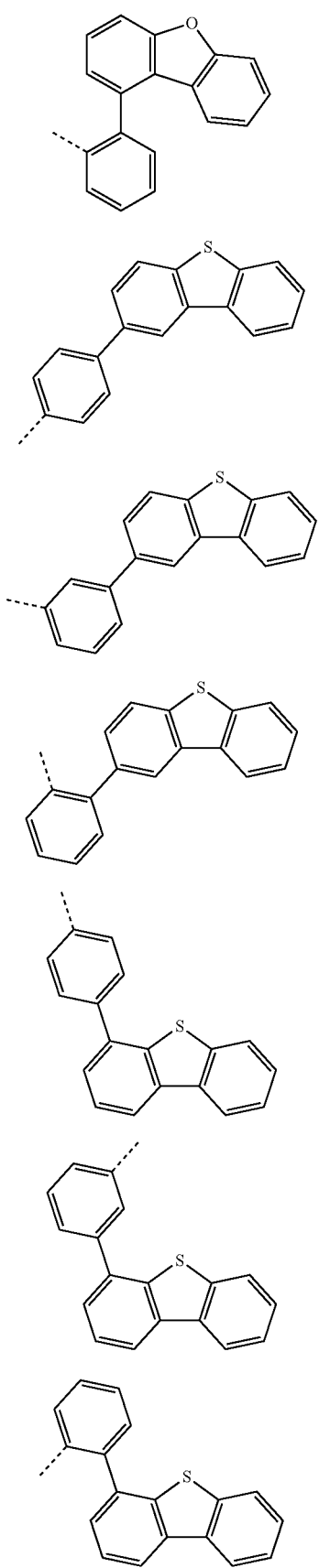
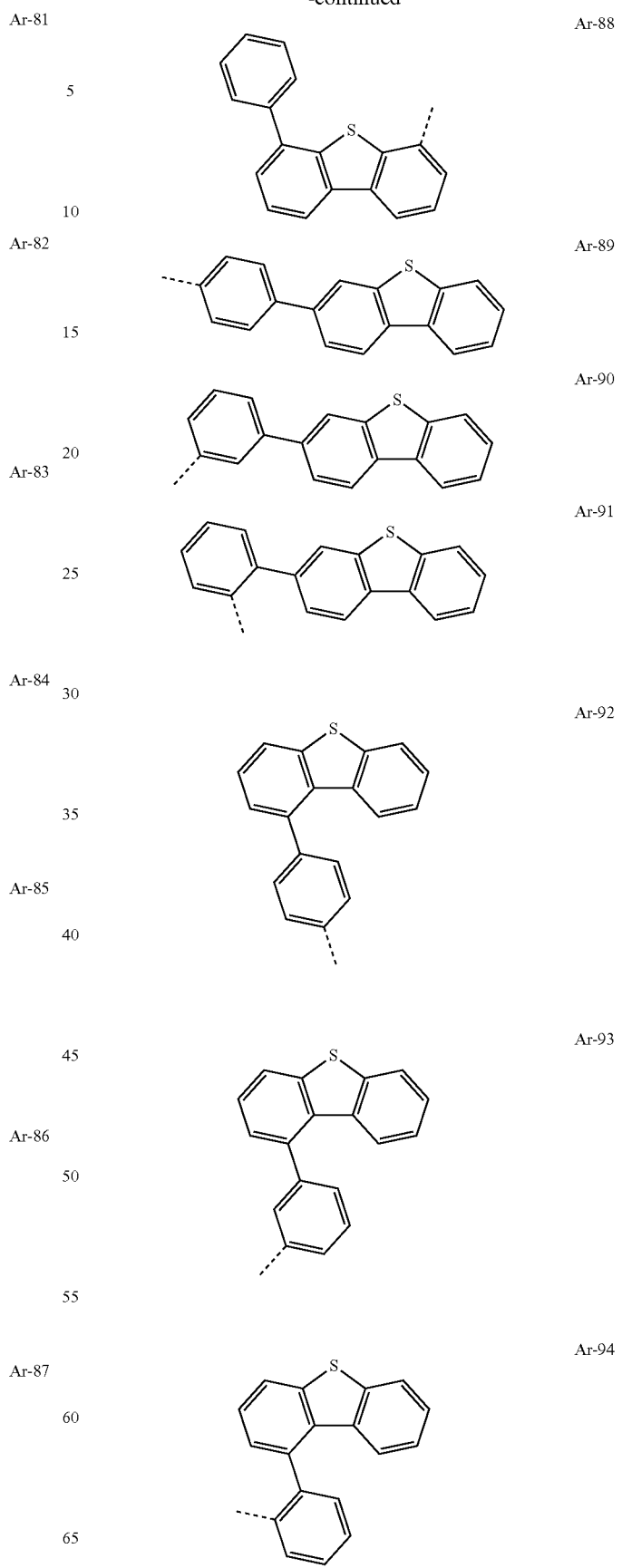

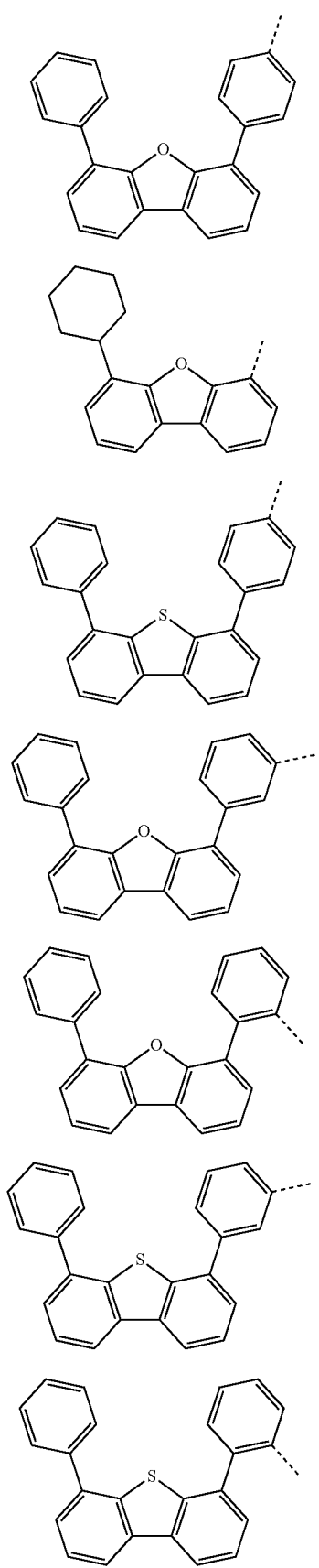
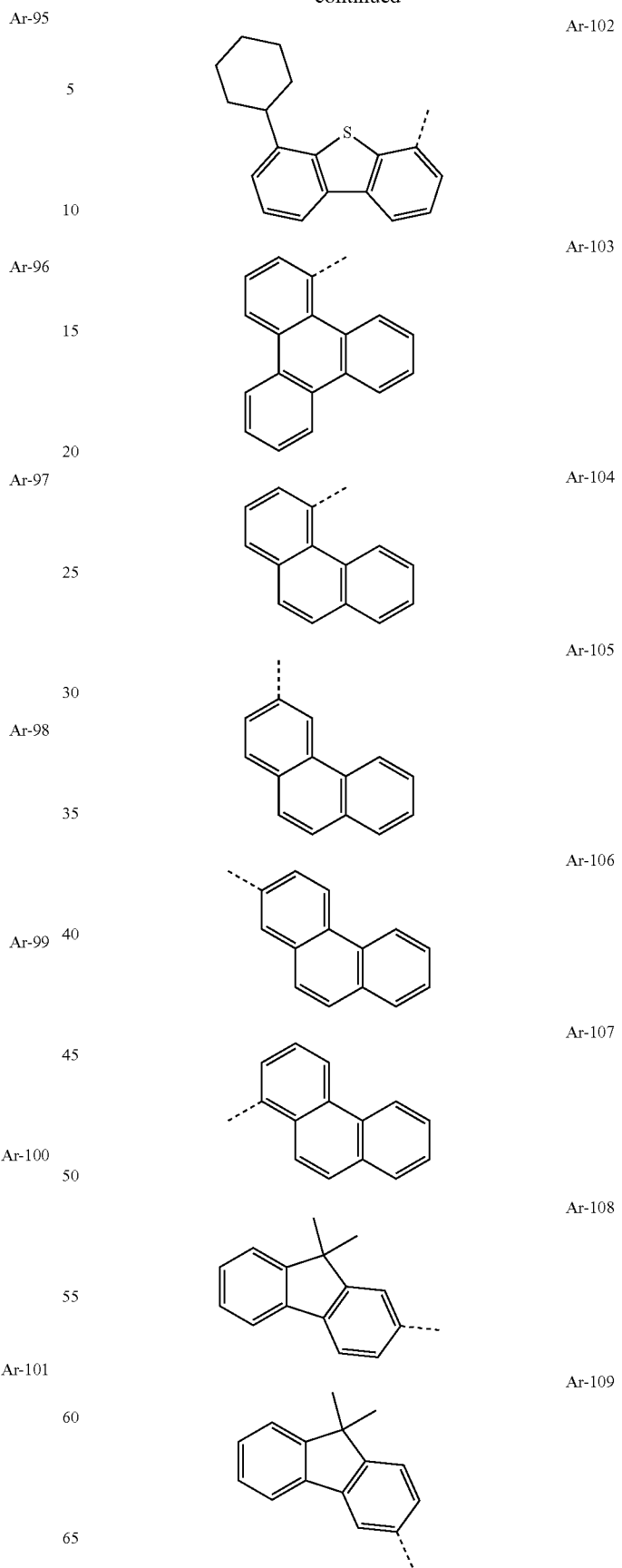

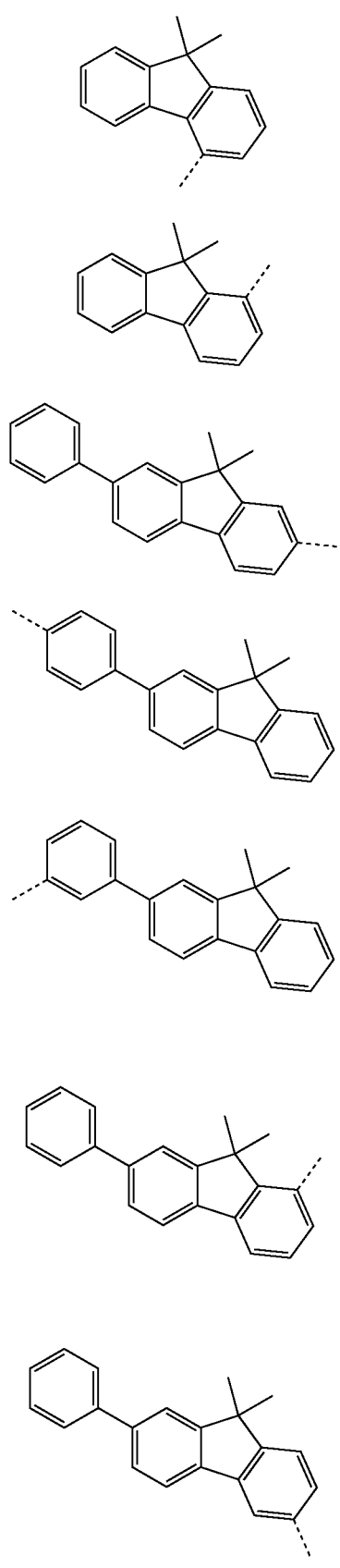
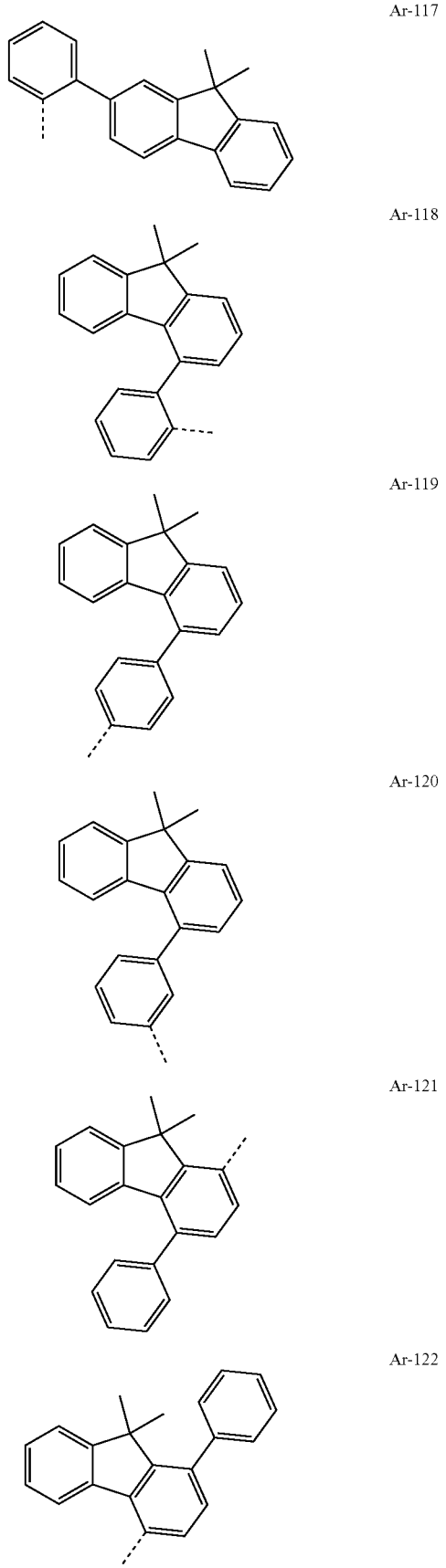

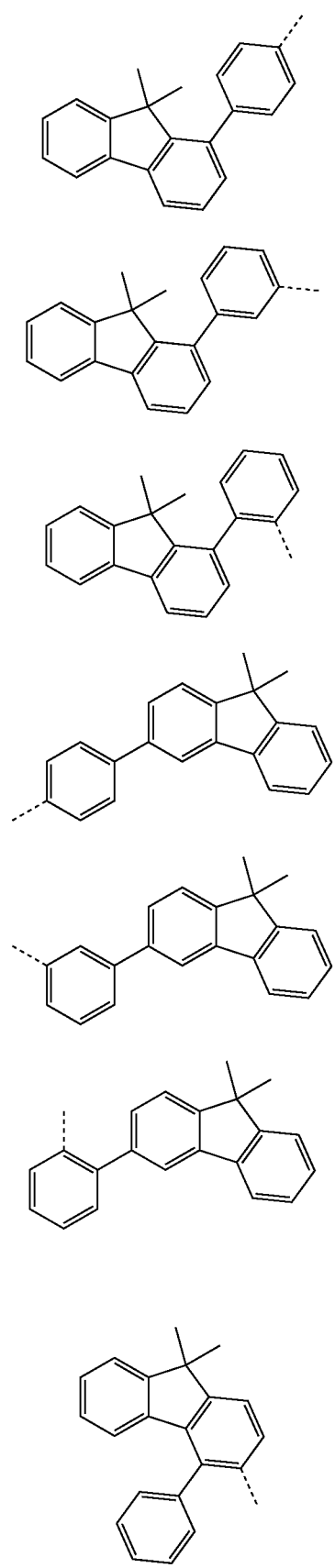
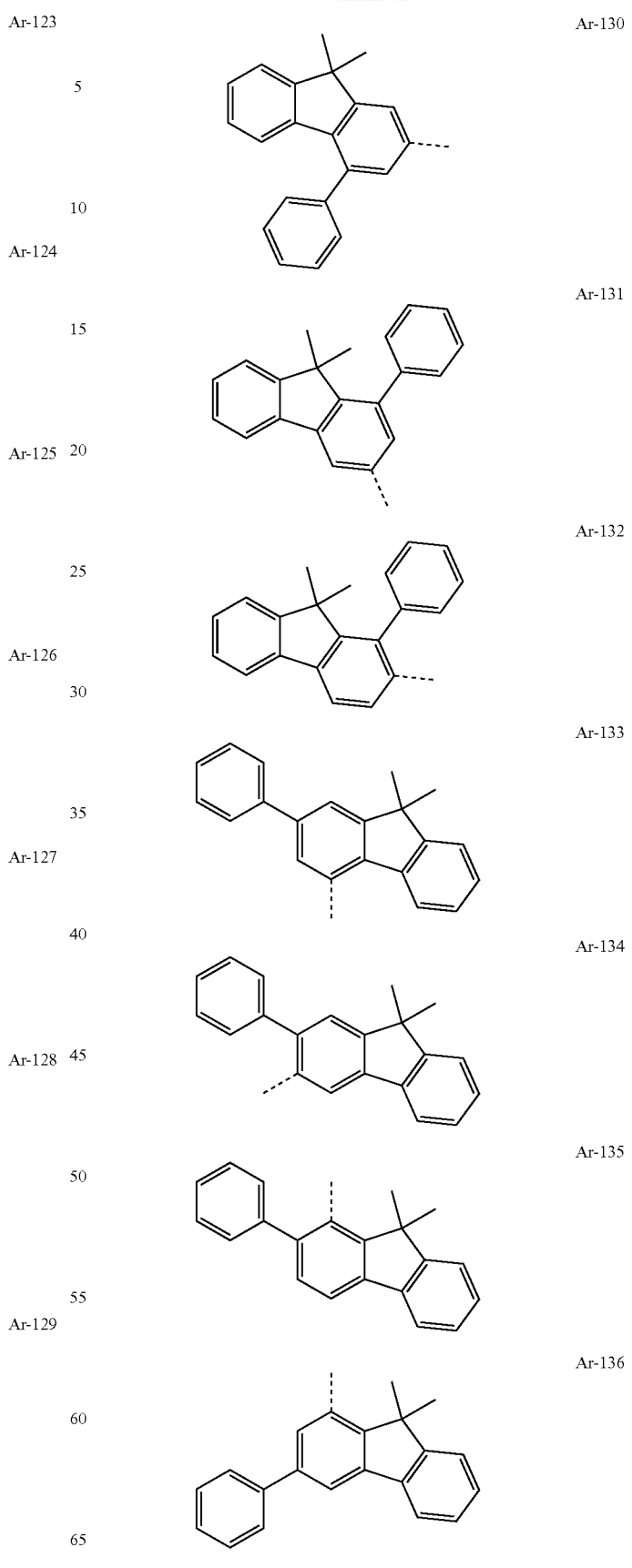

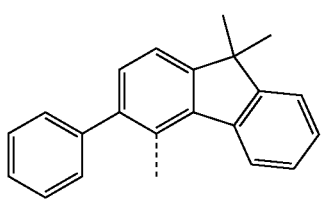 Ar-137
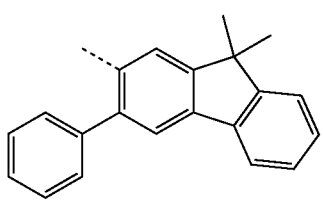 Ar-138
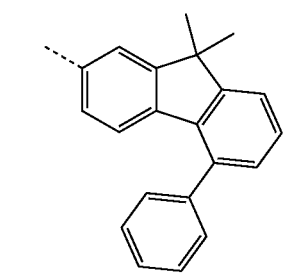 Ar-139
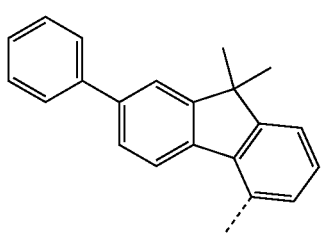 Ar-140
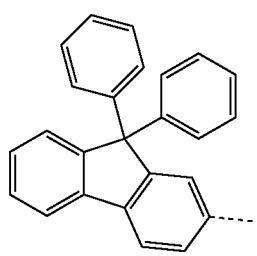 Ar-141
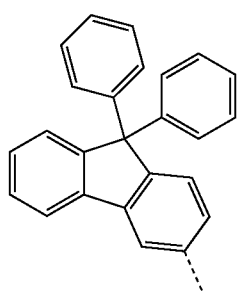 Ar-142
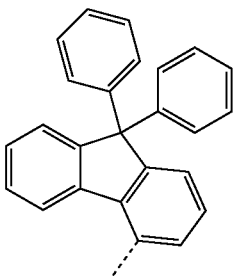 Ar-143
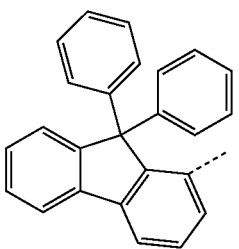 Ar-144
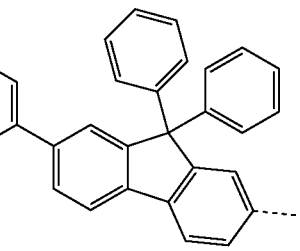 Ar-145
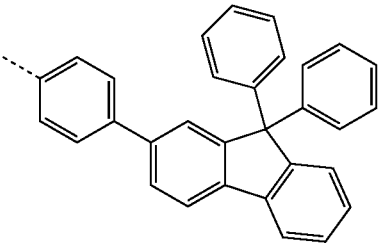 Ar-146
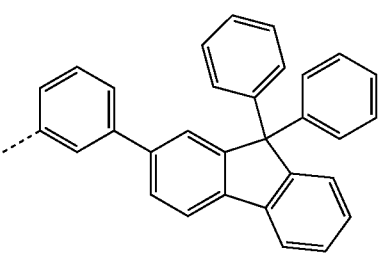 Ar-147
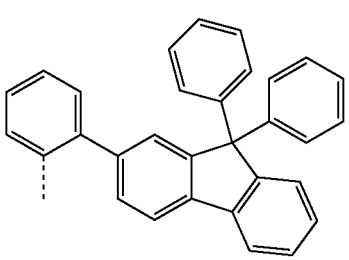 Ar-148

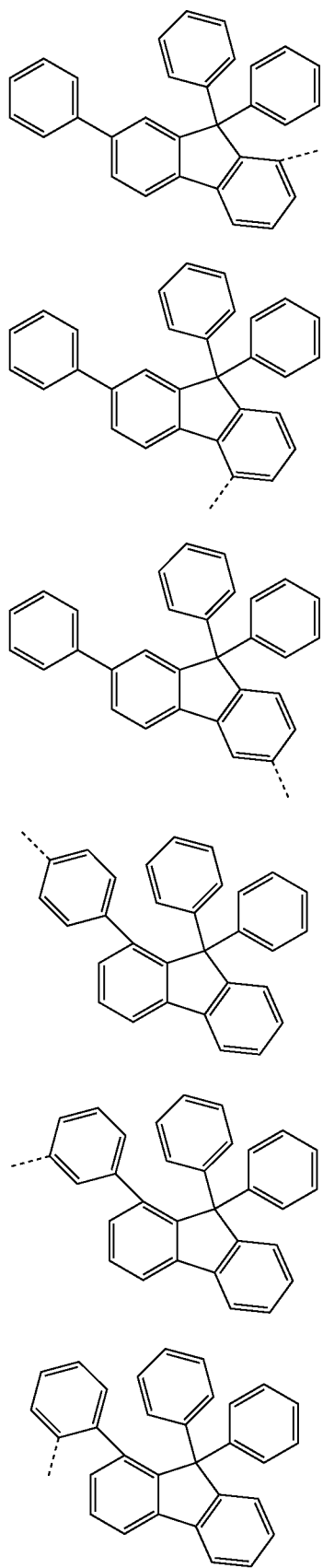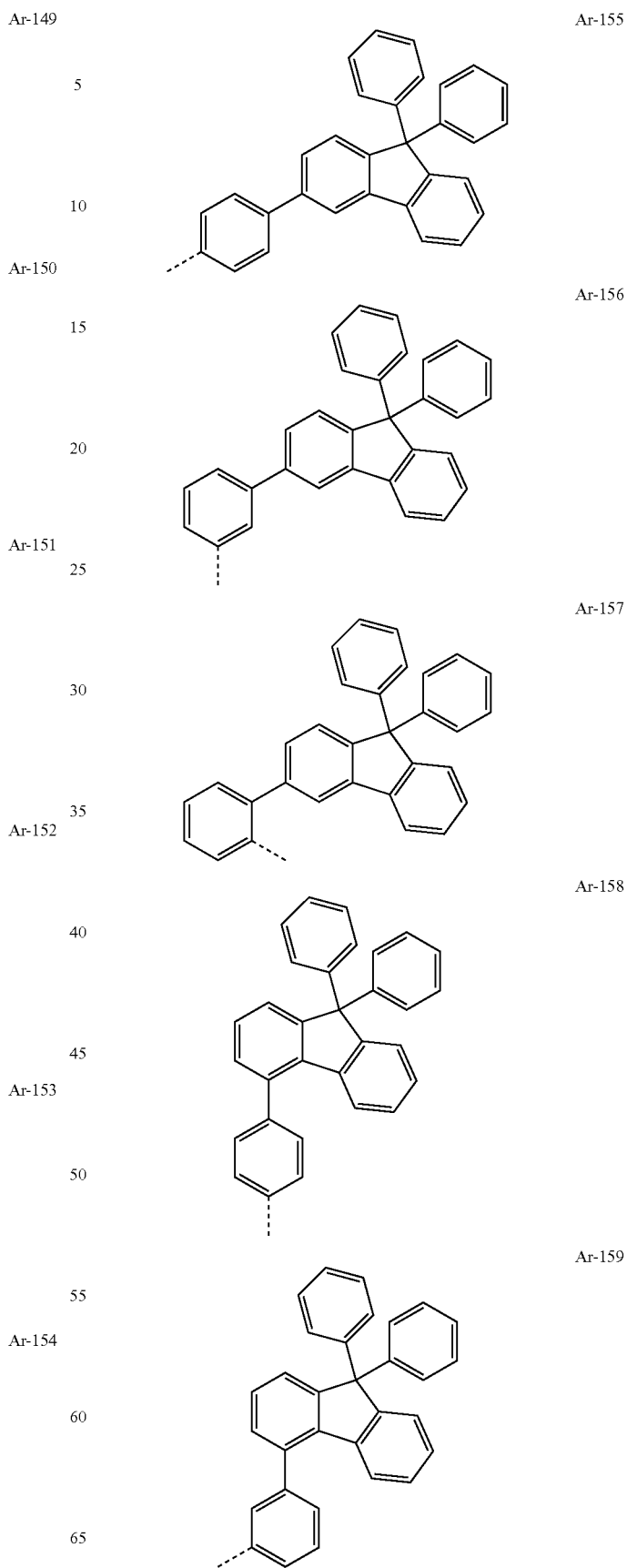

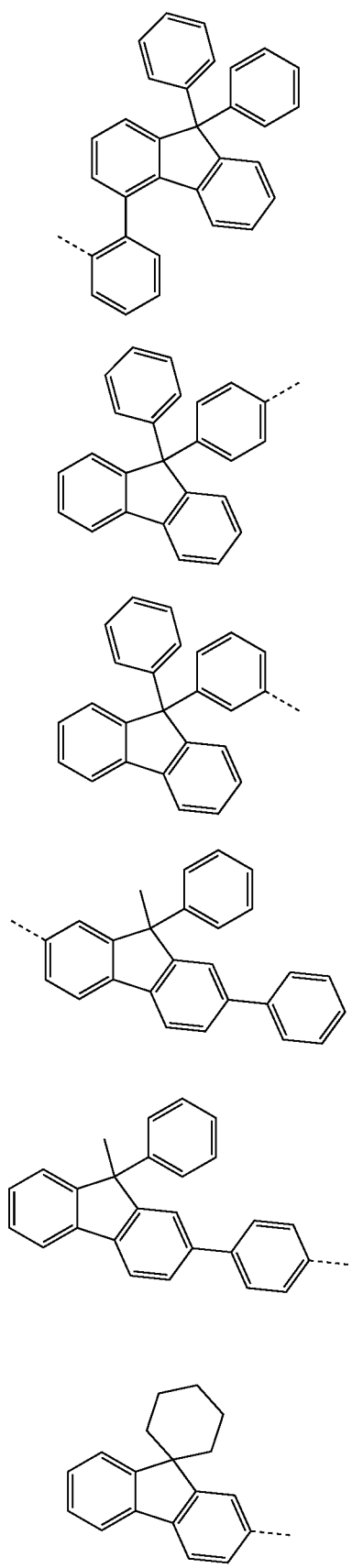
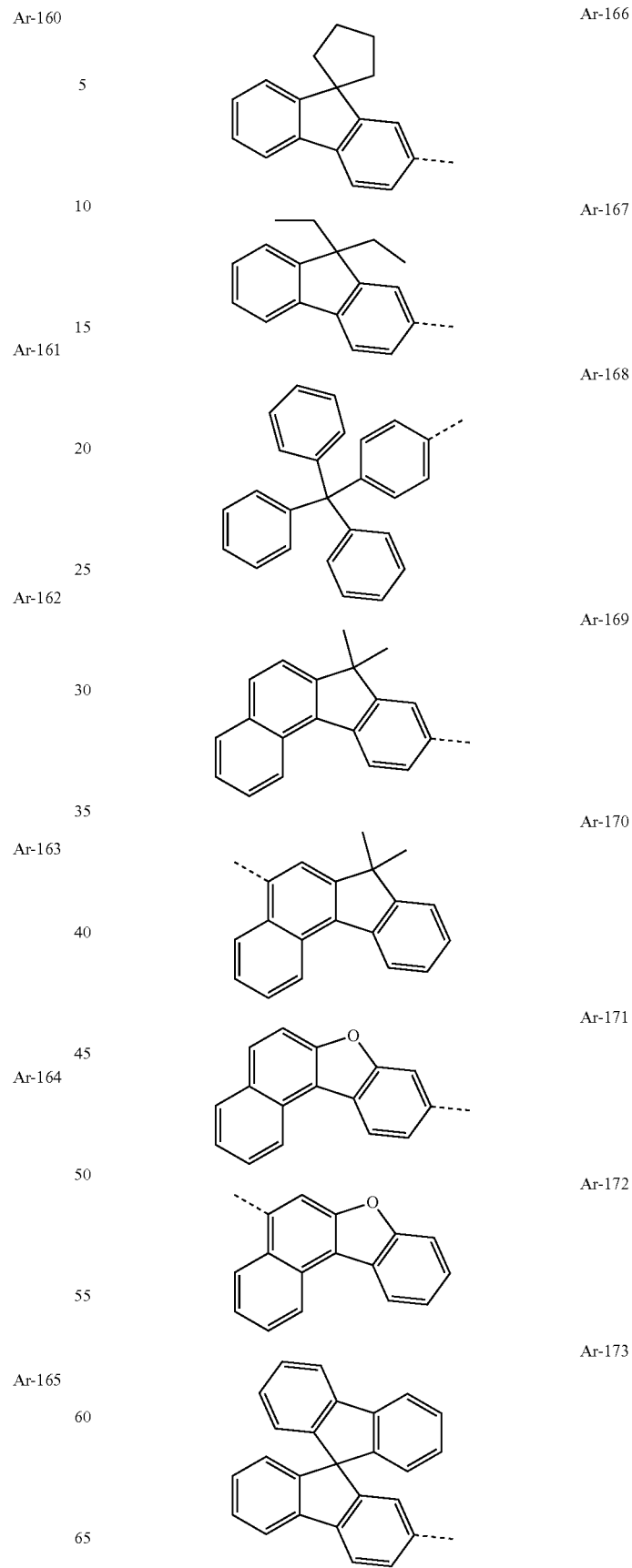

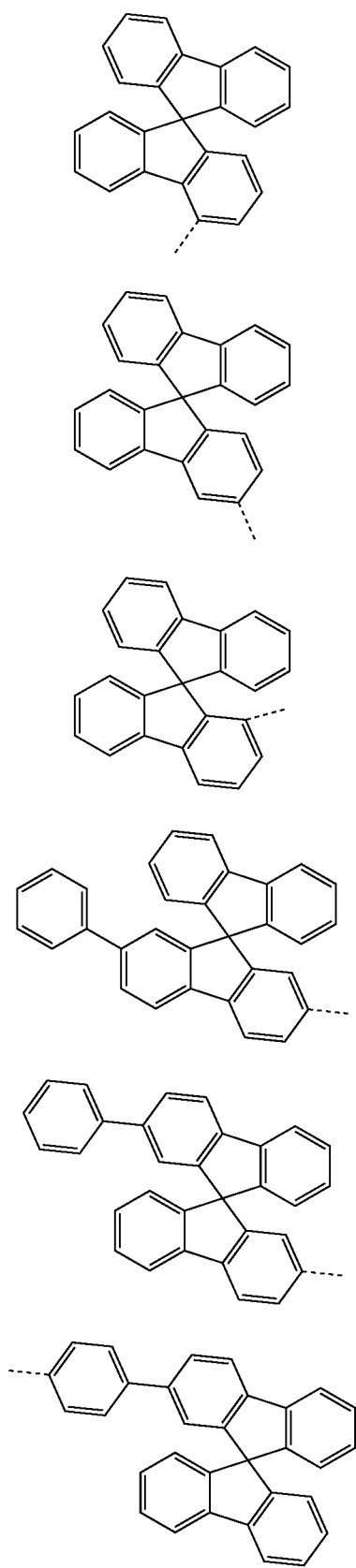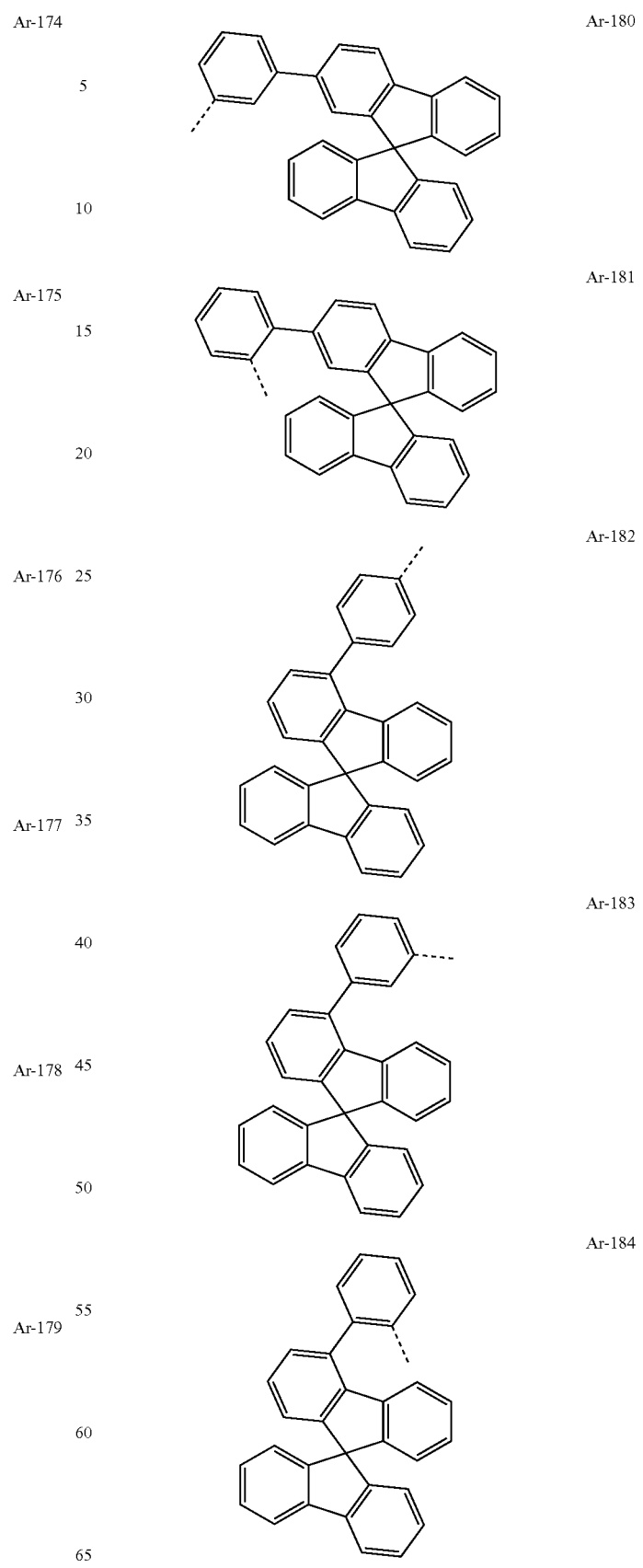

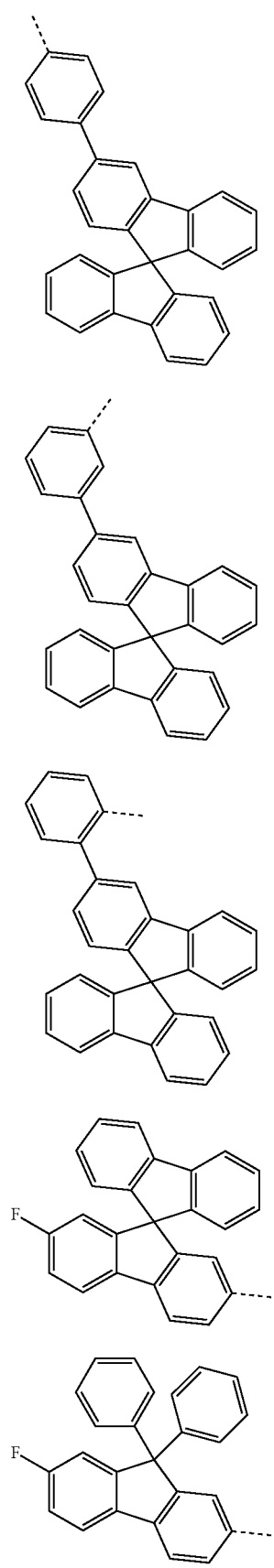
Ar-185
Ar-186
Ar-187
Ar-188
Ar-189
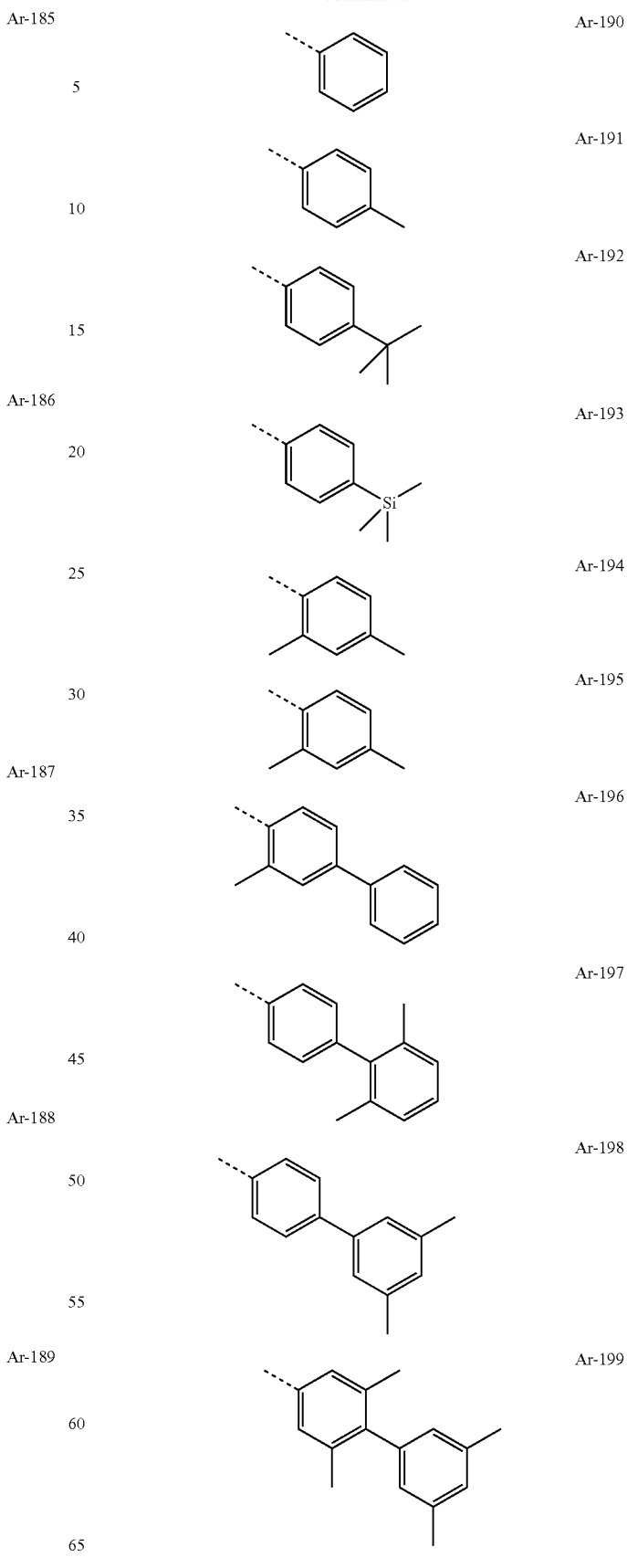
Ar-190
Ar-191
Ar-192
Ar-193
Ar-194
Ar-195
Ar-196
Ar-197
Ar-198
Ar-199

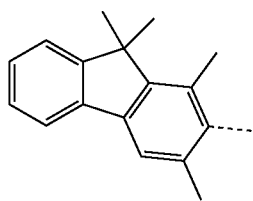
Ar-200

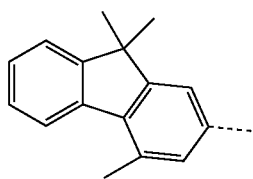
Ar-201

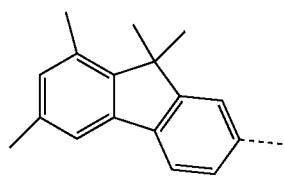
Ar-202

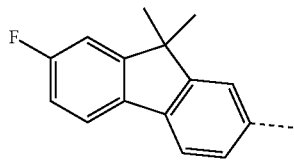
Ar-203

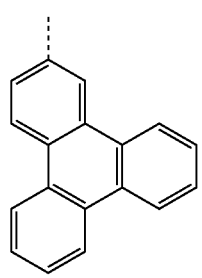
Ar-204 which may be substituted by $R^5$ radicals at the unsubstituted positions shown, but are preferably unsubstituted at these positions, and which are bonded to the rest of the formula (I) via the dotted bond.

$R^1$ is preferably the same or different at each instance and is selected from F, $Si(R^6)_3$, straight-chain alkyl groups having 1 to 20 carbon atoms, branched or cyclic alkyl groups having 3 to 20 carbon atoms, aromatic ring systems having 6 to 24 aromatic ring atoms, and heteroaromatic ring systems having 5 to 24 aromatic ring atoms; where the alkyl groups mentioned, the aromatic ring systems mentioned and the heteroaromatic ring systems mentioned may each be substituted by one or more $R^6$ radicals; and where two $R^1$ groups bonded to the same carbon atom may be joined to one another to form a ring, giving rise to a spiro carbon atom. In this case, the result is preferably a cyclopropyl, cyclobutyl, cyclopentyl, cyclohexyl or cycloheptyl ring comprising a spiro carbon atom.

$R^2$, $R^3$ and $R^4$ are preferably the same or different at each instance and are selected from H, D, F, CN, $Si(R^6)_3$, straight-chain alkyl groups having 1 to 20 carbon atoms, branched or cyclic alkyl groups having 3 to 20 carbon atoms, aromatic ring systems having 6 to 24 aromatic ring atoms and heteroaromatic ring systems having 5 to 24 aromatic ring atoms; where the alkyl groups mentioned, the aromatic ring systems mentioned and the heteroaromatic ring systems mentioned may each be substituted by one or more $R^6$ radicals; and where one or more $CH_2$ groups in the alkyl groups mentioned may be replaced by —C≡C—, —$R^6$C=$CR^6$—, $Si(R^6)_2$, C=O, C=$NR^6$, —$NR^6$—, —O—, —S—, —C(=O)O— or —C(=O)$NR^6$—. More preferably, $R^2$ is H or an aromatic ring system which has 6 to 24 aromatic ring atoms and may be substituted by one or more $R^6$ radicals, or a heteroaromatic ring system which has 5 to 24 aromatic ring atoms and may be substituted by one or more $R^6$ radicals, most preferably H. More preferably, in addition, $R^3$ is H or an aromatic ring system which has 6 to 24 aromatic ring atoms and may be substituted by one or more $R^6$ radicals, or a heteroaromatic ring system which has 5 to 24 aromatic ring atoms and may be substituted by one or more $R^6$ radicals, most preferably H.

$R^5$ is preferably the same or different at each instance and is selected from H, D, $Si(R^6)_3$, straight-chain alkyl groups having 1 to 20 carbon atoms, branched or cyclic alkyl groups having 3 to 20 carbon atoms, aromatic ring systems having 6 to 24 aromatic ring atoms, and heteroaromatic ring systems having 5 to 24 aromatic ring atoms; where the alkyl groups mentioned, the aromatic ring systems mentioned and the heteroaromatic ring systems mentioned may each be substituted by one or more $R^6$ radicals, where $R^5$ and substituents bonded to $R^5$ do not contain any carbazole group. More preferably, $R^5$ is H or an aromatic ring system which has 6 to 24 aromatic ring atoms and may be substituted by one or more $R^6$ radicals, where substituents bonded to $R^5$ do not contain any carbazole group; most preferably, $R^5$ is H.

$R^6$ is preferably the same or different at each instance and is selected from H, D, F, CN, $Si(R^7)_3$, straight-chain alkyl groups having 1 to 20 carbon atoms, branched or cyclic alkyl groups having 3 to 20 carbon atoms, aromatic ring systems having 6 to 24 aromatic ring atoms and heteroaromatic ring systems having 5 to 24 aromatic ring atoms; where the alkyl groups mentioned, the aromatic ring systems mentioned and the heteroaromatic ring systems mentioned may each be substituted by one or more $R^7$ radicals; and where one or more $CH_2$ groups in the alkyl groups mentioned may be replaced by —C≡C—, —$R^7$C=$CR^7$—, $Si(R^7)_2$, C=O, C=$NR^7$, —$NR^7$—, —O—, —S—, —C(=O)O— or —C(=O)$NR^7$—.

Index i is preferably 0 or 1, more preferably 0.

Index k is preferably 1. For compounds of this kind, improved performance data are obtained on use in electronic devices, especially in OLEDs, even more especially on use as matrix materials for phosphorescent emitters in OLEDs. These improvements relate especially to the efficiency, lifetime and operating voltage of the devices.

Preferred compounds correspond to one of the following formulae (I-1) to (I-12):

Formula (I-1)

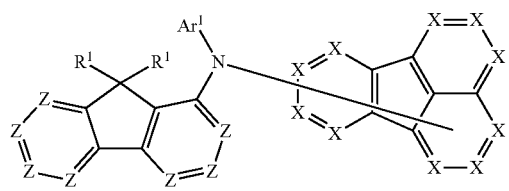

Formula (1-2)
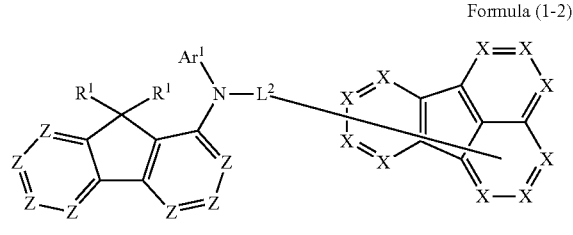
Formula (1-3)
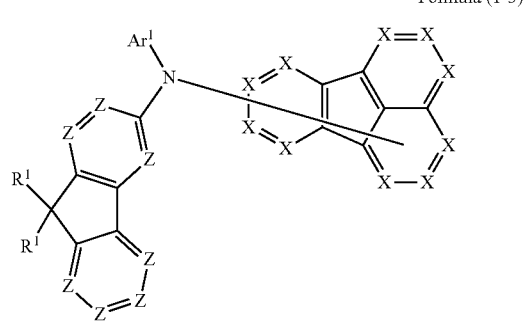
Formula (1-4)
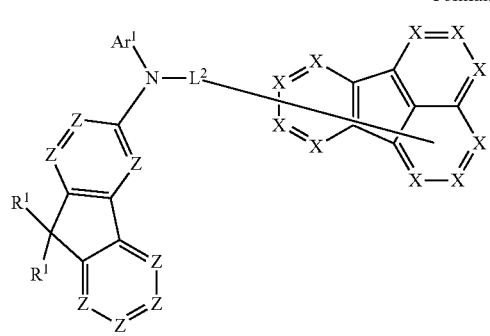
Formula (1-5)
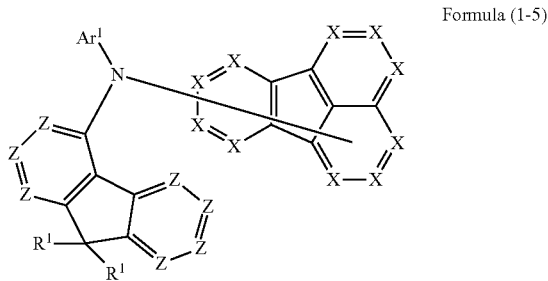
Formula (1-6)
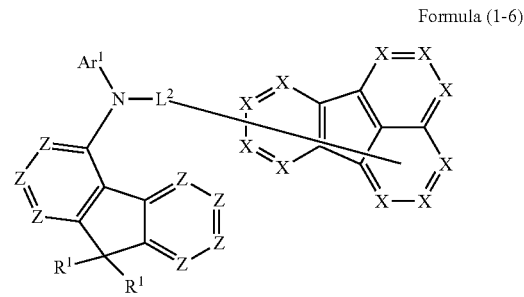
Formula (1-7)
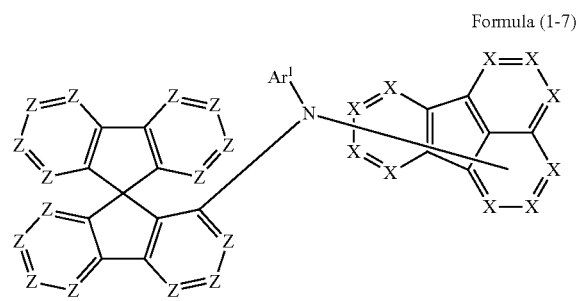
Formula (1-8)
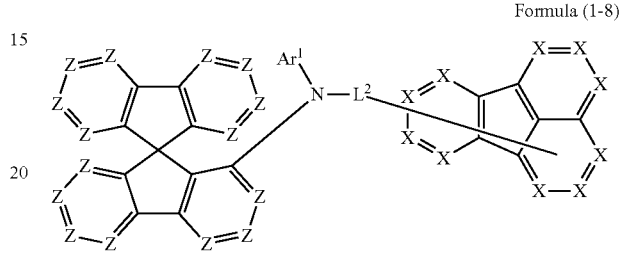
Formula (1-9)
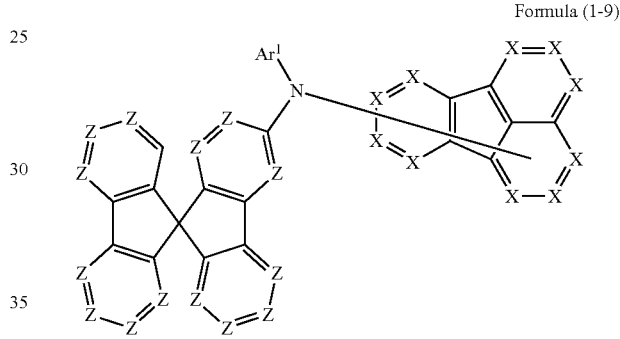
Formula (1-10)
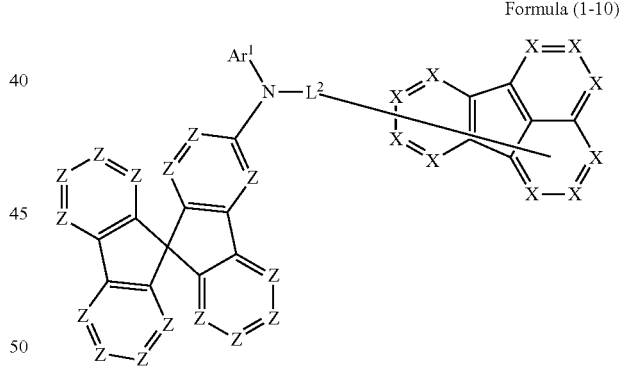
Formula (1-11)
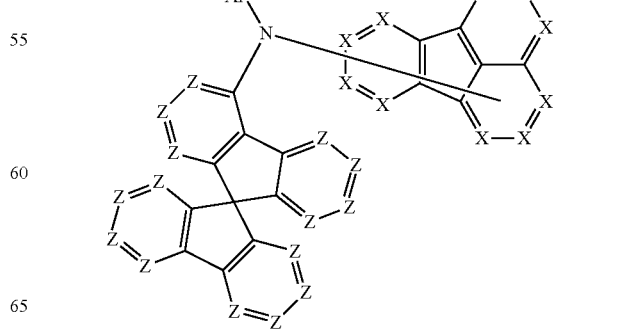

Formula (1-12)

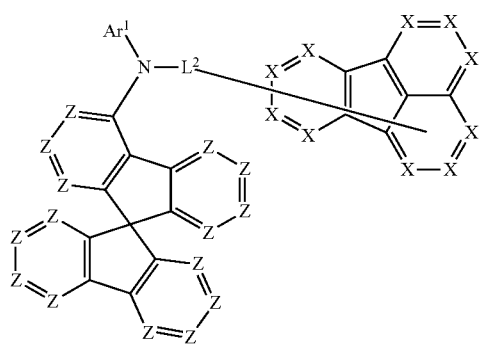

where the symbols that occur are as defined above. Preferably, the above-specified preferred embodiments of the variables apply to the formulae. It is especially preferable that the fluoranthene group is bonded in position 3, as defined above. It is also especially preferably the case that Z is $CR^2$, and/or X is $CR^3$ or C, where X is C in the specific case when the nitrogen atom or the $L^2$ group is bonded to the X in question; and/or that $L^2$ is defined according to the abovementioned preferred embodiments; and/or that $Ar^1$ is defined according to the abovementioned preferred embodiments.

Particularly preferred among the above-specified formulae are the formulae (I-1), (I-2), (I-5), (I-6), (I-7), (I-8), (I-11) and (I-12), even more preferred are the formulae (I-5) and (I-6), and most preferred is the formula (I-6). Preferred compounds of the formula (I) are depicted below:

1

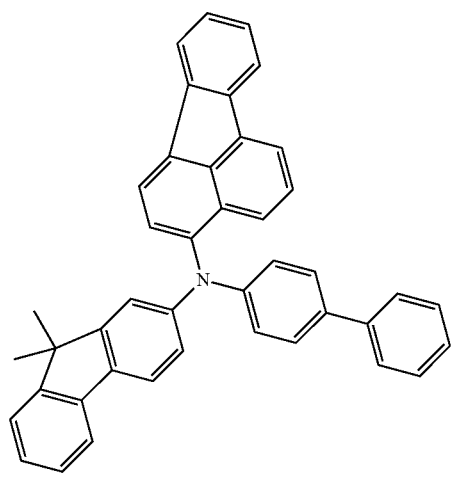

2

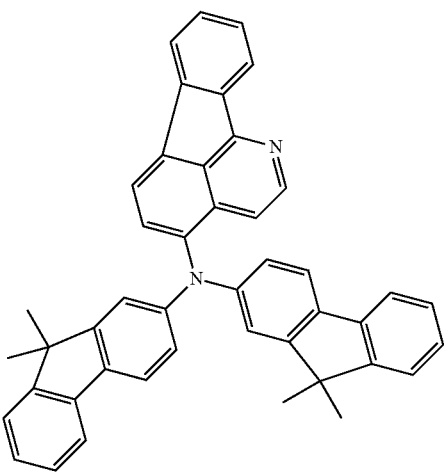

3

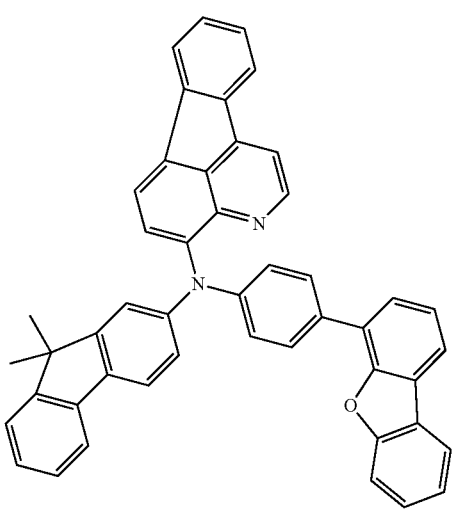

4

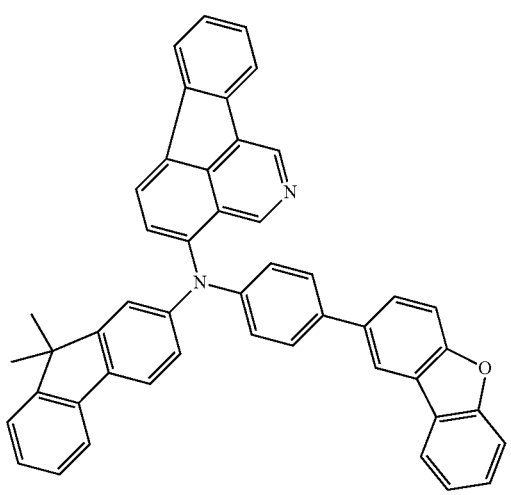

5
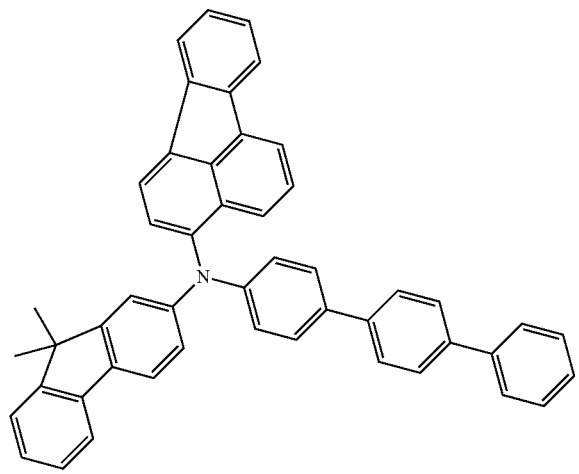
6
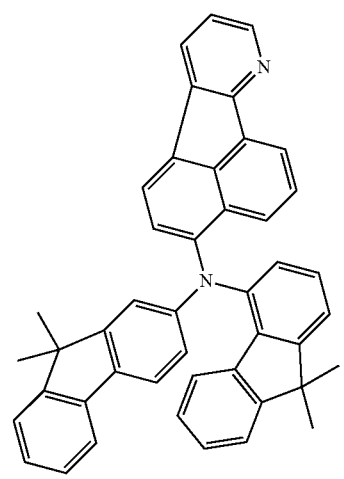
7
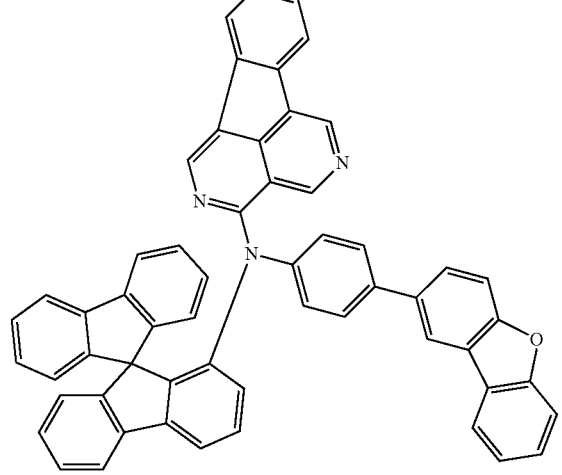
8
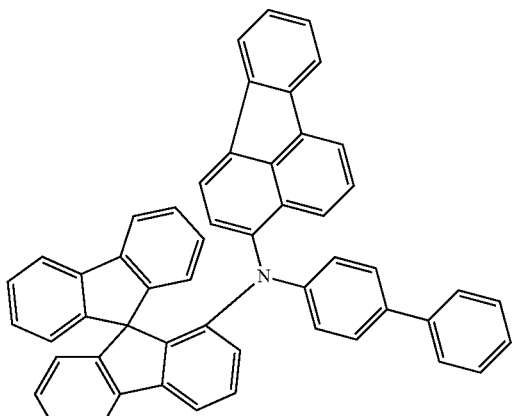
9
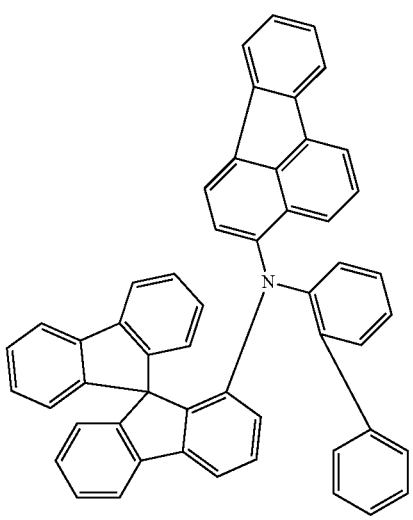
10
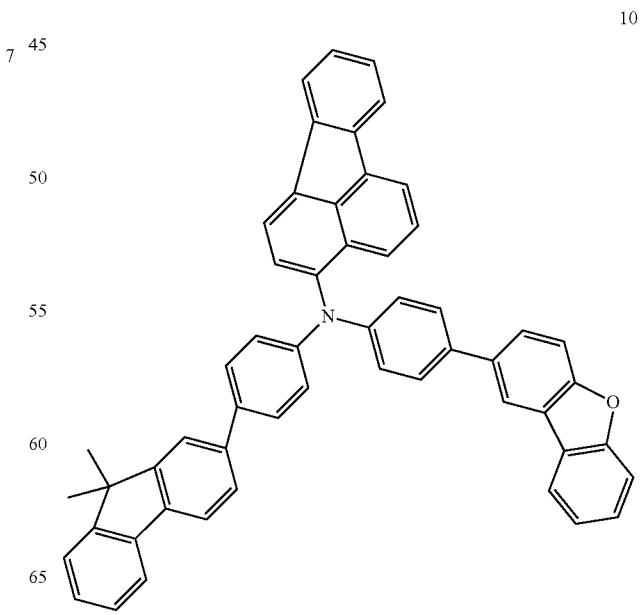

11
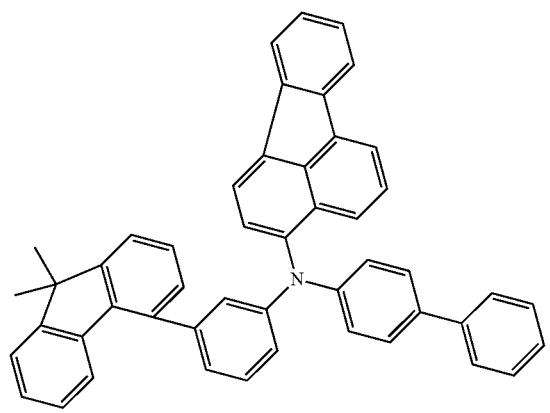
14
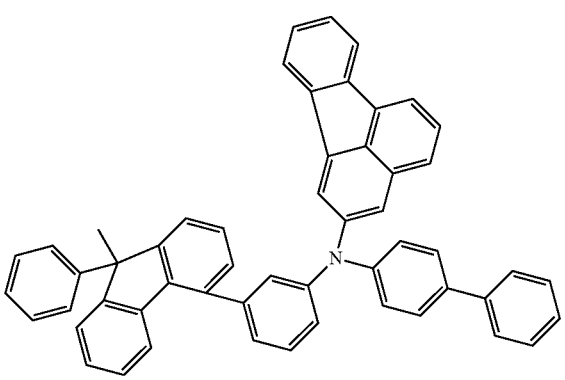
12
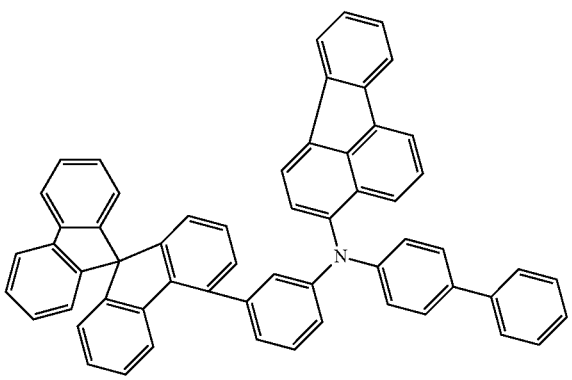
15
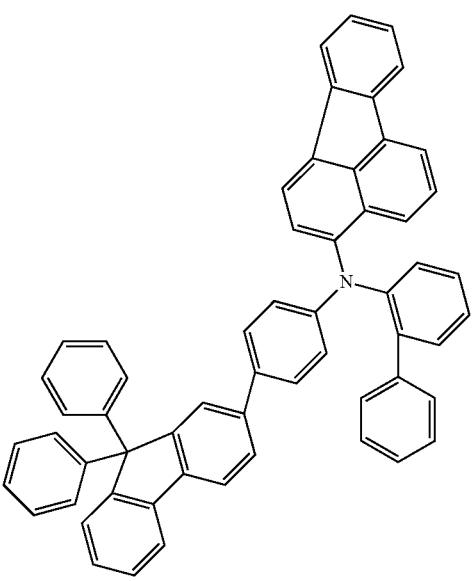
13
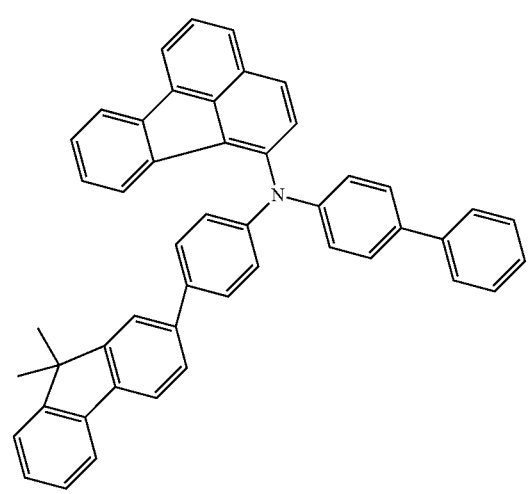
16

17
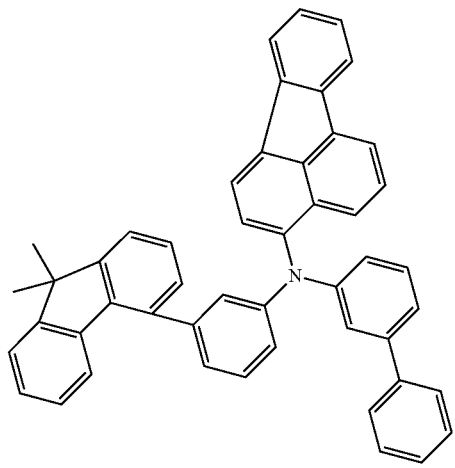
18
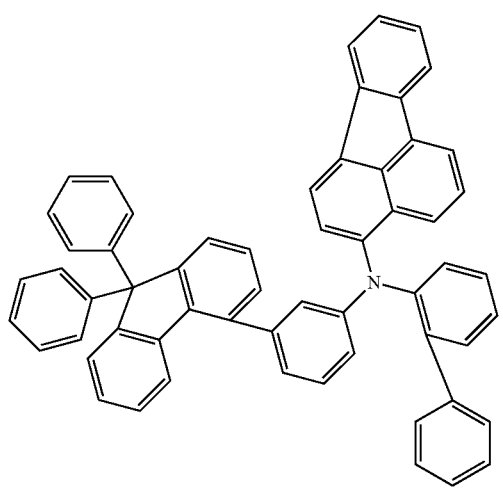
19
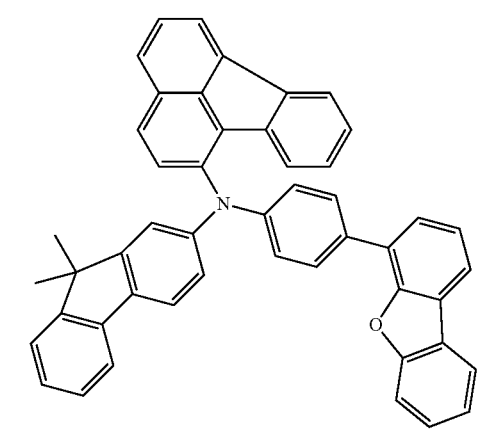
20
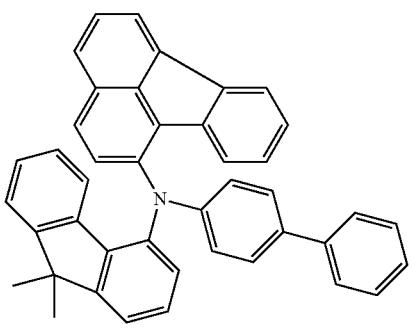
21
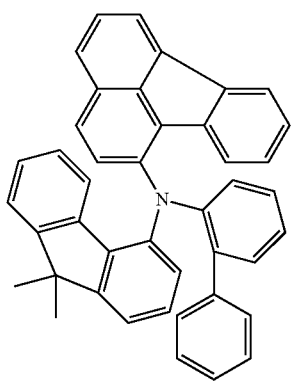
22
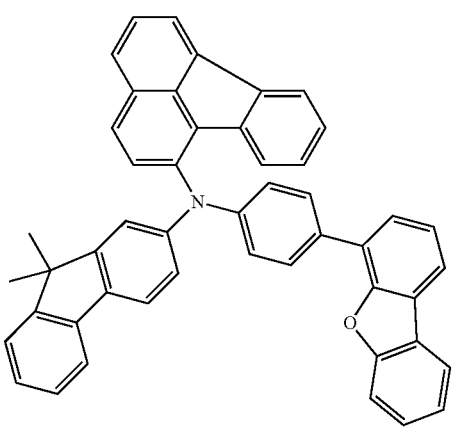
23
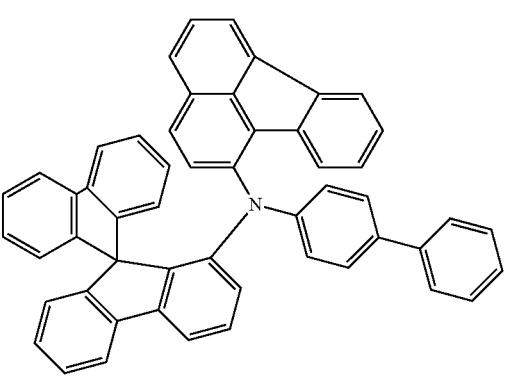

24
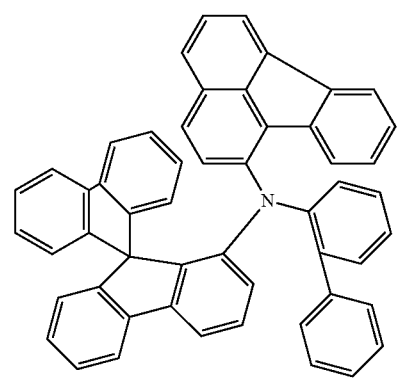
25
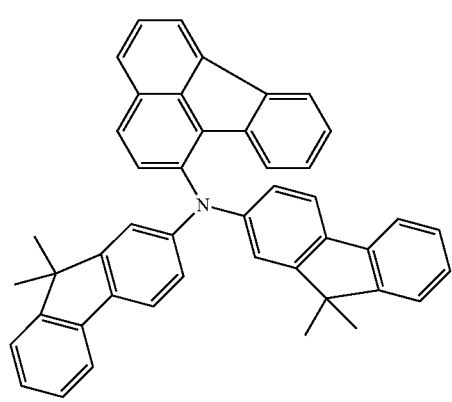
26
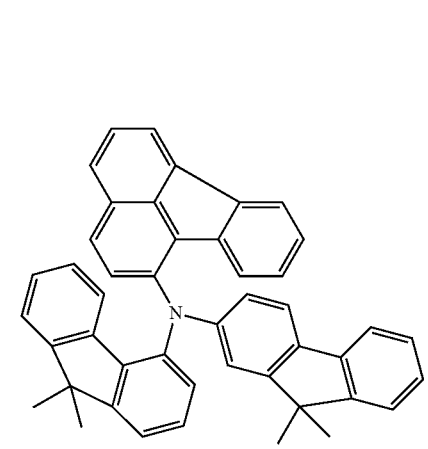
27
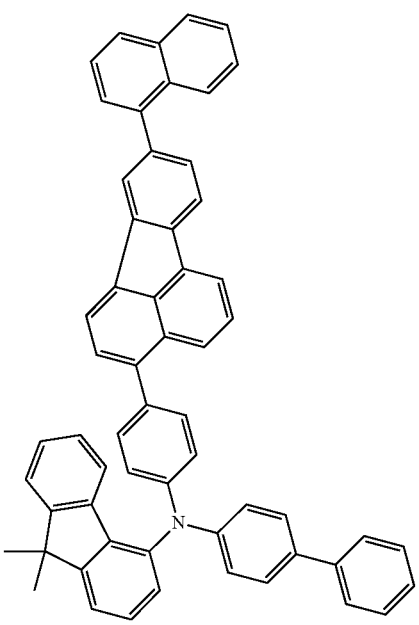
28
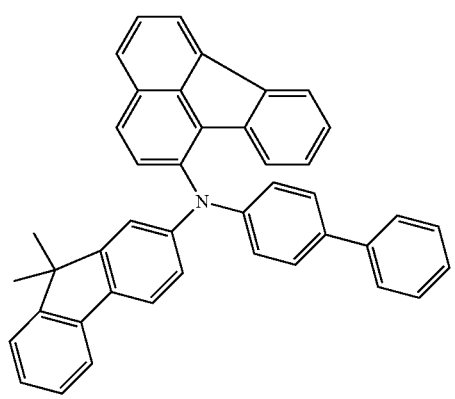
29
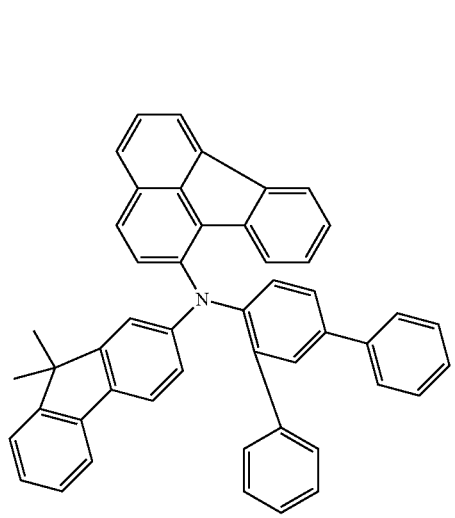

-continued
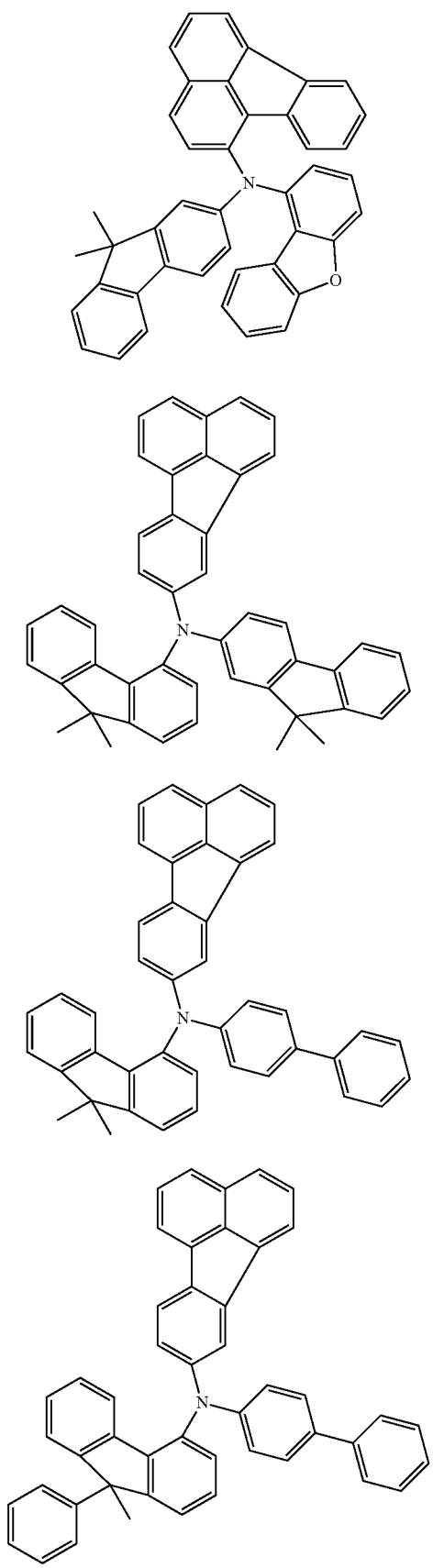
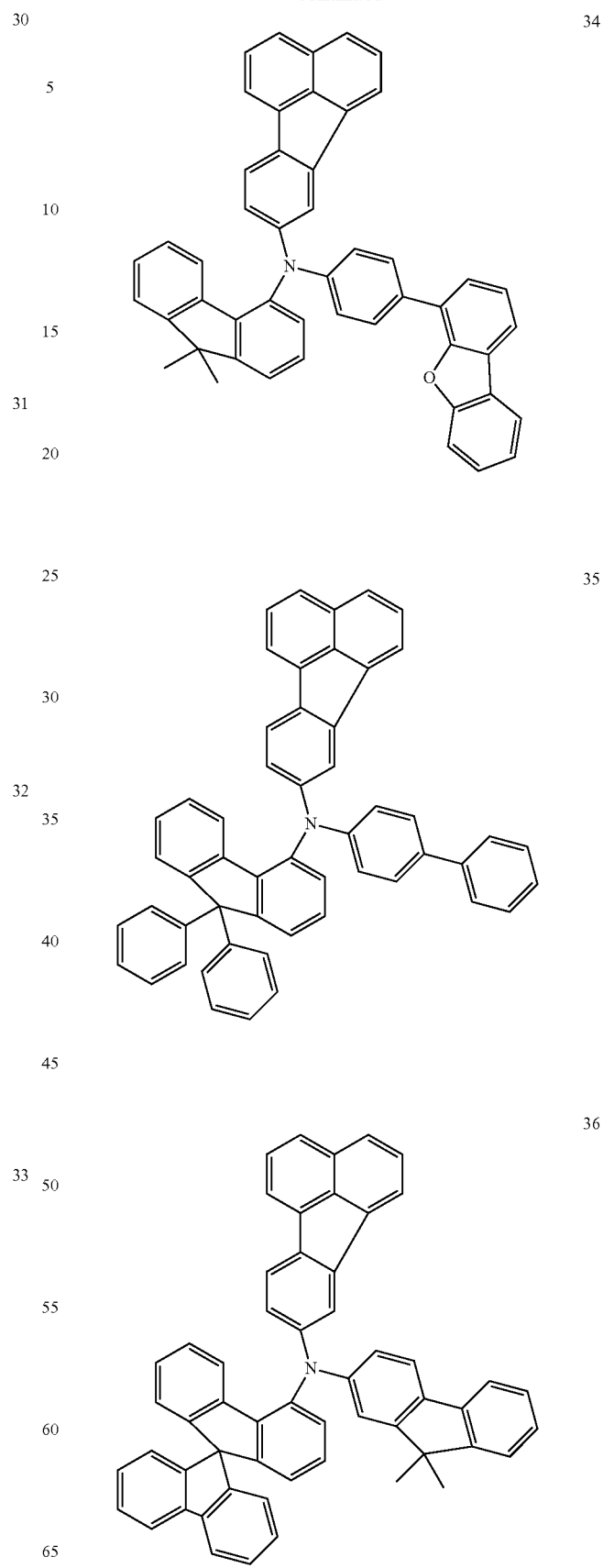

37
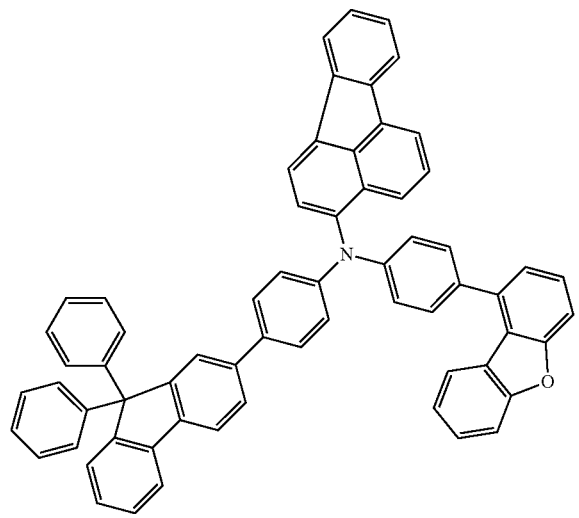
38
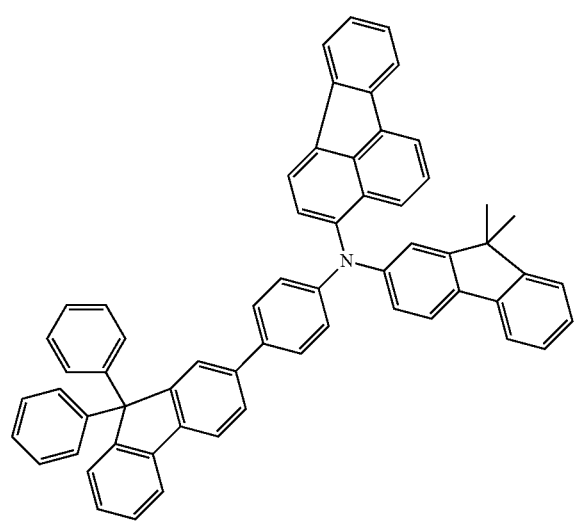
39
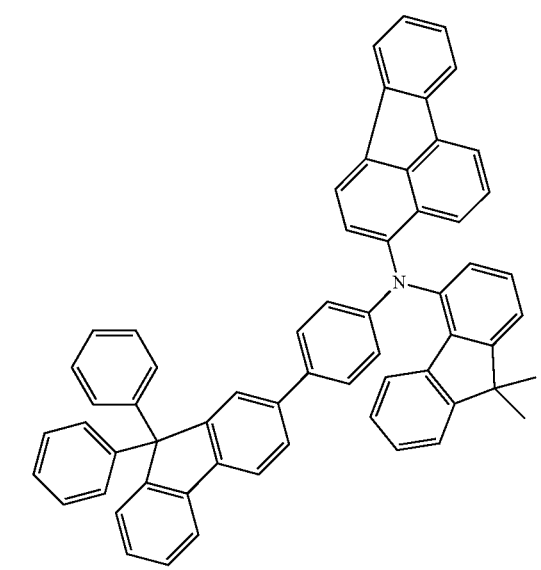
40
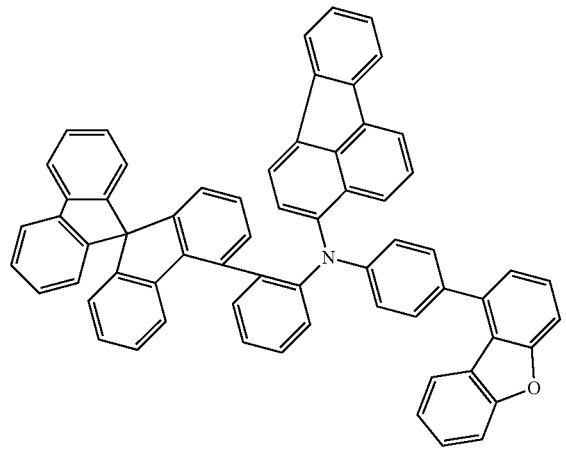
41
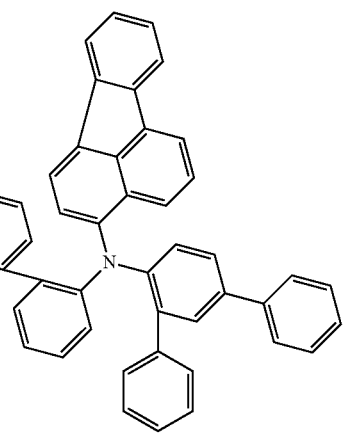
42

43
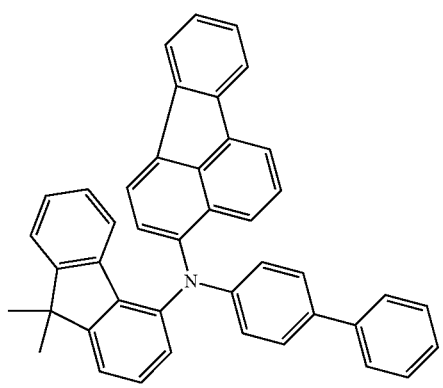
44
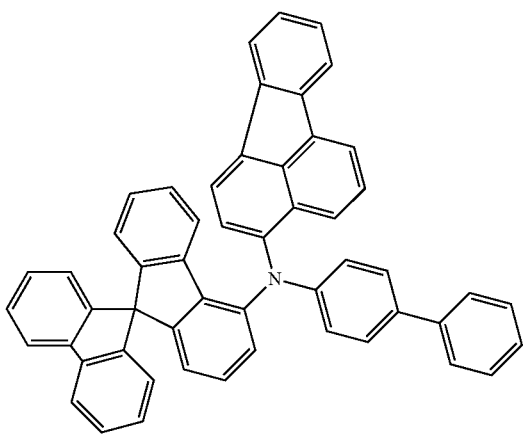
45
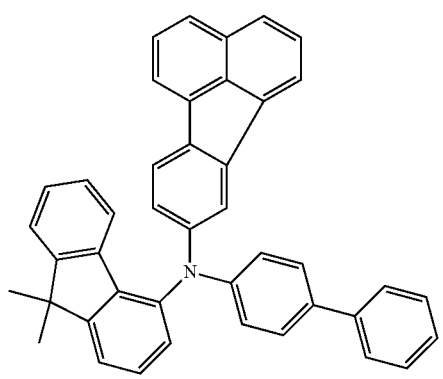
46
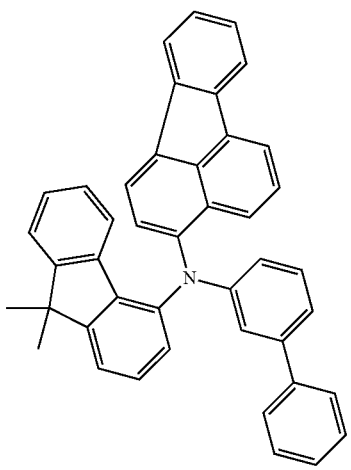
47
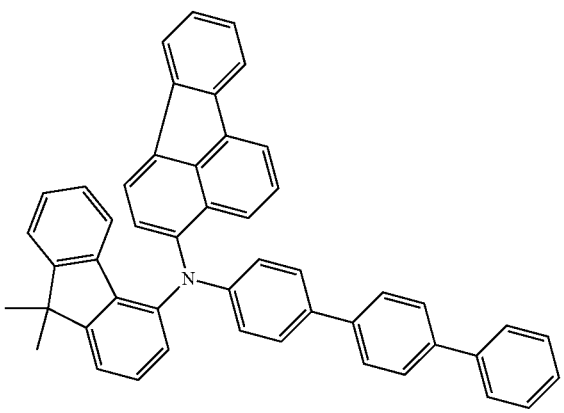
48
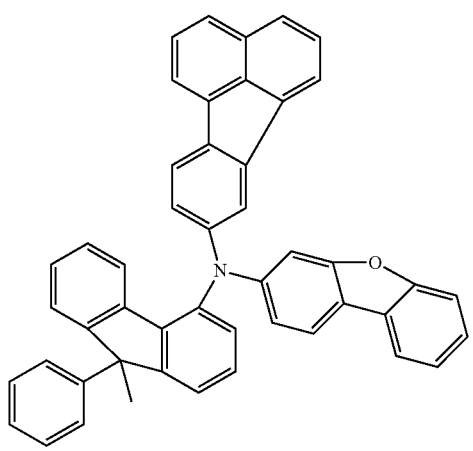

49
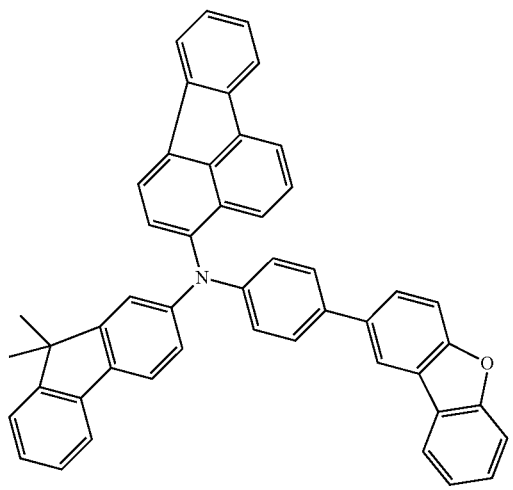
50
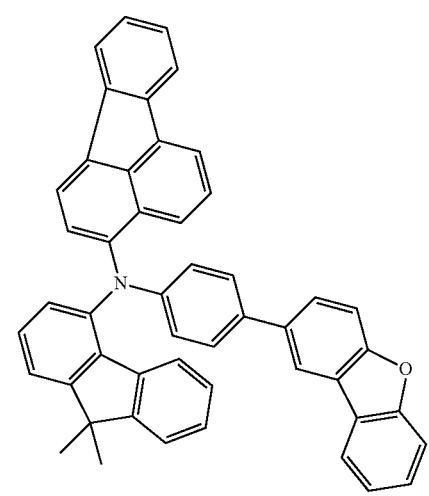
51
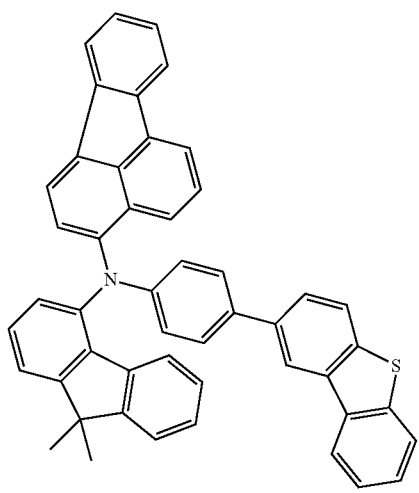
52
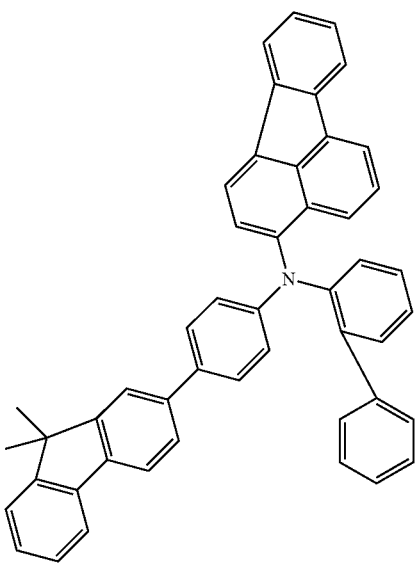
53
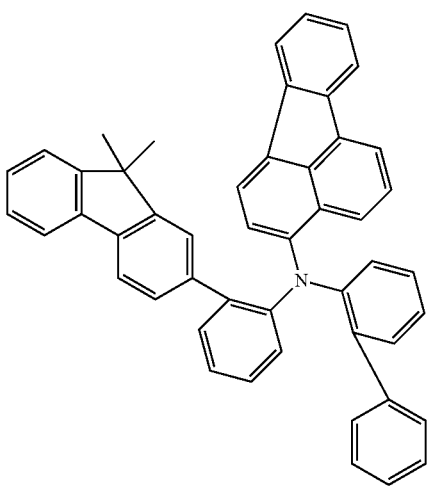
54
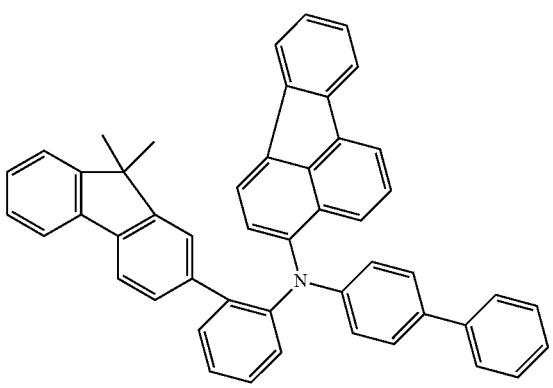

55
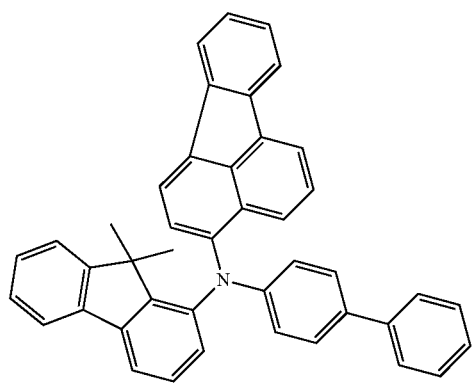
56
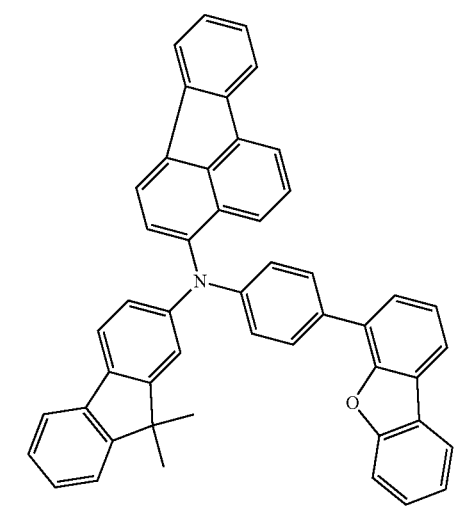
57
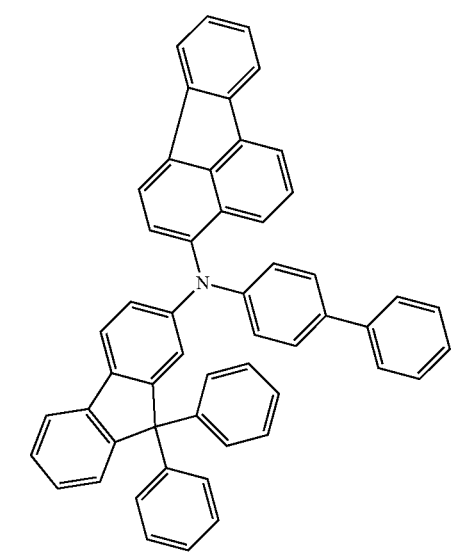
58
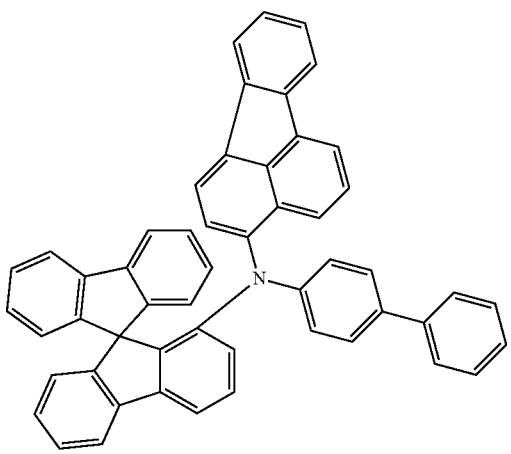
59
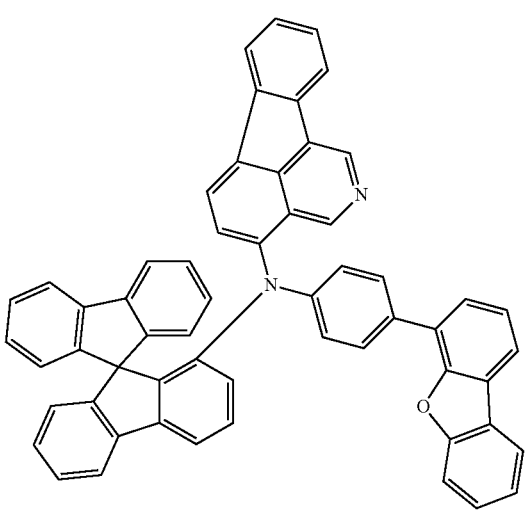
60
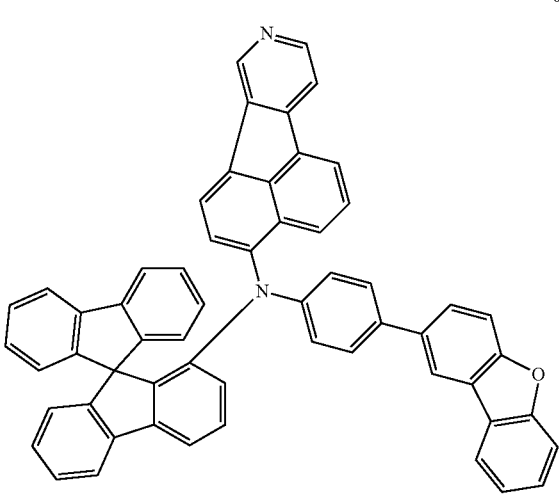

61
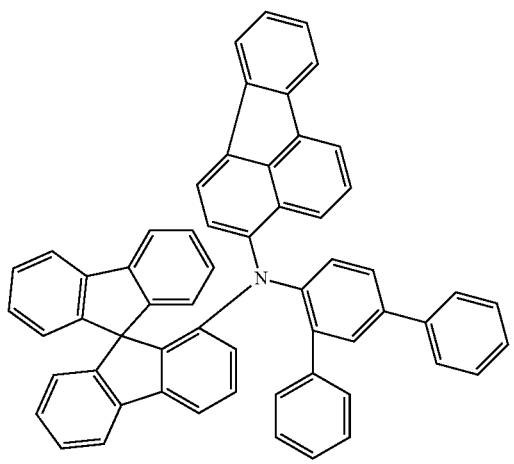
62
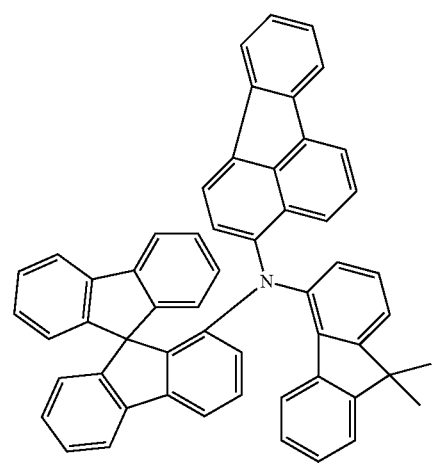
63
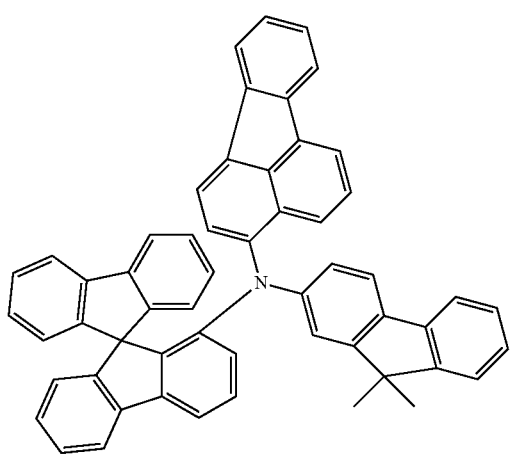
64
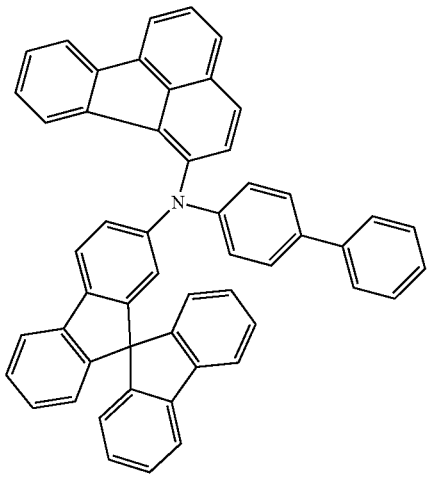
65
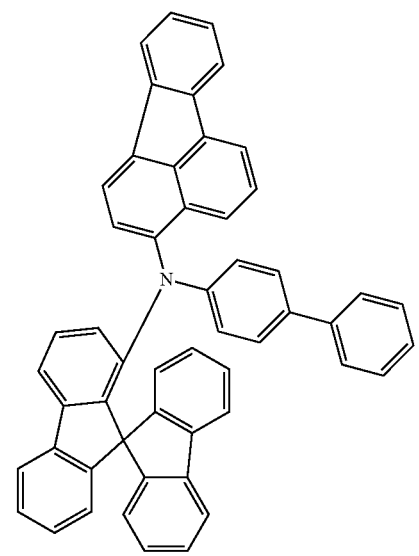
66
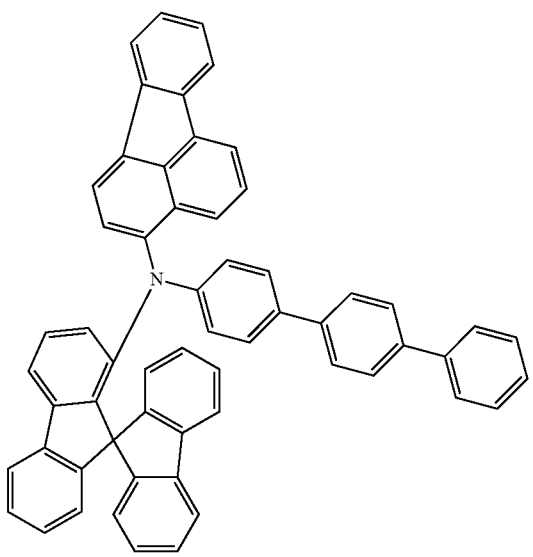

67
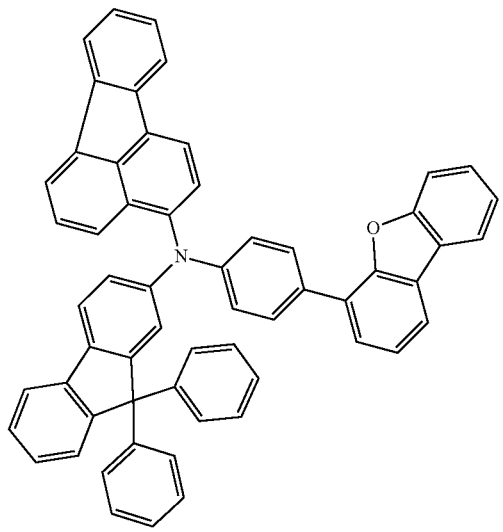
68
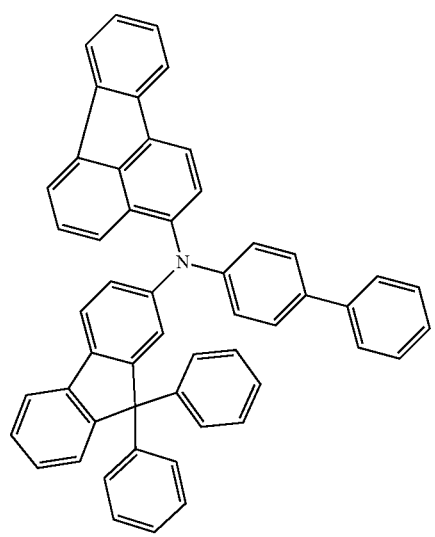
69
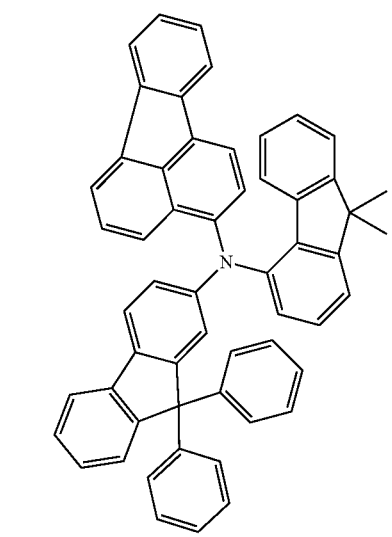
70
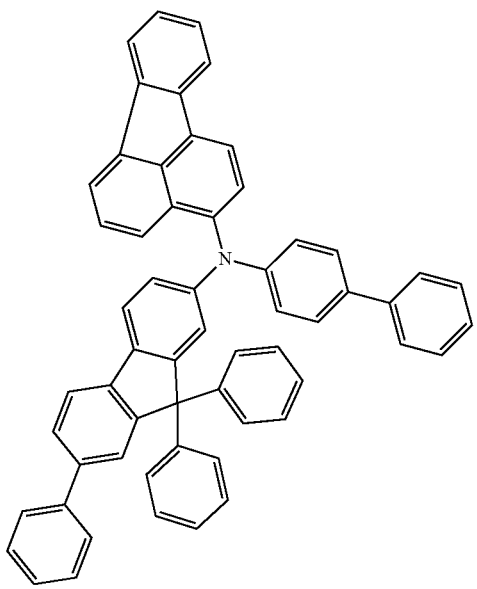
71
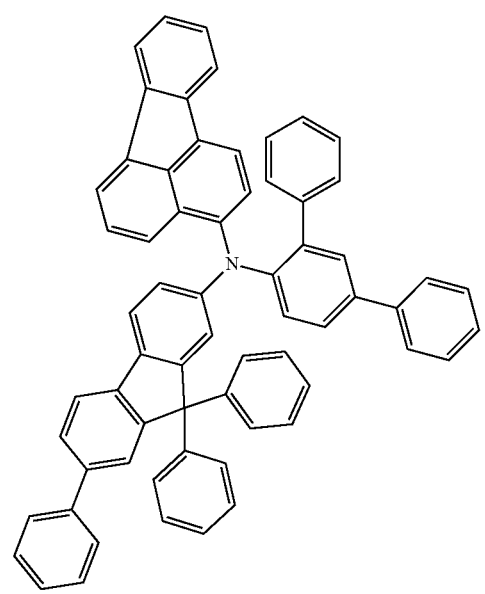

72
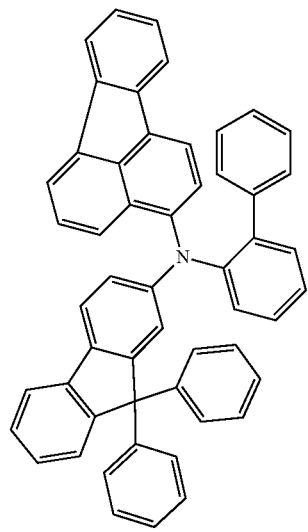
73
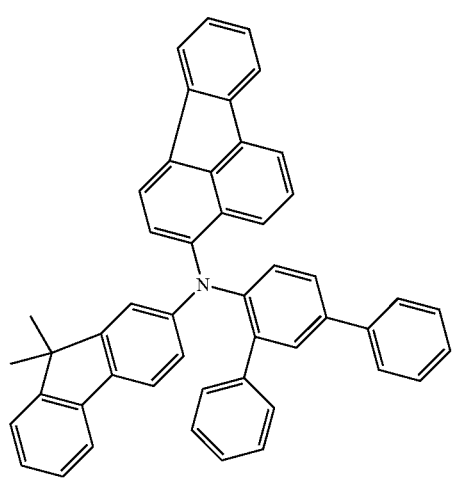
74
75
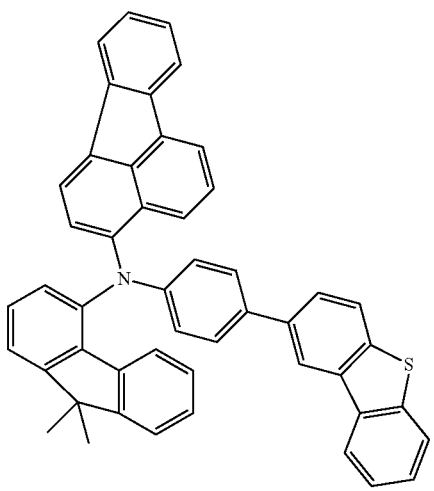
76
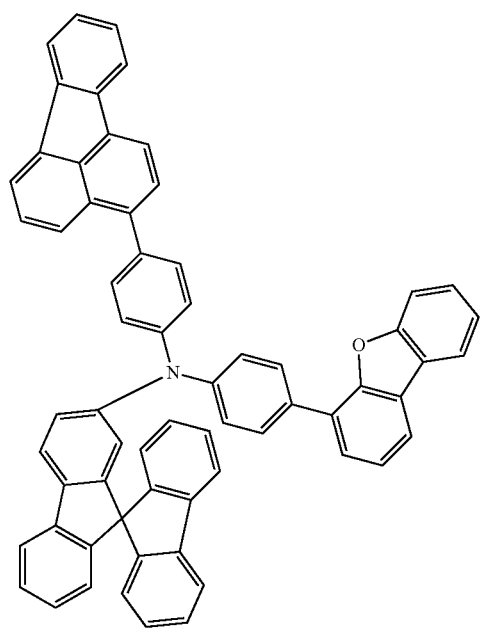

77
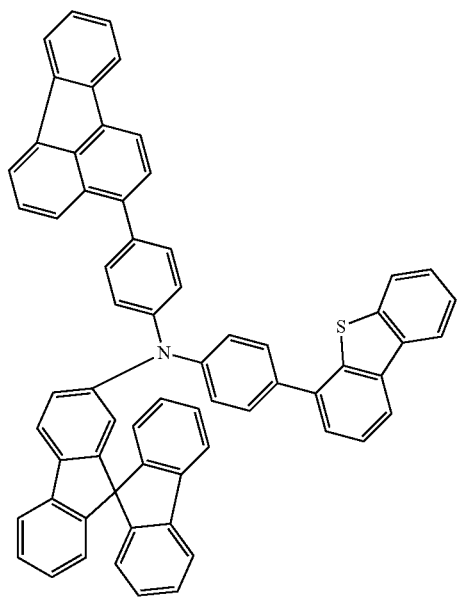
78
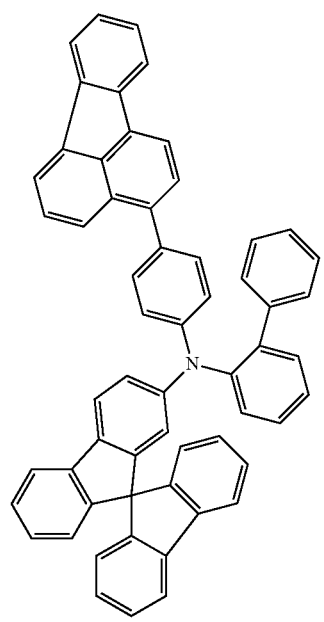
79
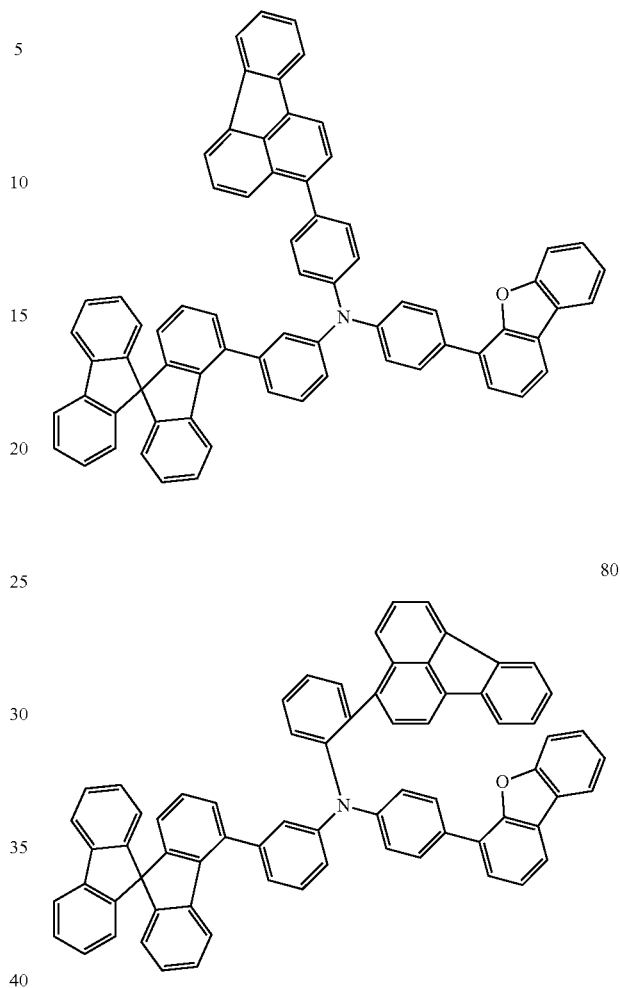
80
81
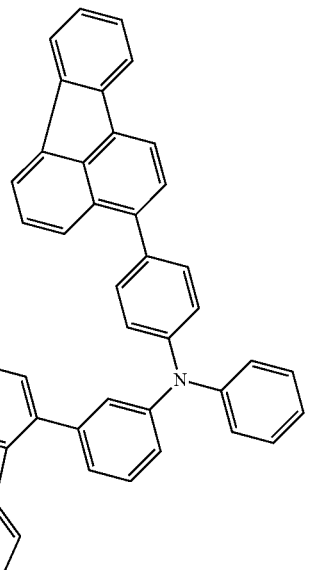

82
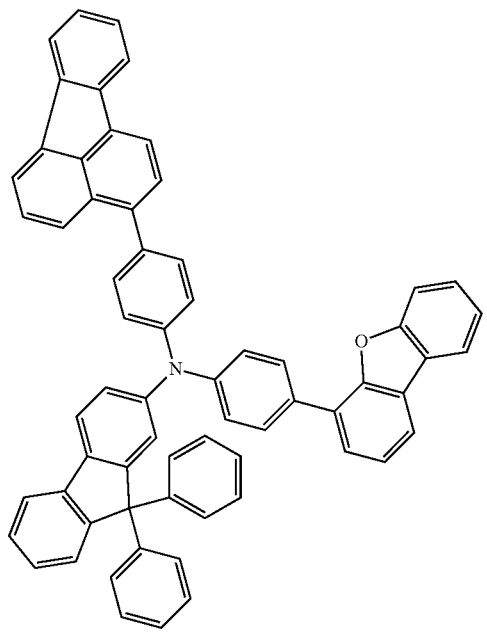
84
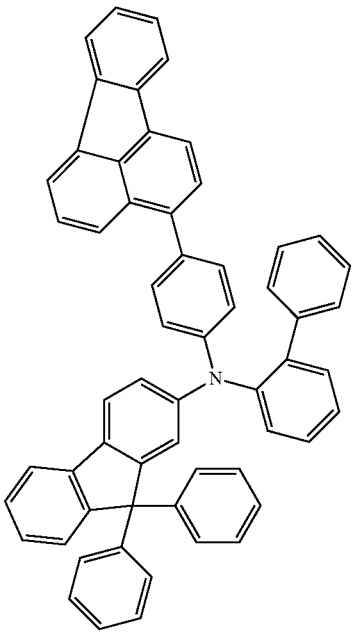
83
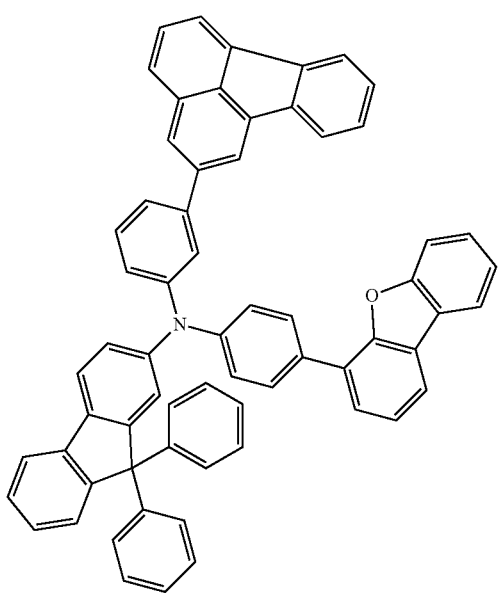
85

86
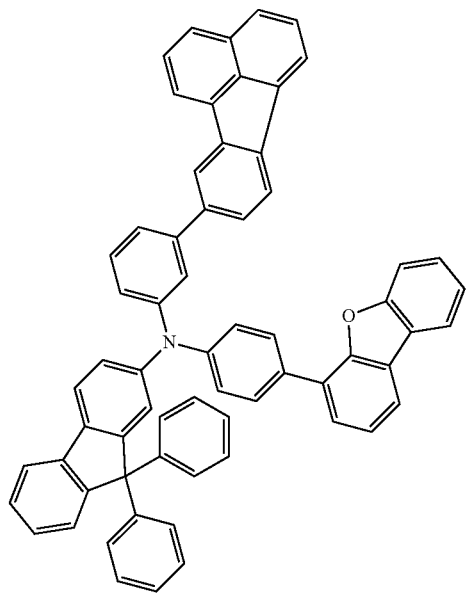
88
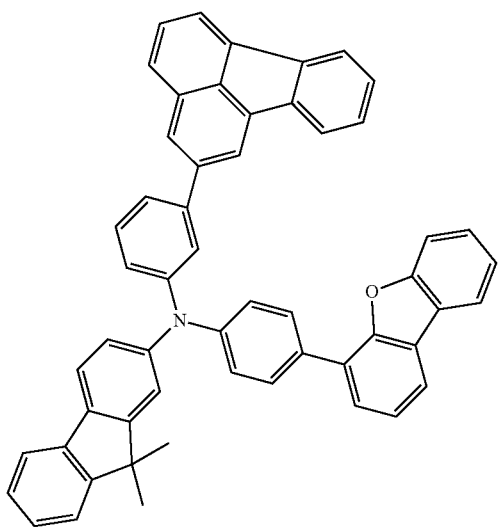
87
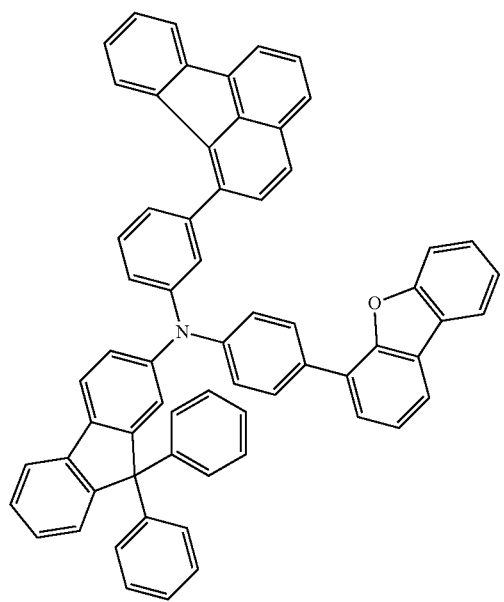
89
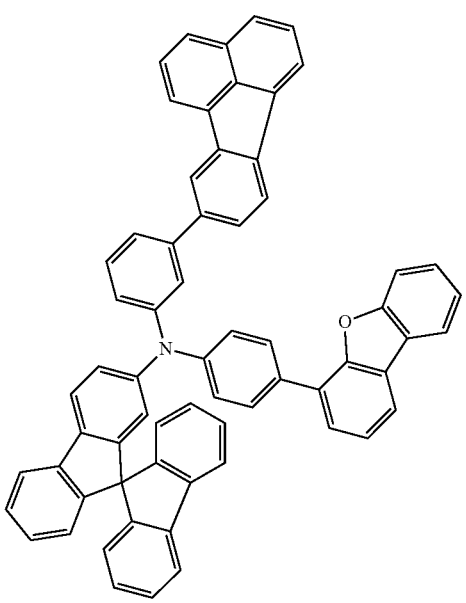

77
-continued
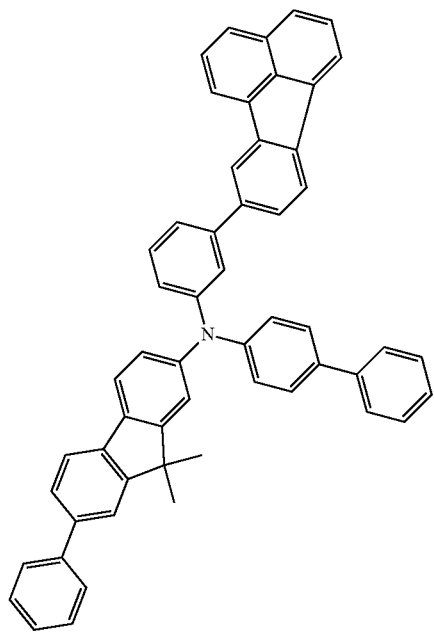
90
78
-continued
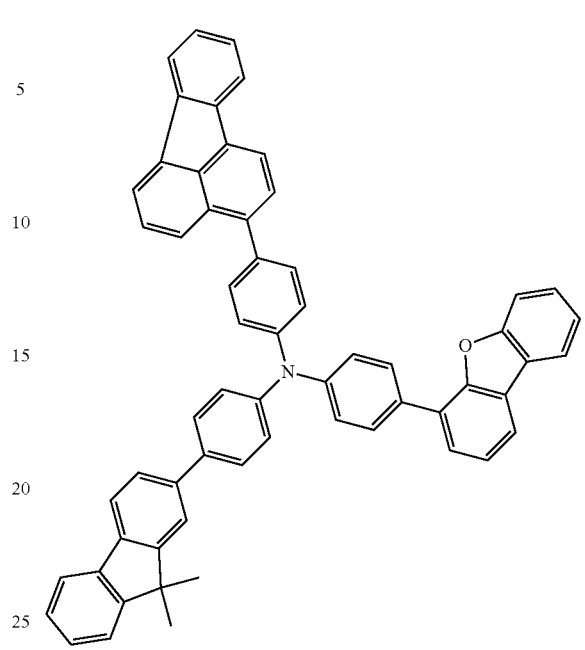
92
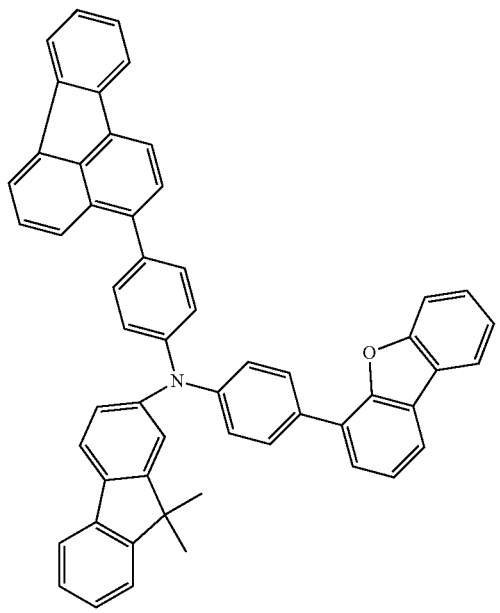
91
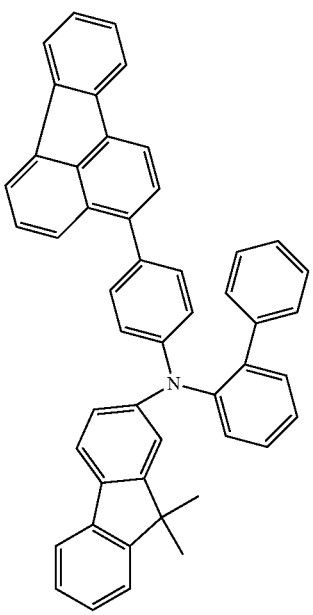
93

94
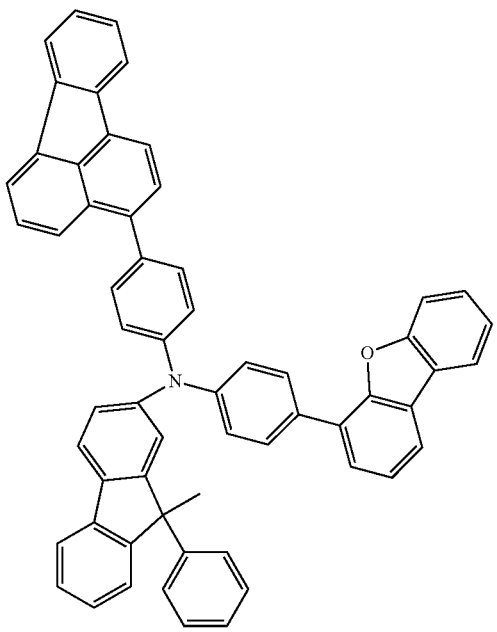
96
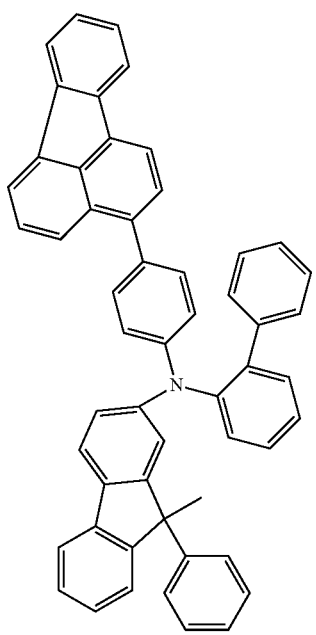
95
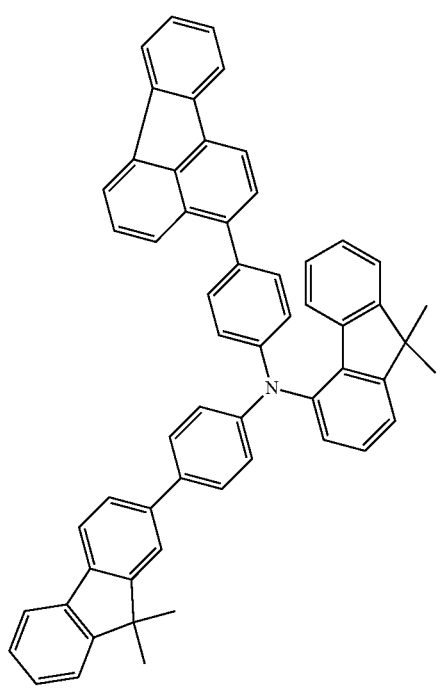
97
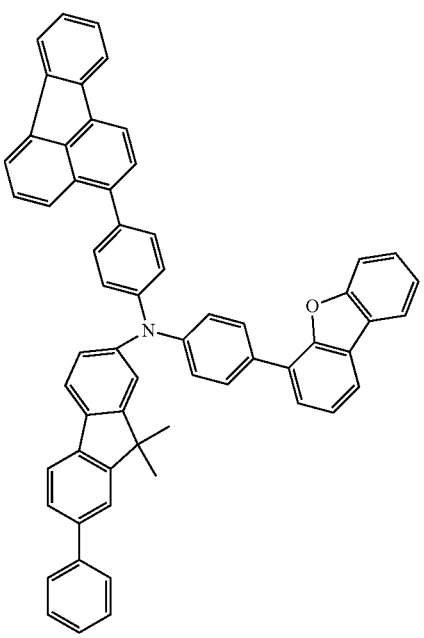

98
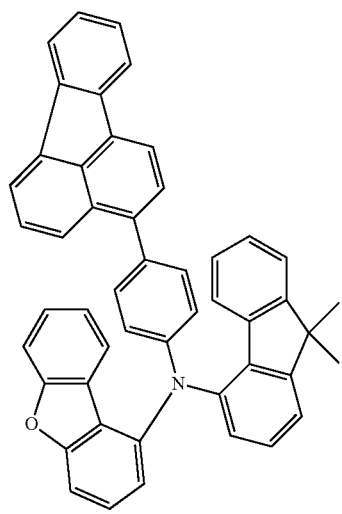
100
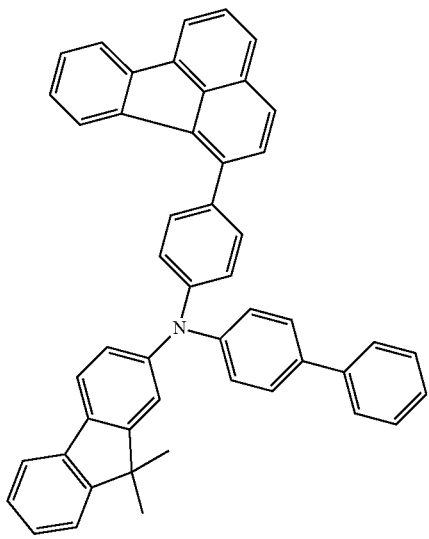
99
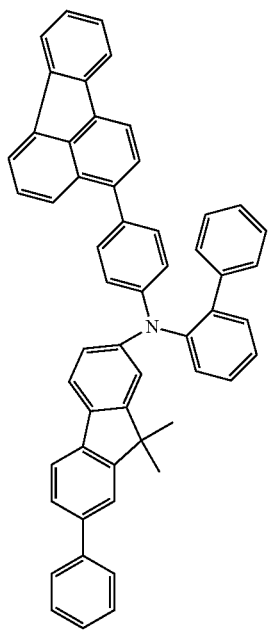
101
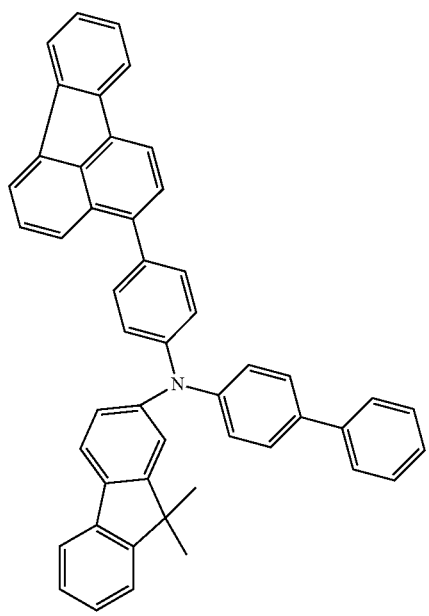

102
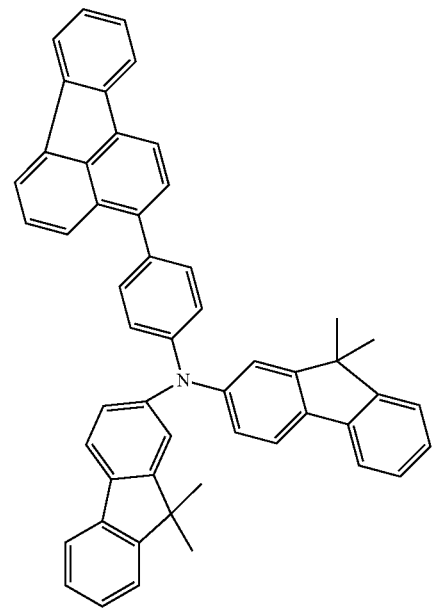
103
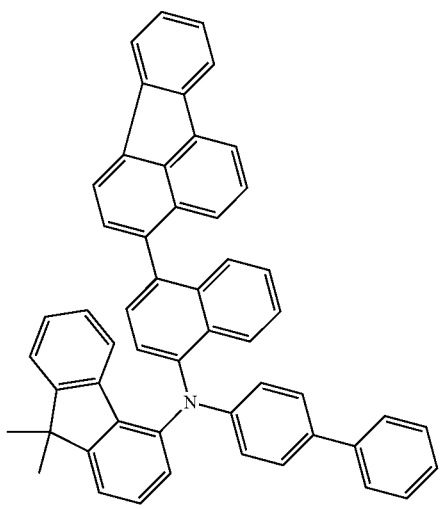
104
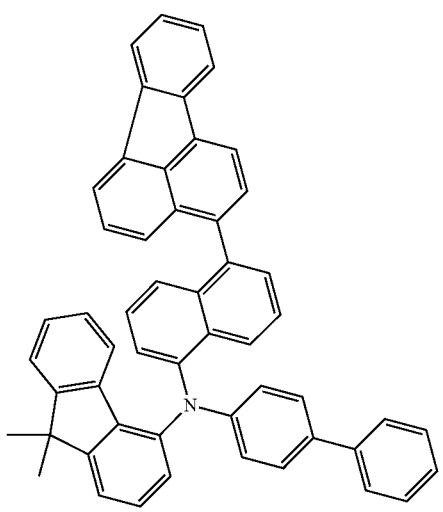
105
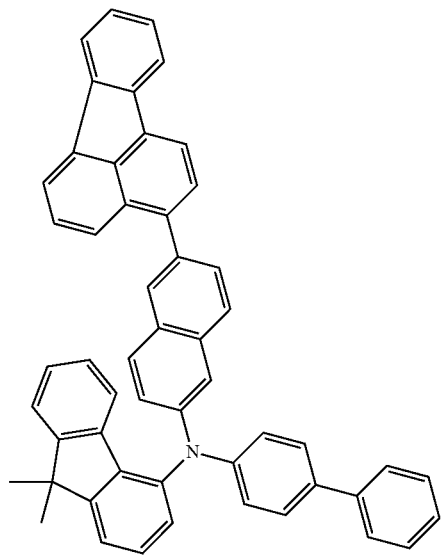
106
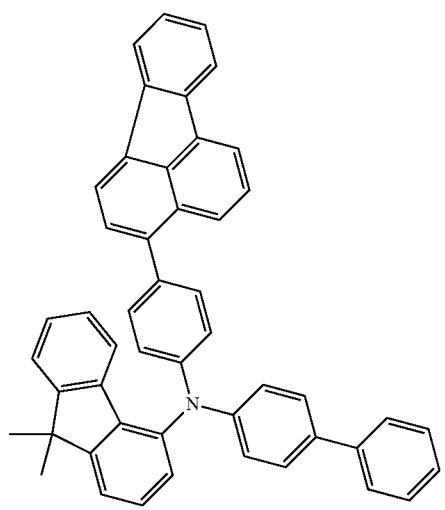
107
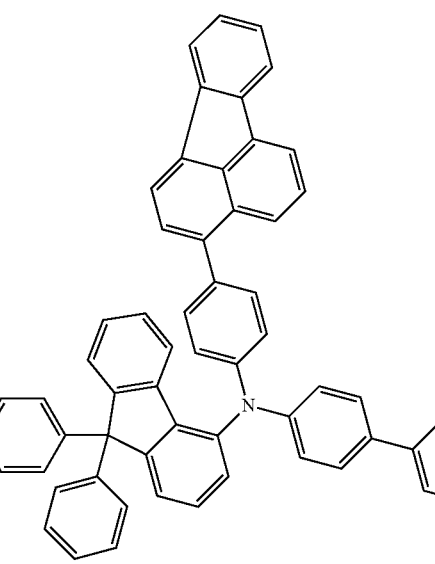

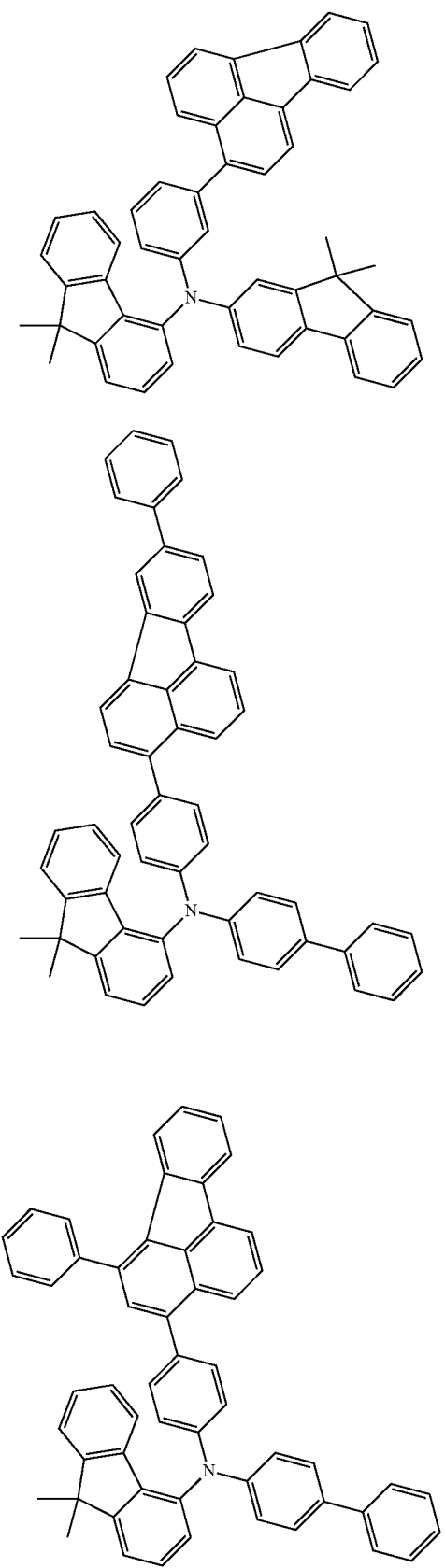
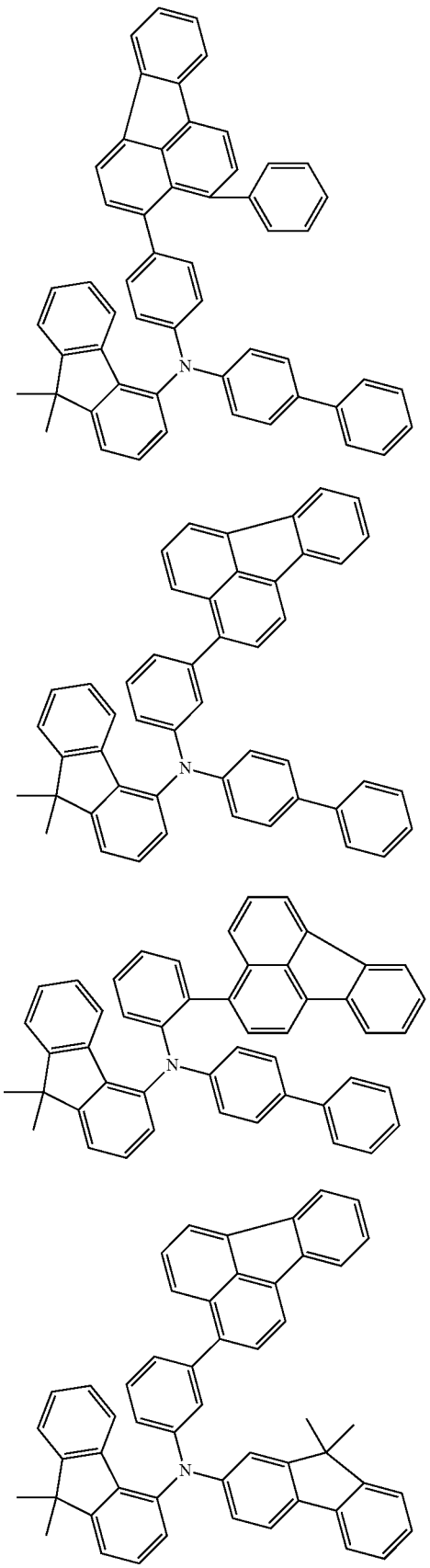

115
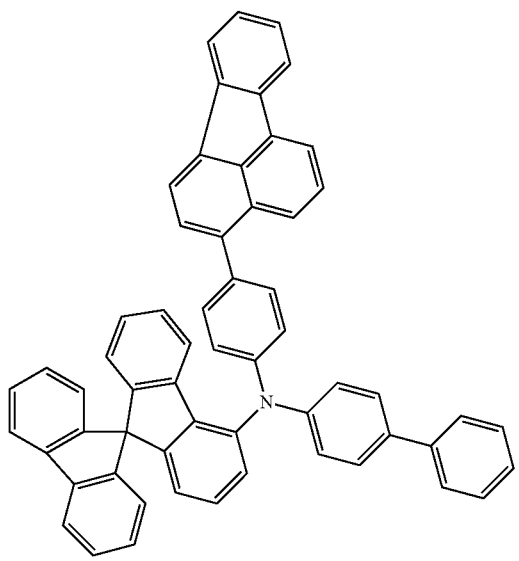
116
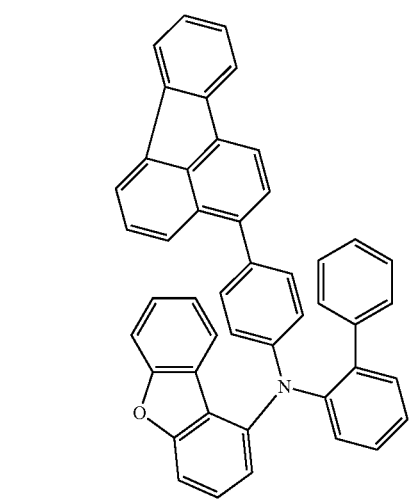
117
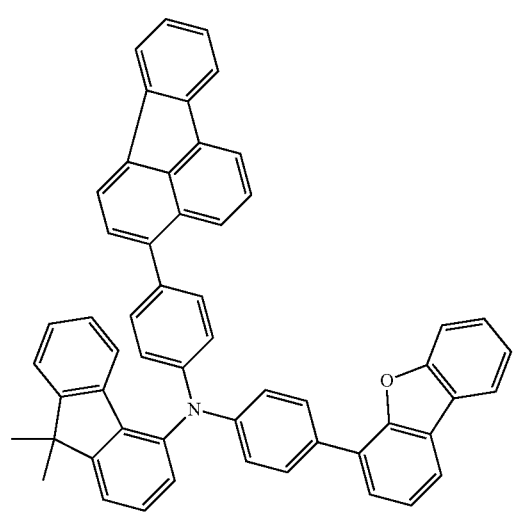
118
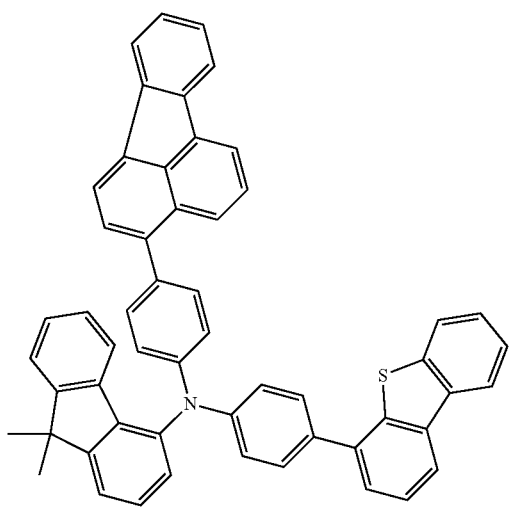
119
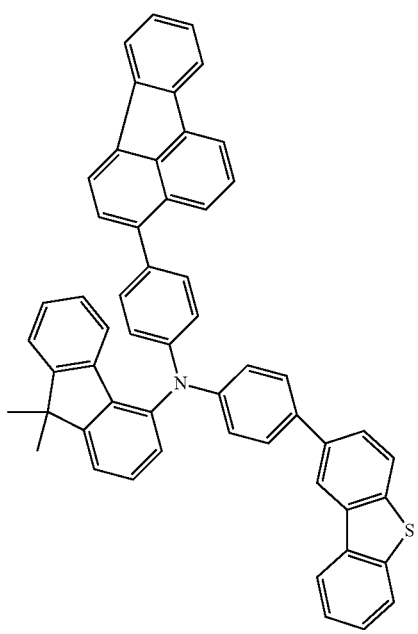

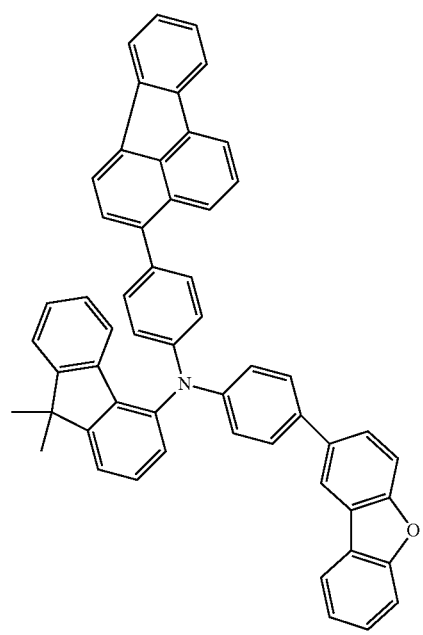
120
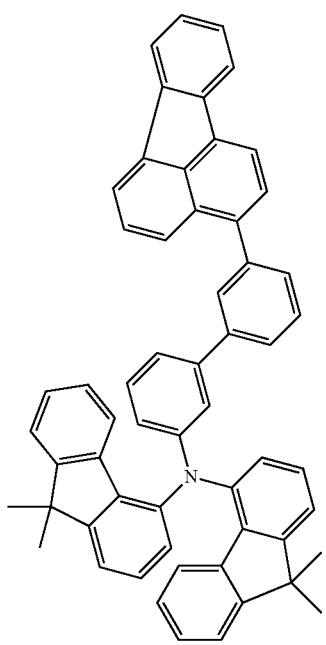
122
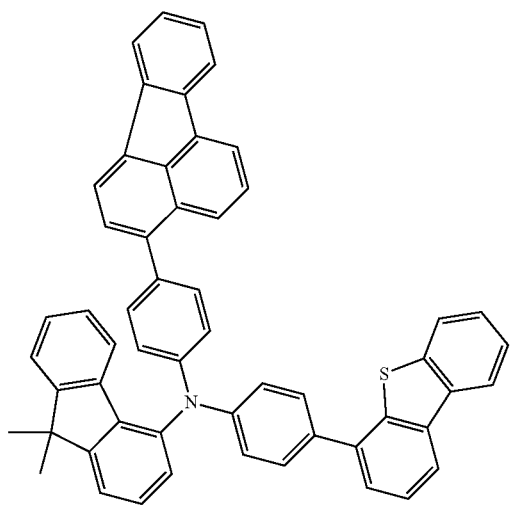
121
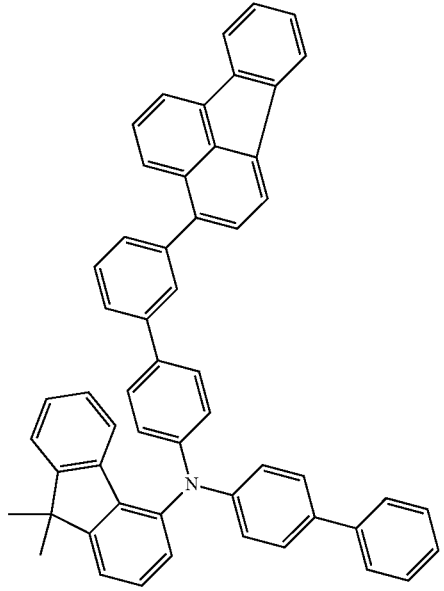
123

91
-continued
124
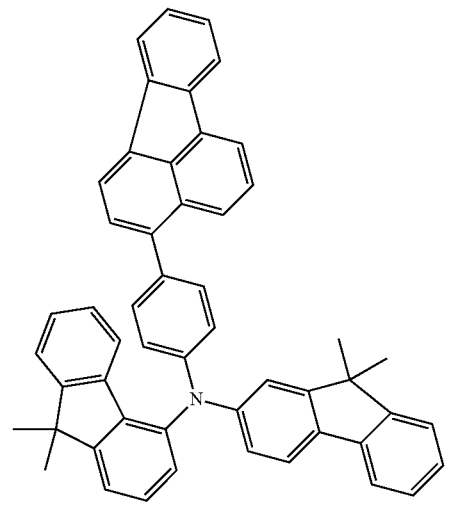
125
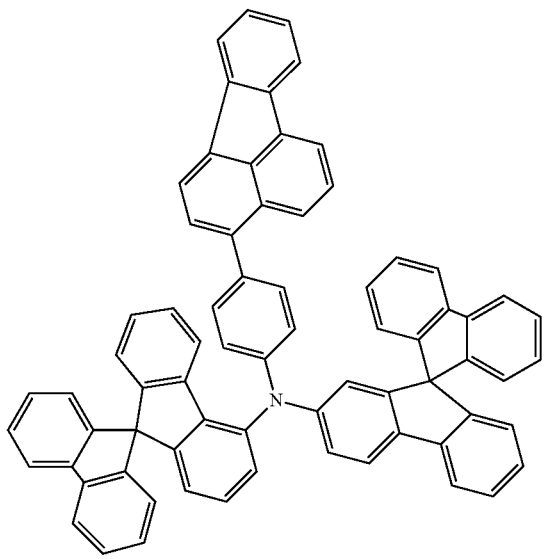
126
92
-continued
127
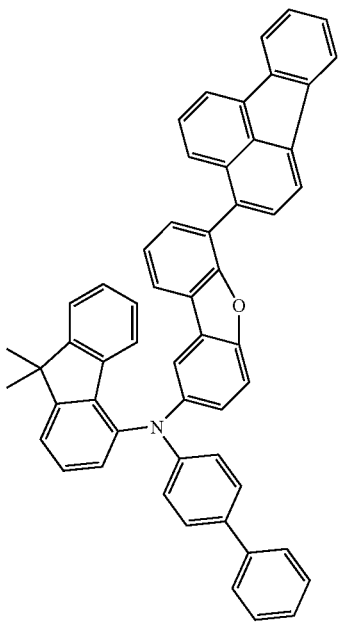
128
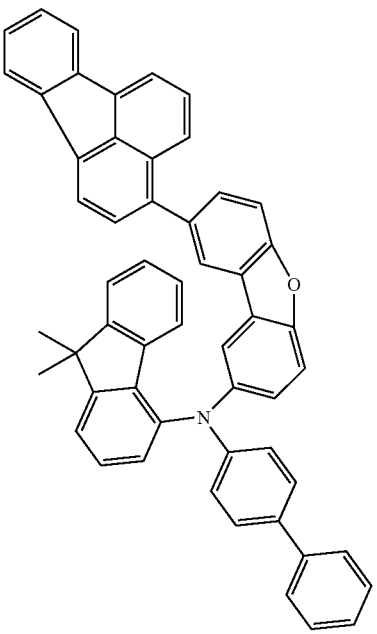

129
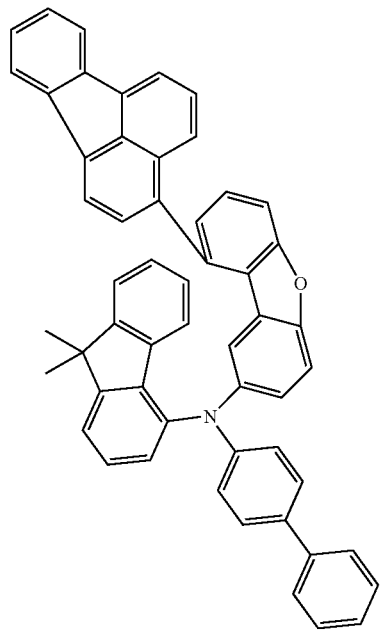
130
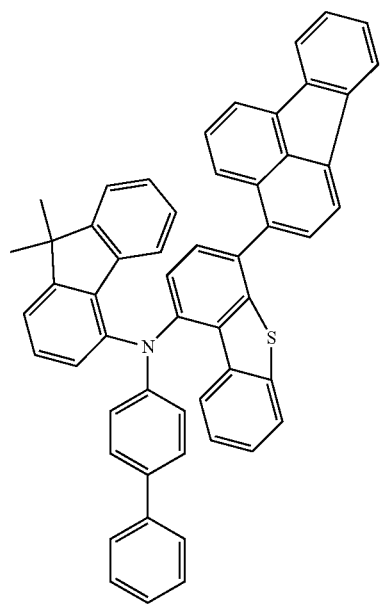
131
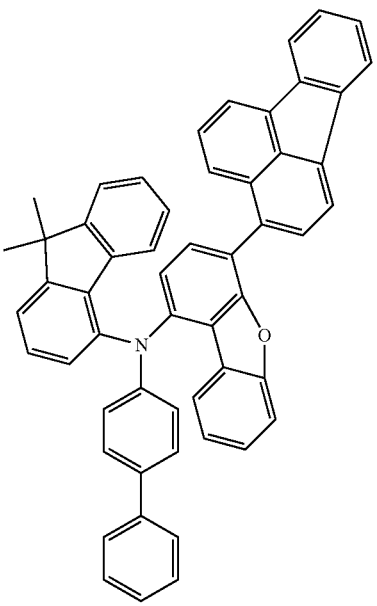
132
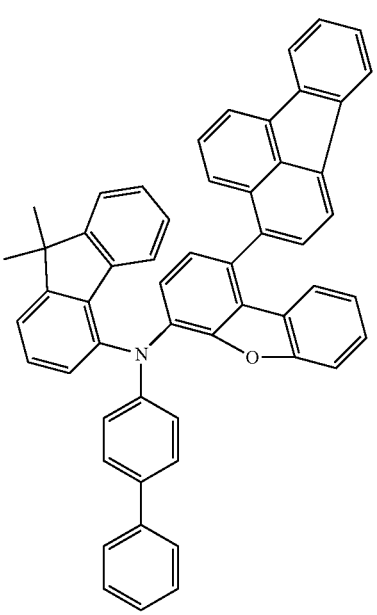
133
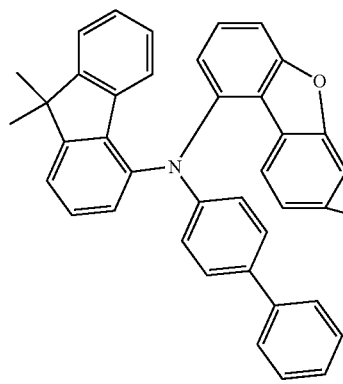

134
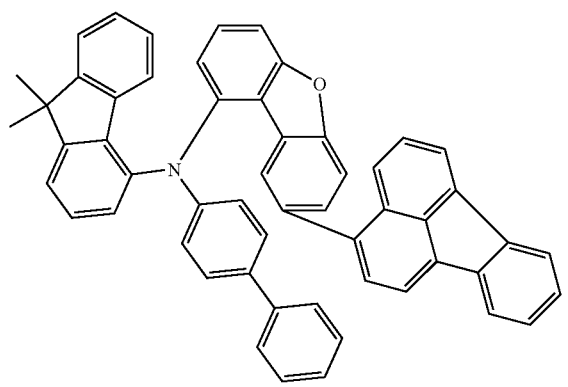
135
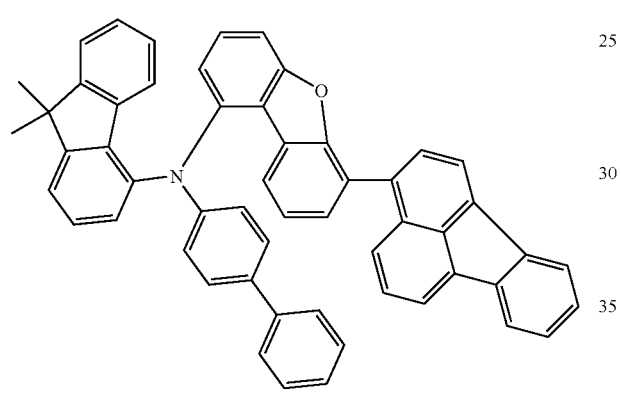
136
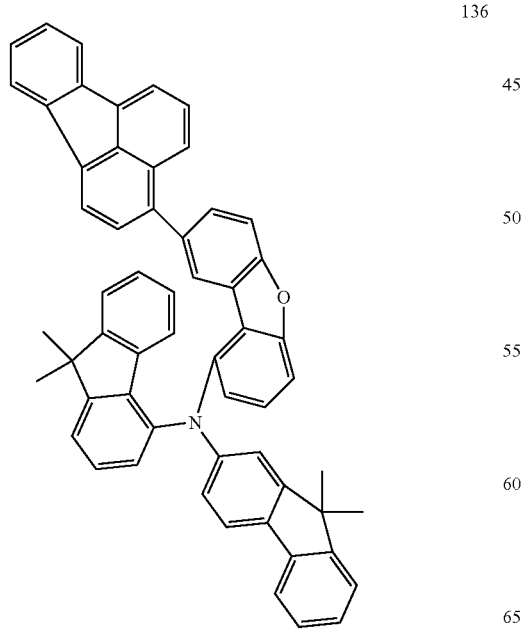
137
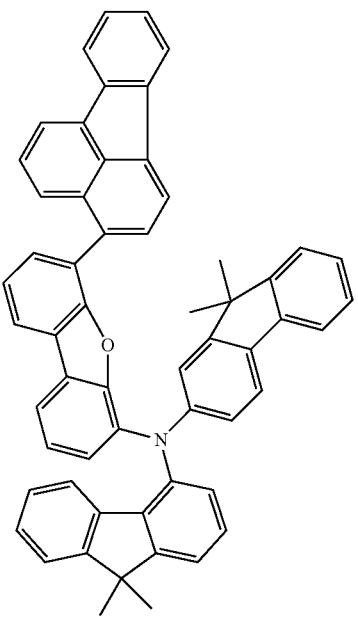
138
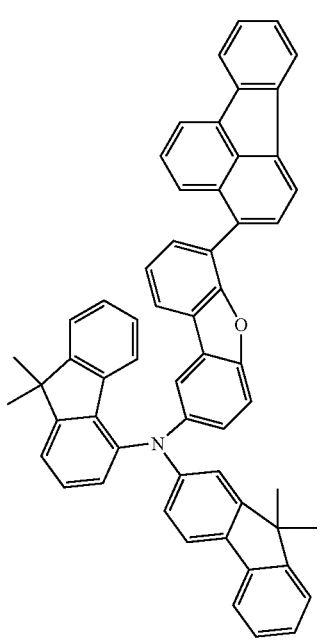

139
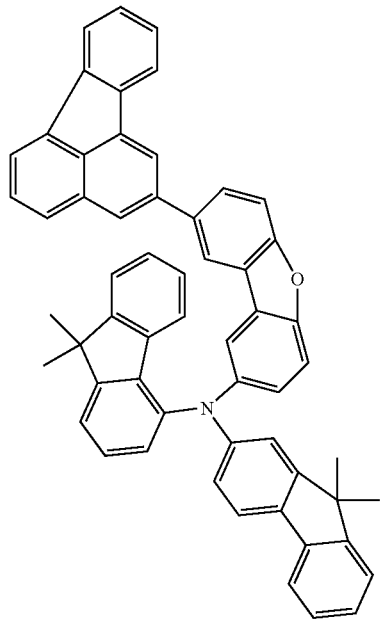
140
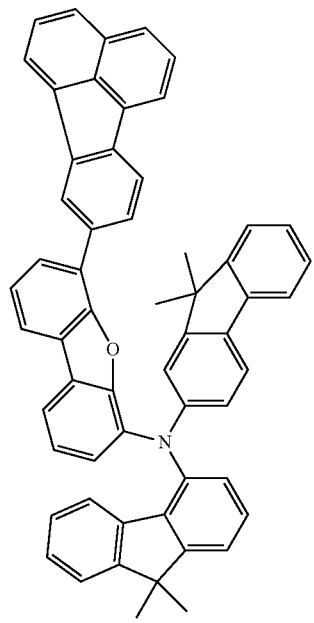
141
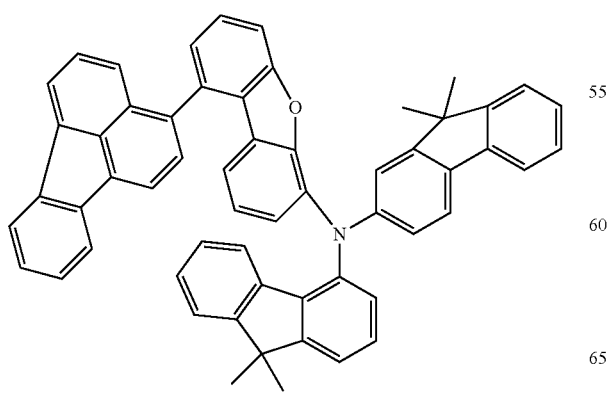
142
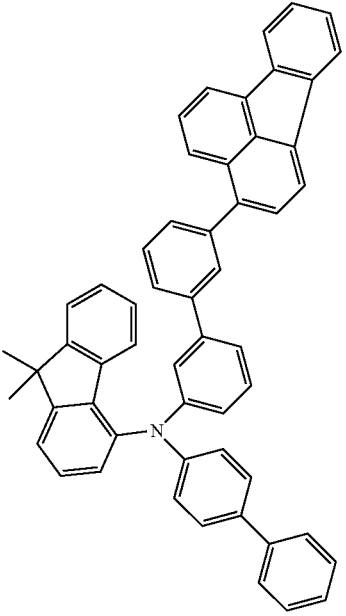
143
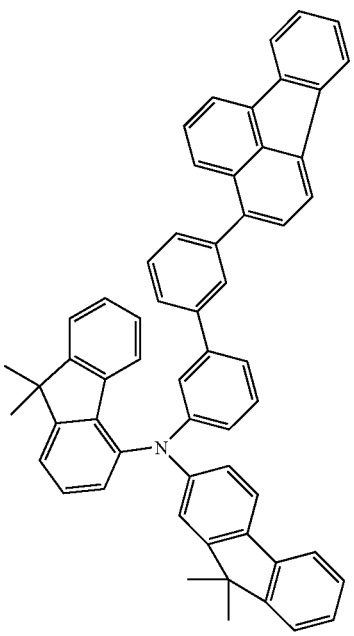

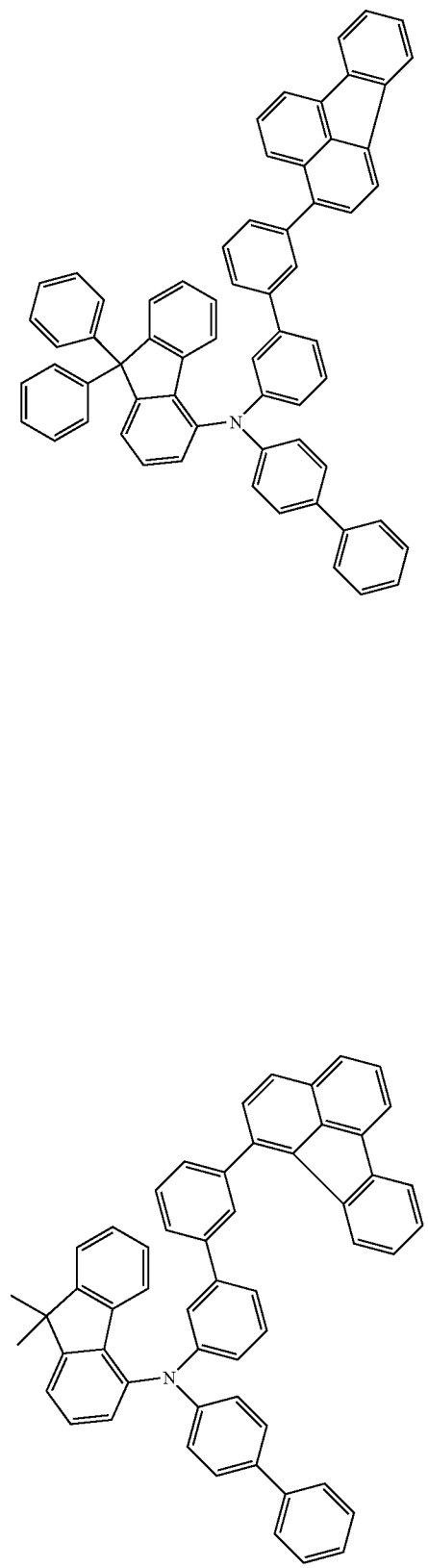
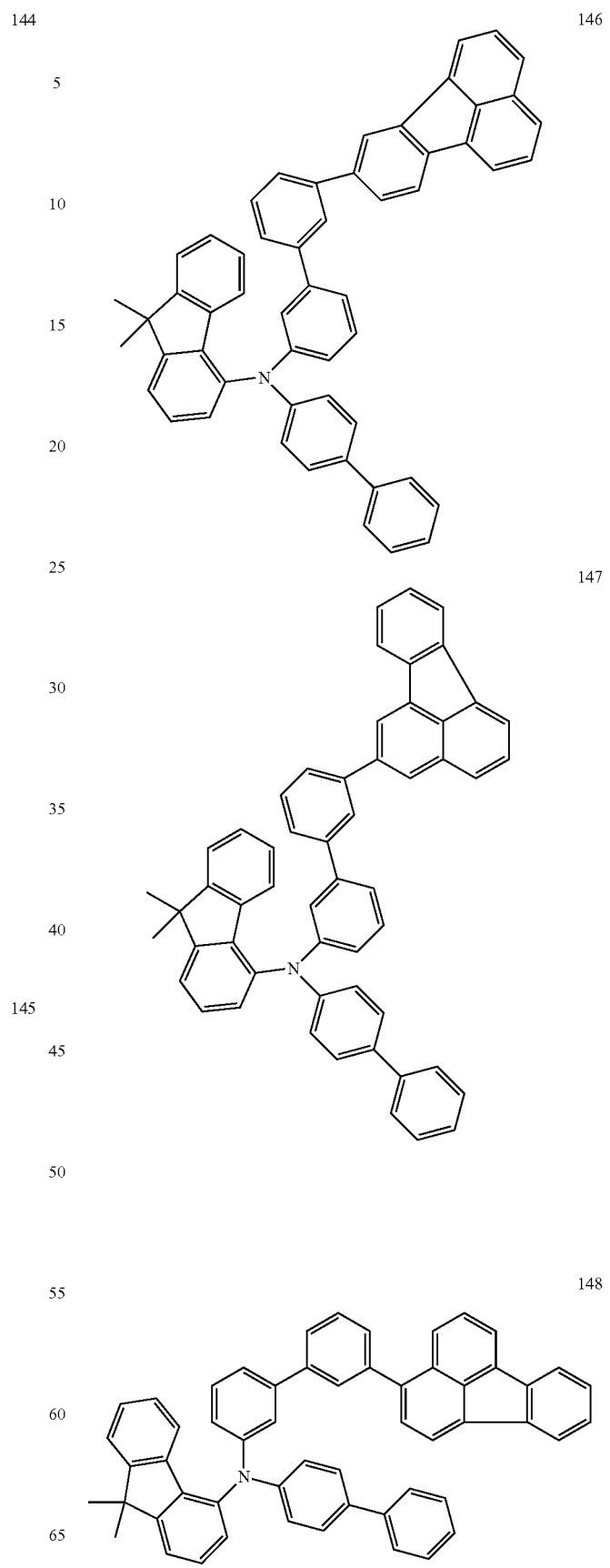

101
-continued
149
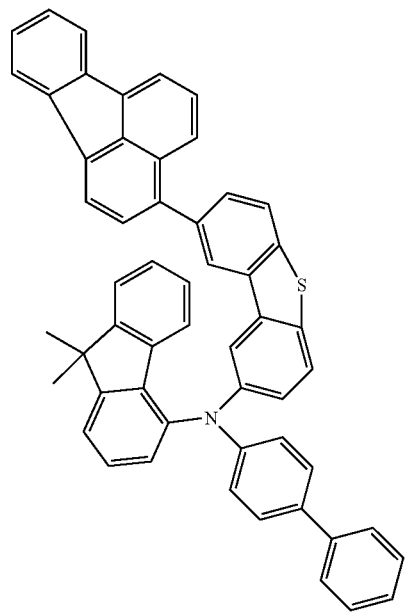
150
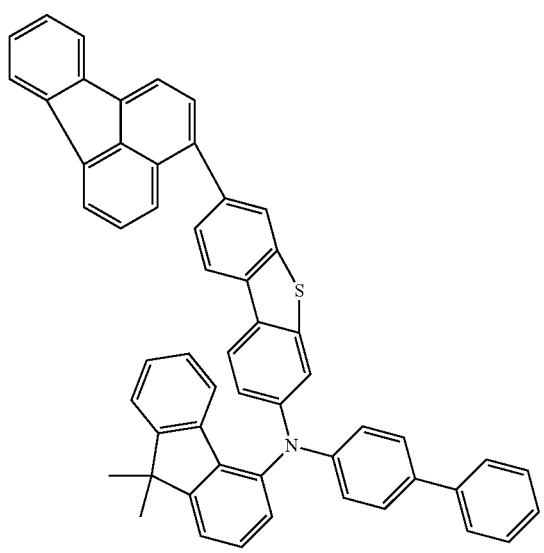
151
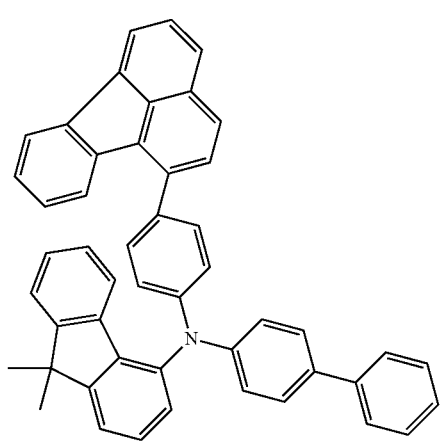
102
-continued
152
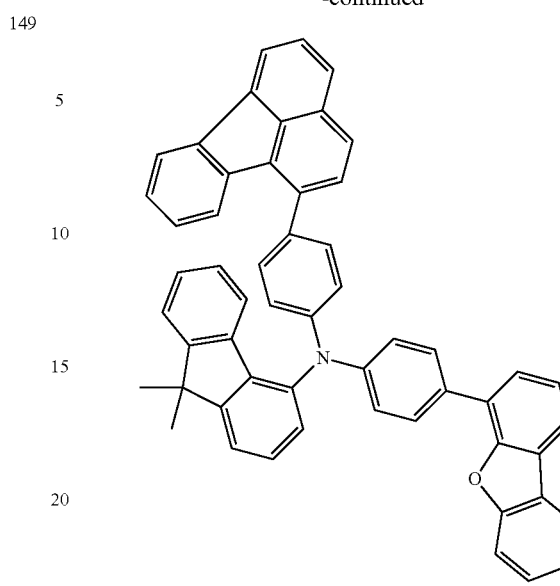
153
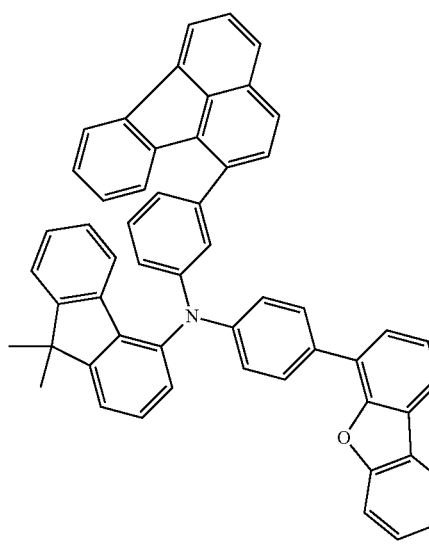
154
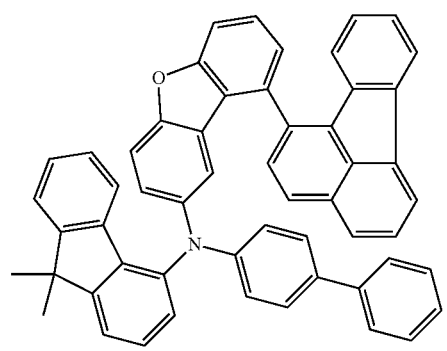

155
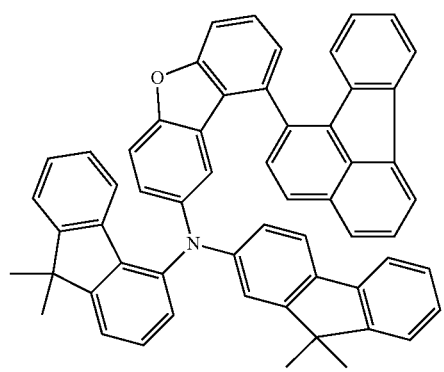
156
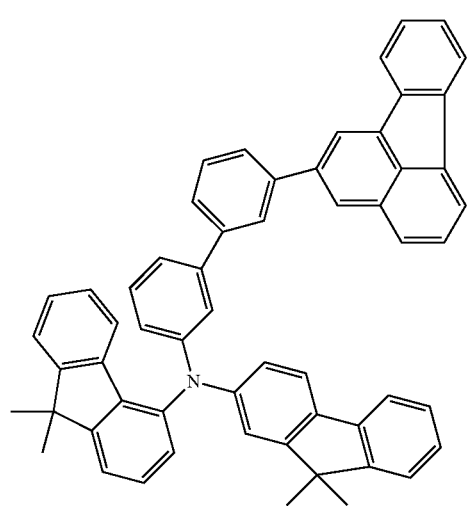
157
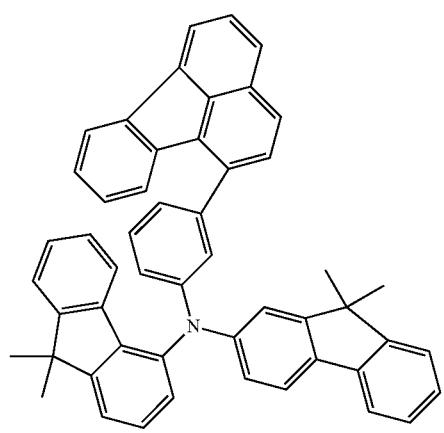
158
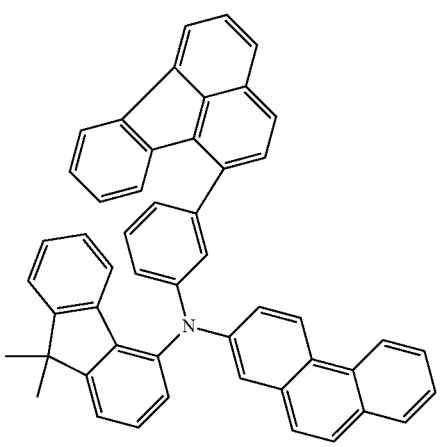
159
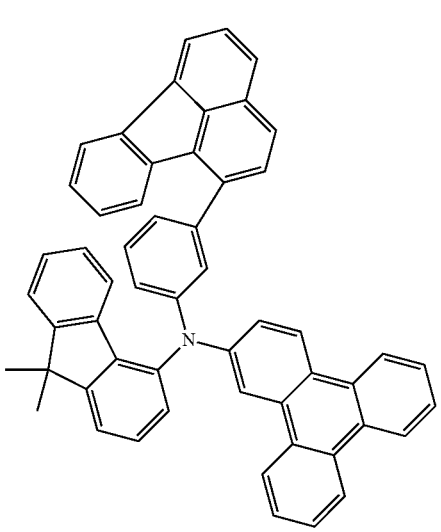
160
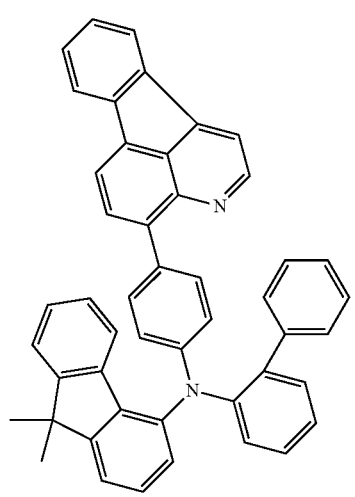

161
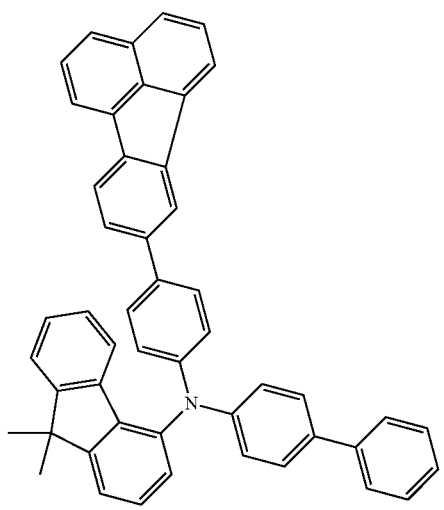
162
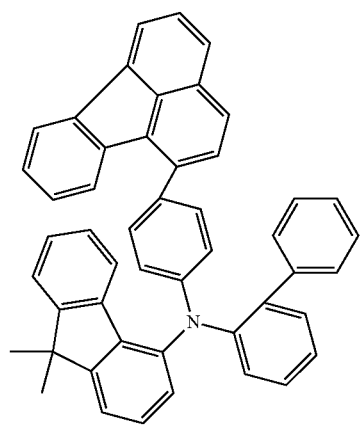
163
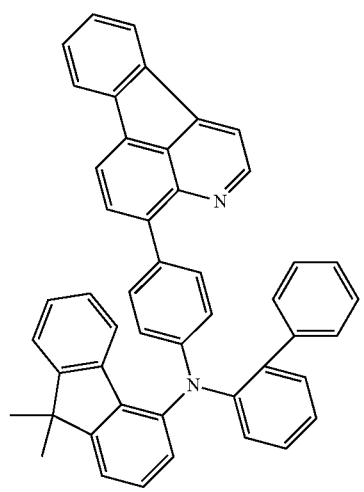
164
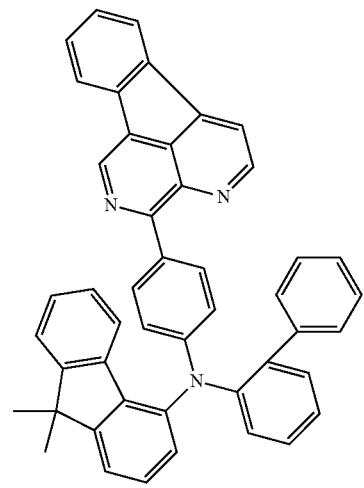
165
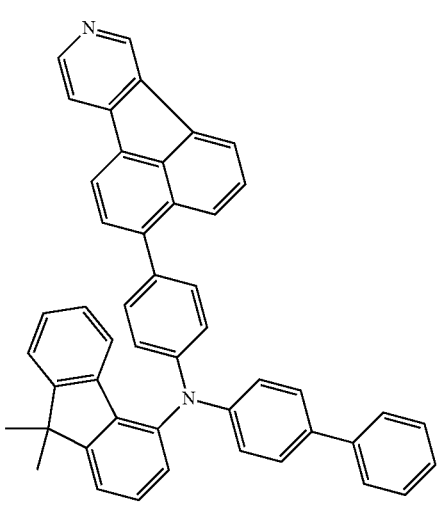
166
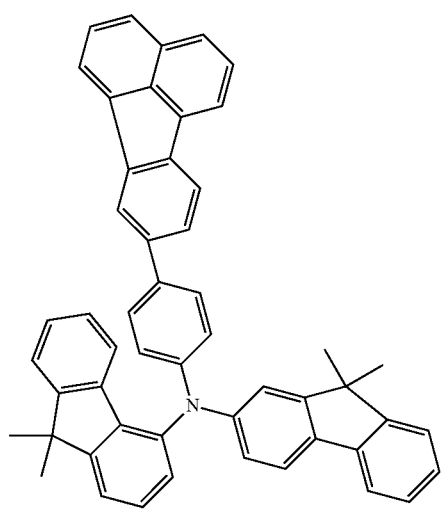

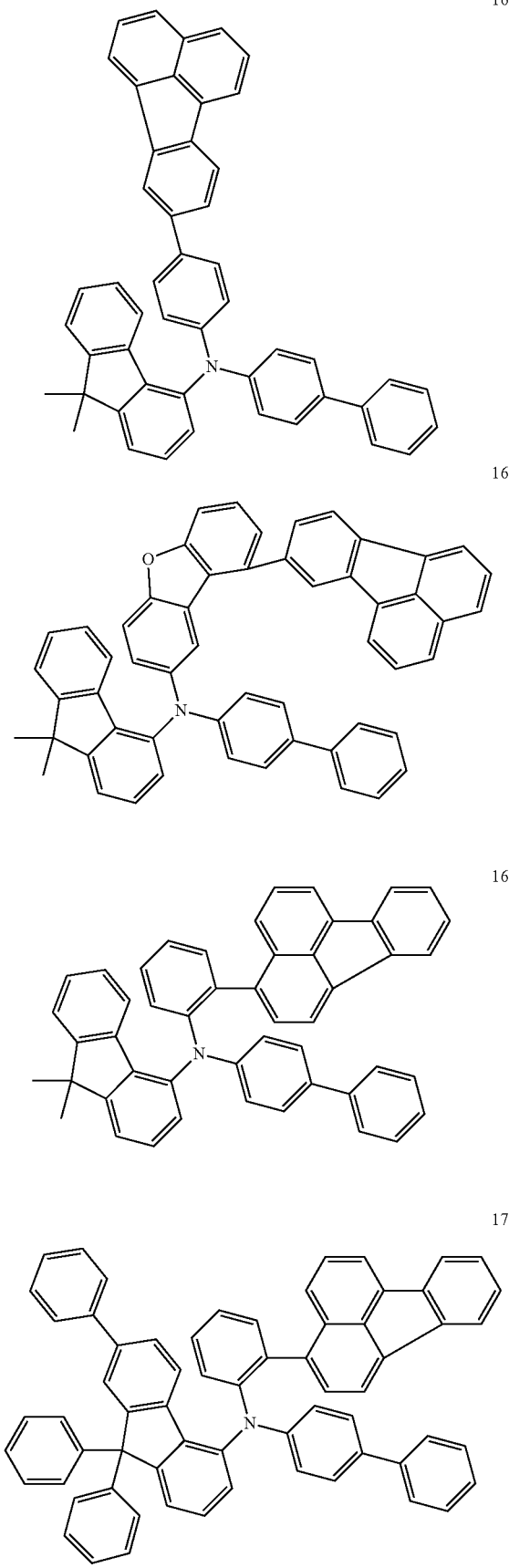
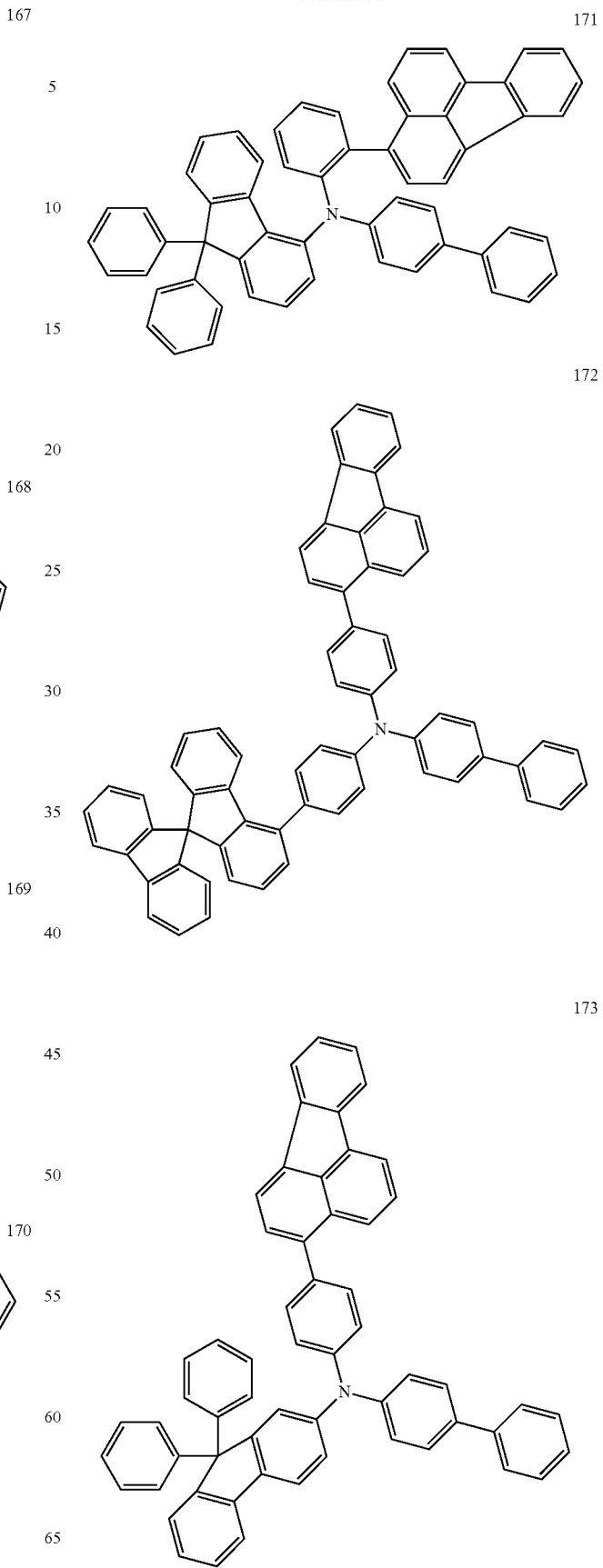

174
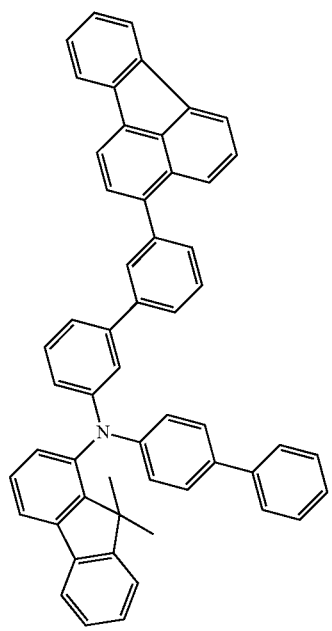
175
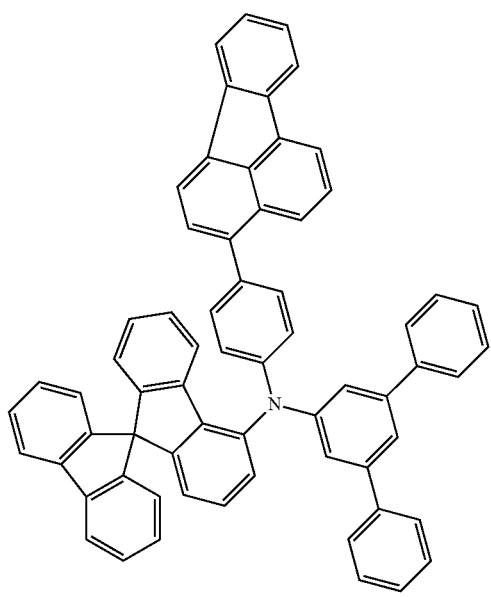
176
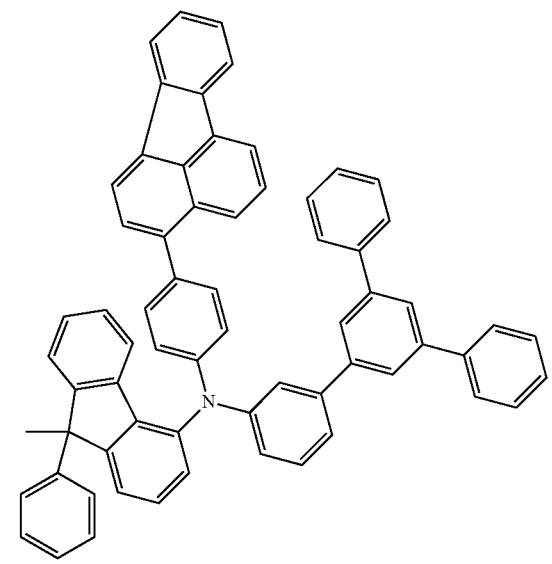
177
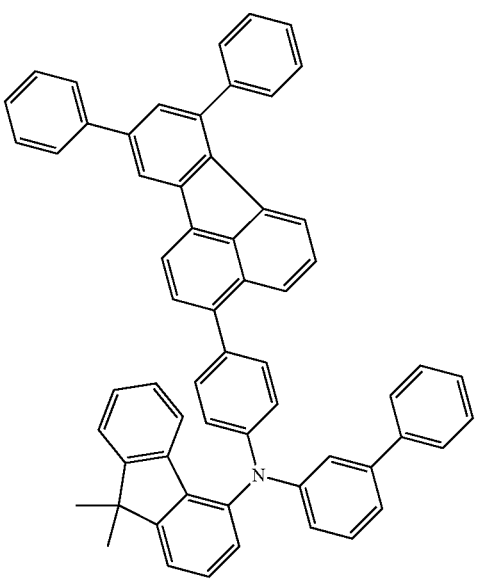

111
-continued
178
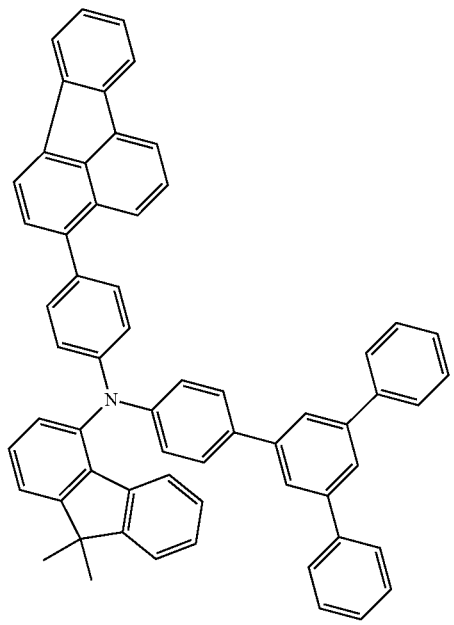
179
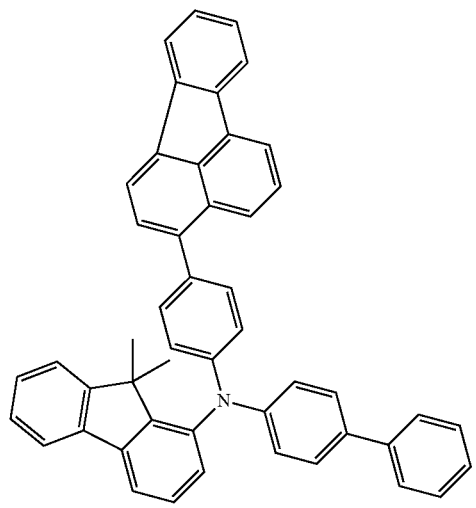
180
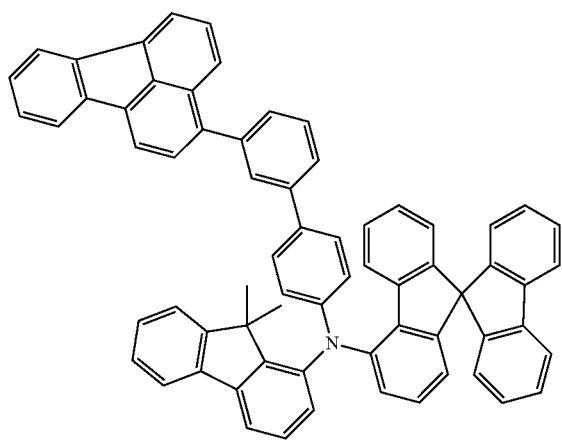
112
-continued
181
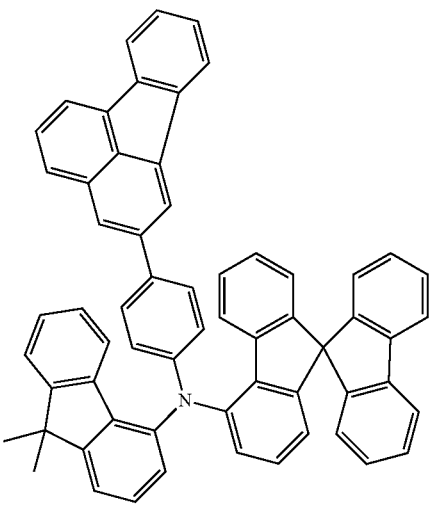
182
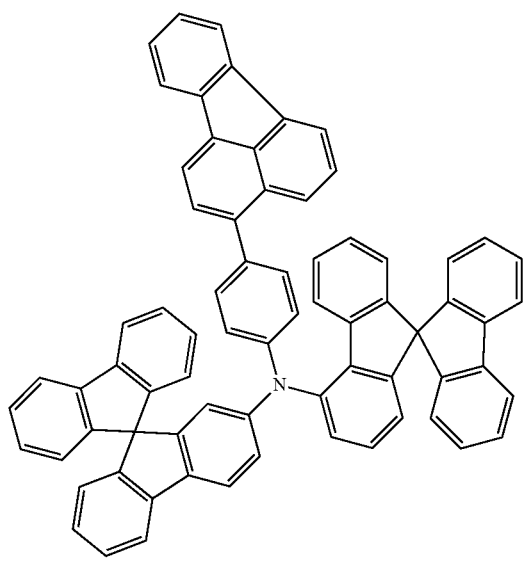
183
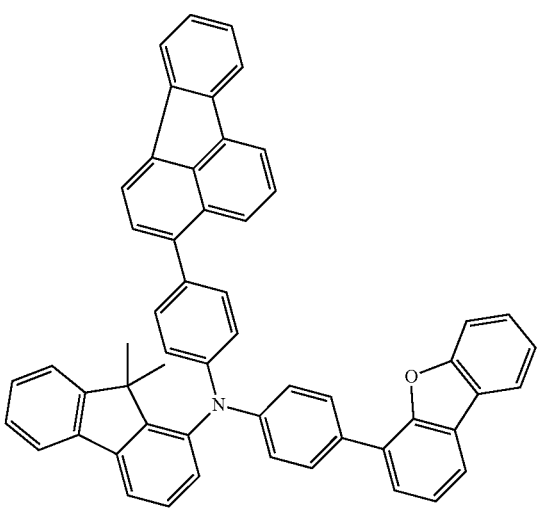

184
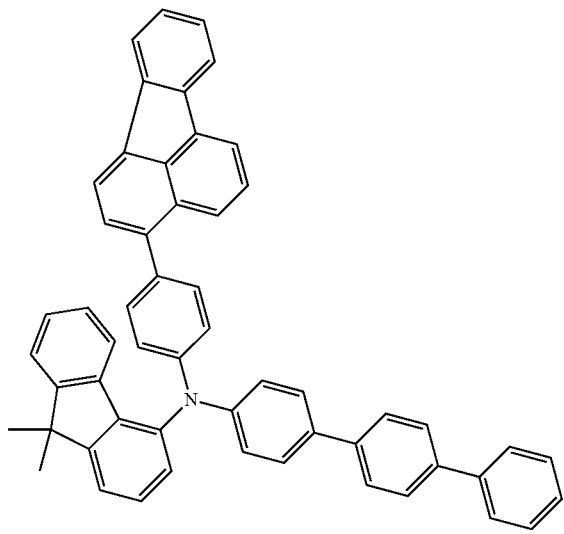
185
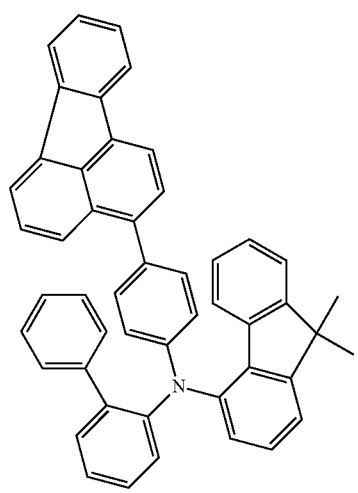
186
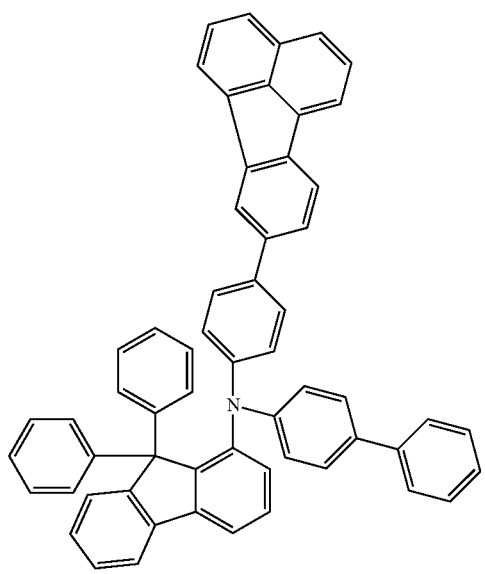
187
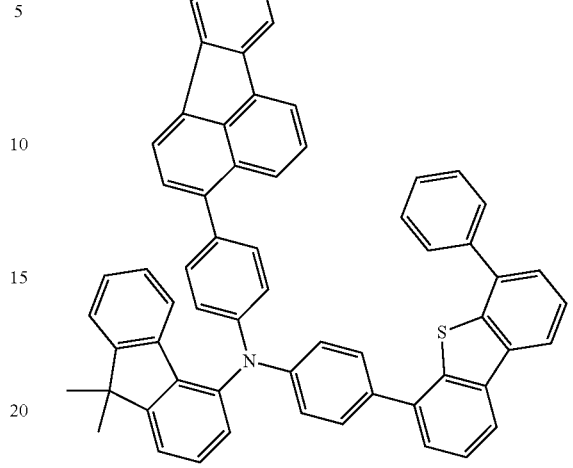
188
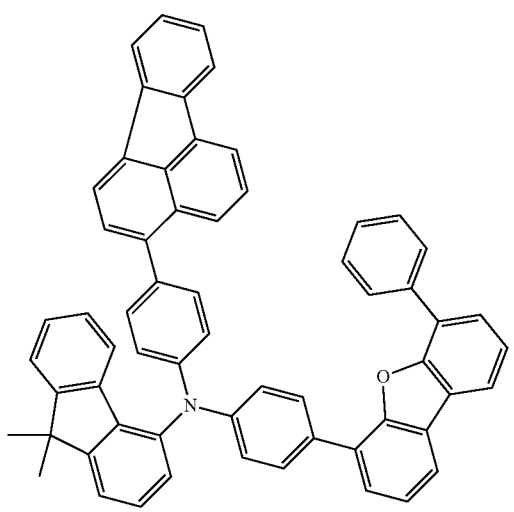
189
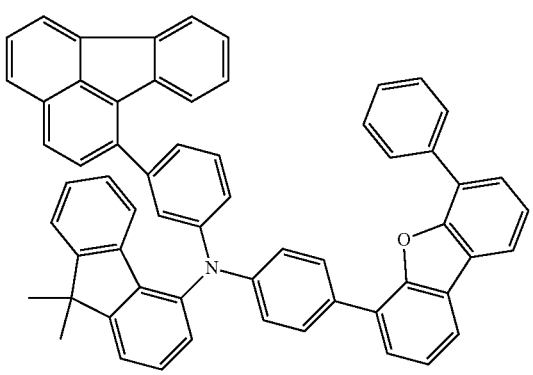

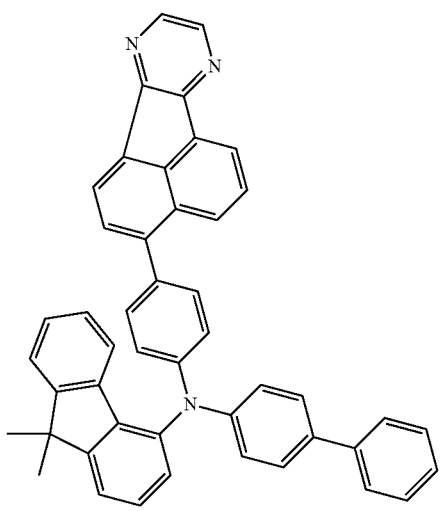
190
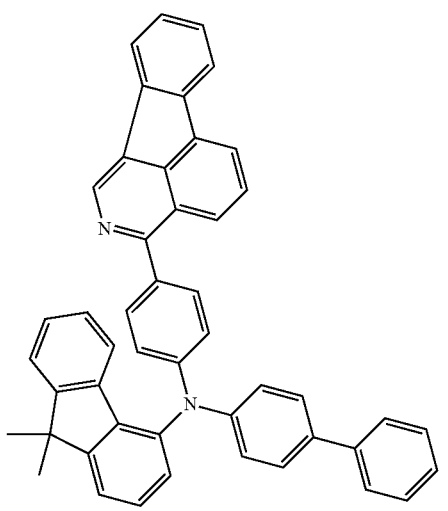
191
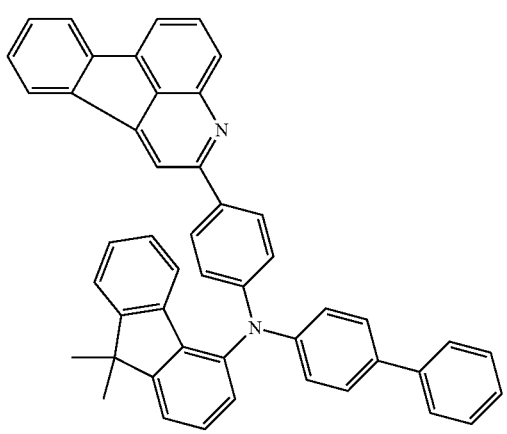
192
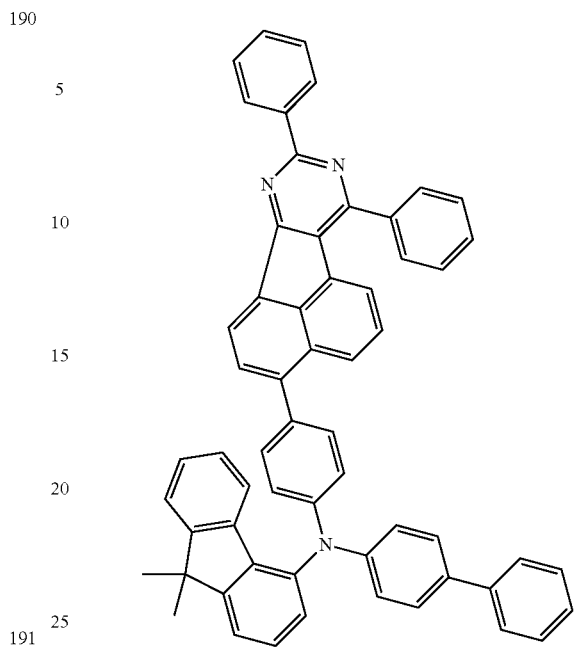
193
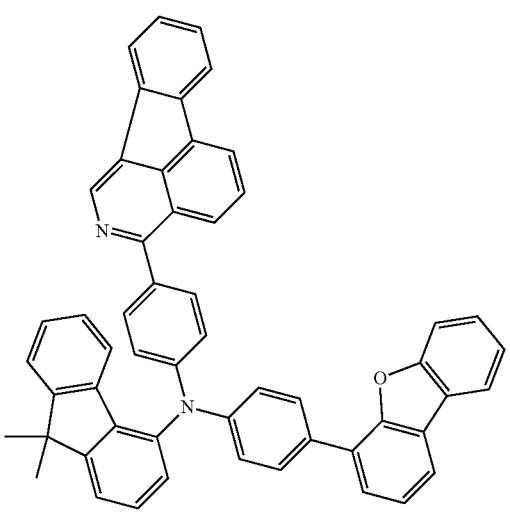
194
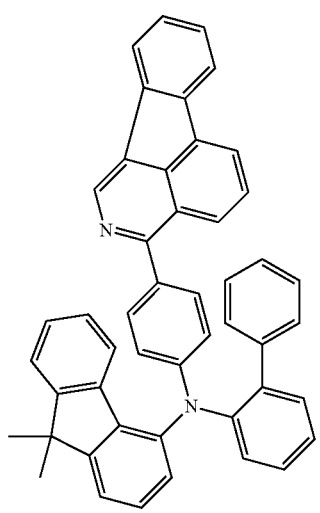
195

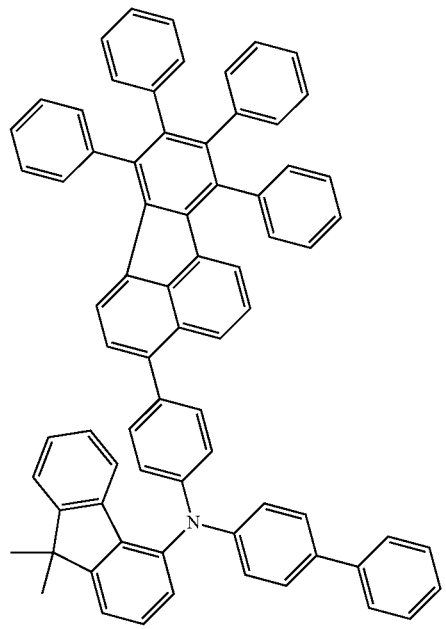
196
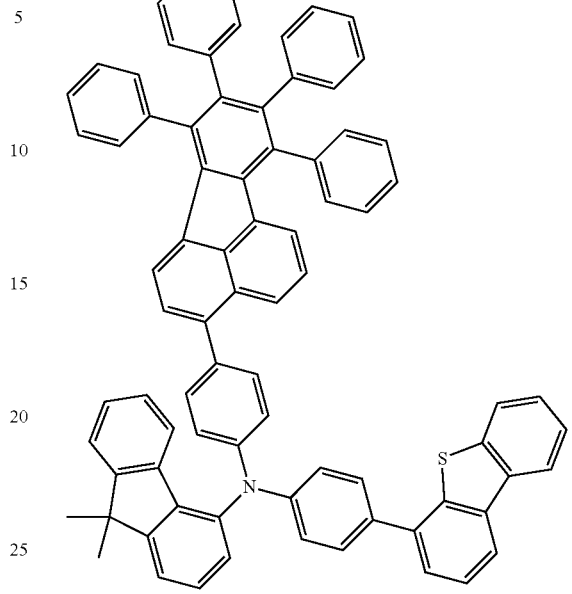
198
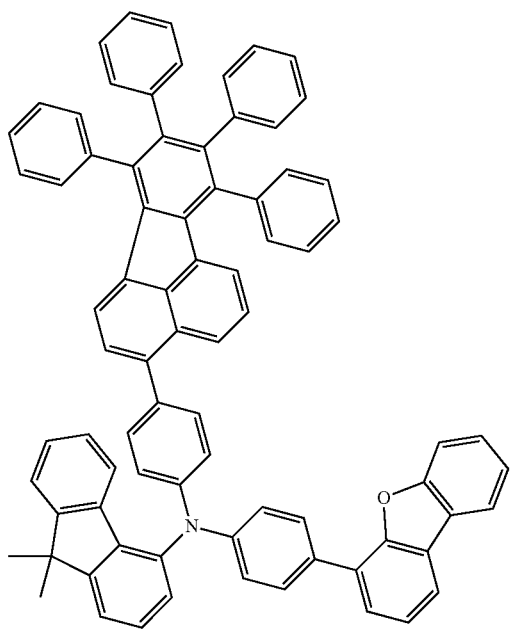
197
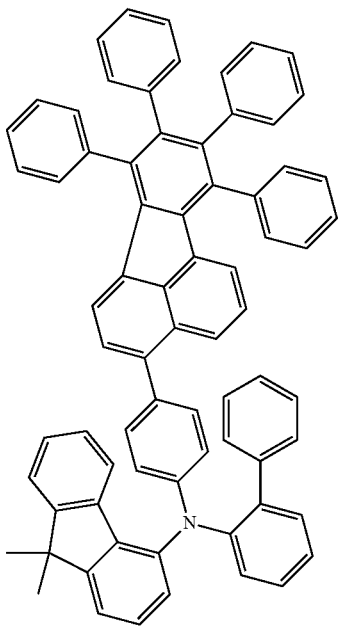
199

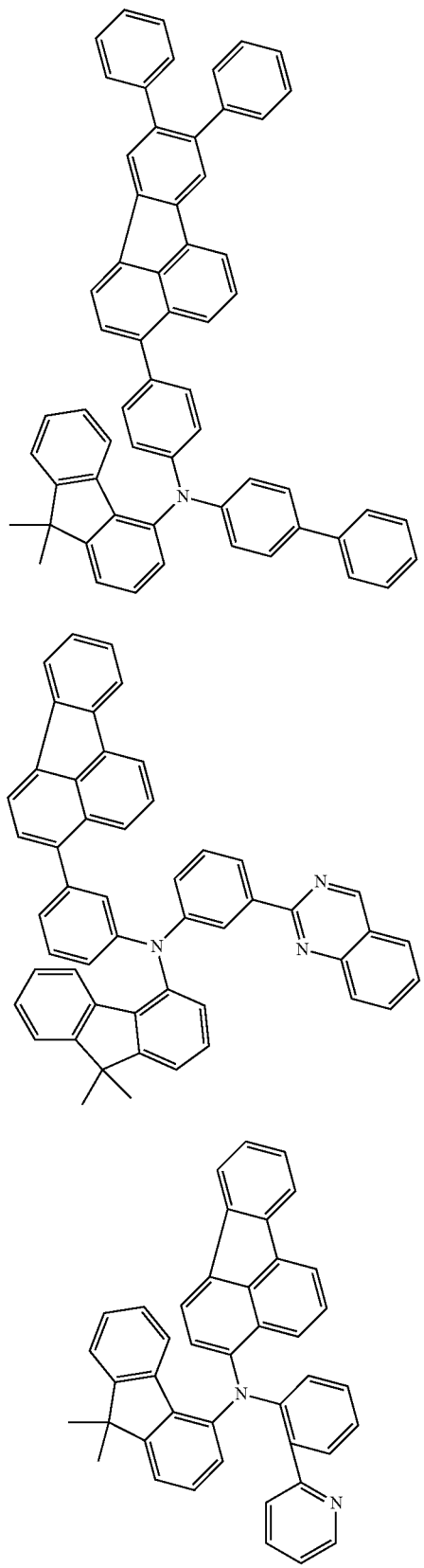
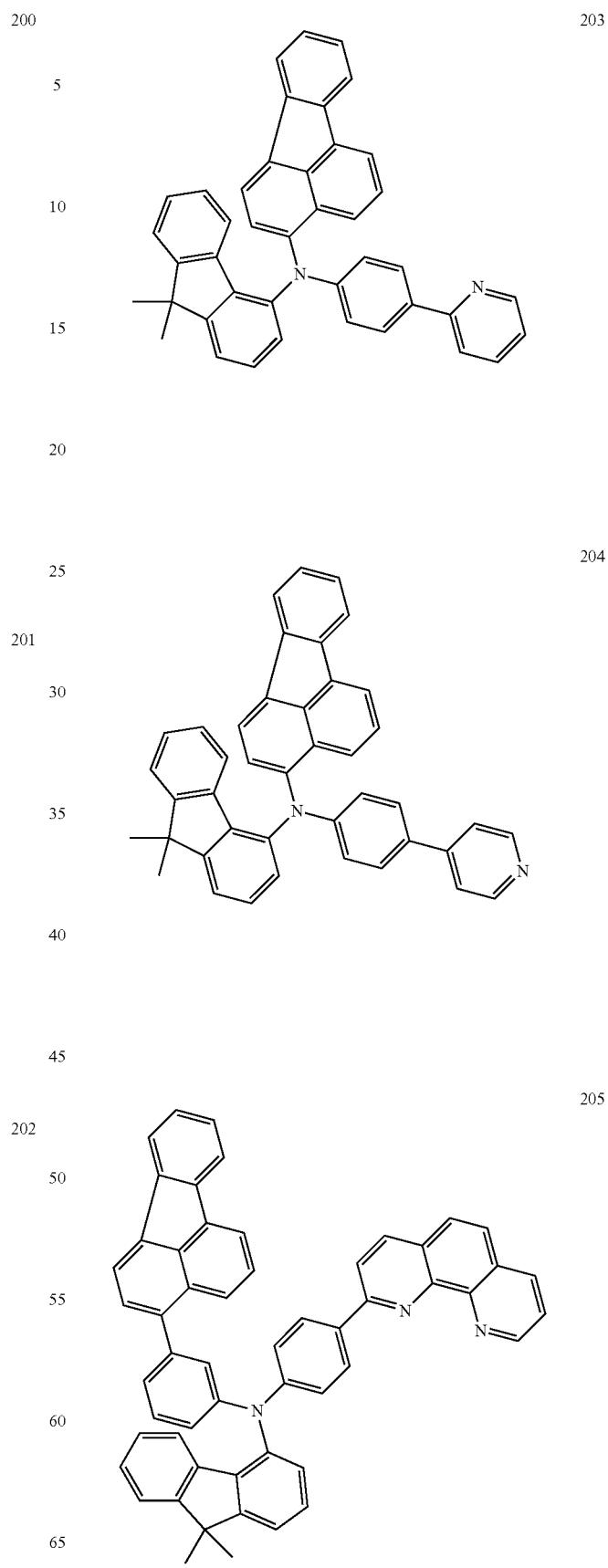

206
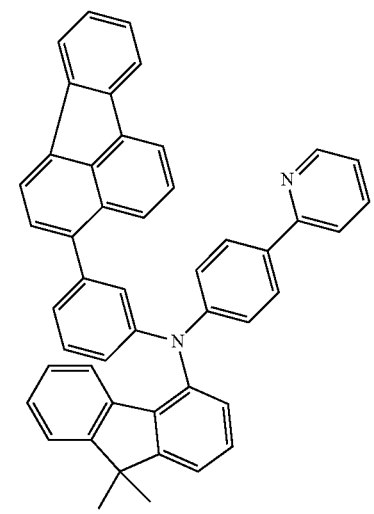
207
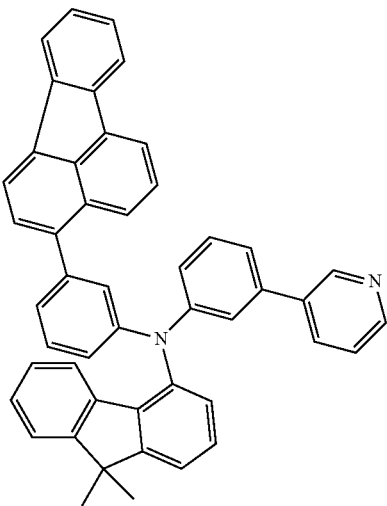
208
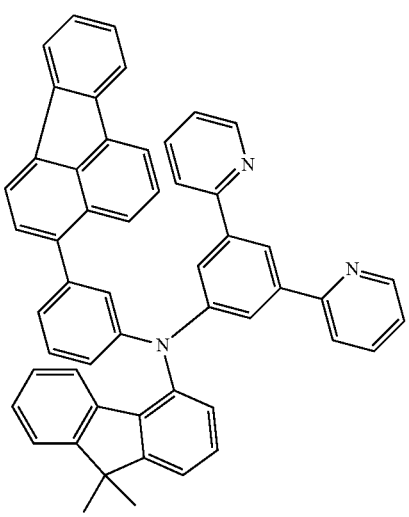
209
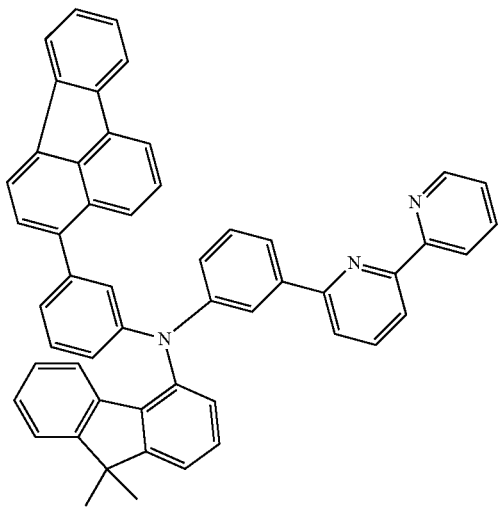
210
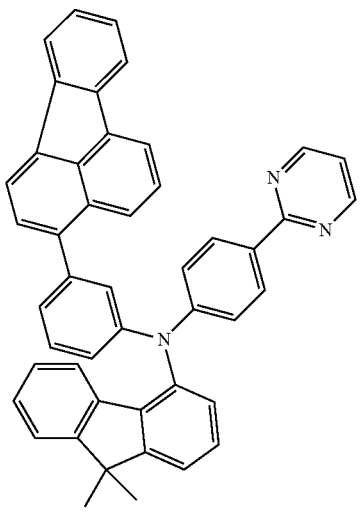
211
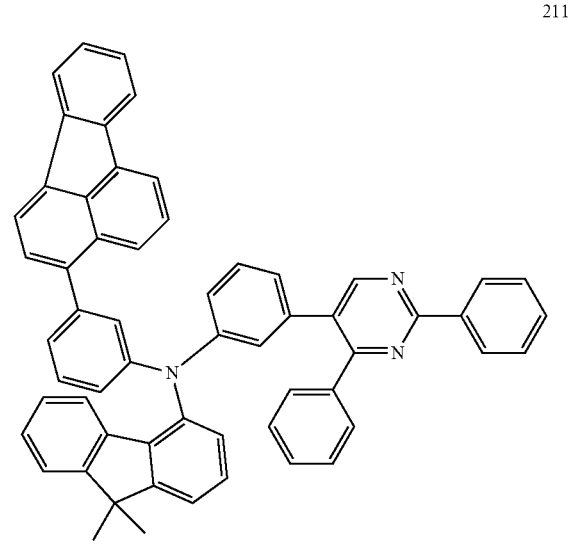

212
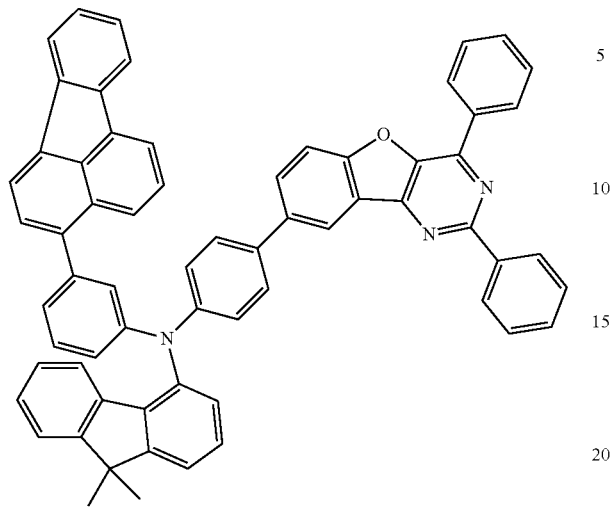
215
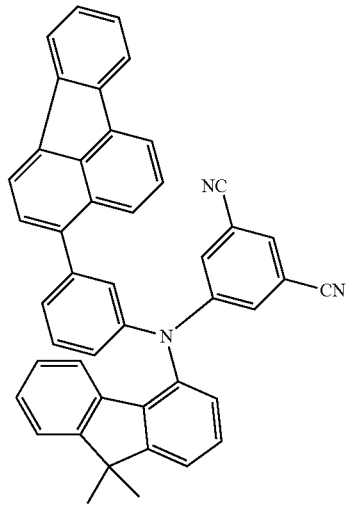
213
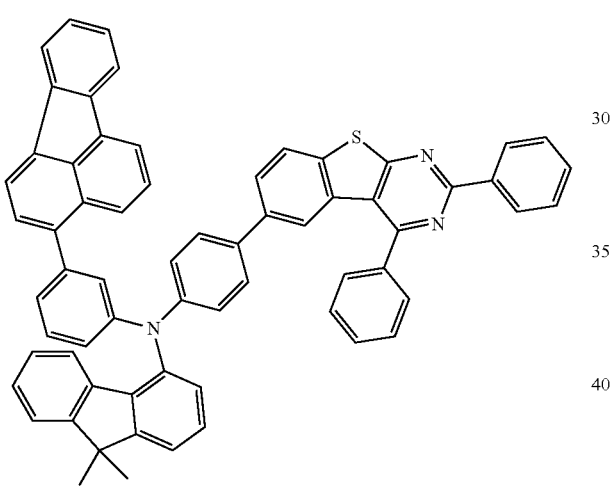
216
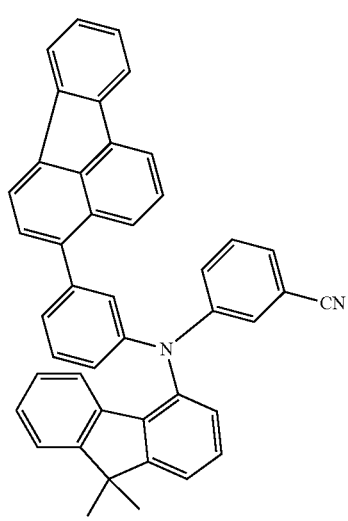
214
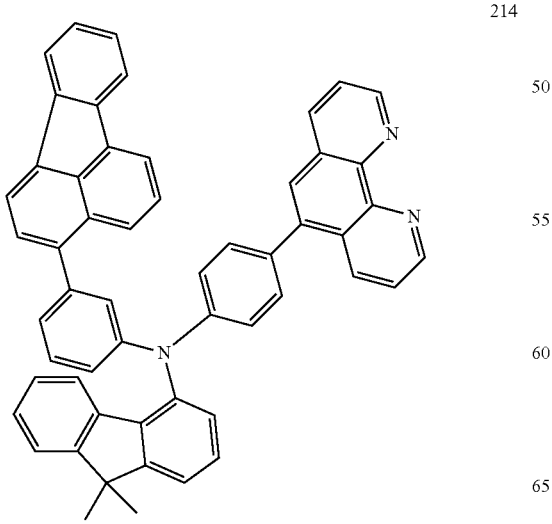
217
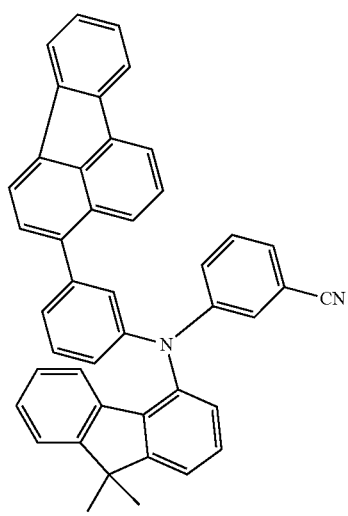

218

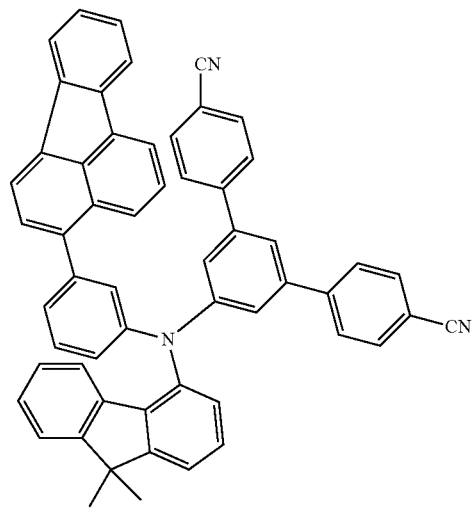

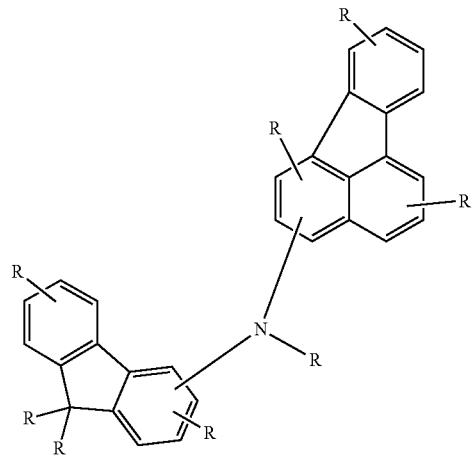

R = optional organic radical
Y = reactive group, preferably Cl, Br or I

The compounds of the formula (I) can be prepared by customary methods of synthetic organic chemistry that are known to those skilled in the art. In the preparation of the compounds, transition metal-catalysed coupling reactions in particular are used, such as Buchwald coupling reactions and Suzuki coupling reactions.

For preparation of compounds of formula (I) in which the fluoranthenyl group is bonded directly to the amino nitrogen atom, the procedure followed is preferably according to the method which follows (Scheme 1). In this case, rather than a fluorenyl group, it is equally possible to use a spirobifluorenyl group.

A fluorenylamine is reacted here in a Buchwald reaction with a fluoranthenyl derivative bearing a reactive group. This affords a compound of formula (I).

For preparation of compounds of formula (I) in which the fluoranthenyl group is bonded to the amino nitrogen via an aromatic linker, the procedure followed is preferably according to one of the two methods which follow (Schemes 2 and 3). In this case, rather than a fluorenyl group, it is equally possible to use a spirobifluorenyl group.

Scheme 1

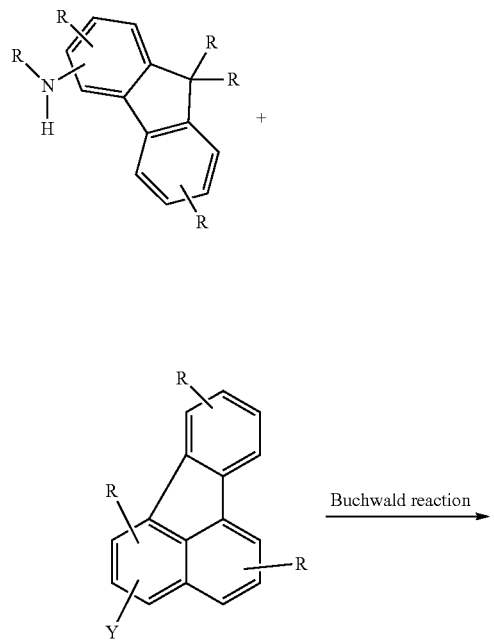

Scheme 2

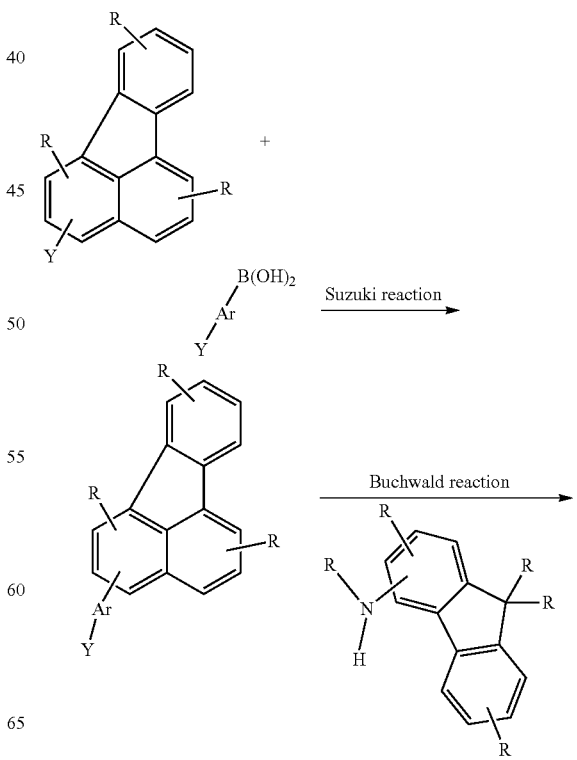

-continued

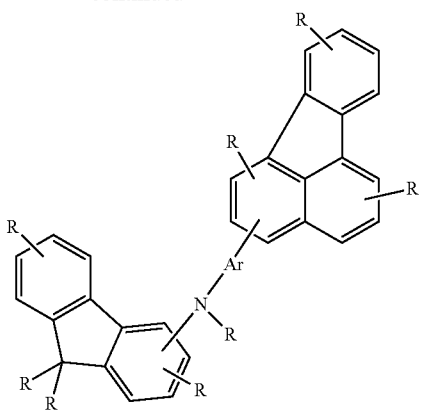

R = optional organic radical
Y = reactive group, preferably Cl, Br or I
Ar = arylene or heteroarylene group A fluoranthenyl derivative bearing a reactive group is reacted here in a Suzuki reaction with an aryl group bearing a further reactive group. In this way, an aryl-substituted fluoranthenyl group is prepared. The latter is subsequently reacted with a fluorenylamine in a Buchwald reaction to give a compound of formula (I).

Scheme 3

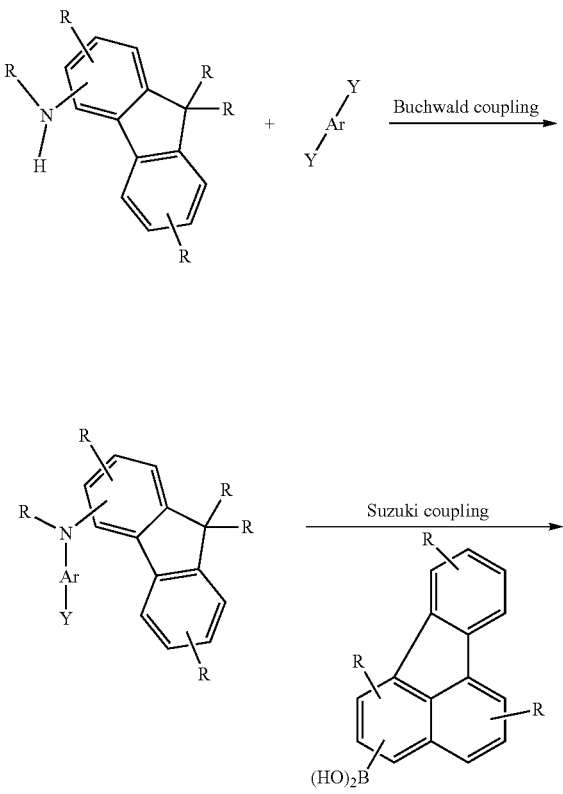

-continued

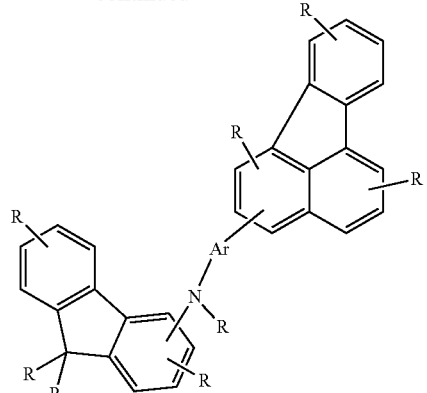

R = optional organic radical
Y = reactive group, preferably Cl, Br or I
Ar = arylene or heteroarylene group According to the variant of Scheme 3, the sequence of the Suzuki coupling and Buchwald coupling steps has been switched with respect to the variant of Scheme 2. In this case, an aryl group having a reactive group is first bound to the amine in a Buchwald coupling on the fluorenylamine. Then, in a subsequent reaction, the fluoranthenyl group is introduced in a Suzuki coupling.

The present invention thus further provides a process for preparing a compound of formula (I), which is characterized in that a fluorenylamine is reacted with an aromatic or heteroaromatic compound in a Buchwald coupling reaction.

In a preferred embodiment of the invention, the aromatic or heteroaromatic compound mentioned comprises a fluoranthenyl group. In an alternative, likewise preferred embodiment of the invention, the aromatic or heteroaromatic compound mentioned does not comprise any fluoranthenyl group. In this case, a fluoranthenyl group is preferably introduced in a subsequent Suzuki reaction.

The above-described compounds, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (I), wherein the bond(s) to the polymer, oligomer or dendrimer may be localized at any desired positions substituted by $R^1$, $R^2$, $R^3$, $R^4$ or $R^5$ in formula (I). According to the linkage of the compound of formula (I), the compound is part of a side chain of the oligomer or polymer or part of the main chain. An oligomer in the context of this invention is understood to mean a compound formed from at least three monomer units. A polymer in the context of the invention is understood to mean a compound formed from at least ten monomer units. The polymers, oligomers or dendrimers of the invention may be conjugated, partly conjugated or nonconjugated. The oligomers or polymers of the invention may be linear, branched or dendritic. In the structures having linear linkage, the units of formula (I) may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of formula (I) to be joined via a trivalent or higher-valency group, for example via a trivalent or higher-valency aromatic or heteroaromatic group, to give a branched or dendritic oligomer or polymer.

For the repeat units of formula (I) in oligomers, dendrimers and polymers, the same preferences apply as described above for compounds of formula (M).

For preparation of the oligomers or polymers, the monomers of the invention are homopolymerized or copolymerized with further monomers. Suitable and preferred comonomers are chosen from fluorenes (for example according to EP 842208 or WO 2000/22026), spirobifluorenes (for example according to EP 707020, EP 894107 or WO 2006/061181), paraphenylenes (for example according to WO 1992/18552), carbazoles (for example according to WO 2004/070772 or WO 2004/113468), thiophenes (for example according to EP 1028136), dihydrophenanthrenes (for example according to WO 2005/014689 or WO 2007/006383), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers typically contain still further units, for example emitting (fluorescent or phosphorescent) units, for example vinyltriarylamines (for example according to WO 2007/068325) or phosphorescent metal complexes (for example according to WO 2006/003000), and/or charge transport units, especially those based on triarylamines.

The polymers and oligomers of the invention are generally prepared by polymerization of one or more monomer types, of which at least one monomer leads to repeat units of the formula (I) in the polymer. Suitable polymerization reactions are known to those skilled in the art and are described in the literature. Particularly suitable and preferred polymerization reactions which lead to formation of C—C or C—N bonds are the Suzuki polymerization, the Yamamoto polymerization, the Stille polymerization and the Hartwig-Buchwald polymerization.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of formula (I) and at least one solvent, preferably an organic solvent. The way in which such solutions can be prepared is known to those skilled in the art and is described, for example, in WO 2002/072714, WO 2003/019694 and the literature cited therein.

The compounds of the invention are suitable for use in electronic devices, especially in organic electroluminescent devices (OLEDs). Depending on the substitution, the compounds are used in different functions and layers.

The invention therefore further provides for the use of the compound of formula (I) in an electronic device. This electronic device is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably organic electroluminescent devices (OLEDs).

The invention further provides, as already set out above, an electronic device comprising at least one compound of formula (I). This electronic device is preferably selected from the abovementioned devices.

It is more preferably an organic electroluminescent device (OLED) comprising anode, cathode and at least one emitting layer, characterized in that at least one organic layer, which may be an emitting layer, a hole transport layer or another layer, comprises at least one compound of formula (I).

Apart from the cathode, anode and emitting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers of the organic electroluminescent device comprising the compound of the formula (I) is preferably as follows: anode-hole injection layer-hole transport layer-optionally further hole transport layer(s)-optionally electron blocker layer-emitting layer-optionally hole blocker layer-electron transport layer-electron injection layer-cathode. It is additionally possible for further layers to be present in the OLED.

The organic electroluminescent device of the invention may contain two or more emitting layers. More preferably, these emission layers in this case have several emission maxima between 380 nm and 750 nm overall, such that the overall result is white emission; in other words, various emitting compounds which may fluoresce or phosphoresce and which emit blue, green, yellow, orange or red light are used in the emitting layers. Especially preferred are three-layer systems, i.e. systems having three emitting layers, where the three layers show blue, green and orange or red emission (for the basic construction see, for example, WO 2005/011013). The compounds of the invention are preferably present here in a hole transport layer, hole injection layer, electron blocker layer, emitting layer, hole-blocking layer and/or electron-transporting layer, more preferably in an emitting layer as matrix material, in a hole blocker layer and/or in an electron transport layer.

It is preferable in accordance with the invention when the compound of formula (I) is used in an electronic device comprising one or more phosphorescent emitting compounds. In this case, the compound may be present in different layers, preferably in a hole transport layer, an electron blocker layer, a hole injection layer, an emitting layer, a hole blocker layer and/or an electron transport layer. More preferably, it is present in an emitting layer in combination with a phosphorescent emitting compound.

The term "phosphorescent emitting compounds" typically encompasses compounds where the emission of light is effected through a spin-forbidden transition, for example a transition from an excited triplet state or a state having a higher spin quantum number, for example a quintet state.

Suitable phosphorescent emitting compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitting compounds, compounds containing copper, molybdenum, tungsten, rhenium, ruthenium, osmium, rhodium, iridium, palladium, platinum, silver, gold or europium, especially compounds containing iridium, platinum or copper. In the context of the present invention, all luminescent iridium, platinum or copper complexes are considered to be phosphorescent emitting compounds.

Examples of the above-described emitting compounds can be found in applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used for phosphorescent OLEDs according to the prior art and as known to those skilled in the art in the field of organic electroluminescent devices are suitable. It is also possible for the person skilled in the art, without exercising inventive skill, to use further phosphorescent complexes in combination with the compounds of formula (I) in organic electroluminescent devices. Further examples are listed in the following table:

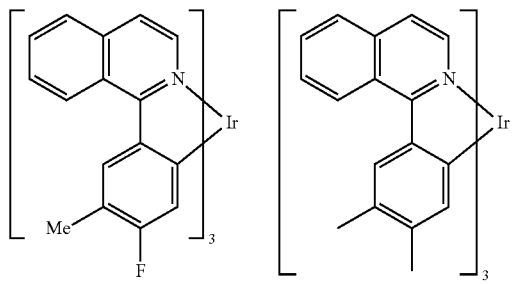

-continued

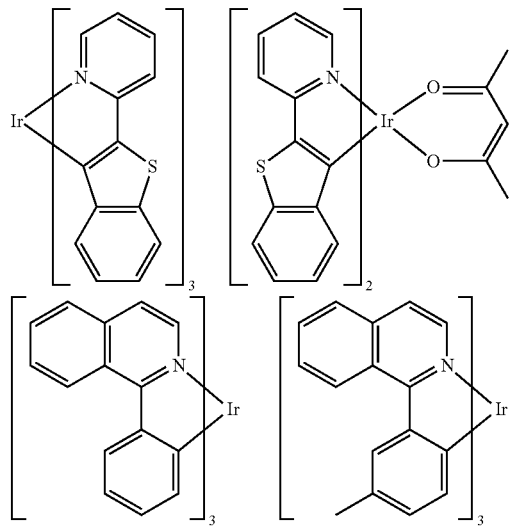

133
-continued
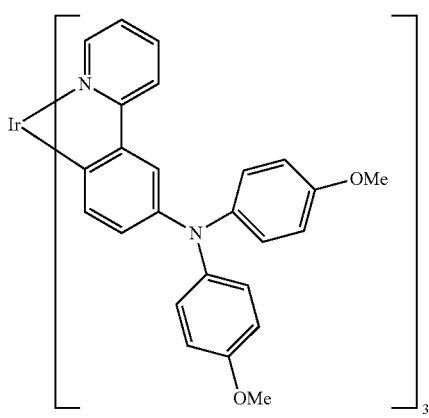
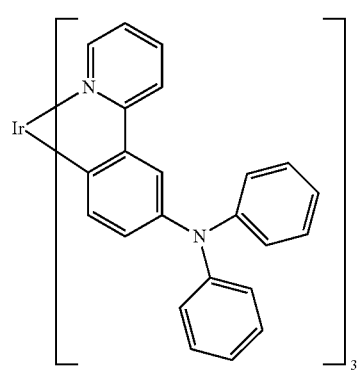
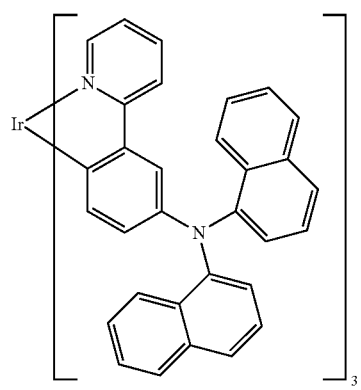
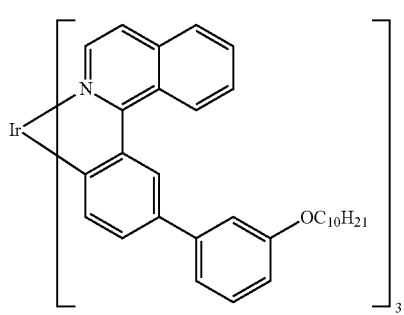
134
-continued
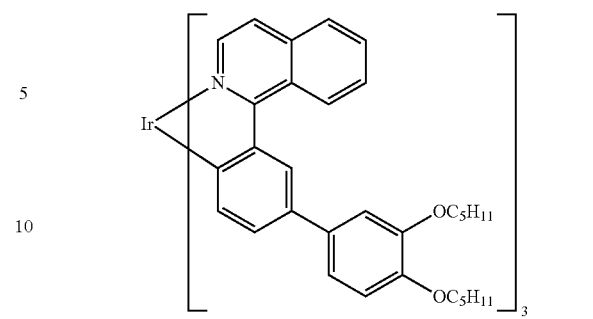
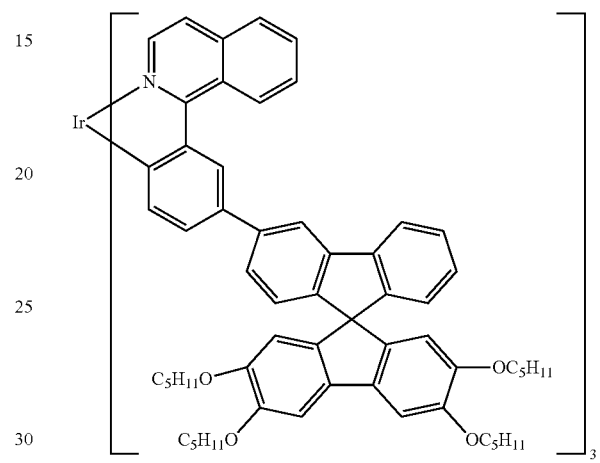
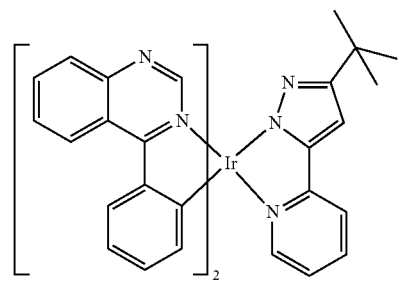
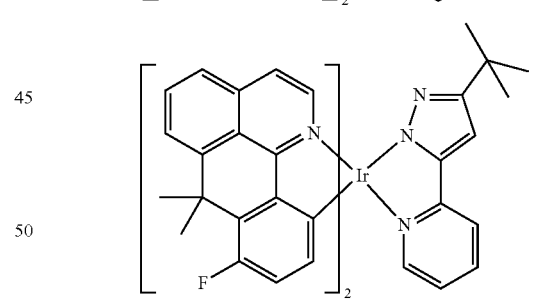
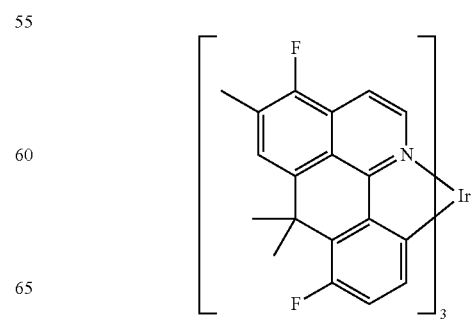

135
-continued
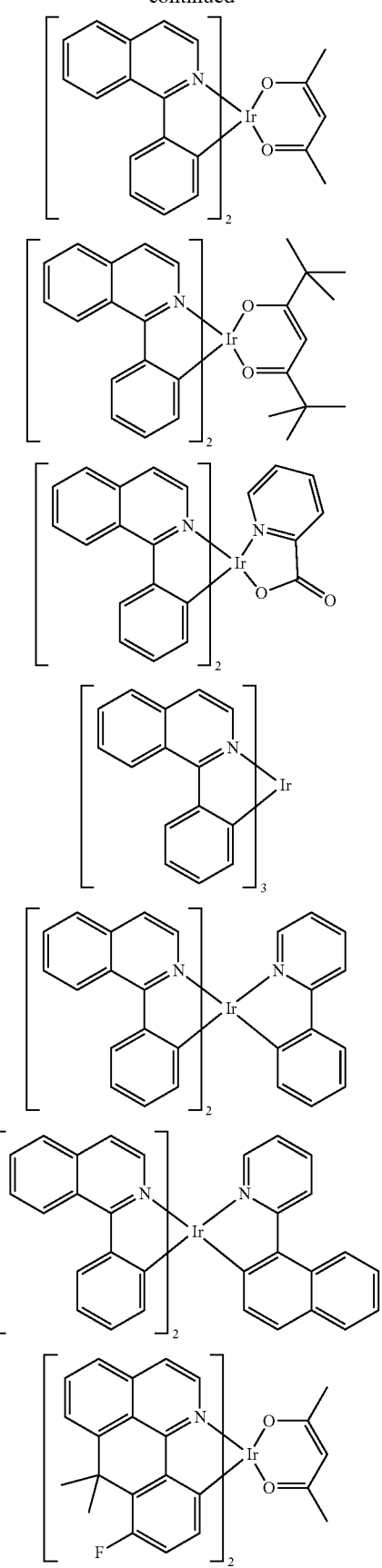
136
-continued
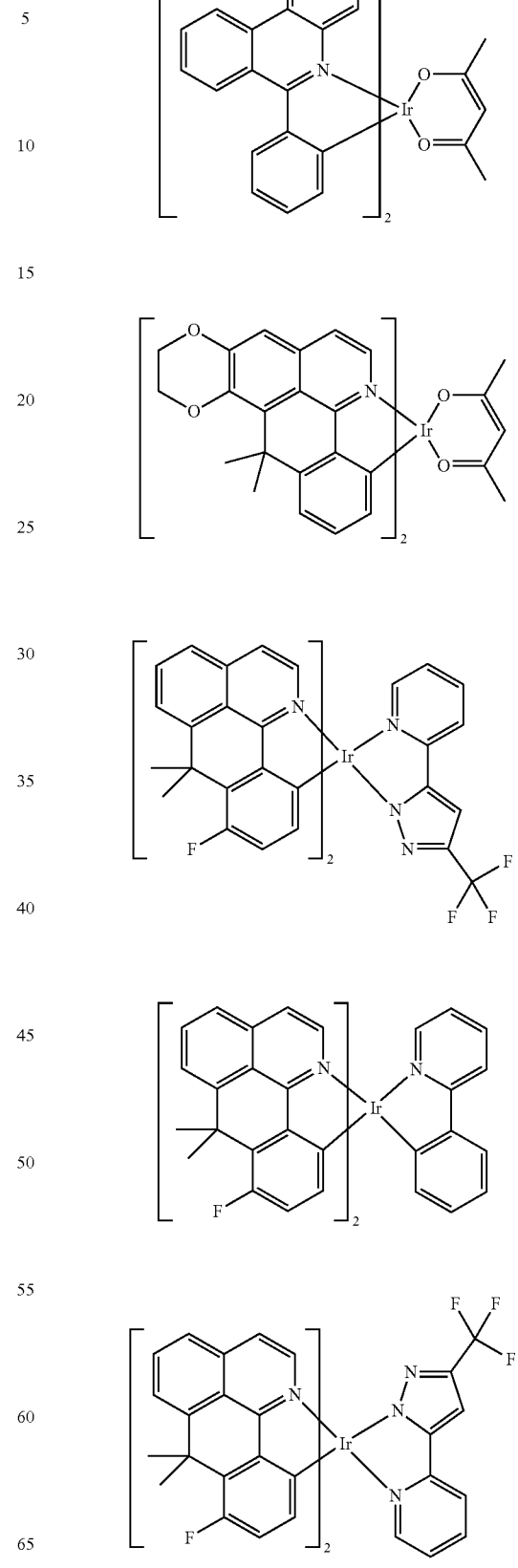

137
-continued
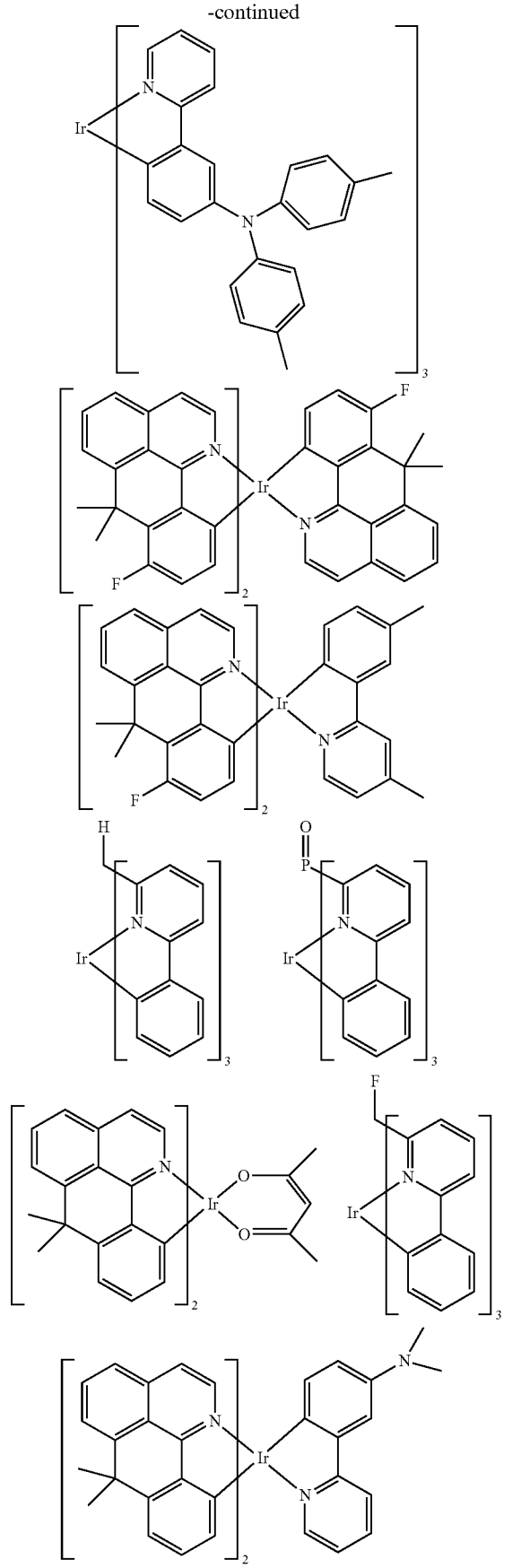
138
-continued
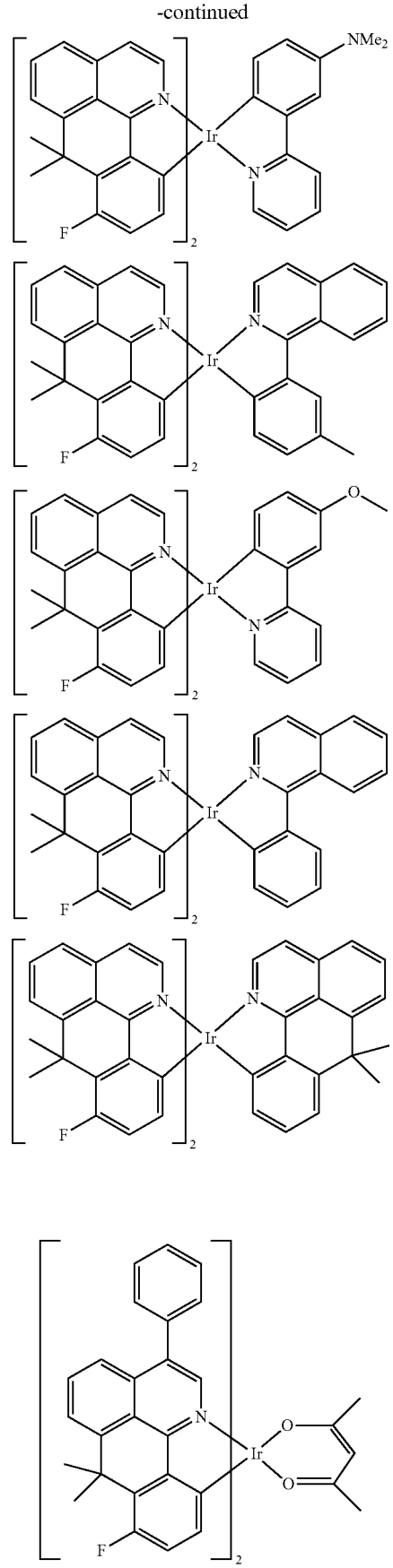

139
-continued
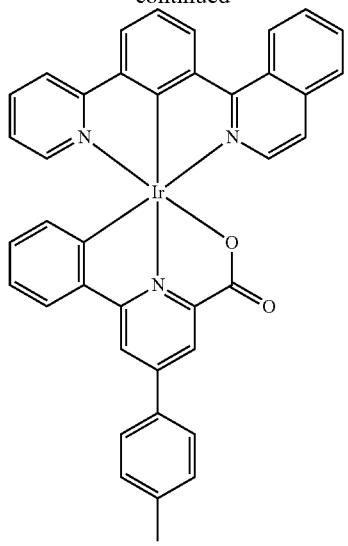
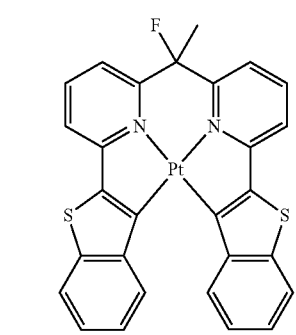
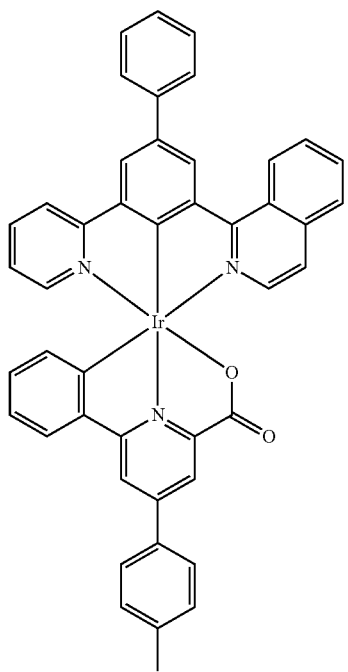
140
-continued
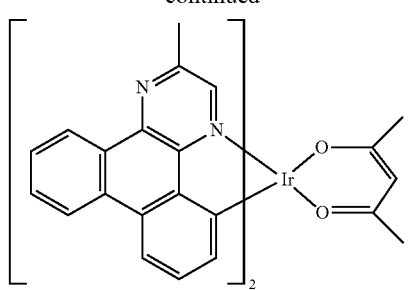
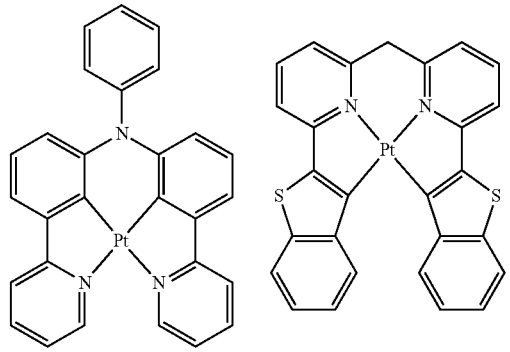
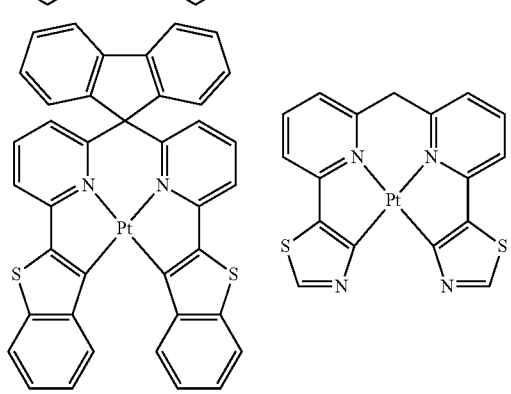
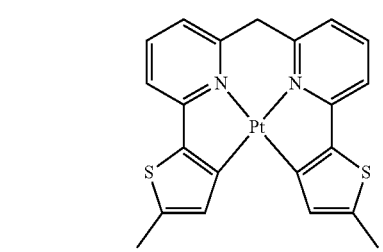
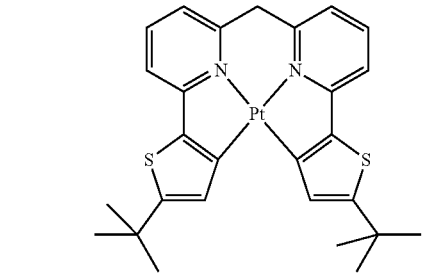

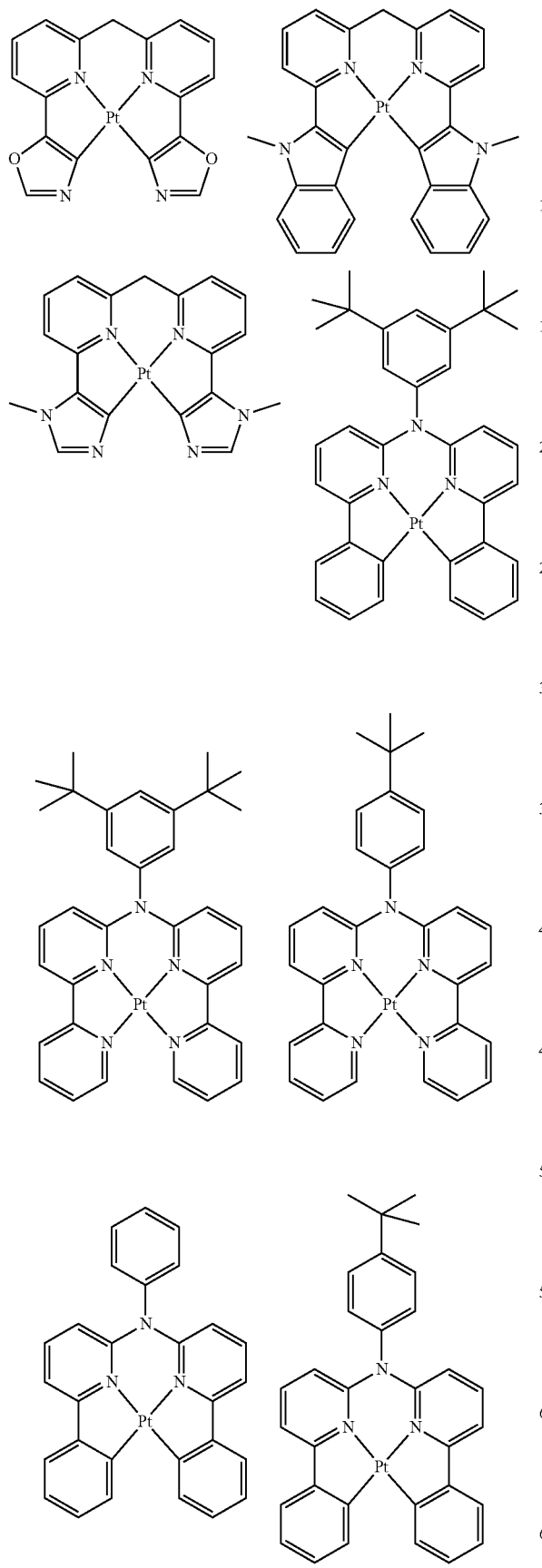
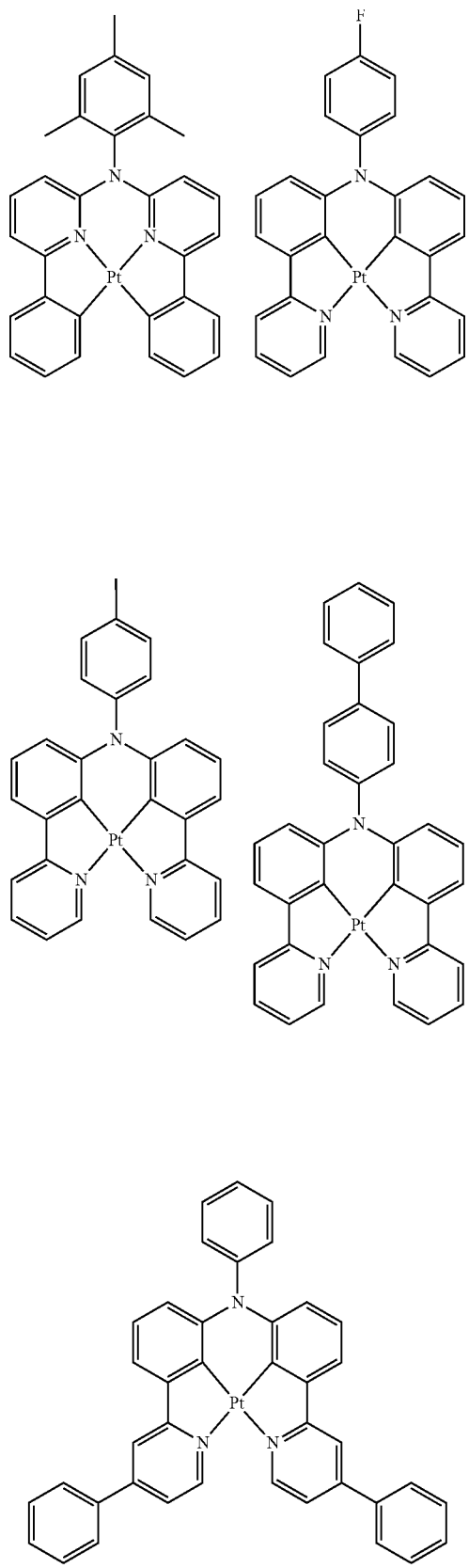

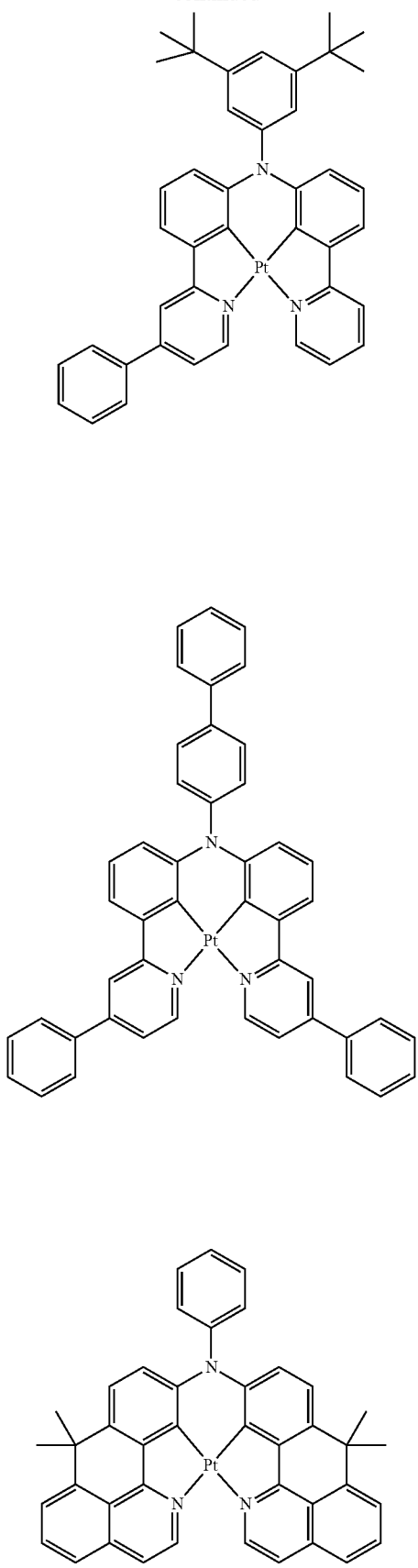
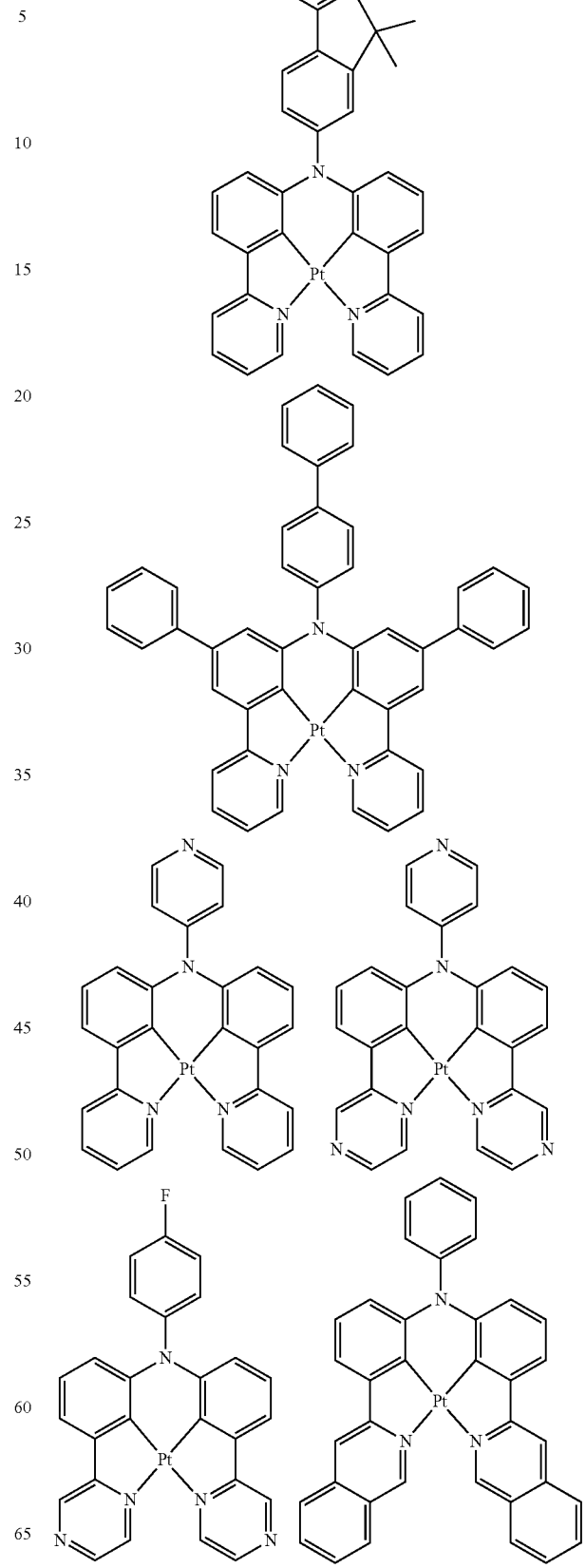

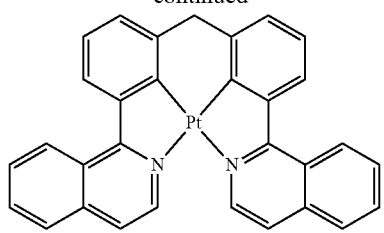
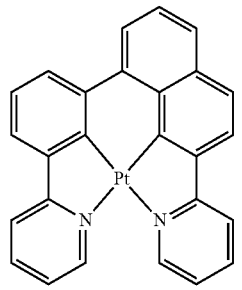
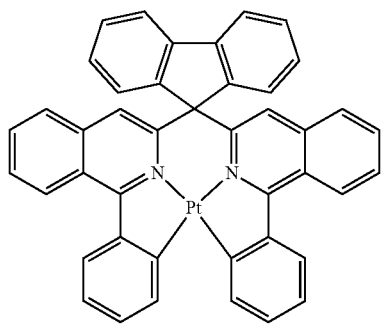
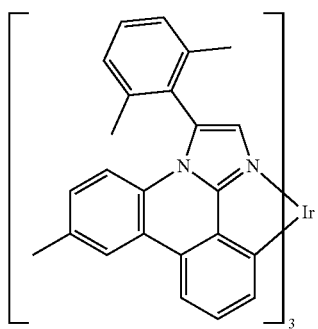
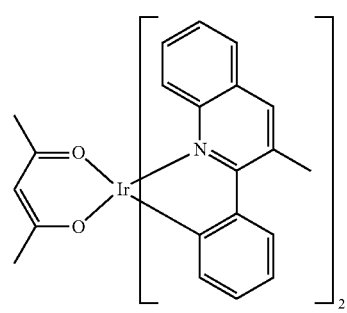
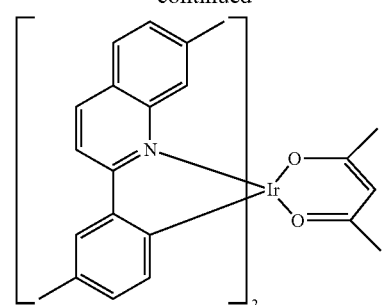
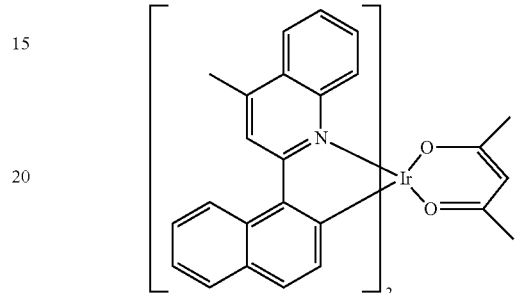
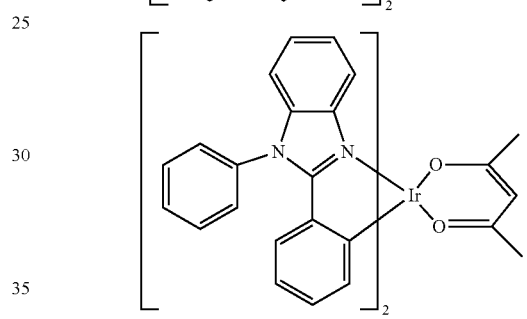
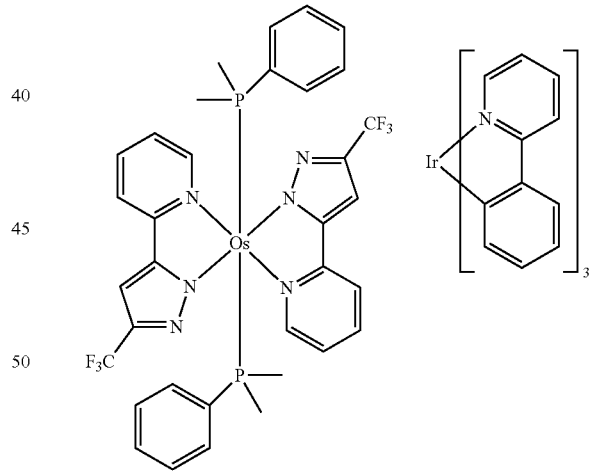
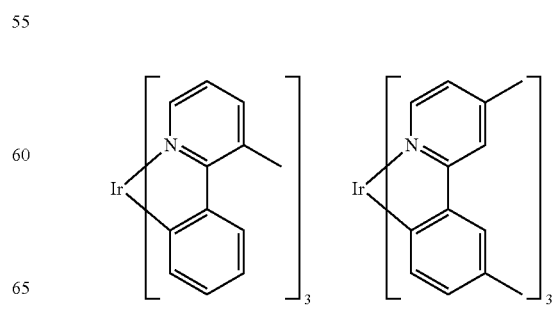

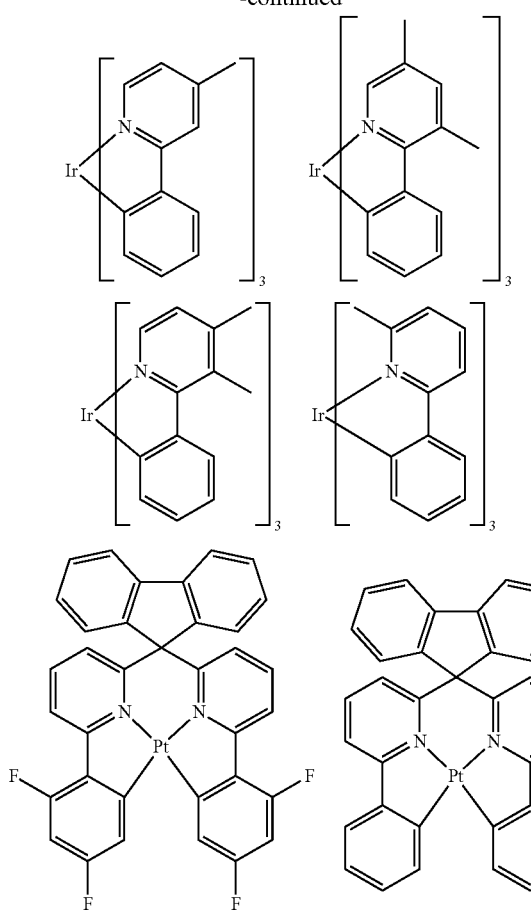
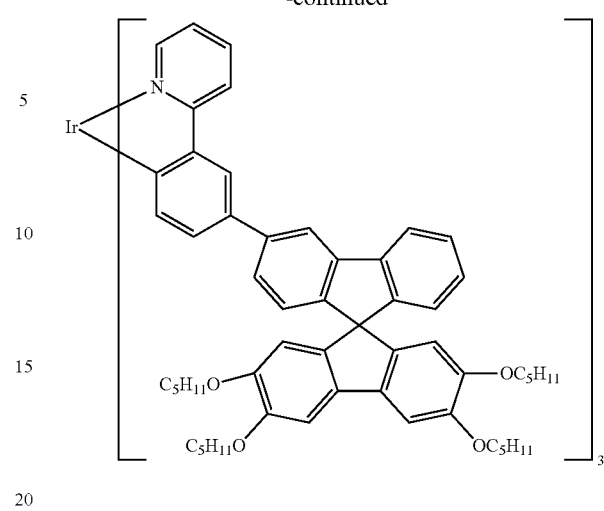
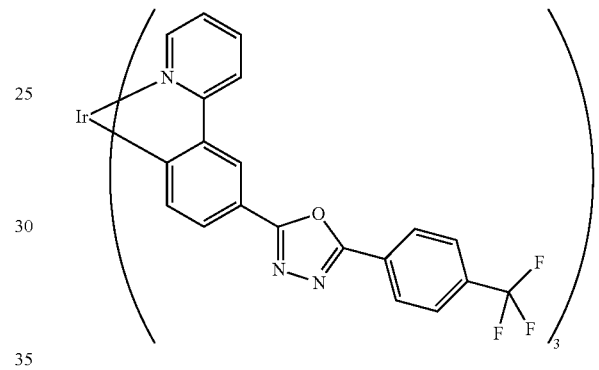
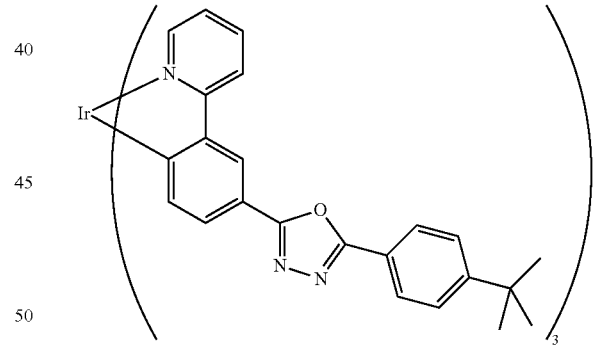
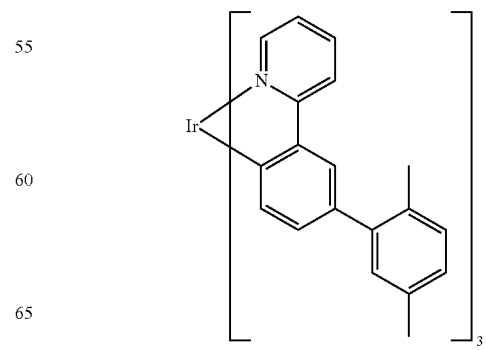

149
-continued
150
-continued
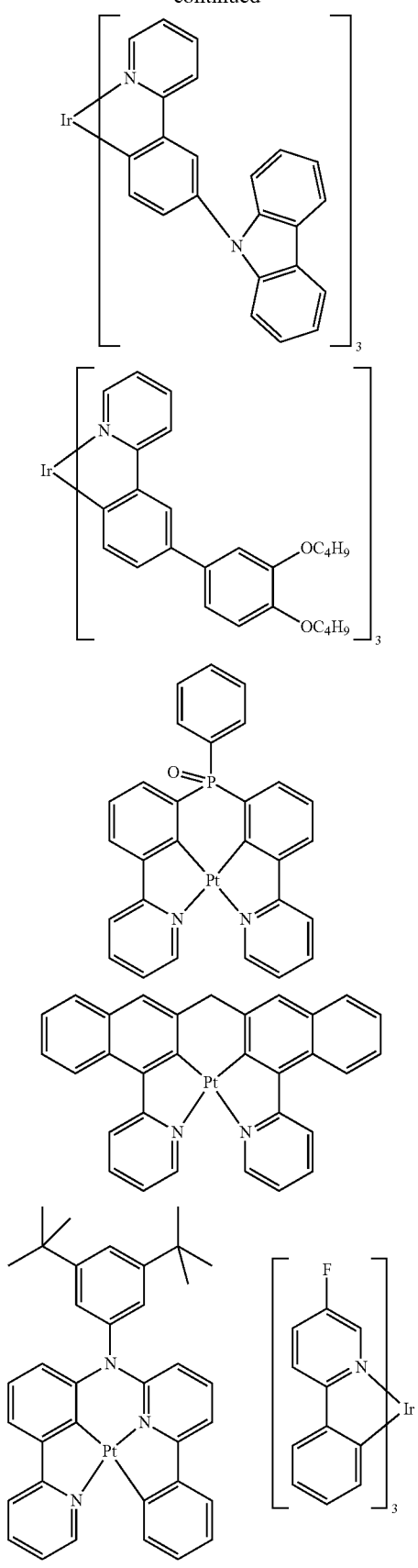
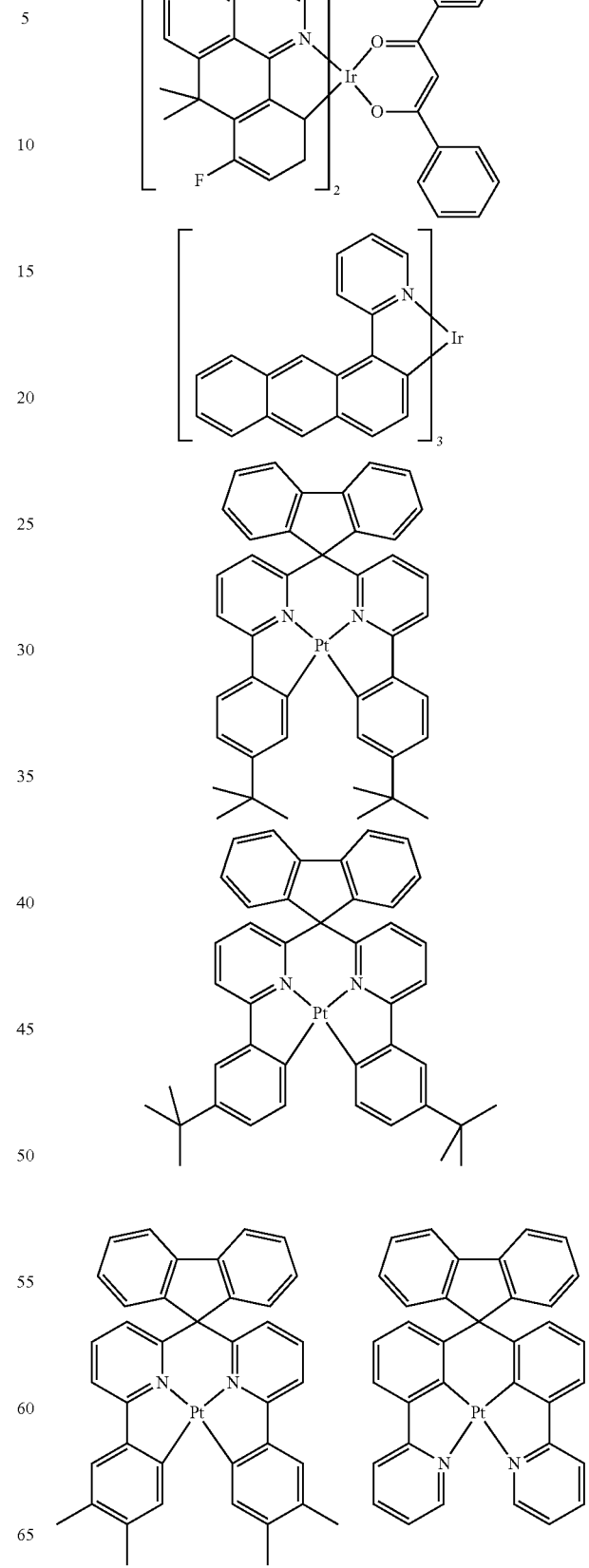

151
-continued
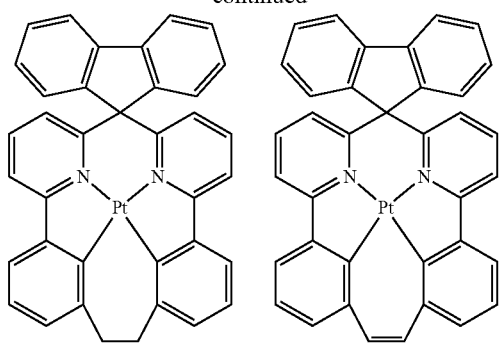
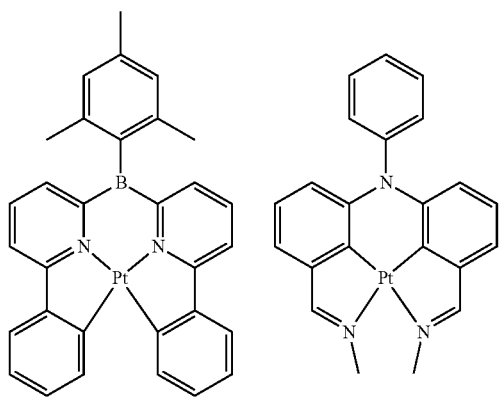
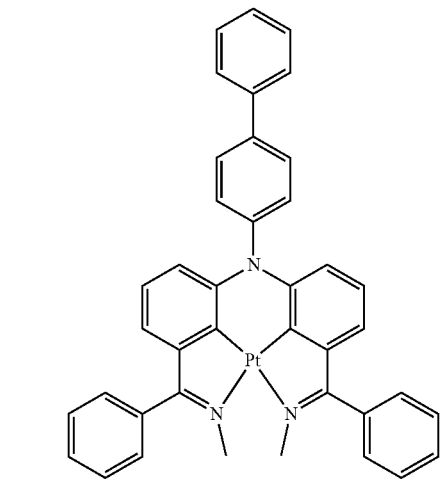
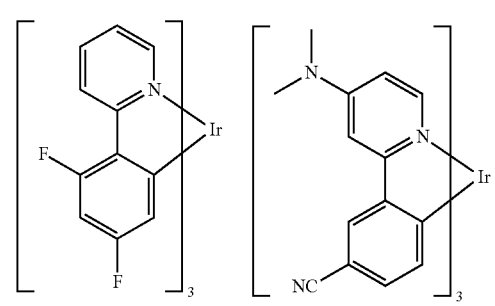
152
-continued
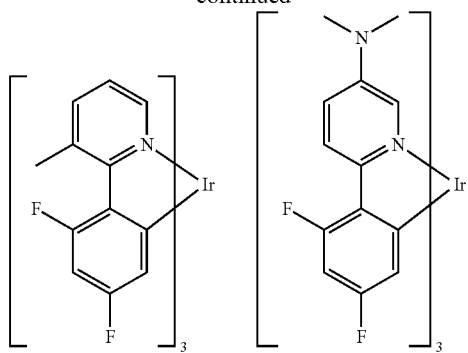
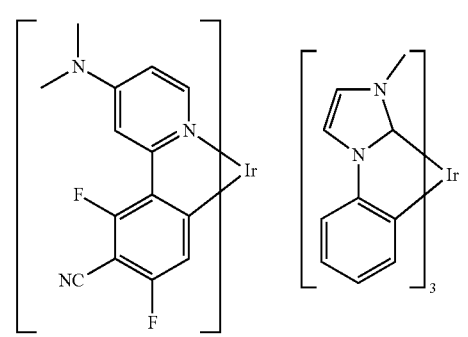
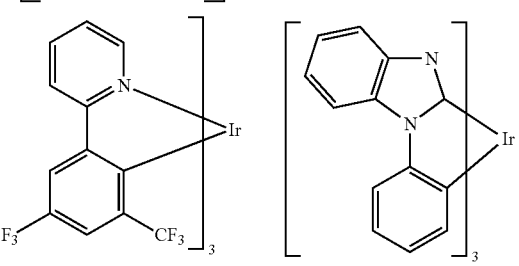
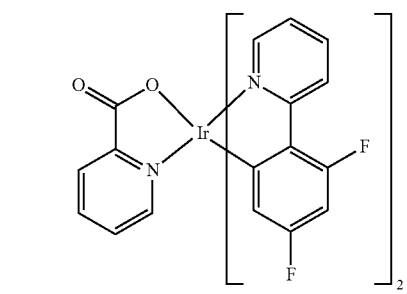
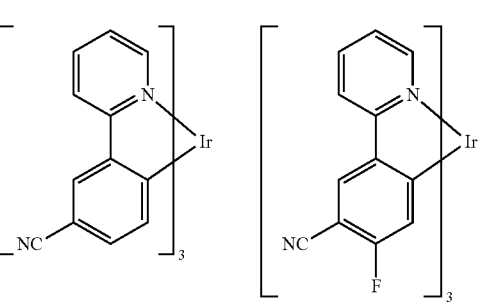

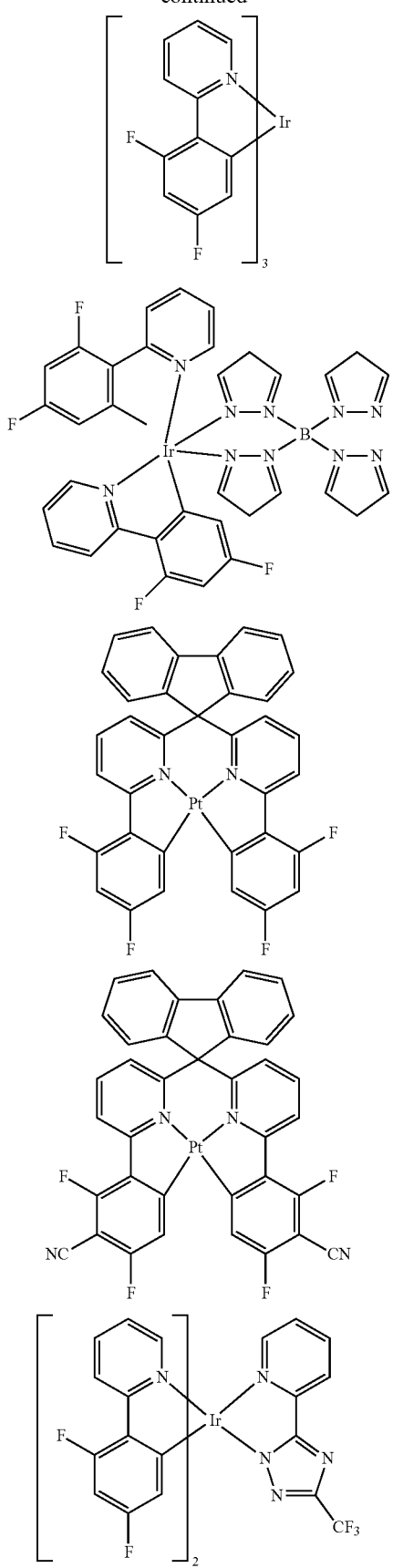
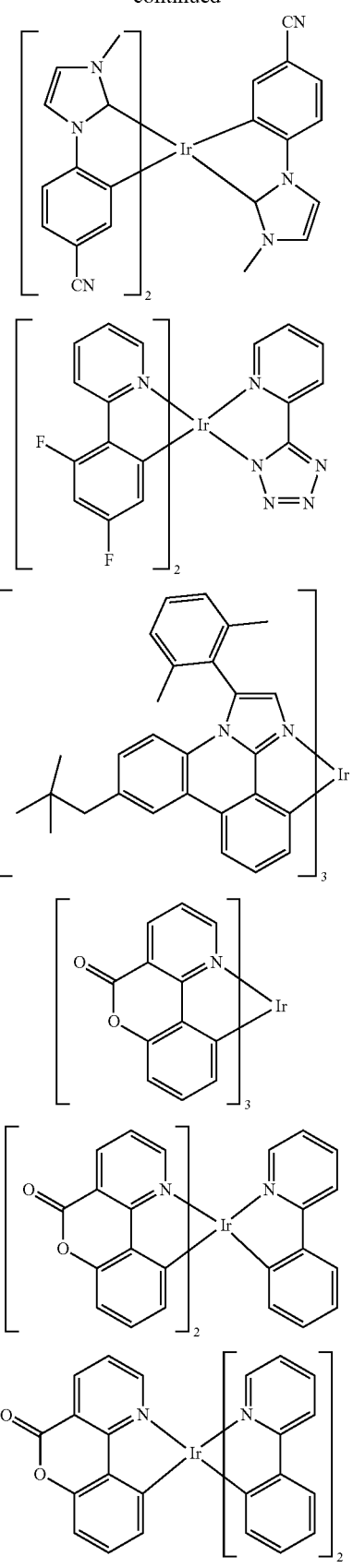

-continued

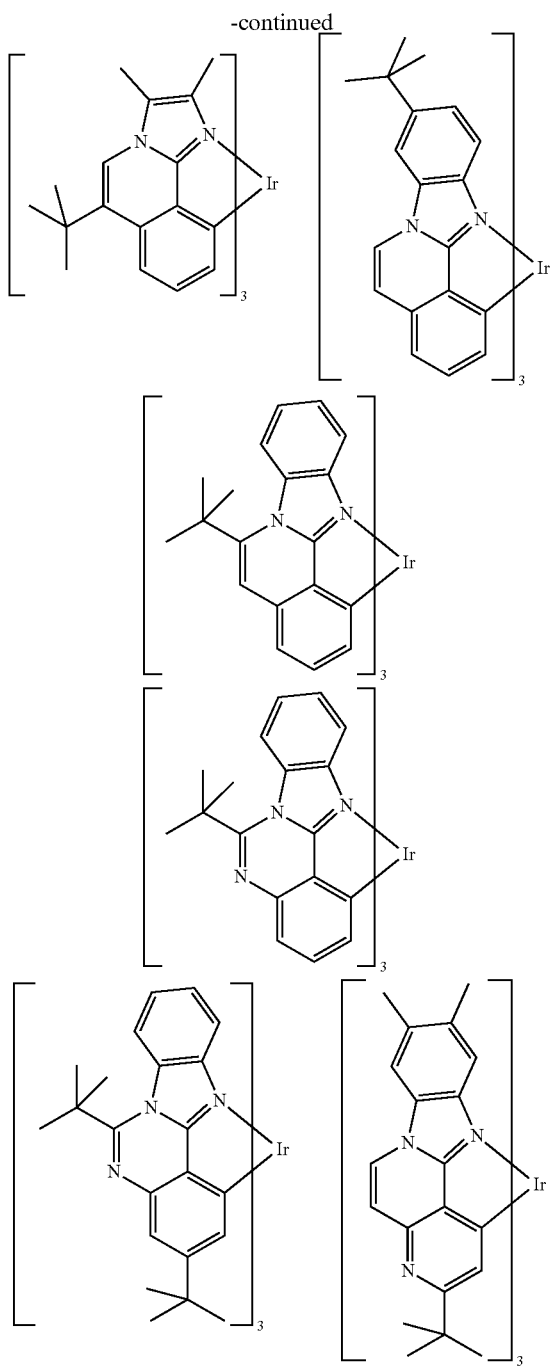

In a preferred embodiment of the present invention, the compound of the formula (I) is used in an emitting layer as matrix material in combination with one or more emitting compounds, preferably phosphorescent emitting compounds. The phosphorescent emitting compound is preferably a red-phosphorescing emitter. This is the most strongly preferred use of the compounds of the formula (I).

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the emitting compound is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of emitting compounds. In this case too, the emitting compounds are generally those compounds having the smaller proportion in the system and the matrix materials are those compounds having the greater proportion in the system. In individual cases, however, the proportion of a single matrix material in the system may be less than the proportion of a single emitting compound.

It is preferable that the compounds of formula (I) are used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The compound of the formula (I) is preferably the matrix material having hole-transporting properties. The desired electron-transporting and hole-transporting properties of the mixed matrix components may, however, also be combined mainly or entirely in a single mixed matrix component, in which case the further mixed matrix component(s) fulfil(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The mixed matrix systems may comprise one or more emitting compounds, preferably one or more phosphorescent emitting compounds. In general, mixed matrix systems are preferably used in phosphorescent organic electroluminescent devices.

Particularly suitable matrix materials which can be used in combination with the compounds of the invention as matrix components of a mixed matrix system are selected from the preferred matrix materials specified below for phosphorescent emitting compounds or the preferred matrix materials for fluorescent emitting compounds, according to what type of emitting compound is used in the mixed matrix system.

Preferred phosphorescent emitting compounds for use in mixed matrix systems are the same as detailed further up as generally preferred phosphorescent emitter materials.

In a preferred embodiment of the invention, the compounds of formula (I) are used as hole-transporting material. In that case, the compounds are preferably present in a hole transport layer, an electron blocker layer or a hole injection layer.

A hole transport layer according to the present application is a layer having a hole-transporting function between the anode and emitting layer.

Hole injection layers and electron blocker layers are understood in the context of the present application to be specific embodiments of hole transport layers. A hole injection layer, in the case of a plurality of hole transport layers between the anode and emitting layer, is a hole transport layer which directly adjoins the anode or is separated therefrom only by a single coating of the anode. An electron blocker layer, in the case of a plurality of hole transport layers between the anode and emitting layer, is that hole transport layer which directly adjoins the emitting layer on the anode side. Preferably, the OLED of the invention comprises two, three or four hole-transporting layers between the anode and emitting layer, at least one of which preferably contains a compound of formula (I), and more preferably exactly one or two contain a compound of formula (I).

If the compound of formula (I) is used as hole transport material in a hole transport layer, a hole injection layer or an electron blocker layer, the compound can be used as pure material, i.e. in a proportion of 100%, in the hole transport layer, or it can be used in combination with one or more further compounds. In a preferred embodiment, the organic layer comprising the compound of the formula (I) then additionally contains one or more p-dopants. p-Dopants used according to the present invention are preferably those organic electron acceptor compounds capable of oxidizing one or more of the other compounds in the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600, WO 2012/095143 and DE 102012209523.

Particularly preferred p-dopants are quinodimethane compounds, azaindenofluorenediones, azaphenalenes, azatriphenylenes, I2, metal halides, preferably transition metal halides, metal oxides, preferably metal oxides containing at least one transition metal or a metal of main group 3, and transition metal complexes, preferably complexes of Cu, Co, Ni, Pd and Pt with ligands containing at least one oxygen atom as bonding site. Preference is further given to transition metal oxides as dopants, preferably oxides of rhenium, molybdenum and tungsten, more preferably $Re_2O_7$, $MoO_3$, $WO_3$ and $ReO_3$.

The p-dopants are preferably in substantially homogeneous distribution in the p-doped layers. This can be achieved, for example, by coevaporation of the p-dopant and the hole transport material matrix.

Preferred p-dopants are especially the following compounds:

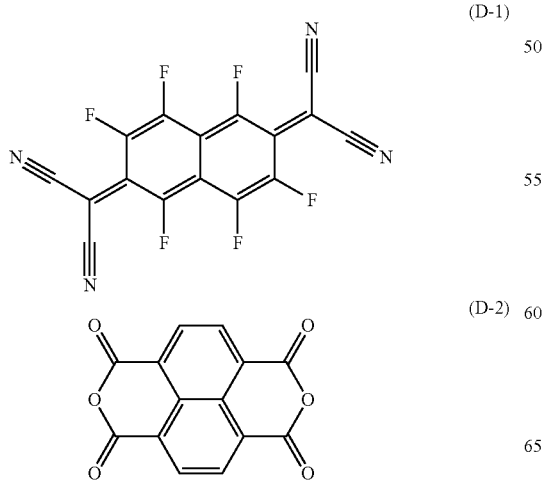

(D-1)

(D-2)

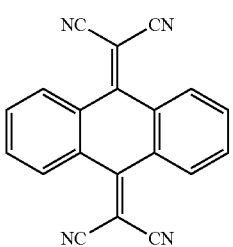

(D-3)

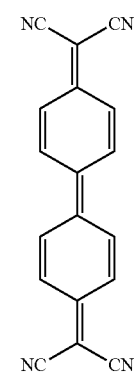

(D-4)

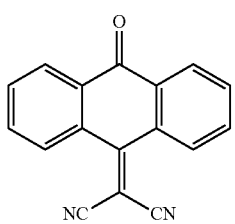

(D-5)

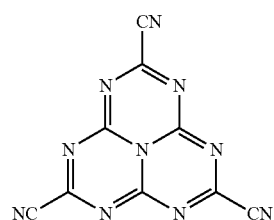

(D-6)

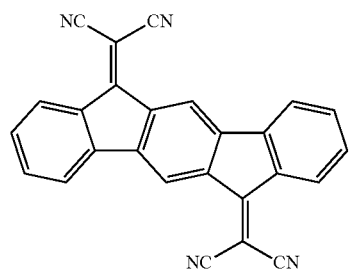

(D-7)

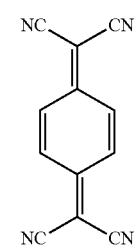

(D-8)

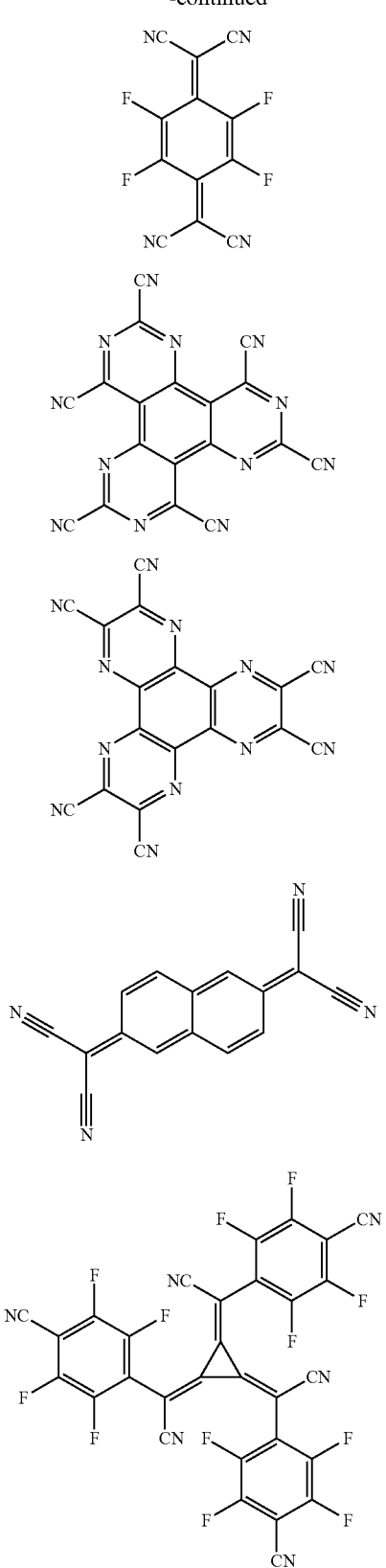

In a further preferred embodiment of the invention, the compound of formula (I) is used as hole transport material in combination with a hexaazatriphenylene derivative as described in US 2007/0092755. Particular preference is given here to using the hexaazatriphenylene derivative in a separate layer.

In a further preferred embodiment, the compounds of the invention are used in one or more layers on the electron transport side, preferably in a hole blocker layer and/or an electron transport layer. In the case of use in an electron transport layer, it is preferable that they are used in combination with a metal complex, preferably a metal quinolinate, more preferably a lithium quinolinate.

Preferred embodiments of the different functional materials in the electronic device are listed hereinafter.

Preferred fluorescent emitting compounds are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthraceneamines, aromatic anthracenediamines, aromatic pyreneamines, aromatic pyrenediamines, aromatic chryseneamines or aromatic chrysenediamines. An aromatic anthraceneamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyreneamines, pyrenediamines, chryseneamines and chrysenediamines are defined analogously, where the diarylamino groups are bonded to the pyrene preferably in the 1 position or 1,6 positions. Further preferred emitting compounds are indenofluoreneamines or -diamines, for example according to WO 2006/108497 or WO 2006/122630, benzoindenofluoreneamines or -diamines, for example according to WO 2008/006449, and dibenzoindenofluoreneamines or -diamines, for example according to WO 2007/140847, and the indenofluorene derivatives having fused aryl groups disclosed in WO 2010/012328. Likewise preferred are the pyrenearylamines disclosed in WO 2012/048780 and in WO 2013/185871. Likewise preferred are the benzoindenofluoreneamines disclosed in WO 2014/037077, the benzofluoreneamines disclosed in WO 2014/106522, the extended benzoindenofluorenes disclosed in WO 2014/111269 and in WO 2017/036574, the phenoxazines disclosed in WO 2017/028940 and WO 2017/028941, and the fluorene derivatives bonded to furan units or to thiophene units that are disclosed in WO 2016/150544.

Useful matrix materials, preferably for fluorescent emitting compounds, include materials of various substance classes. Preferred matrix materials are selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulfoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another. Preference is further given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, the pyrene compounds disclosed in EP 1749809, EP 1905754 and US 2012/0187826, the benzanthracenylanthracene compounds disclosed in WO 2015/158409, the indenobenzofurans disclosed in WO 2017/025165, and the phenanthrylanthracenes disclosed in WO 2017/036573.

Preferred matrix materials for phosphorescent emitting compounds are, as well as the compounds of the formula (I), aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109, WO 2011/000455 or WO 2013/041176, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, or lactams, for example according to WO 2011/116865 or WO 2011/137951.

Suitable charge transport materials as usable in the hole injection or hole transport layer or electron blocker layer or in the electron transport layer of the electronic device of the invention are, as well as the compounds of the formula (I), for example, the compounds disclosed in Y. Shirota et al., Chem. Rev. 2007, 107(4), 953-1010, or other materials as used in these layers according to the prior art.

Preferably, the inventive OLED comprises two or more different hole-transporting layers. The compound of the formula (I) may be used here in one or more of or in all the hole-transporting layers. In a preferred embodiment, the compound of the formula (I) is used in exactly one or exactly two hole-transporting layers, and other compounds, preferably aromatic amine compounds, are used in the further hole-transporting layers present. Further compounds which are used alongside the compounds of the formula (I), preferably in hole-transporting layers of the OLEDs of the invention, are especially indenofluoreneamine derivatives (for example according to WO 06/122630 or WO 06/100896), the amine derivatives disclosed in EP 1661888, hexaazatriphenylene derivatives (for example according to WO 01/049806), amine derivatives with fused aromatics (for example according to U.S. Pat. No. 5,061,569), the amine derivatives disclosed in WO 95/09147, monobenzoindenofluoreneamines (for example according to WO 08/006449), dibenzoindenofluoreneamines (for example according to WO 07/140847), spirobifluoreneamines (for example according to WO 2012/034627 or WO 2013/120577), fluoreneamines (for example according to WO 2014/015937, WO 2014/015938, WO 2014/015935 and WO 2015/082056), spirodibenzopyranamines (for example according to WO 2013/083216), dihydroacridine derivatives (for example according to WO 2012/150001), spirodibenzofurans and spirodibenzothiophenes, for example according to WO 2015/022051, WO 2016/102048 and WO 2016/131521, phenanthrenediarylamines, for example according to WO 2015/131976, spirotribenzotropolones, for example according to WO 2016/087017, spirobifluorenes with meta-phenyldiamine groups, for example according to WO 2016/078738, spirobisacridines, for example according to WO 2015/158411, xanthenediarylamines, for example according to WO 2014/072017, and 9,10-dihydroanthracene spiro compounds with diarylamino groups according to WO 2015/086108.

Materials used for the electron transport layer may be any materials as used according to the prior art as electron transport materials in the electron transport layer. Especially suitable are aluminium complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the above-mentioned compounds as disclosed in JP 2000/053957, WO 2003/060956, WO 2004/028217, WO 2004/080975 and WO 2010/072300.

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, Li$_2$O, BaF$_2$, MgO, NaF, CsF, Cs$_2$CO$_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/NiO$_x$, Al/PtO$_x$) may also be preferred. For some applications, at least one of the electrodes has to be transparent or partly transparent in order to enable the irradiation of the organic material (organic solar cell) or the emission of light (OLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The device is structured appropriately (according to the application), contact-connected and finally sealed, in order to rule out damaging effects by water and air.

In a preferred embodiment, the electronic device is characterized in that one or more layers are coated by a sublimation process. In this case, the materials are applied by vapour deposition in vacuum sublimation systems at an initial pressure of less than 10$^{-5}$ mbar, preferably less than 10$^{-6}$ mbar. In this case, however, it is also possible that the initial pressure is even lower, for example less than 10$^{-7}$ mbar.

Preference is likewise given to an electronic device, characterized in that one or more layers are coated by the OVPD (organic vapour phase deposition) method or with the aid of a carrier gas sublimation. In this case, the materials are applied at a pressure between 10$^{-5}$ mbar and 1 bar. A special case of this method is the OVJP (organic vapour jet printing) method, in which the materials are applied directly by a nozzle and thus structured (for example M. S. Arnold et al., Appl. Phys. Lett. 2008, 92, 053301).

Preference is additionally given to an electronic device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of formula (I) are needed. High solubility can be achieved by suitable substitution of the compounds.

It is further preferable that an electronic device of the invention is produced by applying one or more layers from solution and one or more layers by a sublimation method.

According to the invention, the electronic devices comprising one or more compounds of formula (I) can be used in displays, as light sources in lighting applications and as light sources in medical and/or cosmetic applications (e.g. light therapy).

WORKING EXAMPLES

A) Synthesis Examples

The syntheses which follow, unless stated otherwise, are conducted under a protective gas atmosphere in dried solvents.

a) Biphenyl-4-yl(9,9-dimethyl-9H-fluoren-1-yl) amine (1a)

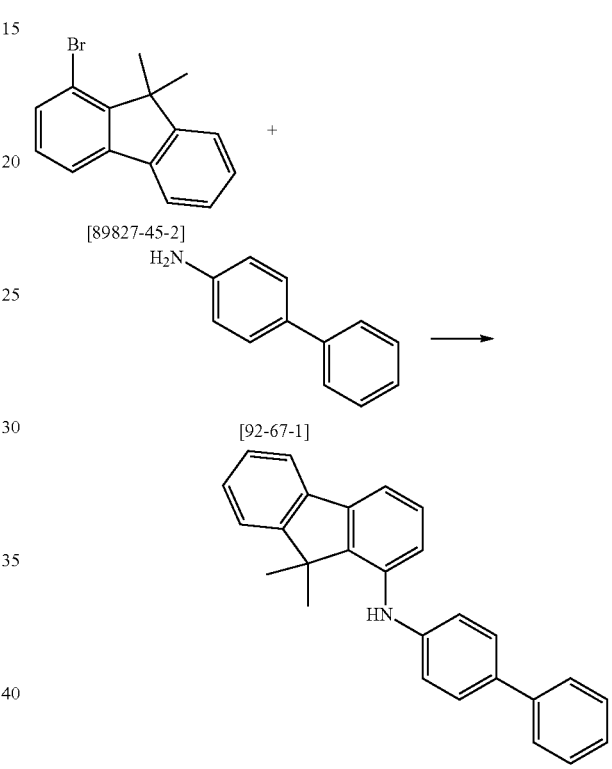

36 g (212 mmol, 1.0 eq) of 4-aminobiphenyl are initially charged together with 57.8 g (177 mmol, 1.0 eq) of 1-bromodimethylfluorene and 2.4 g (212 mmol, 1.20 eq) of sodium t-pentoxide [14593-46-5] in 600 ml of absolute toluene and degassed for 30 minutes. Subsequently, 398 mg (1.77 mmol, 0.01 eq) of palladium(II) acetate [3375-31-3] and 1.46 g (3.56 mmol, 0.02 eq) of 2-dicyclohexylphosphino-2',6'-dimethoxybiphenyl SPHOS [657408-07-6] are added and the mixture is heated under reflux overnight. After the reaction has ended, the mixture is cooled down to room temperature and extracted with 500 ml of water. Subsequently, the aqueous phase is washed three times with toluene, the combined organic phases are dried over sodium sulfate and the solvent is removed on a rotary evaporator. The brown residue is taken up in about 200 ml of toluene and filtered through silica gel. For further purification, a recrystallization from toluene/heptane is conducted.

Yield: 59 g (164 mmol), 79% of theory.

The following are prepared analogously:

| Eintrag | Edukt 1 | Edukt 2 | Produkt 3 | Ausbeute [%] |
|---|---|---|---|---|
| 2a | [92-67-1] | [942615-32-9] | | 65 |
| 3a | [90-41-5] | [942615-32-9] | | 63 |
| 4a | [18998-24-5] | [942615-32-9] | | 60 |
| 5a | [92-67-1] | [1161009-88-6] | | 62 |

-continued

| Eintrag | Edukt 1 | Edukt 2 | Produkt 3 | Ausbeute [%] |
|---|---|---|---|---|
| 6a | [90-41-5] | [171408-76-7] | | 64 |
| 7a | [90-41-5] | [1361305-36-3] | | 68 |
| 8a | [18998-24-8] | [942615-32-9] | | 71 |
| 9a | [18998-24-8] | [320-31-2] | | 72 |

-continued

| Eintrag | Edukt 1 | Edukt 2 | Produkt 3 | Ausbeute [%] |
|---|---|---|---|---|
| 10a | [18998-24-8] | [574750-04-0] | | 83 |
| 11a | [18998-24-8] | [1225053-54-2] | | 64 |
| 12a | [578027-21-1] | [942615-32-9] | | 67 |

-continued
| Eintrag | Edukt 1 | Edukt 2 | Produkt 3 | Ausbeute [%] |
|---|---|---|---|---|
| 13a | 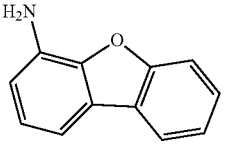 [50548-43-1] | 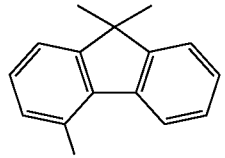 [942615-32-9] | 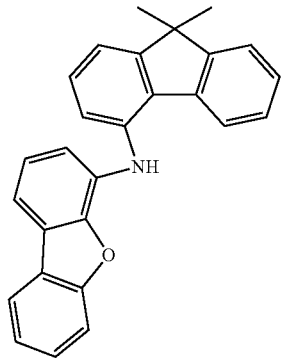 [SMILES: CC1(C)c2ccccc2-c2c(Nc3cccc4c3oc3ccccc34)cccc21] | 56 |
| 14a | 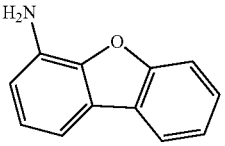 [50548-43-1] | 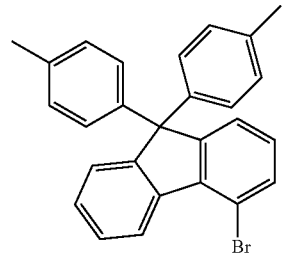 | 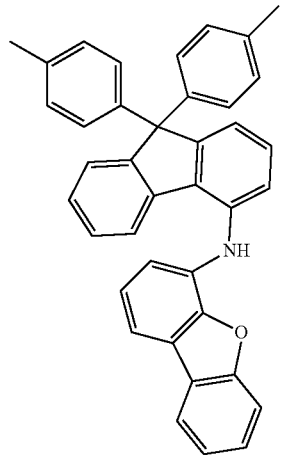 | 75 |
| 15a | 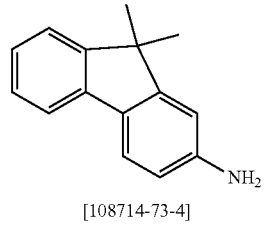 [SMILES: CC1(C)c2ccccc2-c2ccc(N)cc21] [108714-73-4] | 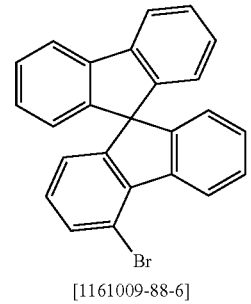 [SMILES: Brc1cccc2c1-c1ccccc1C21c2ccccc2-c2ccccc21] [1161009-88-6] | 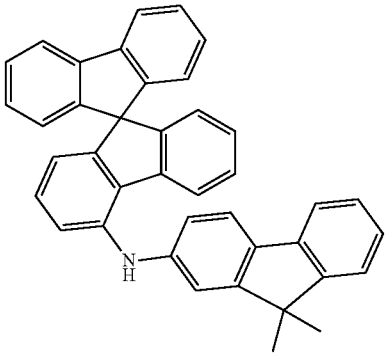 [SMILES: CC1(C)c2ccccc2-c2ccc(Nc3cccc4c3-c3ccccc3C43c4ccccc4-c4ccccc43)cc21] | 85 |
| 16a | 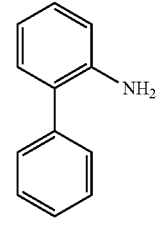 [90-41-5] | 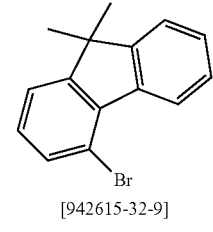 [SMILES: CC1(C)c2ccccc2-c2c(Br)cccc21] [942615-32-9] | 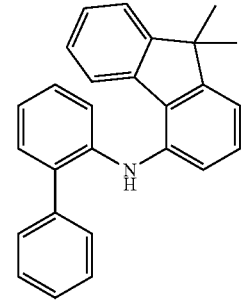 [SMILES: CC1(C)c2ccccc2-c2c(Nc3ccccc3-c3ccccc3)cccc21] | 69 |

-continued
| Eintrag | Edukt 1 | Edukt 2 | Produkt 3 | Ausbeute [%] |
|---|---|---|---|---|
| 17a | 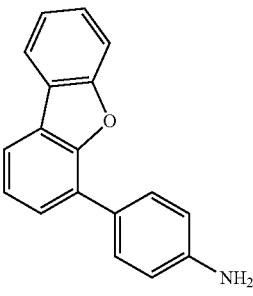 [578027-21-1] | 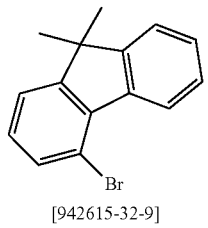 [SMILES: CC1(C)c2ccccc2-c2c(Br)cccc21] [942615-32-9] | 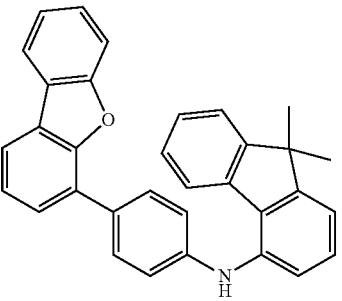 [SMILES: CC1(C)c2ccccc2-c2c(Nc3ccc(-c4cccc5c4oc4ccccc45)cc3)cccc21] | 67 |
| 18a | 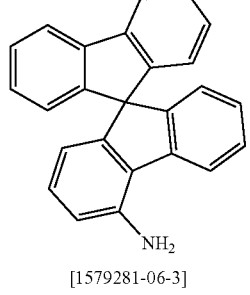 [1579281-06-3] | 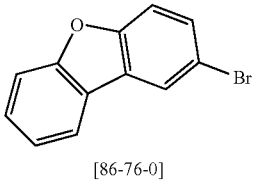 [SMILES: Brc1ccc2oc3ccccc3c2c1] [86-76-0] | 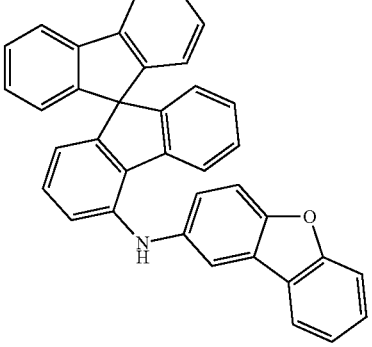 | 88 |
| 19a | 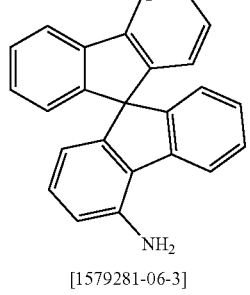 [1579281-06-3] | 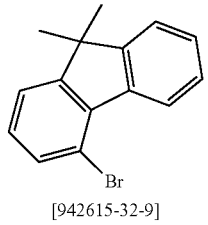 [SMILES: CC1(C)c2ccccc2-c2c(Br)cccc21] [942615-32-9] | 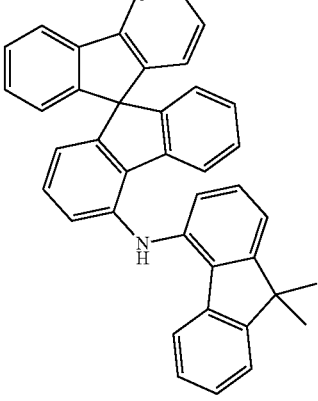 | 81 |
| 20a | 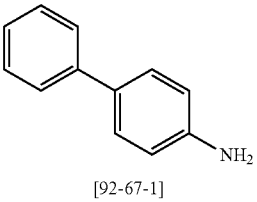 [SMILES: Nc1ccc(-c2ccccc2)cc1] [92-67-1] | 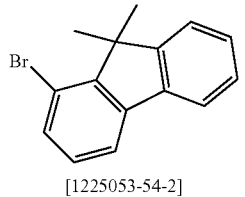 [SMILES: CC1(C)c2ccccc2-c2cccc(Br)c21] [1225053-54-2] | 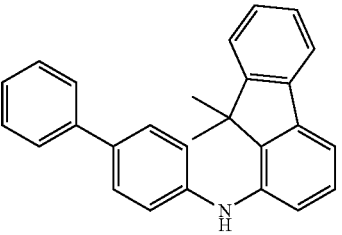 [SMILES: CC1(C)c2ccccc2-c2cccc(Nc3ccc(-c4ccccc4)cc3)c21] | 77 |

| Eintrag | Edukt 1 | Edukt 2 | Produkt 3 | Aus-beute [%] |
|---|---|---|---|---|
| 21a | 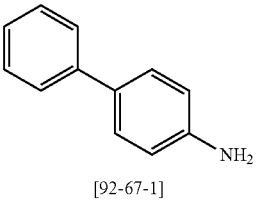 [SMILES: Nc1ccc(-c2ccccc2)cc1] [92-67-1] | 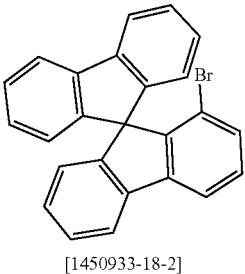 [SMILES: Brc1cccc2c1C1(c3ccccc3-c3ccccc31)c1ccccc1-2] [1450933-18-2] | 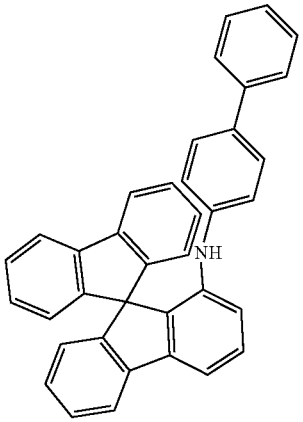 [SMILES: c1ccc(-c2ccc(Nc3cccc4c3C3(c5ccccc5-c5ccccc53)c3ccccc3-4)cc2)cc1] | 70 |
| 22a | 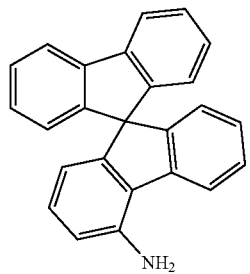 [1579281-06-3] | 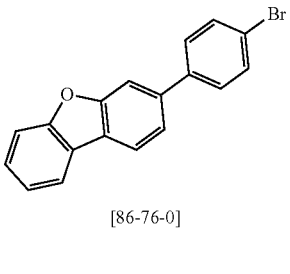 [SMILES: Brc1ccc(-c2ccc3c(c2)oc2ccccc23)cc1] [86-76-0] | 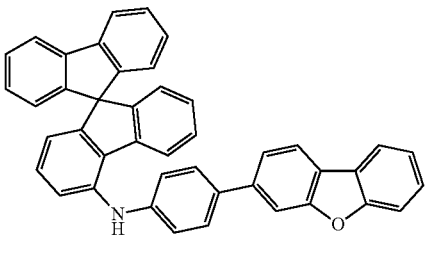 [SMILES: c1ccc2c(c1)-c1ccccc1C21c2ccccc2-c2c(Nc3ccc(-c4ccc5c(c4)oc4ccccc45)cc3)cccc21] | 84 |
| 23a | 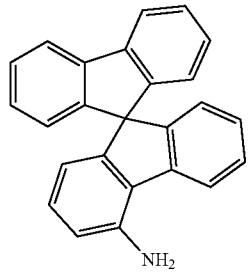 [1579281-06-3] | 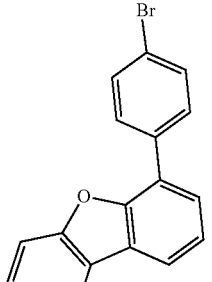 [955959-84-9] | 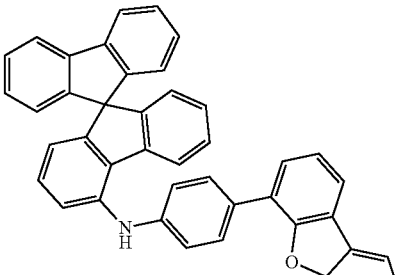 | 91 |
| 24a | 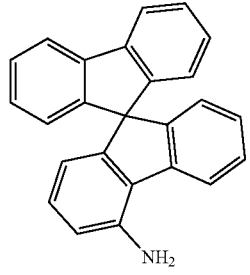 [1579281-06-3] | 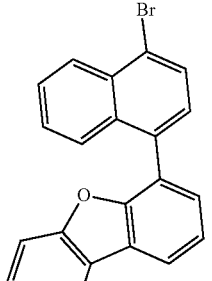 [1297532-85-4] | 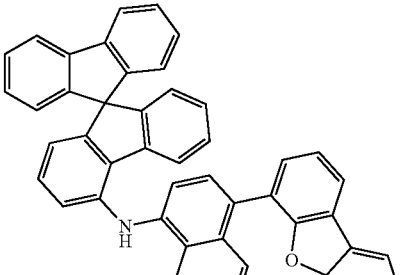 | 74 |

-continued
| Eintrag | Edukt 1 | Edukt 2 | Produkt 3 | Ausbeute [%] |
|---|---|---|---|---|
| 25a | 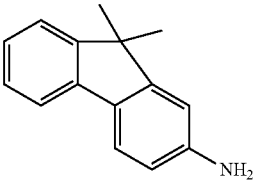 [108714-73-4] | 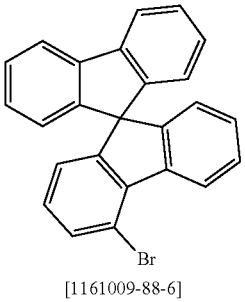 [SMILES: Brc1cccc2c1-c1ccccc1C21c2ccccc2-c2ccccc21] [1161009-88-6] | 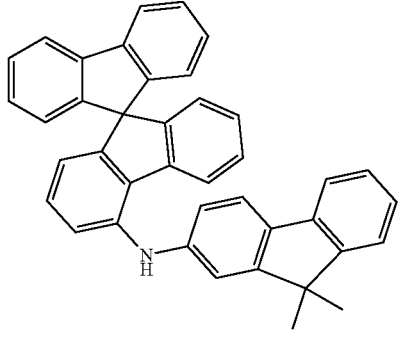 [SMILES: CC1(C)c2ccccc2-c2ccc(Nc3cccc4c3-c3ccccc3C43c4ccccc4-c4ccccc43)cc21] | 85 |
| 26a | 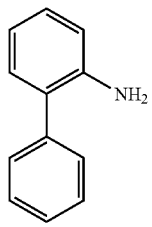 [90-41-5] | 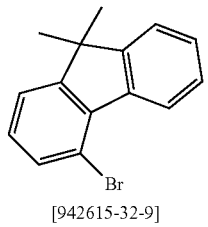 [SMILES: CC1(C)c2ccccc2-c2c(Br)cccc21] [942615-32-9] | 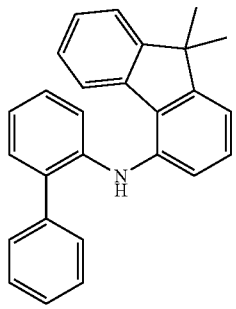 [SMILES: CC1(C)c2ccccc2-c2c(Nc3ccccc3-c3ccccc3)cccc21] | 69 |
| 27a | 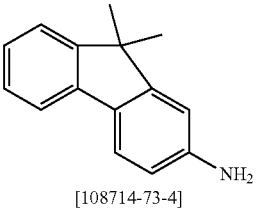 [SMILES: CC1(C)c2ccccc2-c2ccc(N)cc21] [108714-73-4] | 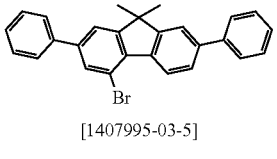 [SMILES: CC1(C)c2cc(-c3ccccc3)ccc2-c2c(Br)cc(-c3ccccc3)cc21] [1407995-03-5] | 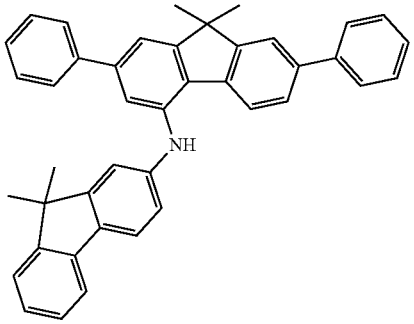 [SMILES: CC1(C)c2ccccc2-c2ccc(Nc3cc(-c4ccccc4)cc4c3-c3ccc(-c5ccccc5)cc3C4(C)C)cc21] | 67 |

-continued

| Eintrag | Edukt 1 | Edukt 2 | Produkt 3 | Ausbeute [%] |
|---|---|---|---|---|
| 28a | [108714-73-4] | [942815-28-3] | | 71 |
| 29a | [92-67-1] | [713125-22-5] | | 70 | b) Biphenyl-4-yl(4-bromophenyl)(9,9-dimethyl-9H-fluoren-4-yl)amine (1b)

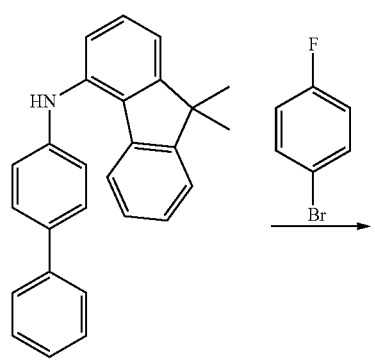

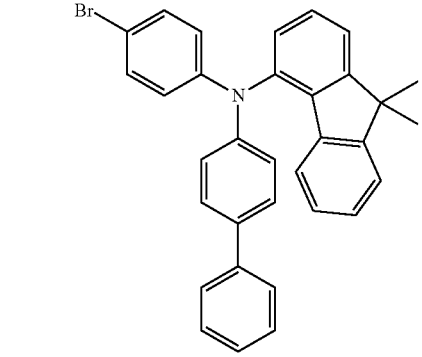

In a 1 l four-neck flask, 51.3 g (142 mmol, 1.00 eq) of biphenyl-4-yl(9,9-dimethyl-9H-fluoren-4-yl)amine and also 75.6 g (426 mmol, 3.00 eq) of 1-bromo-4-fluorobenzene [460-00-4] and 92.5 g (284 mmol, 2.00 eq) of caesium carbonate [534-17-8] are initially charged, and 500 ml of dimethylacetamide are added. The reaction mixture is stirred at 150° C. for three days. After the reaction has ended, the mixture is cooled down to room temperature and the solids are filtered off through Celite. The mother liquor is concentrated and the precipitated solids, after filtration, are extracted by stirring with hot methanol.

Yield: 43 g (135 mmol), 95% of theory.

The following were prepared analogously:
| Eintrag | Edukt 3 | Produkt 5 | Ausbeute [%] |
|---|---|---|---|
| 2b | 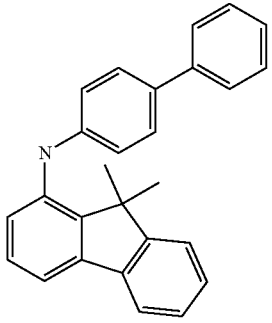 [SMILES: CC1(C)c2ccccc2-c2cccc(Nc3ccc(-c4ccccc4)cc3)c21] | 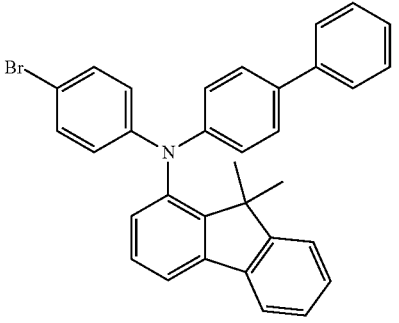 [SMILES: CC1(C)c2ccccc2-c2cccc(N(c3ccc(Br)cc3)c3ccc(-c4ccccc4)cc3)c21] | 78 |
| 3b | 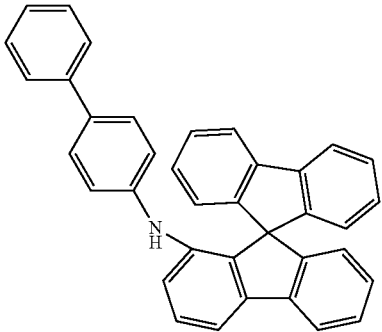 [SMILES: c1ccc(-c2ccc(Nc3cccc4c3C3(c5ccccc5-c5ccccc53)c3ccccc3-4)cc2)cc1] | 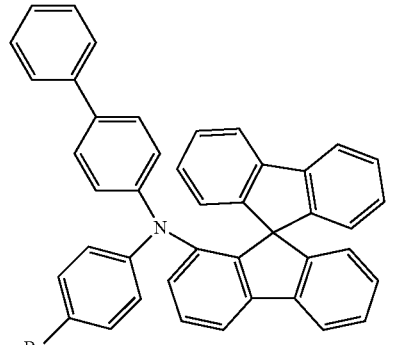 | 26 |
| 4b | 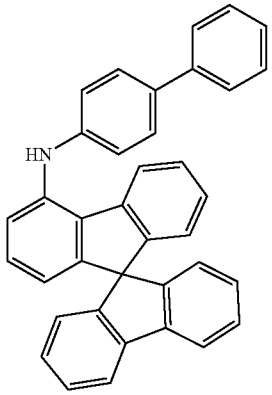 [SMILES: c1ccc(-c2ccc(Nc3cccc4c3-c3ccccc3C43c4ccccc4-c4ccccc43)cc2)cc1] | 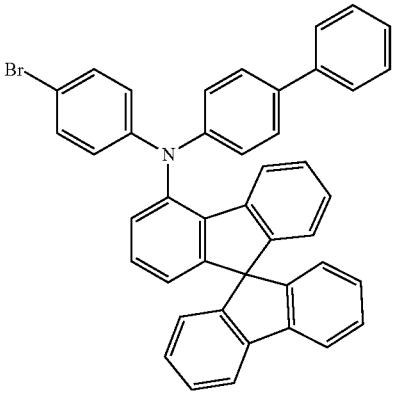 [SMILES: Brc1ccc(N(c2ccc(-c3ccccc3)cc2)c2cccc3c2-c2ccccc2C32c3ccccc3-c3ccccc32)cc1] | 84 |

| Eintrag | Edukt 3 | Produkt 5 | Ausbeute [%] |
|---|---|---|---|
| 5b | 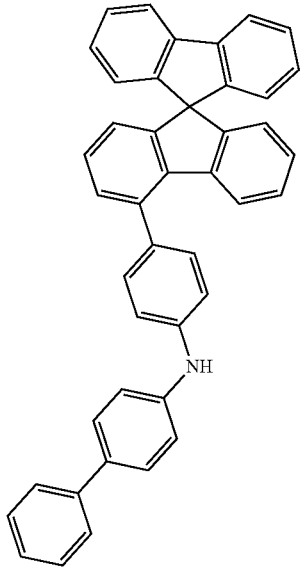 [SMILES: c1ccc(-c2ccc(Nc3ccc(-c4cccc5c4-c4ccccc4C54c5ccccc5-c5ccccc54)cc3)cc2)cc1] | 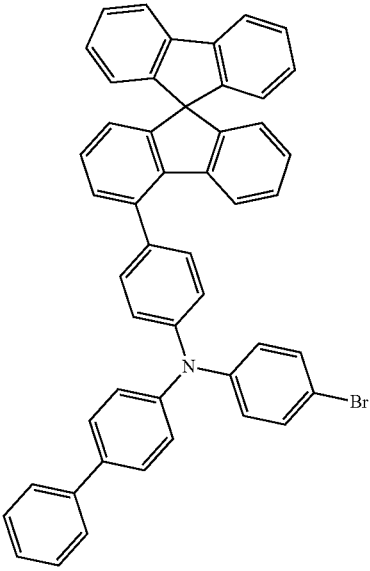 [SMILES: Brc1ccc(N(c2ccc(-c3ccccc3)cc2)c2ccc(-c3cccc4c3-c3ccccc3C43c4ccccc4-c4ccccc43)cc2)cc1] | 68 |
| 6b | 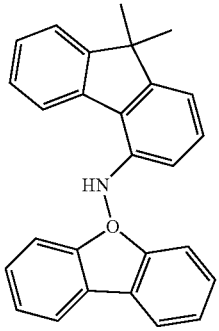 | 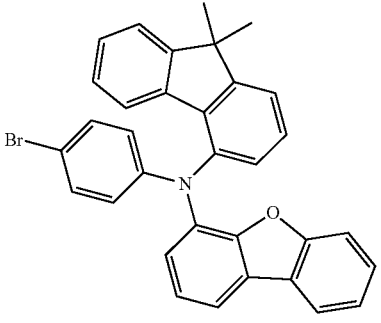 [SMILES: CC1(C)c2ccccc2-c2c(N(c3ccc(Br)cc3)c3cccc4c3oc3ccccc34)cccc21] | 67 |
| 7b | 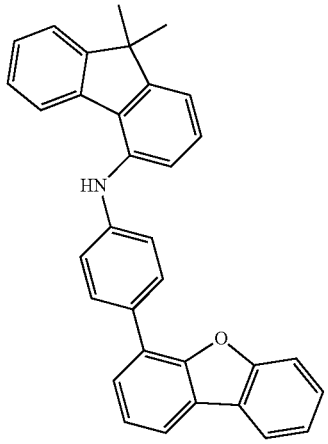 [SMILES: CC1(C)c2ccccc2-c2c(Nc3ccc(-c4cccc5c4oc4ccccc45)cc3)cccc21] | 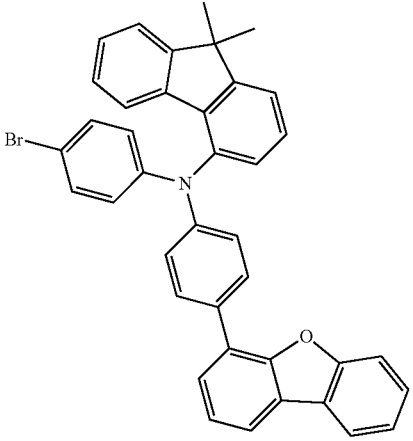 [SMILES: CC1(C)c2ccccc2-c2c(N(c3ccc(Br)cc3)c3ccc(-c4cccc5c4oc4ccccc45)cc3)cccc21] | 44 |

-continued

| Eintrag | Edukt 3 | Produkt 5 | Ausbeute [%] |
|---|---|---|---|
| 8d | | | 59 |
| 9d | | | 65 |
| 10b | | | 67 |
| 11b | | | 71 |

| Eintrag | Edukt 3 | Produkt 5 | Ausbeute [%] |
|---|---|---|---|
| 12b | 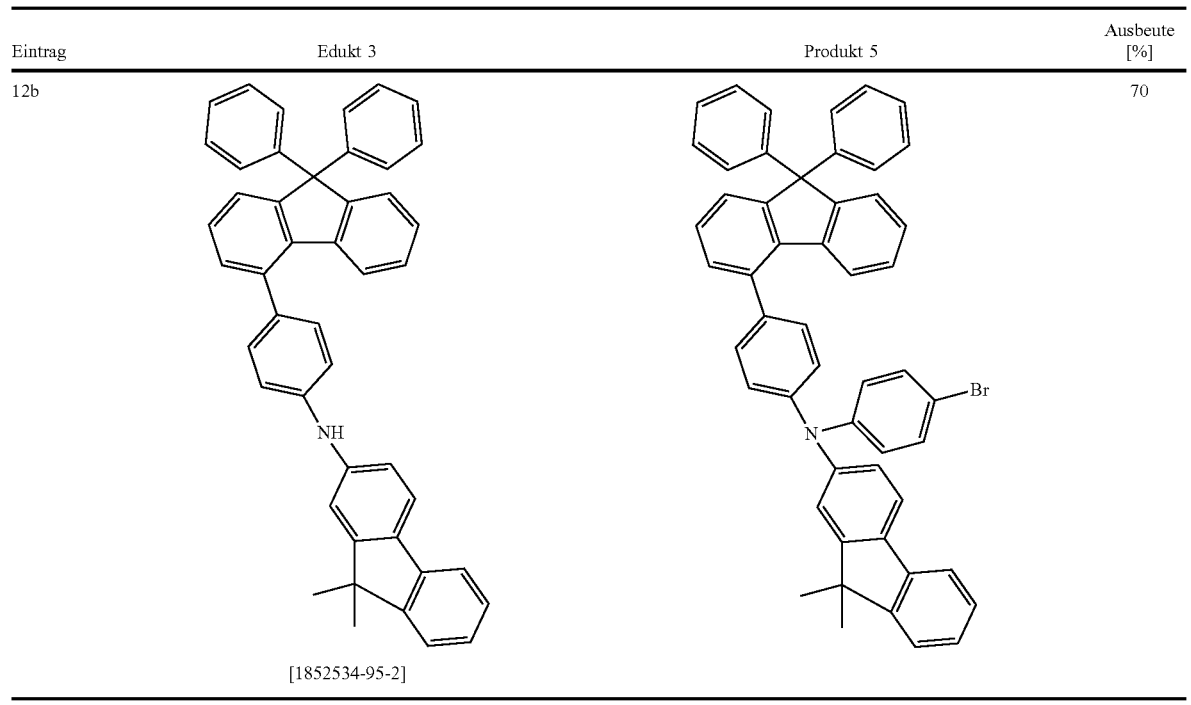 [1852534-95-2] | | 70 | c) Biphenyl-4-yl(9,9-dimethyl-9H-fluoren-1-yl)(4-fluoranthen-3-ylphenyl)amine (1)

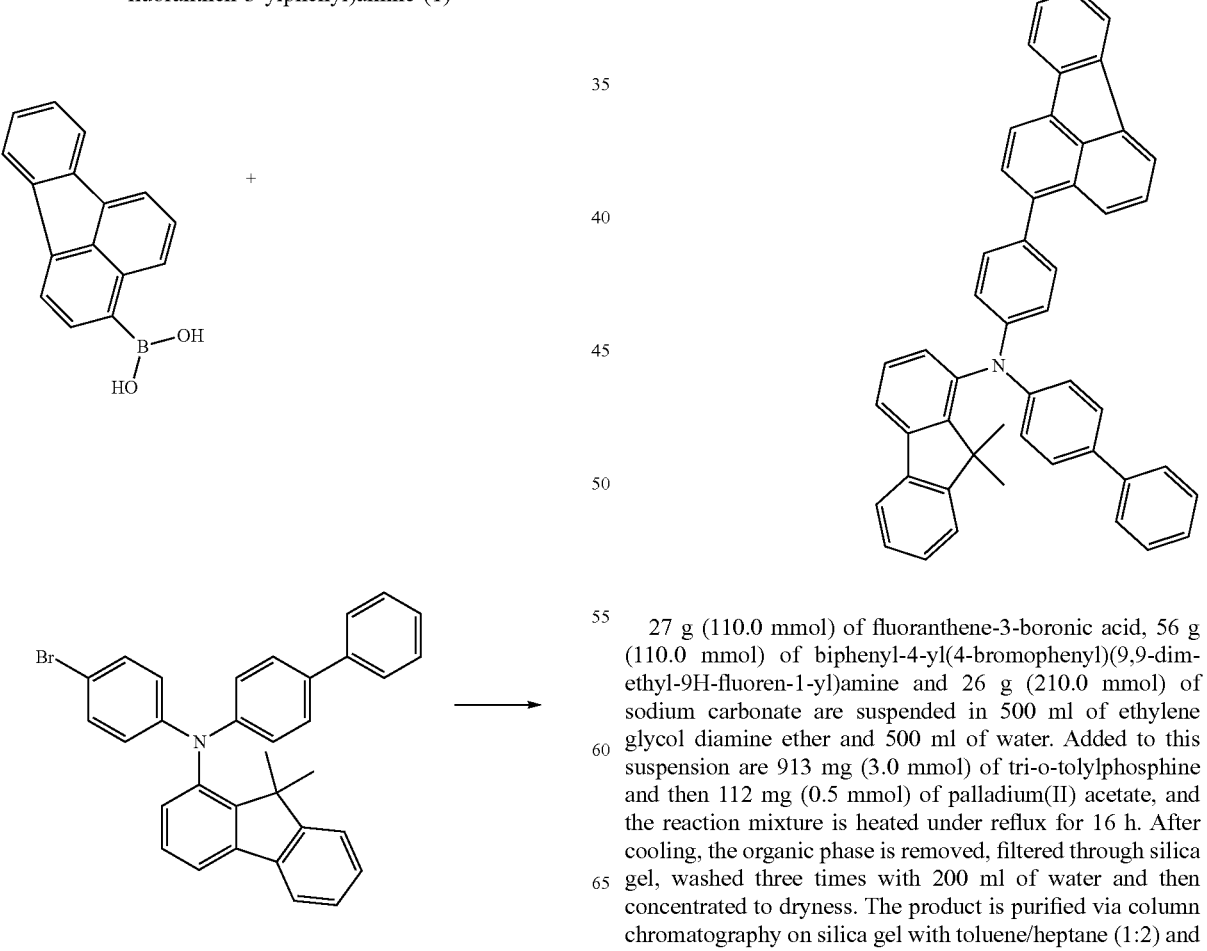

27 g (110.0 mmol) of fluoranthene-3-boronic acid, 56 g (110.0 mmol) of biphenyl-4-yl(4-bromophenyl)(9,9-dimethyl-9H-fluoren-1-yl)amine and 26 g (210.0 mmol) of sodium carbonate are suspended in 500 ml of ethylene glycol diamine ether and 500 ml of water. Added to this suspension are 913 mg (3.0 mmol) of tri-o-tolylphosphine and then 112 mg (0.5 mmol) of palladium(II) acetate, and the reaction mixture is heated under reflux for 16 h. After cooling, the organic phase is removed, filtered through silica gel, washed three times with 200 ml of water and then concentrated to dryness. The product is purified via column chromatography on silica gel with toluene/heptane (1:2) and finally sublimed under high vacuum (p=5×10$^{-7}$ mbar) (99.9% purity). The yield is 56 g (88 mmol), corresponding to 80% of theory.

The following compounds are prepared in an analogous manner:

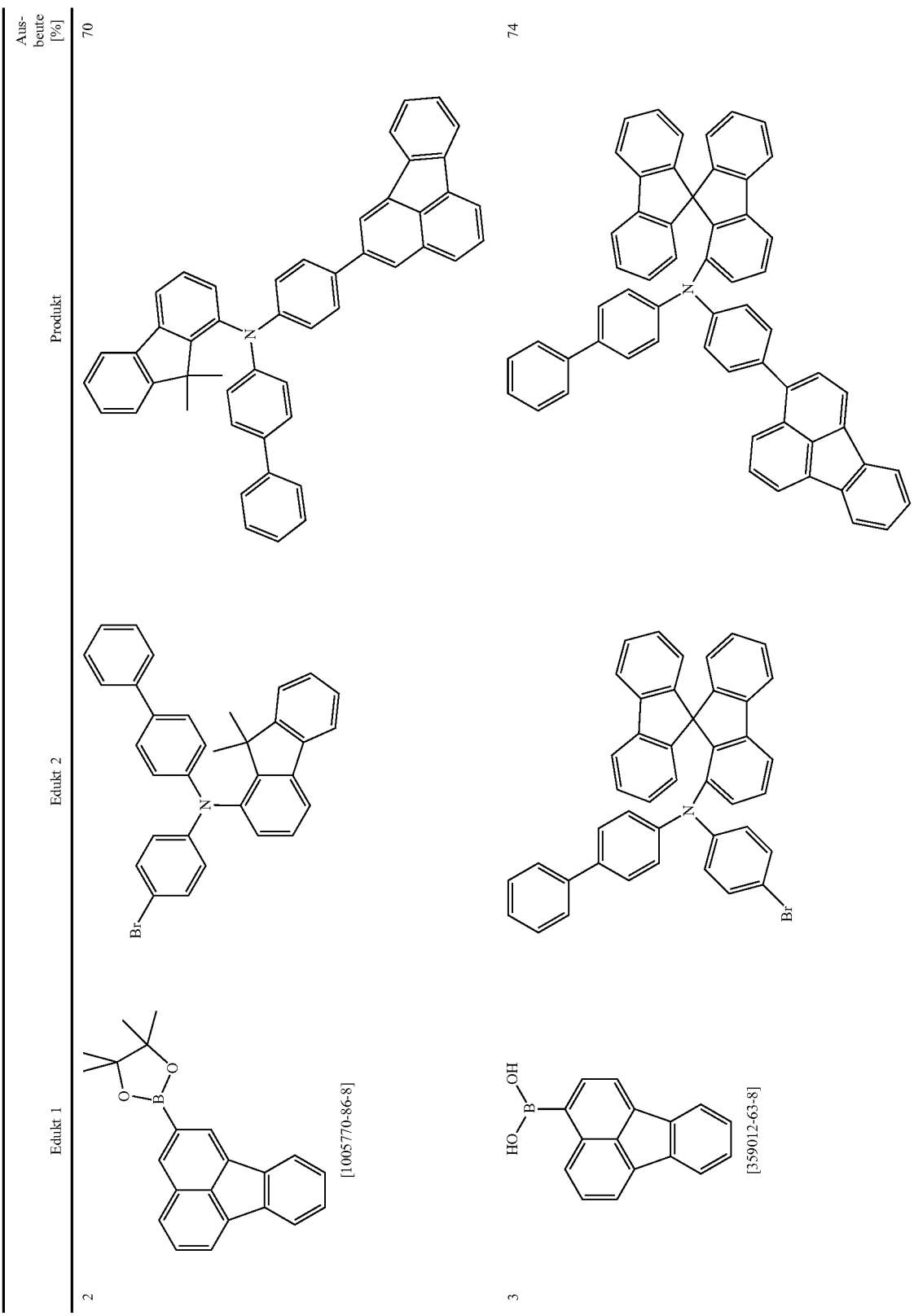

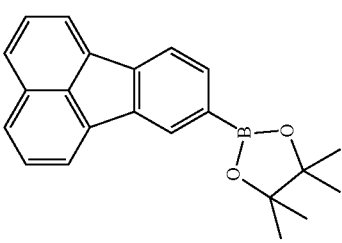

| | Edukt 1 | Edukt 2 | Produkt | Ausbeute [%] |
|---|---|---|---|---|
| 6 | 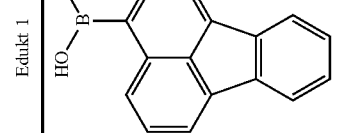 [359012-63-8] | 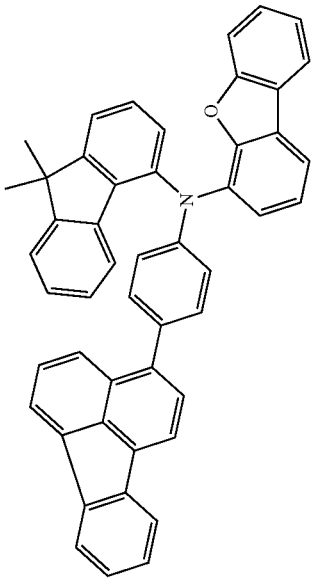 | 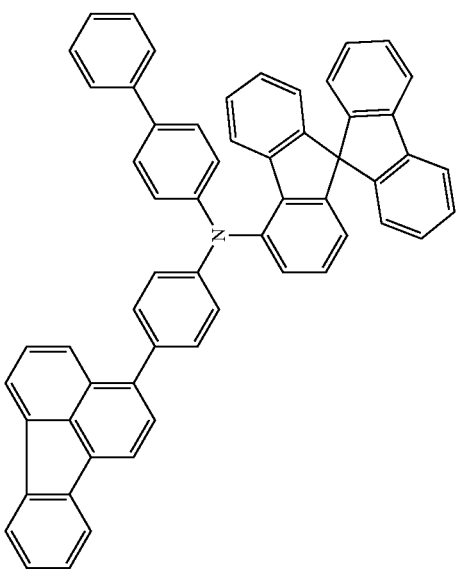 | 71 |
| 7 | 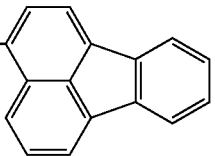 [359012-63-8] | 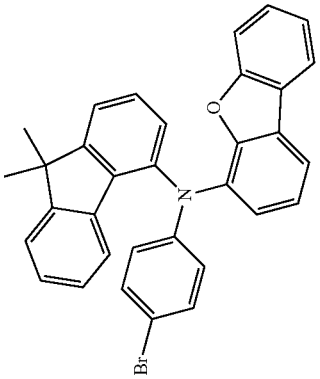 | 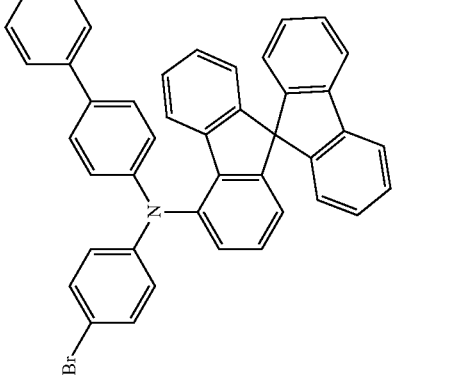 | 64 |

| | Edukt 1 | Edukt 2 | Produkt | Ausbeute [%] |
|---|---|---|---|---|
| 8 | [370084-57-4] | | | 67 |
| 9 | [359012-63-8] | | | 68 |

| Edukt 1 | Edukt 2 | Produkt | Ausbeute [%] |
|---|---|---|---|
| 10 [944418-47-7] | | | 73 |
| 11 [1232029-14-3] | | | 66 |

| | Edukt 1 | Edukt 2 | Produkt | Ausbeute [%] |
|---|---|---|---|---|
| 12 | [1005770-98-8] | | | 70 |
| 13 | [359012-63-8] | | | 72 |

| | Edukt 1 | Edukt 2 | Produkt | Ausbeute [%] |
|---|---|---|---|---|
| 14 | fluoranthene-B(OH)$_2$ [359012-63-8] | bis(di-tert-butylfluorenyl)(4-bromophenyl)amine | corresponding triarylamine product | 76 |
| 15 | fluoranthene-B(OH)$_2$ [359012-63-8] | (9,9-diphenylfluorenyl)(4-biphenyl)(4-bromophenyl)amine | corresponding triarylamine product | 71 |

| | Edukt 1 | Edukt 2 | Produkt | Ausbeute [%] |
|---|---|---|---|---|
| 16 | B(OH)₂-fluoranthene [359012-63-8] | dibenzofuran-Br with N(biphenyl)(dimethylfluorenyl) | coupled product | 75 |
| 17 | B(OH)₂-fluoranthene [359012-63-8] | dibenzothiophene-Br with N(biphenyl)(dimethylfluorenyl) | coupled product | 68 |

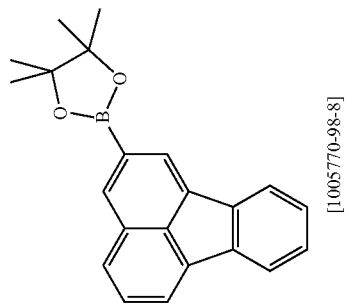

-continued

| | Edukt 1 | Edukt 2 | Produkt | Ausbeute [%] |
|---|---|---|---|---|
| 20 | fluoranthene-B(OH)₂ [359012-63-8] | Br-dibenzofuran-N(biphenyl)(9,9-dimethylfluorenyl) | fluoranthene-dibenzofuran-N(biphenyl)(9,9-dimethylfluorenyl) | 69 |
| 21 | fluoranthene-Bpin [944418-47-7] | Cl-dibenzofuran-N(biphenyl)(9,9-dimethylfluorenyl) 37f | fluoranthene-dibenzofuran-N(biphenyl)(9,9-dimethylfluorenyl) | 68 |

| Edukt 1 | Edukt 2 | Produkt | Ausbeute [%] |
|---|---|---|---|
| 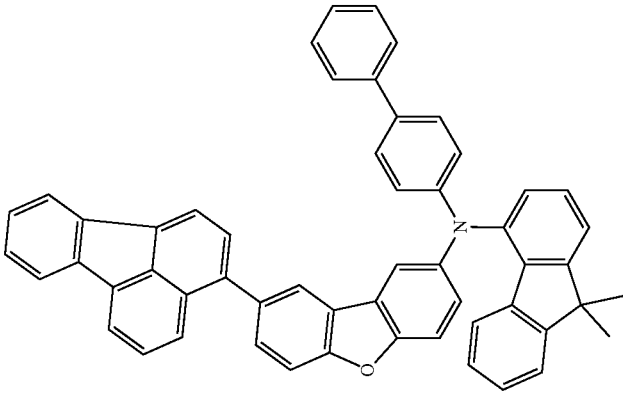 [359012-63-8] | 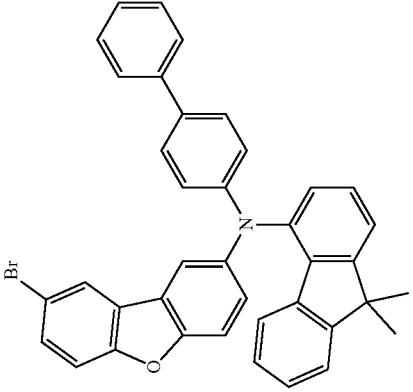 | | 60 |
| 22 | | | |

| | Edukt 1 | Edukt 2 | Produkt | Ausbeute [%] |
|---|---|---|---|---|
| 23 | 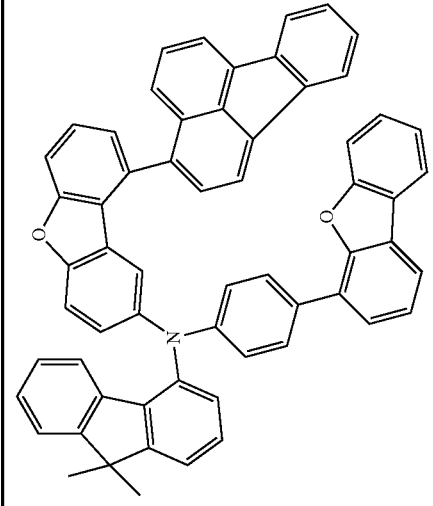 [359012-63-8] | 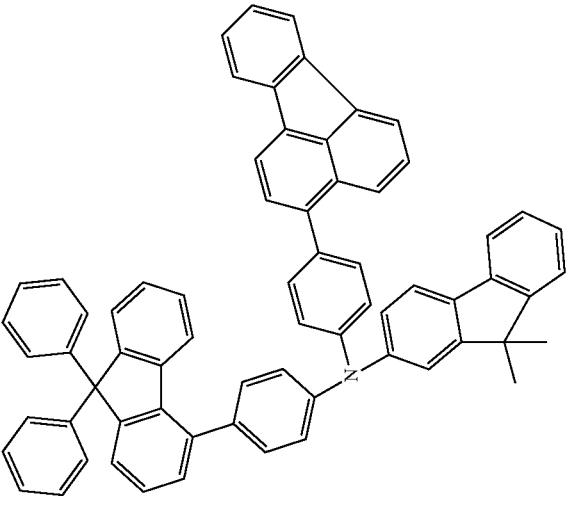 | 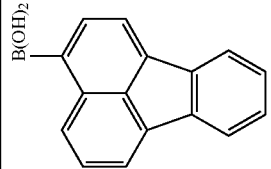 | 65 |
| 24 | 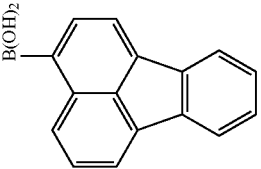 [359012-63-8] | | | 67 |

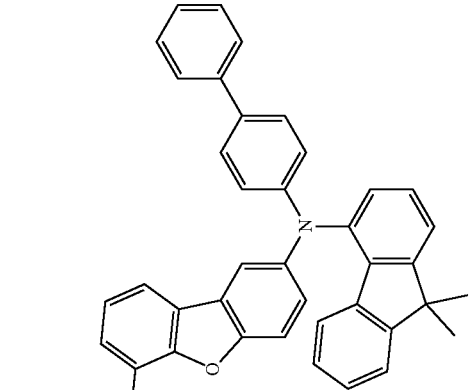

d) 3-(4-Chlorophenyl)fluoranthene (1d)

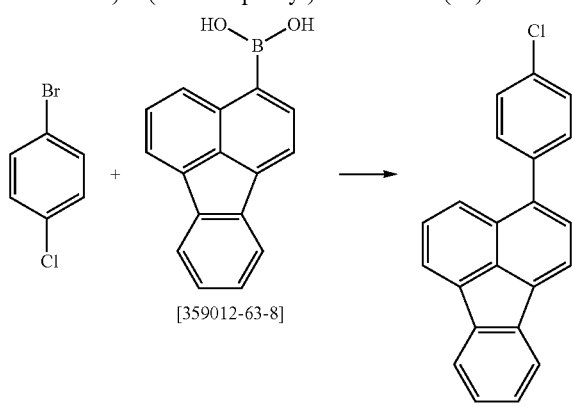

[359012-63-8]

30 g (156 mmol) of 1-bromo-4-chlorobenzene, 37 g (150 mmol) of fluoranthenyl-3-boronic acid and 36 g (340 mmol) of sodium carbonate are suspended in 1000 ml of ethylene glycol diamine ether and 280 ml of water. 1.8 g (1.5 mmol) of tetrakis(triphenylphosphine)palladium(0) are added to this suspension, and the reaction mixture is heated under reflux for 16 h. After cooling, the organic phase is removed, filtered through silica gel, washed three times with 200 ml of water and then concentrated to dryness. The yield is 30 g (97 mmol), corresponding to 65% of theory. The following compounds are prepared in an analogous manner:

| | Edukt 1 | Edukt 2 | Produkt | Ausbeutein % |
|---|---|---|---|---|
| 2d | 4-bromochlorobenzene | acenaphthylene-Bpin [1005770-98-8] | fluoranthene-4-chlorophenyl | 70 |
| 3d | 3-bromochlorobenzene | acenaphthylene-Bpin [1005770-98-8] | fluoranthene-3-chlorophenyl | 71 |
| 4d | 3-bromochlorobenzene | fluoranthenyl-3-boronic acid [359012-63-8] | 3-(3-chlorophenyl)fluoranthene | 74 |

-continued
| | Edukt 1 | Edukt 2 | Produkt | Ausbeutein % |
|---|---|---|---|---|
| 5d | 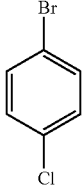 | 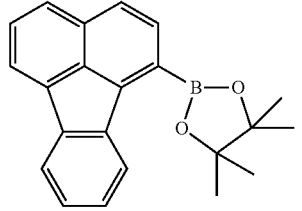<br>[1005770-97-7] | 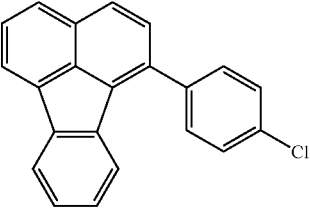 [SMILES: Clc1ccc(-c2ccc3cccc4c3c2-c2ccccc2-4)cc1] | 77 |
| 6d | 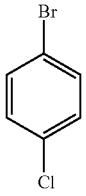 | 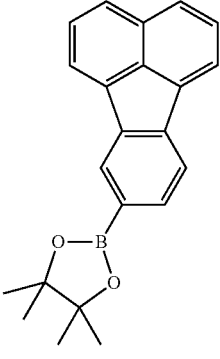<br>[944418-47-7] | 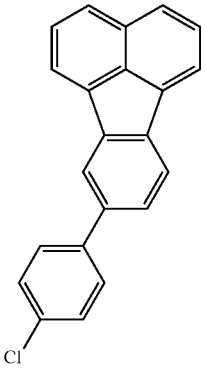 [SMILES: Clc1ccc(-c2ccc3c(c2)-c2cccc4cccc-3c24)cc1] | 73 |
| 7d | 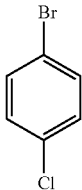 | 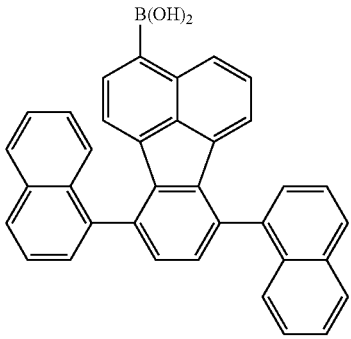<br>[370084-57-4] | 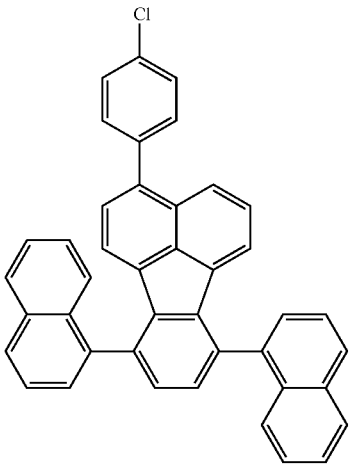 [SMILES: Clc1ccc(-c2ccc3c4c(cccc24)-c2c(-c4cccc5ccccc45)ccc(-c4cccc5ccccc45)c2-3)cc1] | 61 |

| Edukt 1 | Edukt 2 | Produkt | Ausbeutein % |
|---|---|---|---|
| 8d [844856-42-4] | [359012-63-8] | | 62 |
| 9d [844856-42-4] | [944418-47-7] | | 72 |
e) 3-(4-Chlorophenyl)-7,10-diphenylfluoranthene (1e)
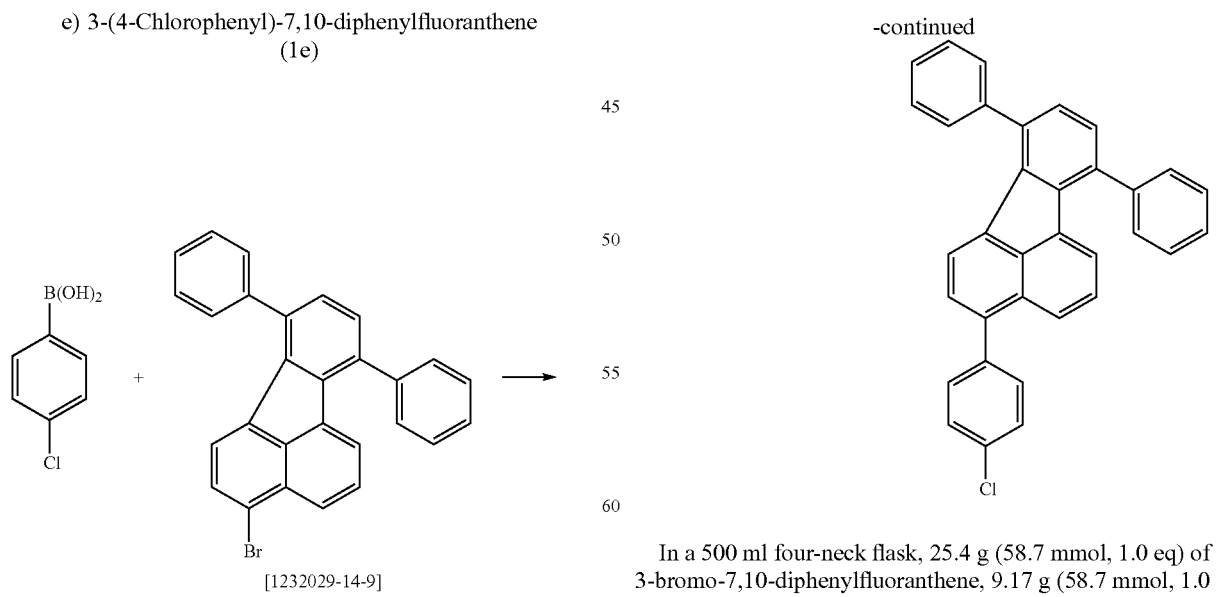
In a 500 ml four-neck flask, 25.4 g (58.7 mmol, 1.0 eq) of 3-bromo-7,10-diphenylfluoranthene, 9.17 g (58.7 mmol, 1.0 eq) of 4-chlorophenylboronic acid (CAS 1679-18-1) and 6.22 g (58.7 mmol, 1.0 eq) of sodium carbonate are dissolved in 150 ml of toluene, 36 ml of ethanol and 77 ml of water. After degassing by means of a nitrogen stream for 30 minutes, 678 mg (0.587 mmol, 0.01 eq) of tetrakis(triphenylphosphine)palladium are added and the mixture is heated at reflux overnight. After the reaction has ended, the phases are separated, the aqueous phase is extracted three times with toluene and the combined organic phases are then washed with water. The organic phases are dried over sodium sulfate and the solution is concentrated on a rotary evaporator. The residue is introduced into 250 ml of ethanol and the solids formed are filtered off with suction.

The yield is 25.6 g (55 mmol), corresponding to 94% of theory.

The following are prepared analogously:

| Verbindung | Edukt 1 | Edukt 2 | Produkt | Ausbeute [%] |
|---|---|---|---|---|
| 1e | 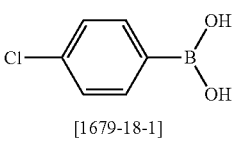 [1554148-65-0] | 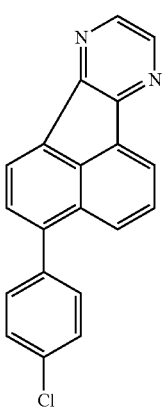 [SMILES: Clc1ccc(-c2ccc3c4c(cccc24)-c2nccnc2-3)cc1] [1679-18-1] | 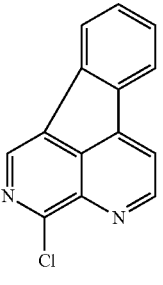 | 91 |
| 2e | 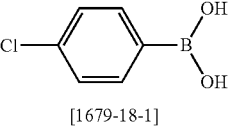 [1195682-94-0] | 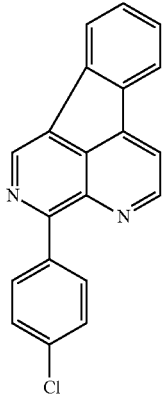 [SMILES: Clc1ccc(-c2ncc3c4c(ccnc24)-c2ccccc2-3)cc1] [1679-18-1] | 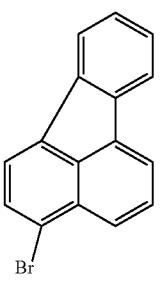 | 32 |
| 3e | 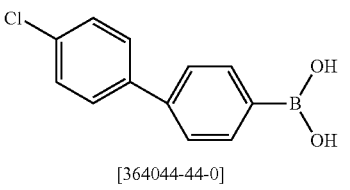 [SMILES: OB(O)c1ccc(-c2ccc(Cl)cc2)cc1] [13438-50-1] | 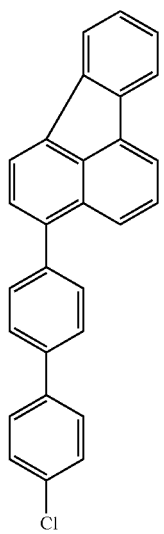 [364044-44-0] |  | 88 |

-continued
| Verbin-dung | Edukt 1 | Edukt 2 | Produkt | Ausbeute [%] |
|---|---|---|---|---|
| 4e | 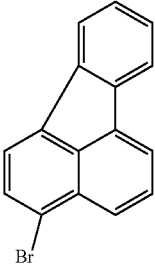 [13438-50-1] | 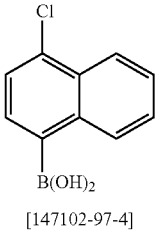 [147102-97-4] | 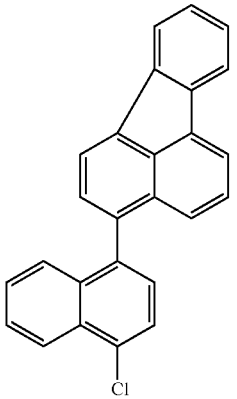 [SMILES: Clc1ccc(-c2ccc3c4c(cccc24)-c2ccccc2-3)c2ccccc12] | 91 |
| 5e | 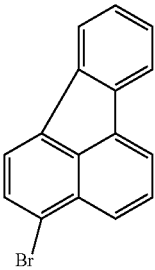 [13438-50-1] | 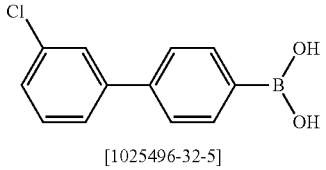 [1025496-32-5] | 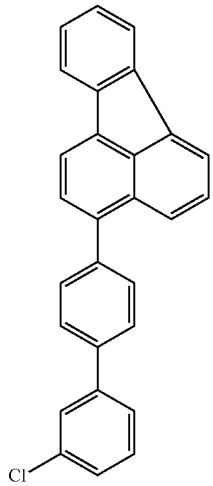 [SMILES: Clc1cccc(-c2ccc(-c3ccc4c5c(cccc35)-c3ccccc3-4)cc2)c1] | 97 |
| 6e | 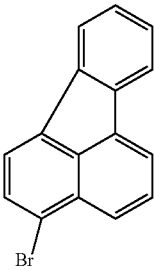 [13438-50-1] | 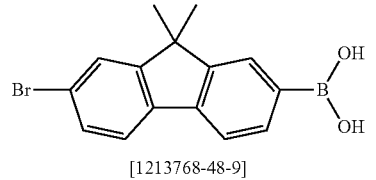 [SMILES: CC1(C)c2cc(Br)ccc2-c2ccc(B(O)O)cc21] [1213768-48-9] | 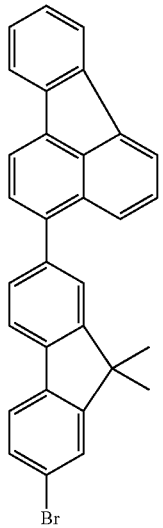 [SMILES: CC1(C)c2cc(Br)ccc2-c2ccc(-c3ccc4c5c(cccc35)-c3ccccc3-4)cc21] | 23 |

-continued

| Verbindung | Edukt 1 | Edukt 2 | Produkt | Ausbeute [%] |
|---|---|---|---|---|
| 7e | 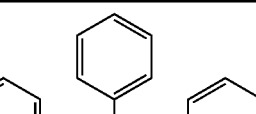 [96765-93-4] | 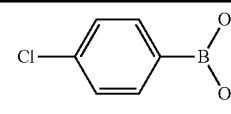 [1679-18-1] | 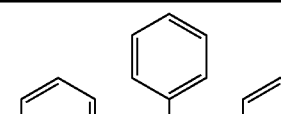 | 86 | f) Biphenyl-4-yl(9,9-dimethyl-9H-fluoren-4-yl)(4-fluoranthen-3-ylphenyl)amine (26)

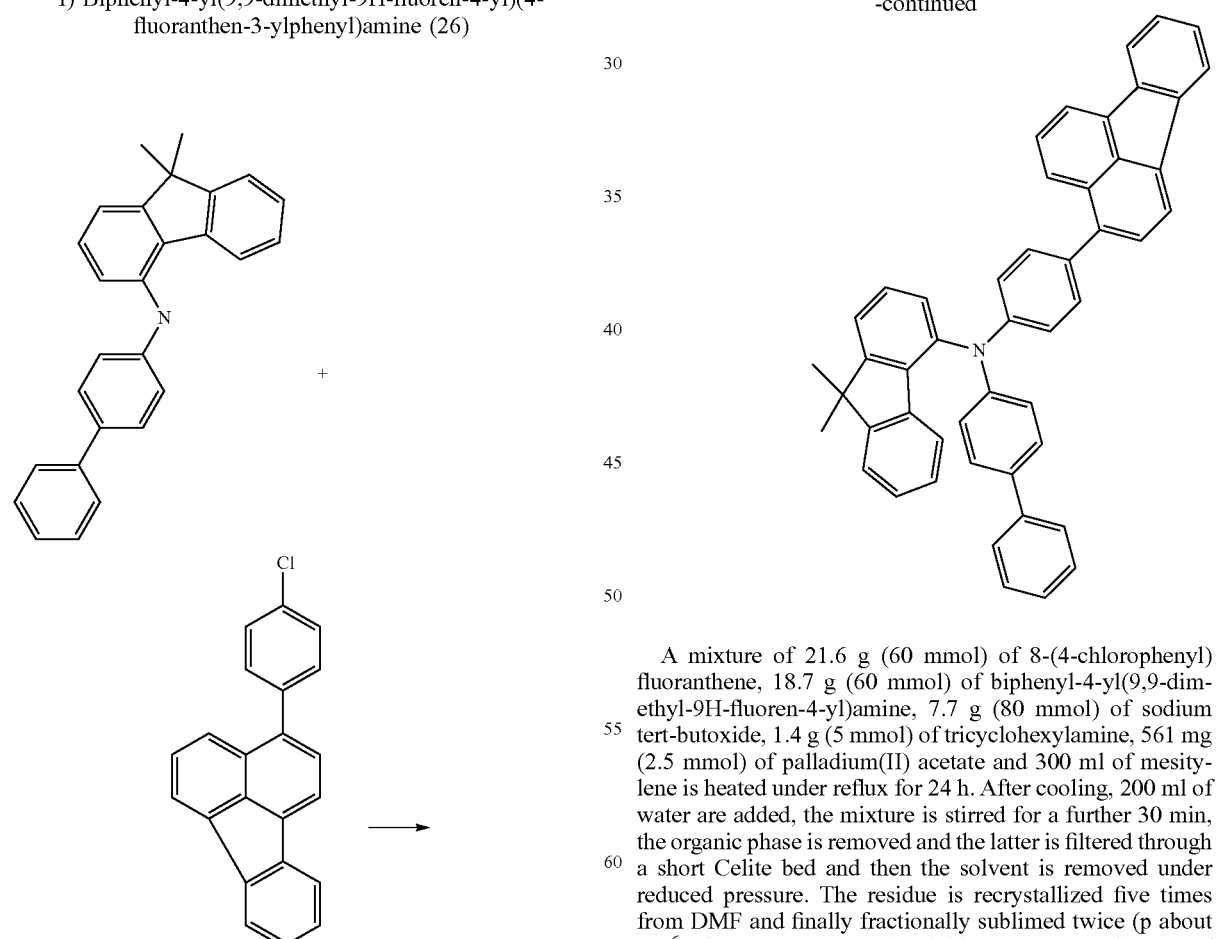

A mixture of 21.6 g (60 mmol) of 8-(4-chlorophenyl)fluoranthene, 18.7 g (60 mmol) of biphenyl-4-yl(9,9-dimethyl-9H-fluoren-4-yl)amine, 7.7 g (80 mmol) of sodium tert-butoxide, 1.4 g (5 mmol) of tricyclohexylamine, 561 mg (2.5 mmol) of palladium(II) acetate and 300 ml of mesitylene is heated under reflux for 24 h. After cooling, 200 ml of water are added, the mixture is stirred for a further 30 min, the organic phase is removed and the latter is filtered through a short Celite bed and then the solvent is removed under reduced pressure. The residue is recrystallized five times from DMF and finally fractionally sublimed twice (p about $10^{-6}$ mbar, T=360-390° C.). Yield: 27 g (42 mmol), 71% of theory: 99.9% by HPLC.

In an analogous manner, the following compounds are obtained:

| Bsp. | Edukt 1 | Edukt 2 | Produkt | Ausbeute [%] |
|---|---|---|---|---|
| 27 | 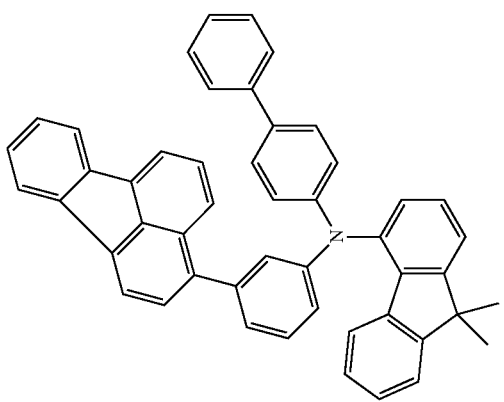 | 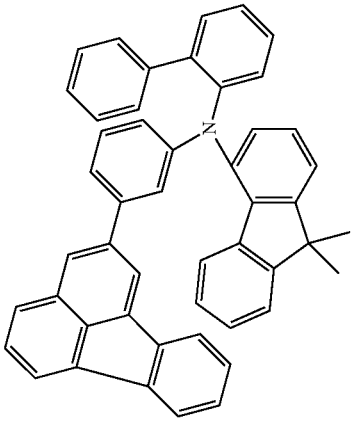 | 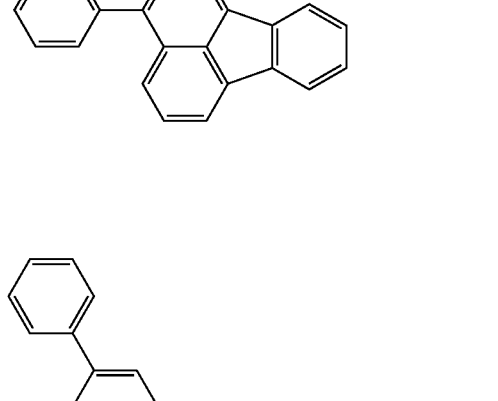 | 68 |
| 28 | 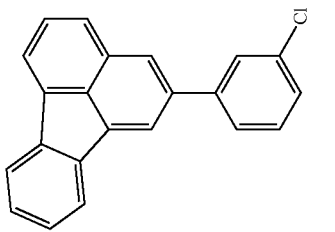 | 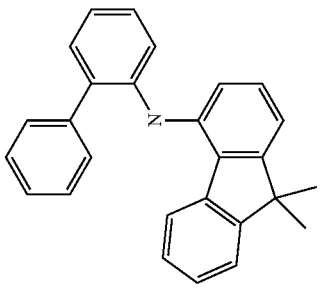 | 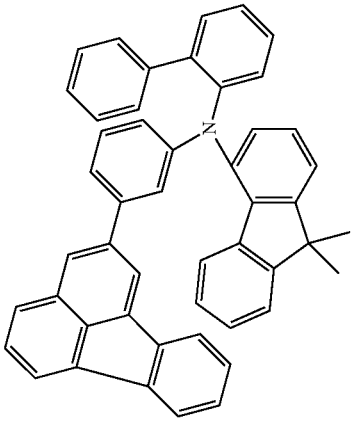 | 72 |

| Bsp. | Edukt 1 | Edukt 2 | Produkt | Ausbeute [%] |
|---|---|---|---|---|
| 29 | | | | 70 |
| 30 | | | | 69 |

| Bsp. | Edukt 1 | Edukt 2 | Produkt | Ausbeute [%] |
|---|---|---|---|---|
| 31 | | | | 74 |
| 32 | | | | 75 |

-continued
| Bsp. | Edukt 1 | Edukt 2 | Produkt | Ausbeute [%] |
|---|---|---|---|---|
| 33 | 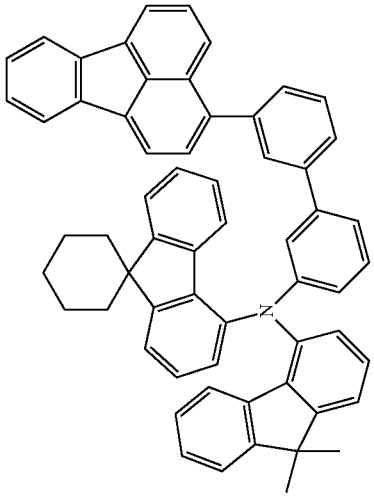 | 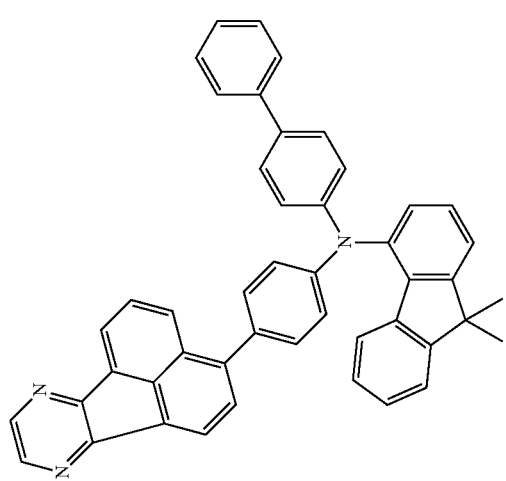 | 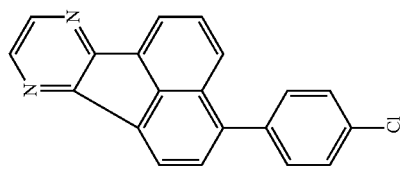 | 72 |
| 34 | 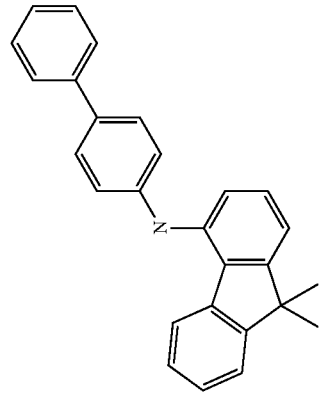 | | | 70 |

| Bsp. | Edukt 1 | Edukt 2 | Produkt | Ausbeute [%] |
|---|---|---|---|---|
| 35 | 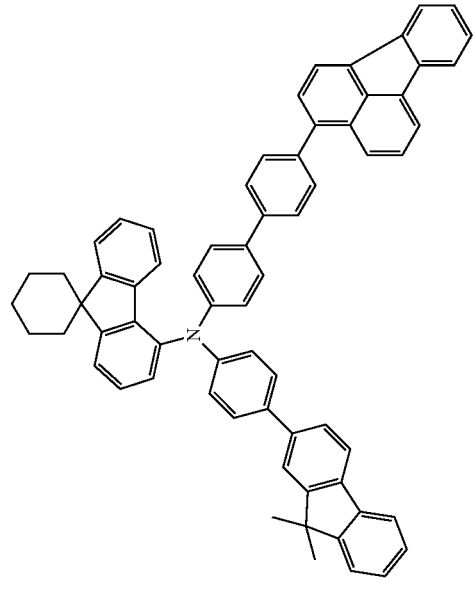 | 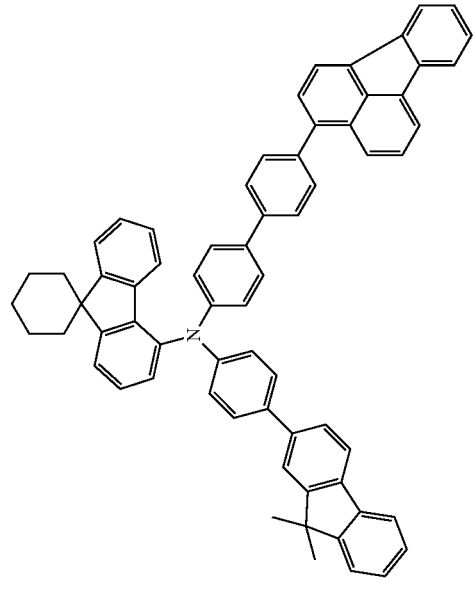 | 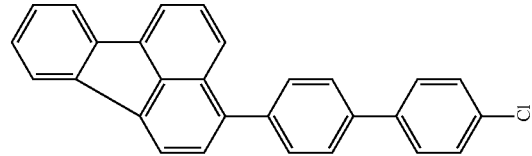 | 75 |

| Bsp. | Edukt 1 | Edukt 2 | Produkt | Ausbeute [%] |
|---|---|---|---|---|
| 36 | 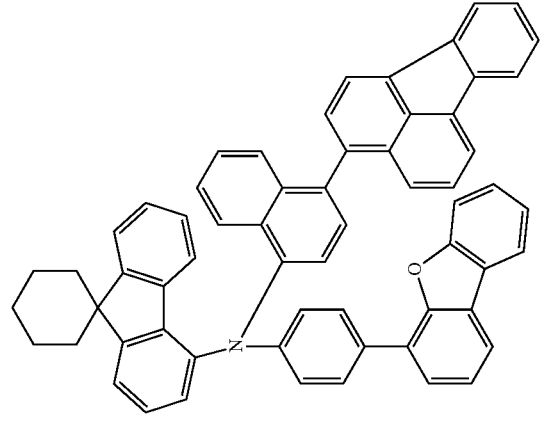 | 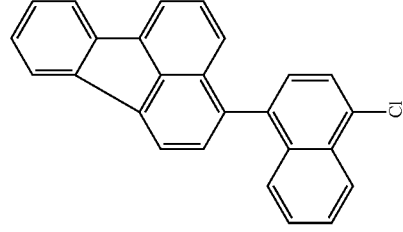 | 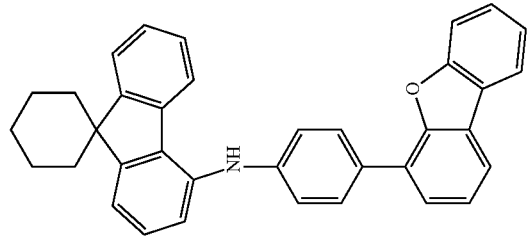 | 63 |

| Bsp. | Edukt 1 | Edukt 2 | Produkt | Ausbeute [%] |
|---|---|---|---|---|
| 37 | 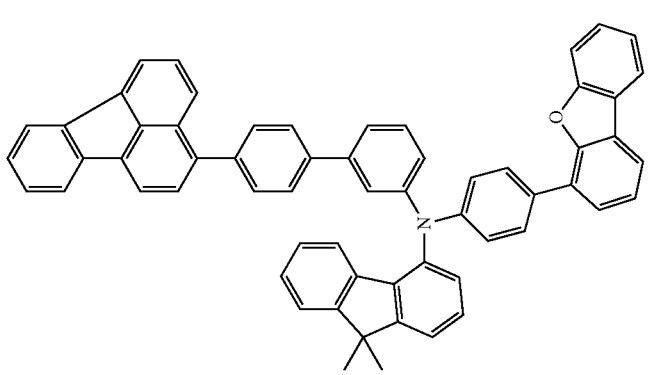 | 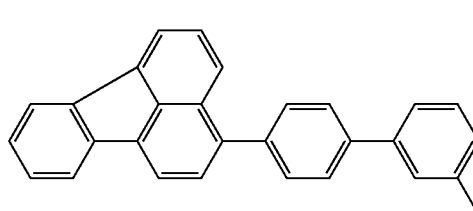 | 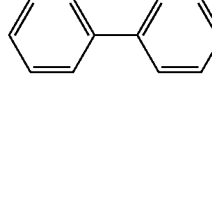 | 73 |

-continued

| Bsp. | Edukt 1 | Edukt 2 | Produkt | Ausbeute [%] |
|---|---|---|---|---|
| 38 | | | | 72 |
| 39 | | | | 77 |

| Bsp. | Edukt 1 | Edukt 2 | Produkt | Ausbeute [%] |
|---|---|---|---|---|
| 40 | 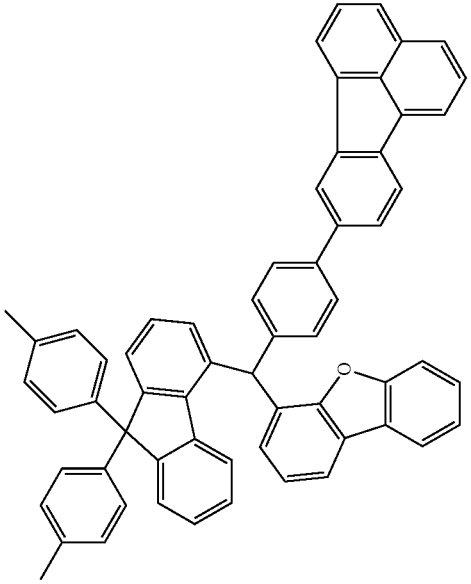 | 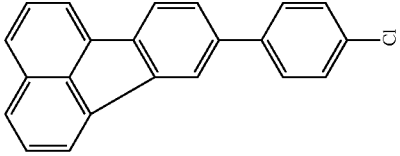 | 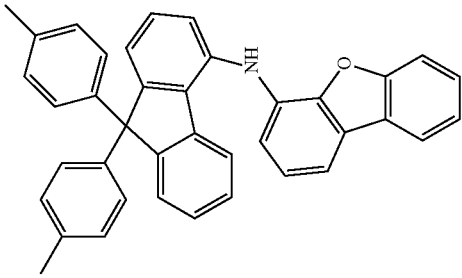 | 72 |

| Bsp. | Edukt 1 | Edukt 2 | Produkt | Ausbeute [%] |
|---|---|---|---|---|
| 41 | 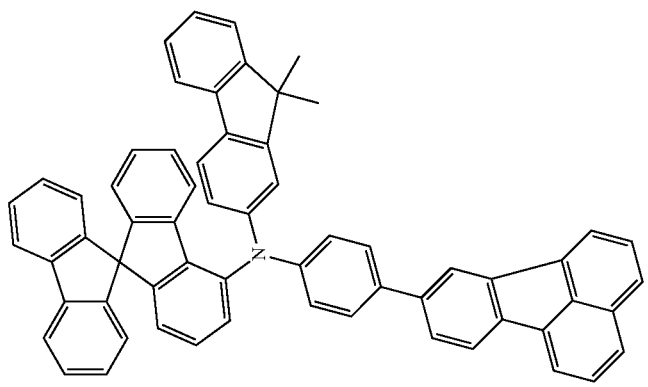 | 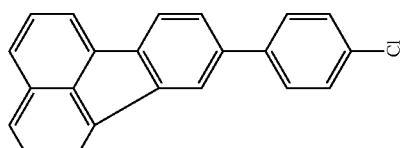 | 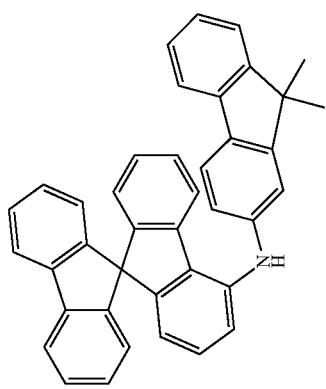 | 63 |

| Bsp. | Edukt 1 | Edukt 2 | Produkt | Ausbeute [%] |
|---|---|---|---|---|
| 42 | 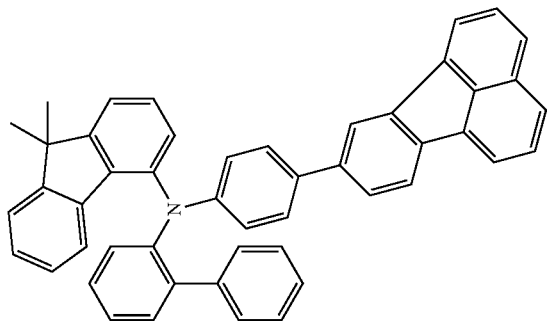 | 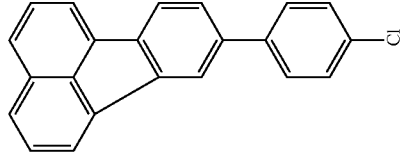 | 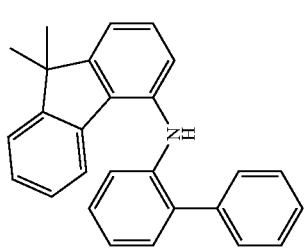 | 67 |

-continued
| Bsp. | Edukt 1 | Edukt 2 | Produkt | Ausbeute [%] |
|---|---|---|---|---|
| 43 | 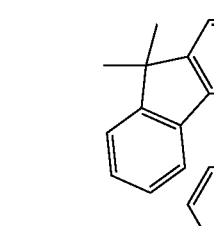 | 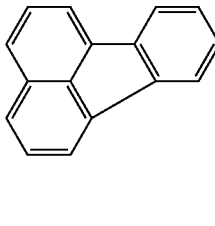 | 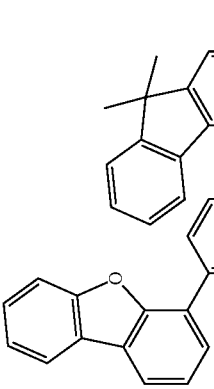 | 60 |

| Bsp. | Edukt 1 | Edukt 2 | Produkt | Ausbeute [%] |
|---|---|---|---|---|
| 44 | | | | 65 |

| Bsp. | Edukt 1 | Edukt 2 | Produkt | Ausbeute [%] |
|---|---|---|---|---|
| 45 | | | | 73 |

| Bsp. | Edukt 1 | Edukt 2 | Produkt | Ausbeute [%] |
|---|---|---|---|---|
| 46 | | | 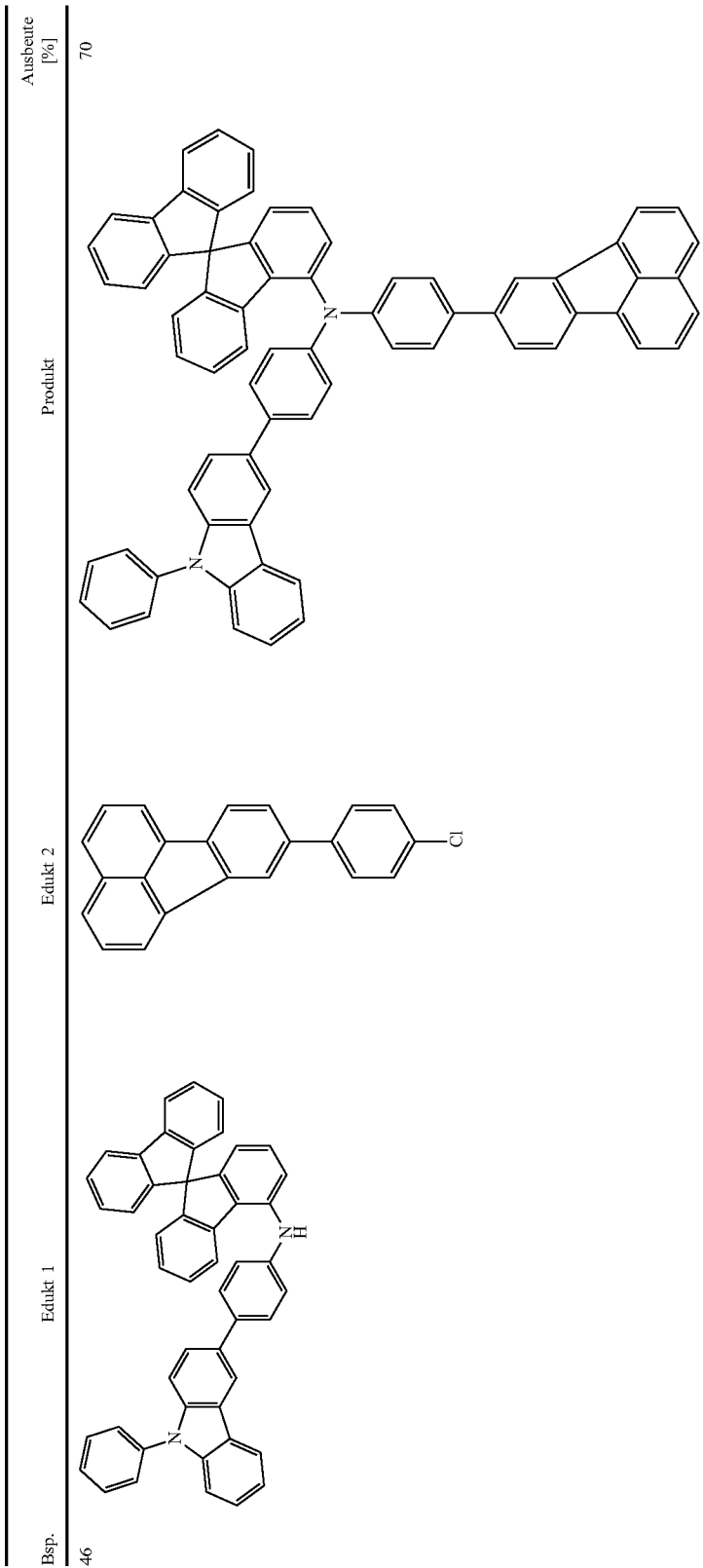 | 70 |

| Bsp. | Edukt 1 | Edukt 2 | Produkt | Ausbeute [%] |
|---|---|---|---|---|
| 47 | | | | 69 |

| Bsp. | Edukt 1 | Edukt 2 | Produkt | Ausbeute [%] |
|---|---|---|---|---|
| 48 | 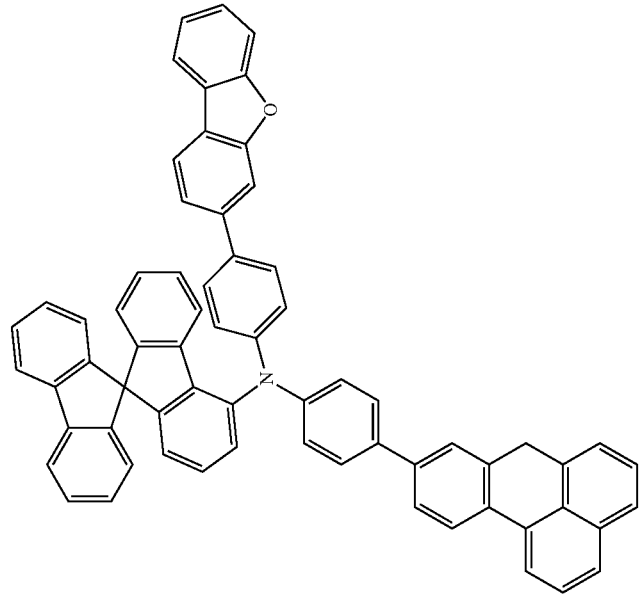 | 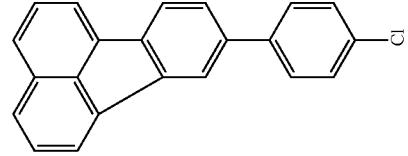 | 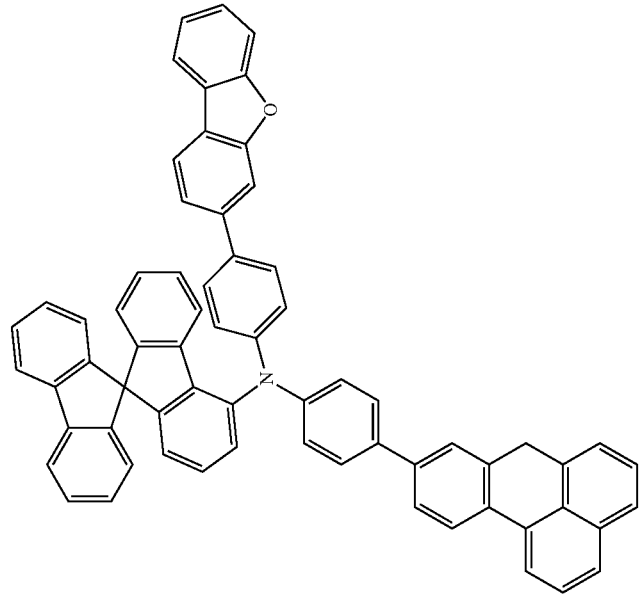 | 77 |

-continued

| Bsp. | Edukt 1 | Edukt 2 | Produkt | Ausbeute [%] |
|---|---|---|---|---|
| 49 | | | | 72 |

| Bsp. | Edukt 1 | Edukt 2 | Produkt | Ausbeute [%] |
|---|---|---|---|---|
| 50 | 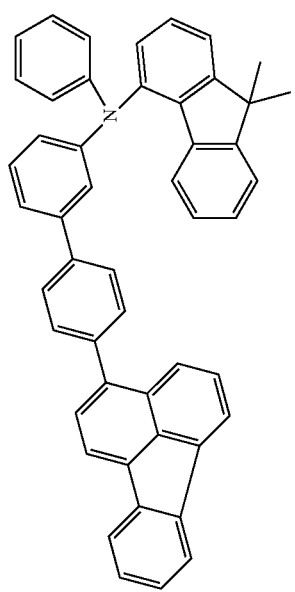 [1776969-70-0] | 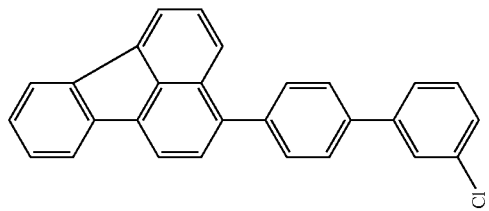 | 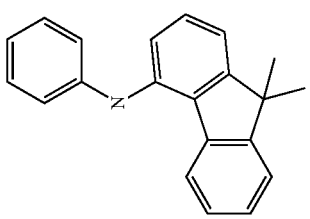 | 70 |

| Bsp. | Edukt 1 | Edukt 2 | Produkt | Ausbeute [%] |
|---|---|---|---|---|
| 51 | 1454679-22-1 | | | 64 |
| 52 | | | | 71 |

-continued

| Bsp. | Edukt 1 | Edukt 2 | Produkt | Ausbeute [%] |
|---|---|---|---|---|
| 53 | | | | 60 |

| Bsp. | Edukt 1 | Edukt 2 | Produkt | Ausbeute [%] |
|---|---|---|---|---|
| 54 | | | | 64 |
| 1f | | [1822311-11-4] | | 61 |

-continued

| Bsp. | Edukt 1 | Edukt 2 | Produkt | Ausbeute [%] |
|---|---|---|---|---|
| 2f | | [1822311-12-5] | | 65 |
| 3f | | [1807916-82-2] | | 67 |

| Bsp. | Edukt 1 | Edukt 2 | Produkt | Ausbeute [%] |
|---|---|---|---|---|
| 4f | | [1643716-58-8] | | 60 |
| 5f | | [1627589-29-9] | | 59 |

-continued

| Bsp. | Edukt 1 | Edukt 2 | Produkt | Ausbeute [%] |
|---|---|---|---|---|
| 6f | (biphenyl-fluorenyl amine) | Cl-dibenzofuran-I [1622207-66-2] | (product with Cl) | 68 |
| 7f | (biphenyl-fluorenyl amine) | Br-dibenzofuran-I [1206544-88-6] | (product with Br) | 61 |

| Bsp. | Edukt 1 | Edukt 2 | Produkt | Ausbeute [%] |
|---|---|---|---|---|
| 8f | (structure) | (structure) [1822311-11-4] | (structure) | 64 |
| 55 | (structure) | (structure) | (structure) | 66 |

-continued

| Bsp. | Edukt 1 | Edukt 2 | Produkt | Ausbeute [%] |
|---|---|---|---|---|
| 56 | | | | 61 |
| 57 | | | | 70 |

| Bsp. | Edukt 1 | Edukt 2 | Produkt | Ausbeute [%] |
|---|---|---|---|---|
| 58 | [30924-53-9] | | | 74 |
| 59 | [13438-50-1] | | | 77 |

| Bsp. | Edukt 1 | Edukt 2 | Produkt | Ausbeute [%] |
|---|---|---|---|---|
| 60 | 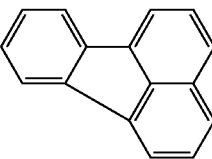 [13438-50-1] | 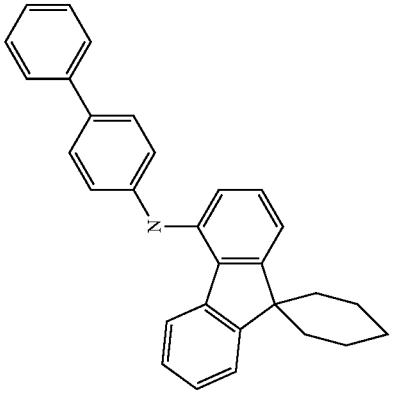 | 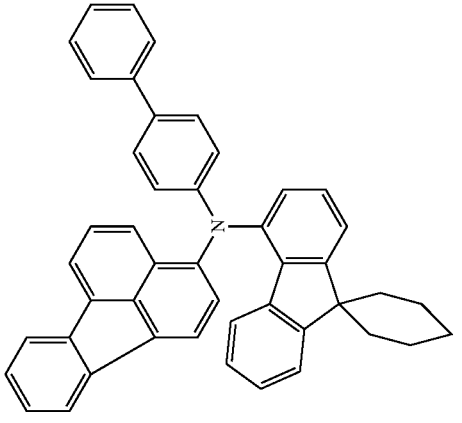 | 72 |
| 61 | 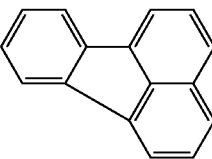 [13438-50-1] | 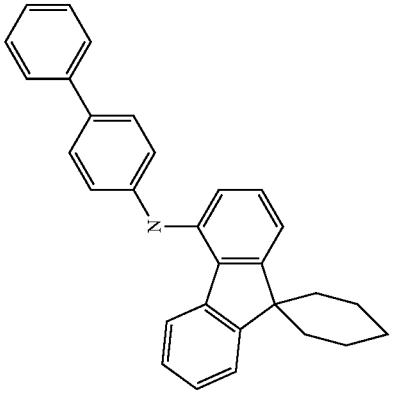 | 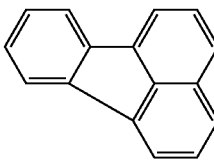 | 71 |

-continued
| Bsp. | Edukt 1 | Edukt 2 | Produkt | Ausbeute [%] |
|---|---|---|---|---|
| 62 | 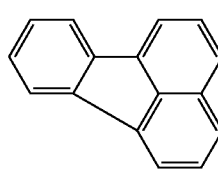 [13438-50-1] | 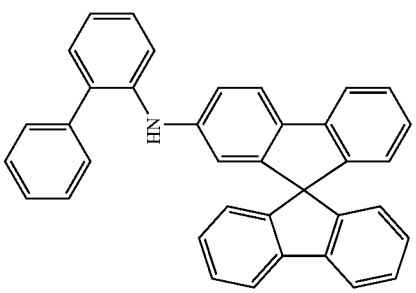 | 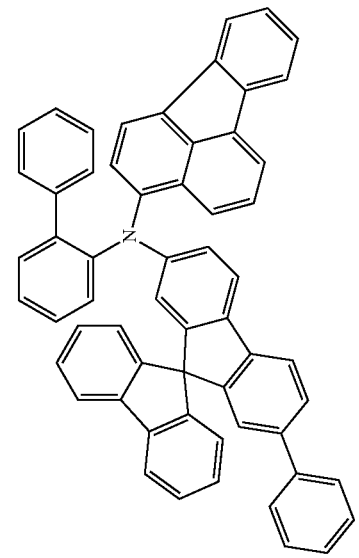 | 78 |
| 63 | 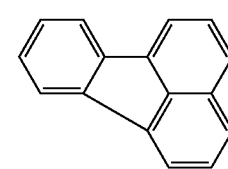 [13438-50-1] | | | 74 |

-continued

| Bsp. | Edukt 1 | Edukt 2 | Produkt | Ausbeute [%] |
|---|---|---|---|---|
| 64 | [1554148-65-0] | | | 79 |
| 65 | [1195682-94-0] | | | 76 |

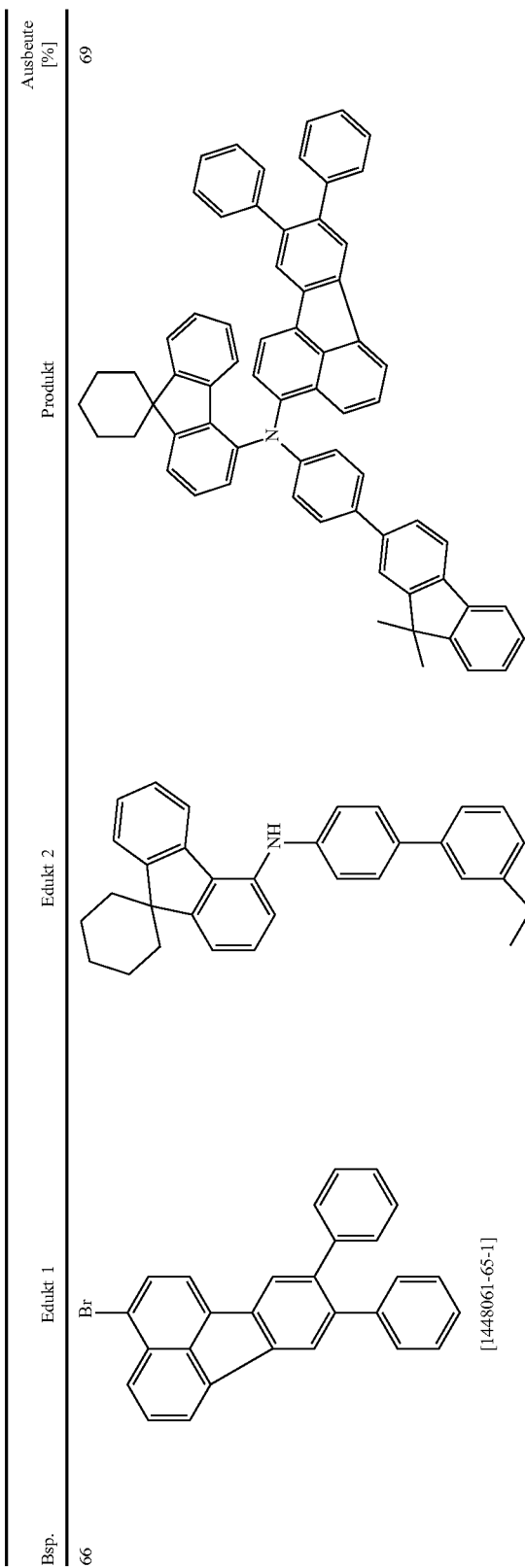

-continued

| Bsp. | Edukt 1 | Edukt 2 | Produkt | Ausbeute [%] |
|---|---|---|---|---|
| 67 | [30924-53-9] | | | 73 |
| 68 | [26886-42-7] | | | 75 |

| Bsp. | Edukt 1 | Edukt 2 | Produkt | Ausbeute [%] |
|---|---|---|---|---|
| 69 | [30924-53-9] | | | 78 |
| 70 | [13438-50-1] | | | 77 |

| Bsp. | Edukt 1 | Edukt 2 | Produkt | Ausbeute [%] |
|---|---|---|---|---|
| 71 | 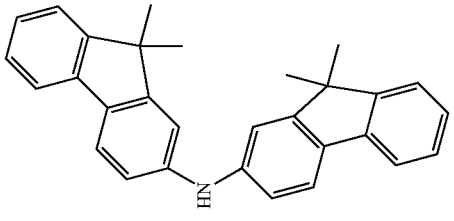 [26885-42-7] | 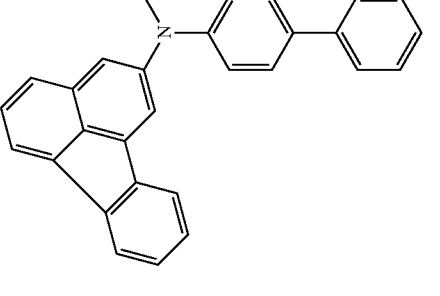 | 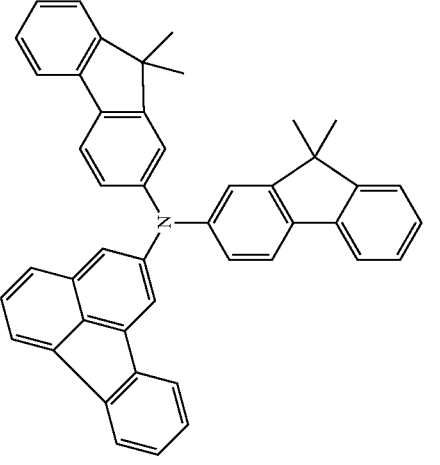 | 72 |
| 72 | 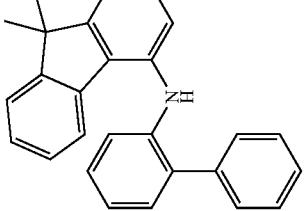 [30924-53-9] | 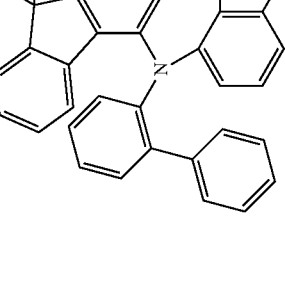 [500717-23-7] | 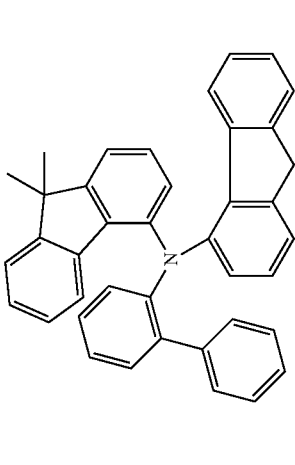 | 72 |

| Bsp. | Edukt 1 | Edukt 2 | Produkt | Ausbeute [%] |
|---|---|---|---|---|
| 73 | | | | 75 |
| 74 | [30924-53-9] | | | 76 |

| Bsp. | Edukt 1 | Edukt 2 | Produkt | Ausbeute [%] |
|---|---|---|---|---|
| 75 | [30924-53-9] | | | 78 |
| 76 | | | | 79 |

| Bsp. | Edukt 1 | Edukt 2 | Produkt | Ausbeute [%] |
|---|---|---|---|---|
| 77 | 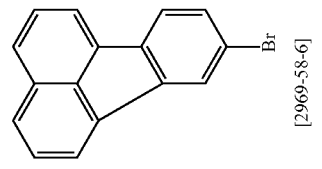 [2969-58-6] | 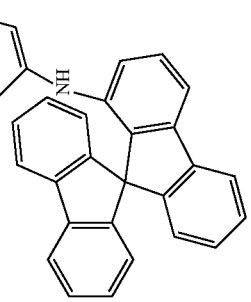 | 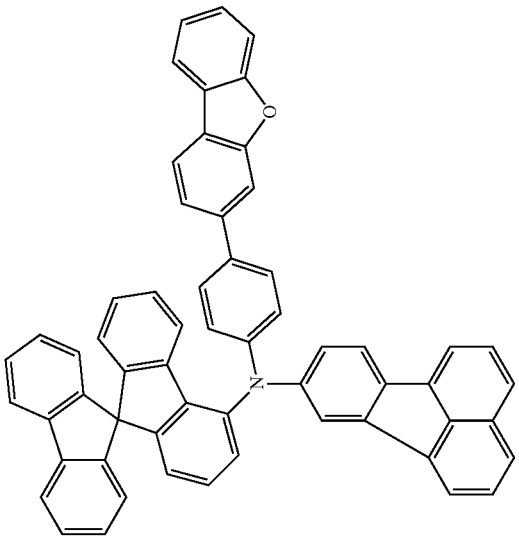 | 72 |
| 78 | 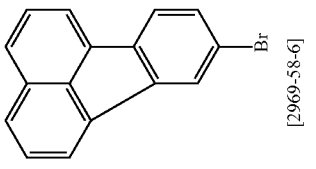 [2969-58-6] | 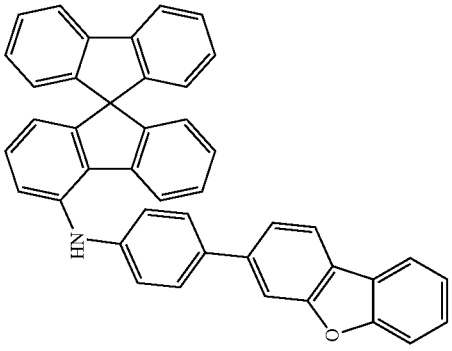 | | 76 |

| Bsp. | Edukt 1 | Edukt 2 | Produkt | Ausbeute [%] |
|---|---|---|---|---|
| 79 | [2969-58-6] | | | 71 |

| Bsp. | Edukt 1 | Edukt 2 | Produkt | Ausbeute [%] |
|---|---|---|---|---|
| 80 | [30924-53-9] | | | 79 |
| 81 | [30924-53-9] | | | 74 |

| Bsp. | Edukt 1 | Edukt 2 | Produkt | Ausbeute [%] |
|---|---|---|---|---|
| 82 | 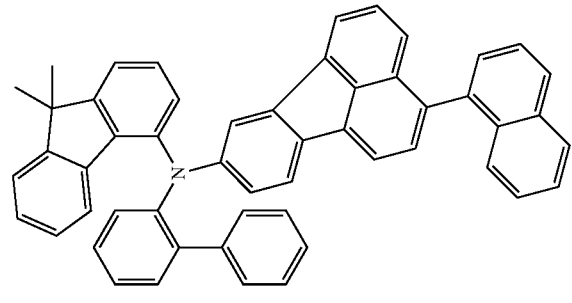 [863878-61-9] | 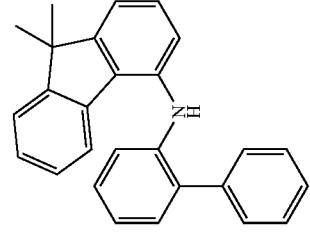 | 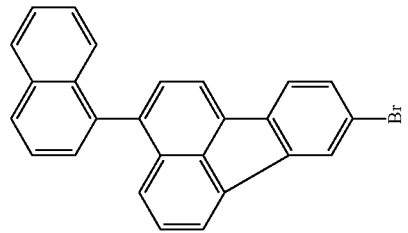 | 77 |

| Bsp. | Edukt 1 | Edukt 2 | Produkt | Ausbeute [%] |
|---|---|---|---|---|
| 83 | 1-bromofluoranthene [30924-53-9] | N-(9,9-dimethylfluoren-2-yl)-9,9-dimethyl-2,7-diphenylfluoren-4-amine | corresponding triarylamine product | 72 |

-continued

| Bsp. | Edukt 1 | Edukt 2 | Produkt | Ausbeute [%] |
|---|---|---|---|---|
| 84 | [30924-53-9] | [1421769-19-6] | | 73 |
| 85 | [30924-53-9] | | | 68 |

-continued
| Bsp. | Edukt 1 | Edukt 2 | Produkt | Ausbeute [%] |
|---|---|---|---|---|
| 86 | 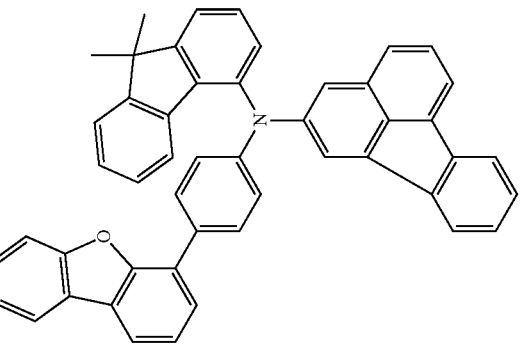 [26885-42-7] | 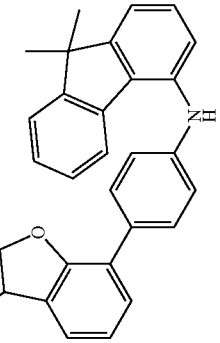 | 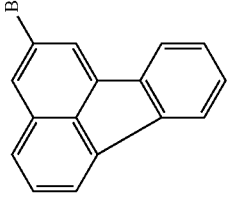 | 60 |

| Bsp. | Edukt 1 | Edukt 2 | Produkt | Ausbeute [%] |
|---|---|---|---|---|
| 87 | 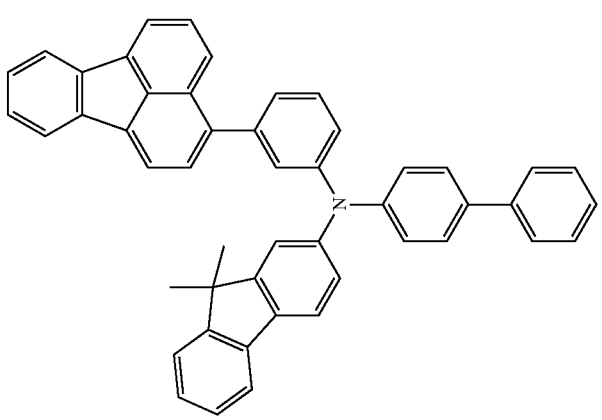 | 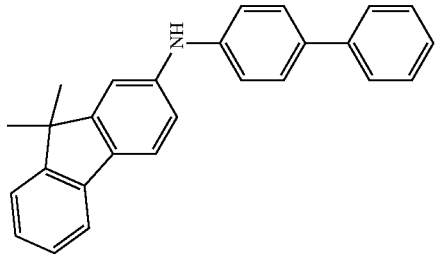 80767-69-1 | 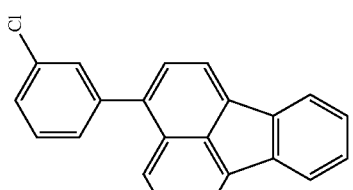 | 71 |

| Bsp. | Edukt 1 | Edukt 2 | Produkt | Ausbeute [%] |
|---|---|---|---|---|
| 88 | (3-chlorophenyl-fluoranthene) | (9,9-dimethyl-N-phenyl-fluoren-2-amine) | (product structure) | 65 |

B) Device Examples

The inventive OLEDs I1 to I10 and the comparative OLEDs C1 to C3 are produced, and their properties are analysed (Tables 1 and 2).

The OLEDs are produced as follows: Glass plaques coated with structured ITO (indium tin oxide) of thickness 50 nm are treated prior to coating with an oxygen plasma, followed by an argon plasma. These plasma-treated glass plaques form the substrates to which the OLEDs are applied.

The OLEDs basically have the following layer structure: substrate/hole injection layer (HIL)/hole transport layer (HTL)/electron blocker layer (EBL)/emission layer (EML)/optional hole blocker layer (HBL)/electron transport layer (ETL) and finally a cathode. The cathode is formed by an aluminium layer of thickness 100 nm. The exact structure of the OLEDs can be found in Table 1. The materials required for production of the OLEDs are shown in Table 3.

All materials are applied by thermal vapour deposition in a vacuum chamber. In this case, the emission layer always consists of at least one matrix material (host material) and an emitting dopant (emitter) which is added to the matrix material(s) in a particular proportion by volume by coevaporation. Details given in such a form as IC5:IC3:TEG2 (55%:35%:10%) mean here that the material IC5 is present in the layer in a proportion by volume of 55%, IC3 in a proportion of 35% and TEG2 in a proportion of 10%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) as a function of luminance, calculated from current-voltage-luminance characteristics (IUL characteristics) assuming Lambertian emission characteristics, and also the lifetime are determined. The electroluminescence spectra are determined at a luminance of 1000 cd/m$^2$, and the CIE 1931 x and y colour coordinates are calculated therefrom. The parameter U1000 in Table 2 refers to the voltage which is required for a luminance of 1000 cd/m$^2$. Finally, EQE1000 refers to the external quantum efficiency at an operating luminance of 1000 cd/m$^2$. The lifetime LT is defined as the time after which the luminance drops from the starting luminance to a certain proportion L1 in the course of operation with constant current. Figures given as L0;j0=a mA/cm$^2$, L1=b % mean that the luminance in the course of operation at a mA/cm$^2$ falls to b % of its starting value after the time LT.

The data obtained for the OLEDs are collated in Table 2.

TABLE 1

Structure of the OLEDs

| Ex. | HIL thickness | HTL thickness | EBL thickness | EML thickness | HBL thickness | ETL thickness |
|---|---|---|---|---|---|---|
| C1 | HATCN 5 nm | SpMA1 125 nm | SpMA3 10 nm | PA1:TER5 (97%:3%) 35 nm | ST2 10 nm | ST2:LiQ (50%:50%) 30 nm |
| C2 | HATCN 5 nm | SpMA1 125 nm | SpMA3 10 nm | PA2:TER5 (97%:3%) 35 nm | ST2 10 nm | ST2:LiQ (50%:50%) 30 nm |
| C3 | HATCN 5 nm | SpMA1 125 nm | SpMA3 10 nm | PA3:TER5 (97%:3%) 35 nm | ST2 10 nm | ST2:LiQ (50%:50%) 30 nm |
| I1 | HATCN 5 nm | SpMA1 125 nm | SpMA3 10 nm | EG26:TER5 (97%:3%) 35 nm | ST2 10 nm | ST2:LiQ (50%:50%) 30 nm |
| I2 | HATCN 5 nm | SpMA1 125 nm | SpMA3 10 nm | EG87:TER5 (97%:3%) 35 nm | ST2 10 nm | ST2:LiQ (50%:50%) 30 nm |
| I3 | HATCN 5 nm | SpMA1 125 nm | SpMA3 10 nm | EG88:TER5 (97%:3%) 35 nm | ST2 10 nm | ST2:LiQ (50%:50%) 30 nm |
| I4 | HATCN 5 nm | SpMA1 125 nm | SpMA3 10 nm | EG23:TER5 (97%:3%) 35 nm | ST2 10 nm | ST2:LiQ (50%:50%) 30 nm |
| I5 | HATCN 5 nm | SpMA1 125 nm | SpMA3 10 nm | EG30:TER5 (97%:3%) 35 nm | ST2 10 nm | ST2:LiQ (50%:50%) 30 nm |
| I6 | HATCN 5 nm | SpMA1 230 nm | SpMA3 20 nm | IC5:IC3:TEG2 (60%:30%:10%) 30 nm | EG18 10 nm | ST2:LiQ (50%:50%) 30 nm |
| I7 | HATCN 5 nm | SpMA1 230 nm | SpMA3 20 nm | IC5:IC3:TEG2 (60%:30%:10%) 30 nm | EG71 10 nm | ST2:LiQ (50%:50%) 30 nm |
| I8 | HATCN 5 nm | SpMA1 230 nm | SpMA3 20 nm | IC5:IC3:TEG2 (60%:30%:10%) 30 nm | EG85 10 nm | ST2:LiQ (50%:50%) 30 nm |
| I9 | HATCN 5 nm | SpMA1 230 nm | SpMA3 20 nm | IC5:IC3:TEG2 (60%:30%:10%) 30 nm | ST2 10 nm | EG3:LiQ (50%:50%) 30 nm |
| I10 | HATCN 5 nm | SpMA1 230 nm | SpMA3 20 nm | IC5:IC3:TEG2 (60%:30%:10%) 30 nm | ST2 10 nm | EG37:LiQ (50%:50%) 30 nm |

TABLE 2

Performance data of the OLEDs

| Ex. | U1000 (V) | EQE 1000 | CIE x/y at 1000 cd/m$^2$ | L$_0$; j$_0$ | L1 % | LT (h) |
|---|---|---|---|---|---|---|
| C1 | 3.4 | 16.8% | 0.67/0.33 | 60 mA/cm$^2$ | 95 | 25 |
| C2 | 3.4 | 16.6% | 0.67/0.33 | 60 mA/cm$^2$ | 95 | 20 |
| C3 | 3.4 | 16.7% | 0.67/0.33 | 60 mA/cm$^2$ | 95 | 15 |
| I1 | 3.5 | 16.0% | 0.67/0.33 | 60 mA/cm$^2$ | 95 | 105 |
| I2 | 3.4 | 16.4% | 0.67/0.33 | 60 mA/cm$^2$ | 95 | 80 |
| I3 | 3.4 | 16.4% | 0.67/0.33 | 60 mA/cm$^2$ | 95 | 45 |
| I4 | 3.5 | 16.2% | 0.67/0.33 | 60 mA/cm$^2$ | 95 | 115 |
| I5 | 3.6 | 16.3% | 0.67/0.33 | 60 mA/cm$^2$ | 95 | 95 |
| I6 | 3.3 | 18.1% | 0.33/0.63 | 40 mA/cm$^2$ | 80 | 220 |
| I7 | 3.4 | 17.5% | 0.33/0.63 | 40 mA/cm$^2$ | 80 | 200 |
| I8 | 3.4 | 17.7% | 0.33/0.63 | 40 mA/cm$^2$ | 80 | 210 |
| I9 | 3.5 | 17.6% | 0.33/0.63 | 40 mA/cm$^2$ | 80 | 215 |
| I10 | 3.6 | 17.3% | 0.33/0.63 | 40 mA/cm$^2$ | 80 | 195 |

TABELLE 3
Strukturformein der verwendeten Materialien
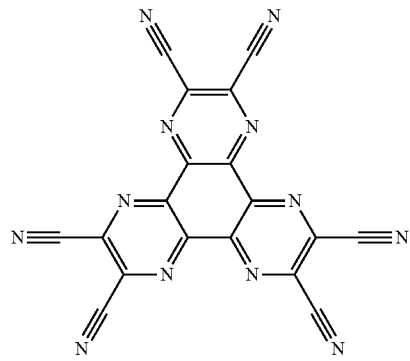
HATCH
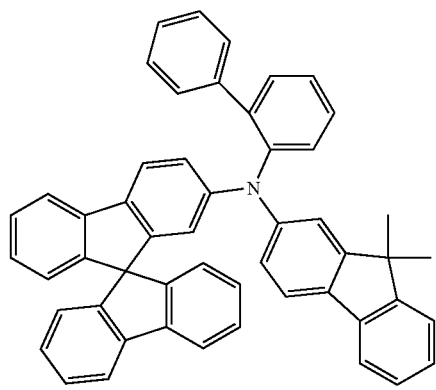
SpMA1
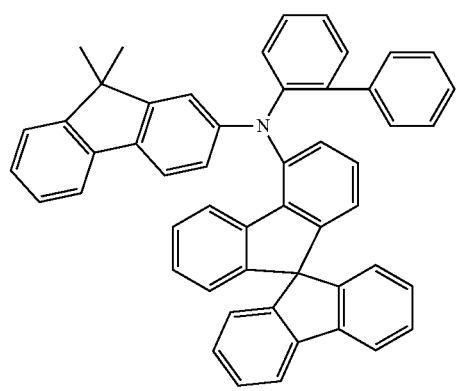
SpMA3
TABELLE 3-continued
Strukturformein der verwendeten Materialien
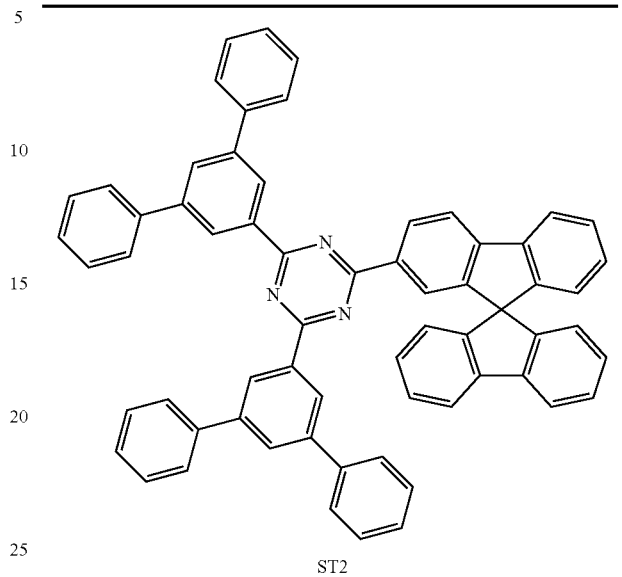
ST2
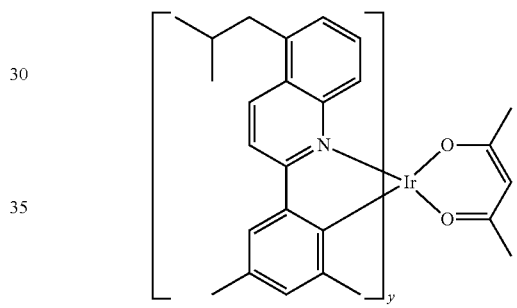
TER5
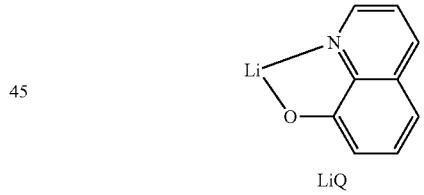
LiQ
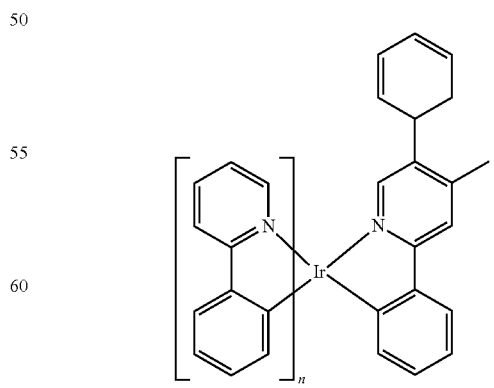
TEG2

TABELLE 3-continued
Strukturformein der verwendeten Materialien
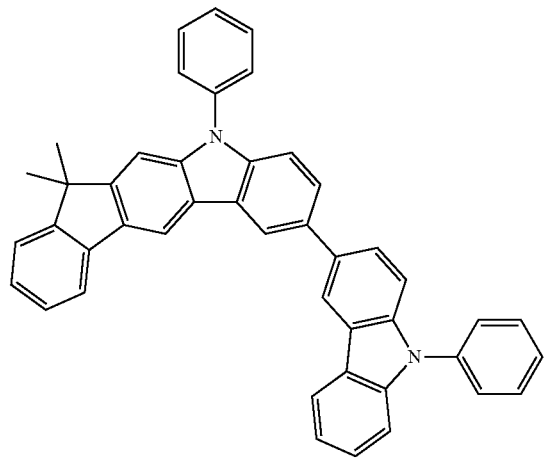
IC3
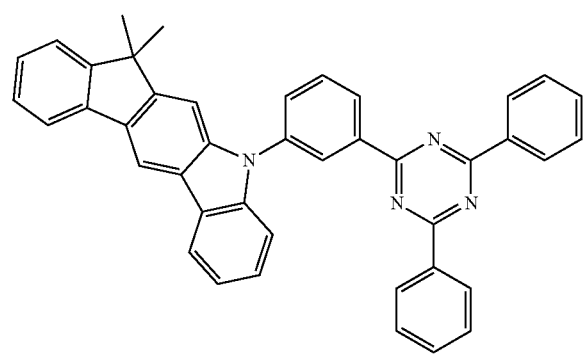
IC5
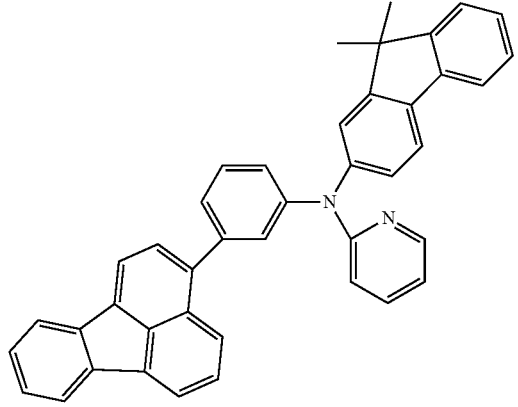
PA1
TABELLE 3-continued
Strukturformein der verwendeten Materialien
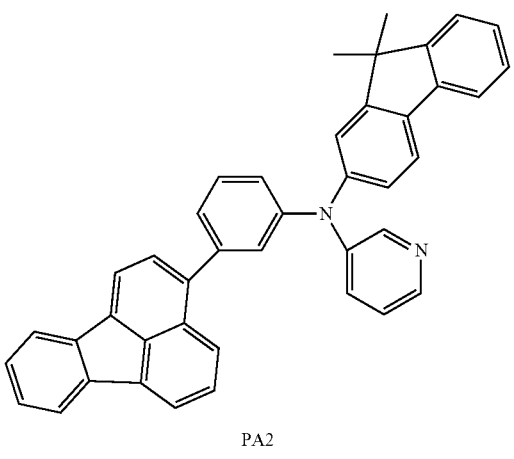 [SMILES: CC1(C)c2ccccc2-c2ccc(N(c3cccnc3)c3cccc(-c4ccc5c6c(cccc46)-c4ccccc4-5)c3)cc21]
PA2
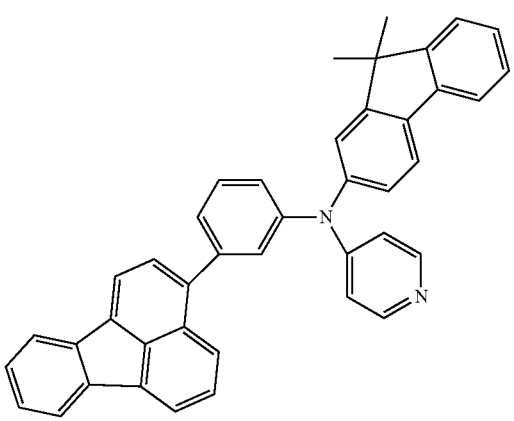
PA3
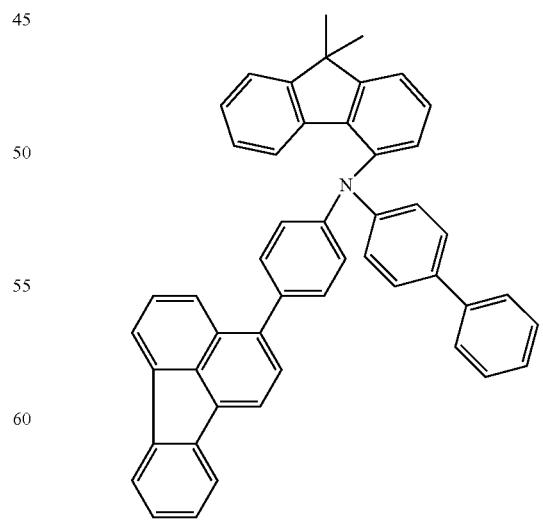
EG26

TABELLE 3-continued
Strukturformein der verwendeten Materialien
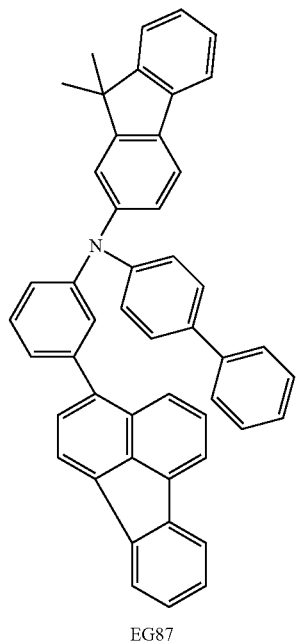 [SMILES: CC1(C)c2ccccc2-c2ccc(N(c3ccc(-c4ccccc4)cc3)c3cccc(-c4ccc5c6c(cccc46)-c4ccccc4-5)c3)cc21]
EG87
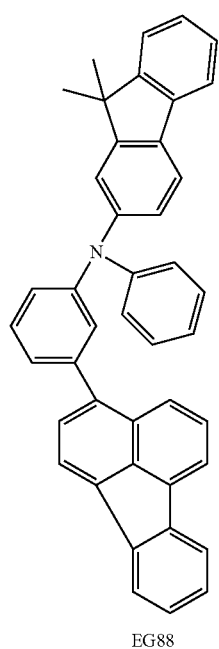 [SMILES: CC1(C)c2ccccc2-c2ccc(N(c3ccccc3)c3cccc(-c4ccc5c6c(cccc46)-c4ccccc4-5)c3)cc21]
EG88
TABELLE 3-continued
Strukturformein der verwendeten Materialien
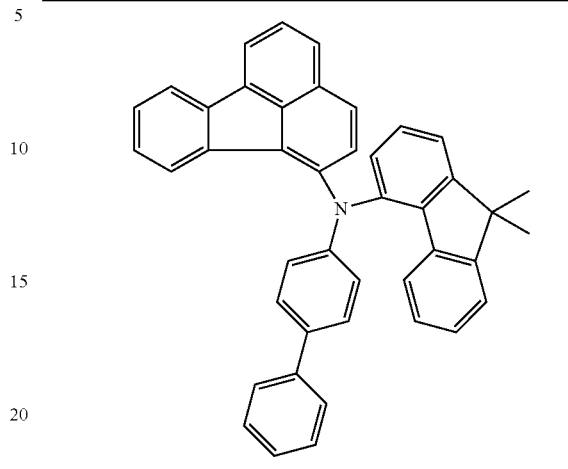
EG85
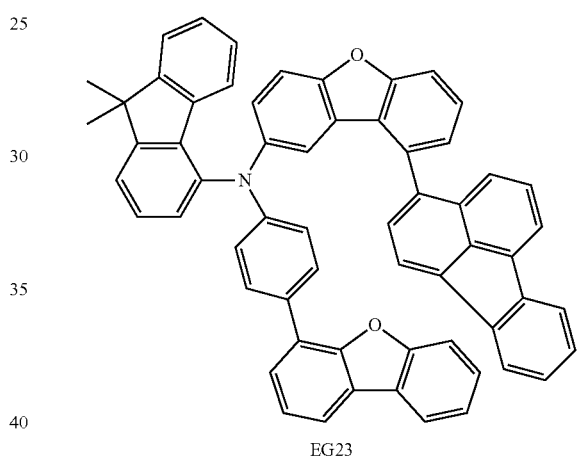
EG23
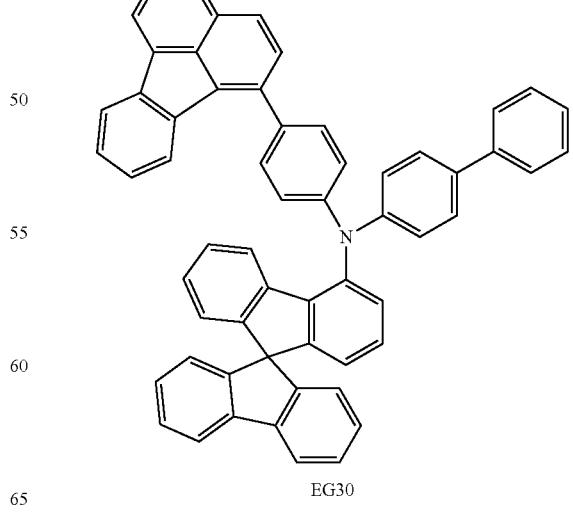
EG30

TABELLE 3-continued

Strukturformeln der verwendeten Materialien

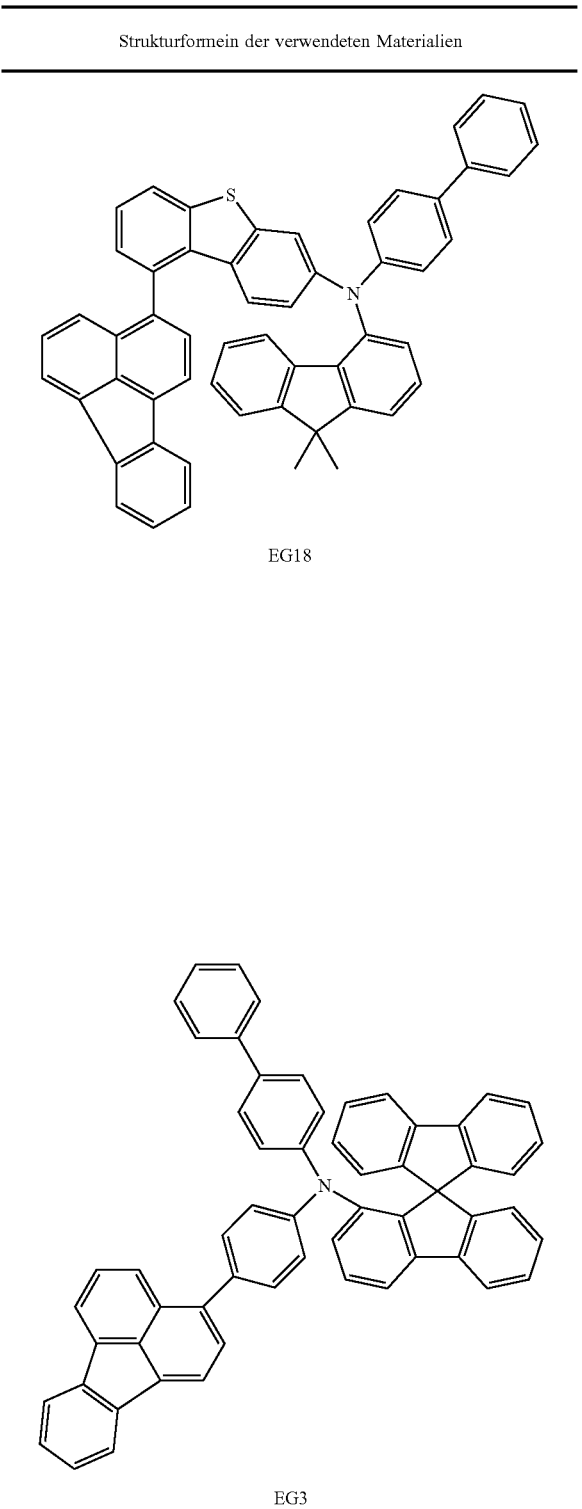

EG18

EG3

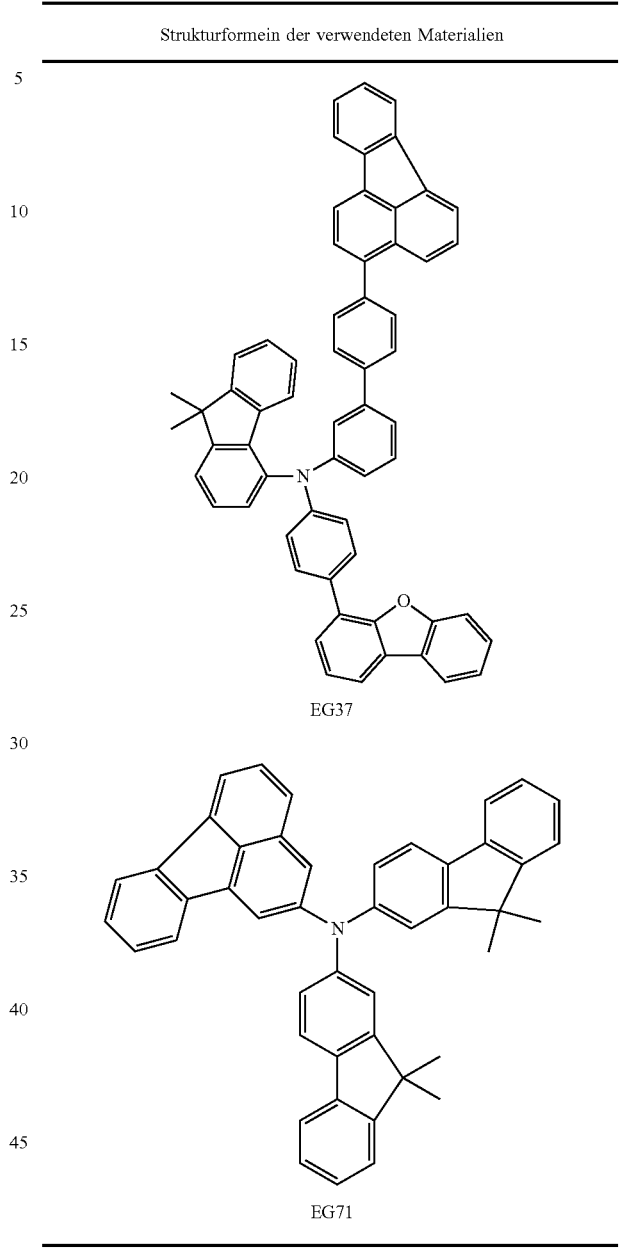

EG37

EG71

In experiments I1 to I5, the materials according to the present application EG26, EG87, EG88, EG23 and EG30 are used as matrix materials for red-phosphorescing emitters in the emitting layer. The OLEDs C1 to C3 differ from the OLEDs I1 to I5 merely by the material used as matrix in the emitting layer (PA1, PA2 and PA3). Otherwise, they are of identical construction. It is found that the inventive OLEDs I1 to I5 all have a distinctly longer lifetime than the comparative OLEDs C1 to C3.

Experiments I6 to I8 show that the inventive compounds (EG18, EG71 and EG85) are of excellent suitability as hole blocker materials.

Experiments I9 and I10 show that the inventive compounds (EG3, EG37) are of excellent suitability as electron transport materials.

The invention claimed is:
1. A compound of formula (I)

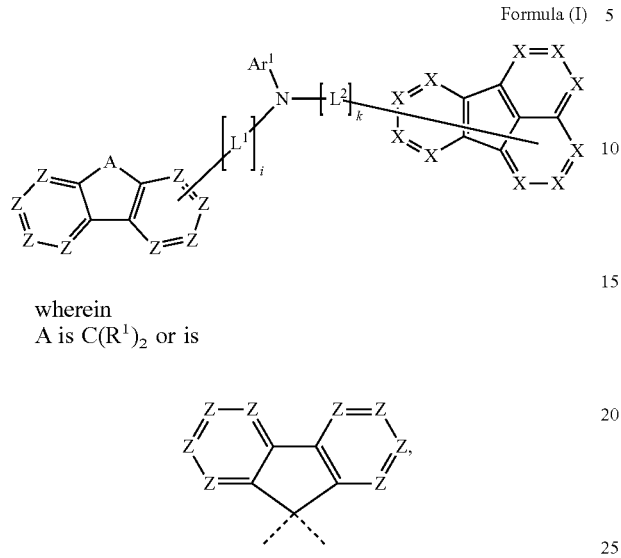

Formula (I)

wherein
A is $C(R^1)_2$ or is where the dotted lines represent the bonds to the six-membered aromatic rings;
Z is the same or different at each instance and is $CR^2$ or N or C, where a Z group is C in the specific case when the $[L^1]_i$ group is bonded to it;
X is the same or different at each instance and is $CR^3$ or N or C, where an X group is C in the specific case when the $[L^2]_k$ group is bonded to it;
$L^1$ is the same or different at each instance and are selected from a divalent group derived from benzene, biphenyl, terphenyl, fluorene, spirobifluorene, indenofluorene, carbazole, dibenzofuran or dibenzothiophene, each optionally substituted by $R^4$ radicals, or a combination of two or more of these groups;
$L^2$ is the same or different at each instance and selected from a divalent group derived from biphenyl, terphenyl, fluorine, spirobifluorene, indenofluorene, carbazole, dibenzofuran or dibenzothiophene, each optionally substituted by $R^4$ radicals, or a combination of two or more of these groups;
$Ar^1$ is an aromatic ring system which has 6 to 24 aromatic ring atoms and may be substituted by one or more $R^5$ radicals, or a heteroaromatic ring system which has 5 to 24 aromatic ring atoms and may be substituted by one or more $R^5$ radicals, where $Ar^1$ does not comprise any nitrogen-containing heteroaryl group bonded directly to the amine nitrogen atom of the formula (I), and where $Ar^1$ and substituents bonded thereto do not contain any carbazole group;
$R^1$, $R^2$, $R^3$, $R^4$ are the same or different at each instance and are selected from H, D, F, $C(=O)R^6$, CN, $Si(R^6)_3$, $P(=O)(R^6)_2$, $OR^6$, $S(=O)R^6$, $S(=O)_2R^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where the alkyl, alkoxy, alkenyl and alkynyl groups mentioned and the aromatic ring systems and heteroaromatic ring systems mentioned may each be substituted by one or more $R^6$ radicals; and where one or more $CH_2$ groups in the alkyl, alkoxy, alkenyl and alkynyl groups mentioned may be replaced by $-R^6C=CR^6-$, $-C\equiv C-$, $Si(R^6)_2$, $C=O$, $C=NR^6$, $-C(=O)O-$, $-C(=O)NR^6-$, $NR^6$, $P(=O)(R^6)$, $-O-$, $-S-$, SO or $SO_2$;
$R^5$ is the same or different at each instance and is selected from H, D, $Si(R^6)_3$, $OR^6$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^5$ radicals may be joined to one another and may form a ring; where the alkyl, alkoxy, alkenyl and alkynyl groups mentioned and the aromatic ring systems and heteroaromatic ring systems mentioned may each be substituted by one or more $R^6$ radicals; and where one or more $CH_2$ groups in the alkyl, alkoxy, alkenyl and alkynyl groups mentioned may be replaced by $-R^6C=CR^6-$, $-C\equiv C-$, $Si(R^6)_2$, $NR^6$, $O-$ or $-S-$;
$R^6$ is the same or different at each instance and is selected from H, D, F, $C(=O)R^7$, CN, $Si(R^7)_3$, $P(=O)(R^7)_2$, $OR^7$, $S(=O)R^7$, $S(=O)_2R^7$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^6$ radicals may be joined to one another and may form a ring; where the alkyl, alkoxy, alkenyl and alkynyl groups mentioned and the aromatic ring systems and heteroaromatic ring systems mentioned may each be substituted by one or more $R^7$ radicals; and where one or more $CH_2$ groups in the alkyl, alkoxy, alkenyl and alkynyl groups mentioned may be replaced by $-R^7C=CR^7-$, $-C\equiv C-$, $Si(R^7)_2$, $C=O$, $C=NR^7$, $-C(=O)O-$, $-C(=O)NR^7-$, $NR^7$, $P(=O)(R^7)$, $-O-$, $-S-$, SO or $SO_2$;
$R^7$ is the same or different at each instance and is selected from H, D, F, CN, alkyl or alkoxy groups having 1 to 20 carbon atoms, alkenyl or alkynyl groups having 2 to 20 carbon atoms, aromatic ring systems having 6 to 40 aromatic ring atoms and heteroaromatic ring systems having 5 to 40 aromatic ring atoms; where two or more $R^7$ radicals may be joined to one another and may form a ring; and where the alkyl, alkoxy, alkenyl and alkynyl groups, aromatic ring systems and heteroaromatic ring systems mentioned may be substituted by F or CN;
i is 0, 1, 2 or 3; and
k is 1, 2 or 3.

2. The compound according to claim 1, wherein the fluoranthene group is bonded in position 3 or 4, where the positions are numbered as follows:

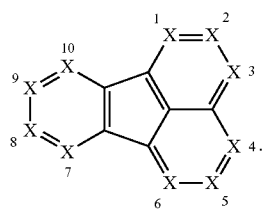

3. The compound according to claim 1, wherein the group of the formula

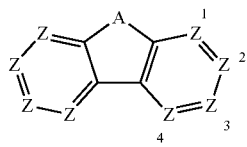

in formula (I) is bonded in one of positions 1, 3 and 4.

4. The compound according to claim 1, wherein $Ar^1$ is selected from the following radicals that are optionally substituted by $R^5$ radicals: phenyl, biphenyl, branched terphenyl, unbranched terphenyl, branched quaterphenyl, unbranched quaterphenyl, fluorenyl, dibenzofuranyl, dibenzothiophenyl, fluorenylphenylene, dibenzofuranylphenylene, dibenzothiophenylphenylene, phenanthrenyl and triphenylyl.

5. The compound according to claim 1, wherein $R^1$ is the same or different at each instance and is selected from F, $Si(R^6)_3$, straight-chain alkyl groups having 1 to 20 carbon atoms, branched or cyclic alkyl groups having 3 to 20 carbon atoms, aromatic ring systems having 6 to 24 aromatic ring atoms, and heteroaromatic ring systems having 5 to 24 aromatic ring atoms; where the alkyl groups mentioned, the aromatic ring systems mentioned and the heteroaromatic ring systems mentioned may each be substituted by one or more $R^6$ radicals; and where two $R^1$ groups bonded to the same carbon atom may be joined to one another to form a ring, giving rise to a spiro carbon atom.

6. The compound according to claim 1, wherein $R^2$, $R^3$ and $R^4$ are the same or different at each instance and are selected from H, D, F, CN, $Si(R^6)_3$, straight-chain alkyl groups having 1 to 20 carbon atoms, branched or cyclic alkyl groups having 3 to 20 carbon atoms, aromatic ring systems having 6 to 24 aromatic ring atoms and heteroaromatic ring systems having 5 to 24 aromatic ring atoms; where the alkyl groups mentioned, the aromatic ring systems mentioned and the heteroaromatic ring systems mentioned may each be substituted by one or more $R^6$ radicals; and where one or more $CH_2$ groups in the alkyl groups mentioned may be replaced by —C≡C—, —$R^6$C=C$R^6$—, $Si(R^6)_2$, C=O, C=N$R^6$, —N$R^6$—, —O—, —S—, —C(=O)O— or —C(=O)N$R^6$—.

7. The compound according to claim 1, wherein $R^5$ is the same or different at each instance and is selected from H, D, $Si(R^6)_3$, straight-chain alkyl groups having 1 to 20 carbon atoms, branched or cyclic alkyl groups having 3 to 20 carbon atoms, aromatic ring systems having 6 to 24 aromatic ring atoms, and heteroaromatic ring systems having 5 to 24 aromatic ring atoms; where the alkyl groups mentioned, the aromatic ring systems mentioned and the heteroaromatic ring systems mentioned may each be substituted by one or more $R^6$ radicals, where $R^5$ and substituents bonded to $R^5$ do not contain any carbazole group.

8. The compound according to claim 1, wherein $R^6$ is the same or different at each instance and is selected from H, D, F, CN, $Si(R^7)_3$, straight-chain alkyl groups having 1 to 20 carbon atoms, branched or cyclic alkyl groups having 3 to 20 carbon atoms, aromatic ring systems having 6 to 24 aromatic ring atoms and heteroaromatic ring systems having 5 to 24 aromatic ring atoms; where the alkyl groups mentioned, the aromatic ring systems mentioned and the heteroaromatic ring systems mentioned may each be substituted by one or more $R^7$ radicals; and where one or more $CH_2$ groups in the alkyl groups mentioned may be replaced by —C≡C—, —$R^7$C=C$R^7$—, $Si(R^7)_2$, C=O, C=N$R^7$, —N$R^7$—, —O—, —S—, —C(=O)O— or —C(=O)N$R^7$—.

9. The compound according to claim 1, wherein i is 0.

10. The compound according to claim 1, wherein k is 1.

11. The compound according to claim 1, wherein the compound corresponds to one of the formulae (I-2), (I-4), (I-6), (I-8), (I-10), or (I-12)

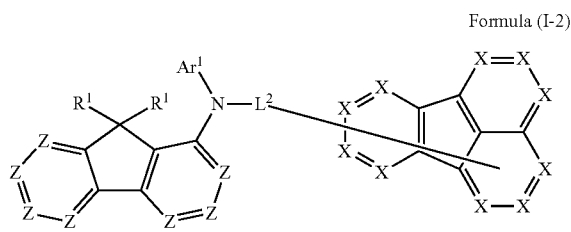

Formula (I-2)

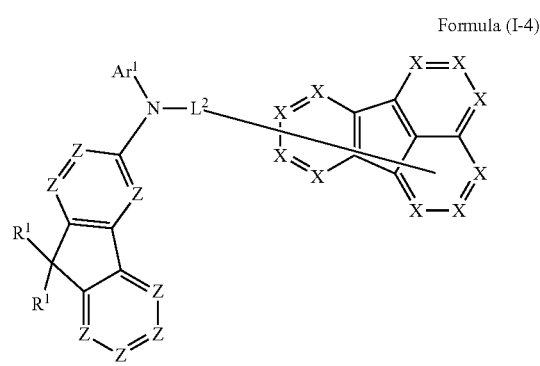

Formula (I-4)

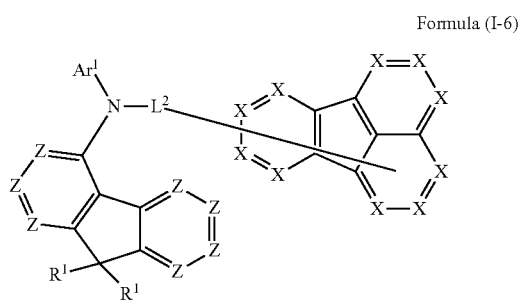

Formula (I-6)

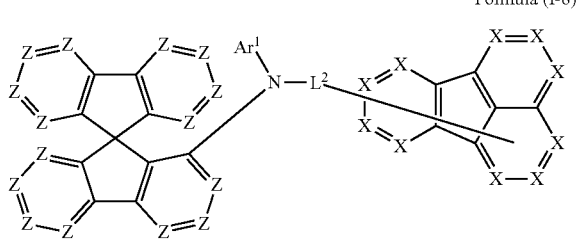

Formula (I-8)

Formula (I-10)

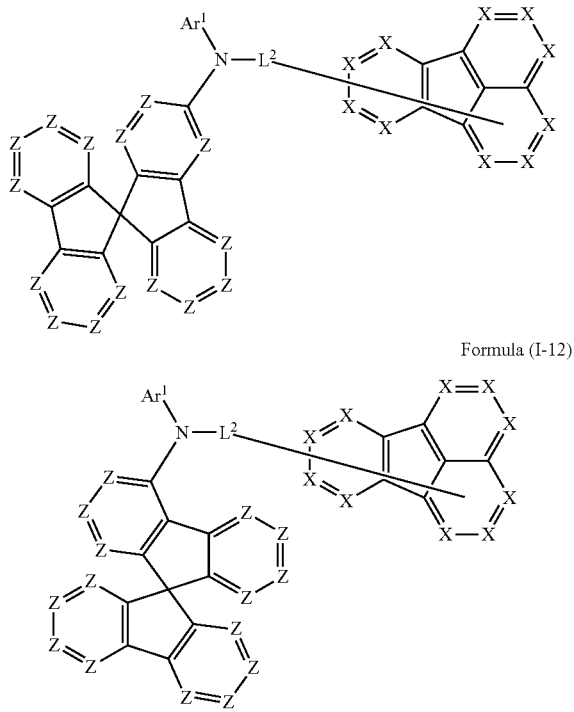

Formula (I-12)

where the variables that occur are as defined in claim 1.

12. A process for preparing a compound of formula (I) according to claim 1, comprising reacting a fluorenylamine with an aromatic or heteroaromatic compound in a Buchwald coupling reaction.

13. An oligomer, polymer or dendrimer containing one or more compounds of formula (I) according to claim 1, wherein the bond(s) to the polymer, oligomer or dendrimer may be localized at any desired positions substituted by $R^1$, $R^2$, $R^3$, $R^4$ or $R^5$ in formula (I).

14. A formulation comprising at least one compound according to claim 1 and at least one solvent.

15. An electronic device comprising at least one compound according to claim 1.

16. The electronic device according to claim 15, wherein the electronic device is an organic electroluminescent device comprising anode, cathode and at least one emitting layer, wherein at least one organic layer of the device, which may be an emitting layer or a hole-transporting layer, comprises the at least one compound.

17. The electronic device according to claim 16, comprising at least one emitting layer comprising a red-emitting phosphorescent emitter, where the at least one compound is present in the emitting layer as matrix material.

18. A method comprising utilizing the compound according to claim 1 in an electronic device.

19. The compound according to claim 1, wherein the fluoranthene group is bonded in position 3 or 4, where the positions are numbered as follows:

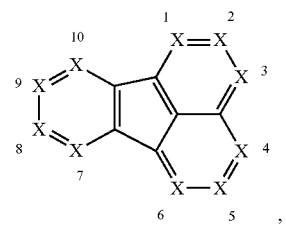

and wherein $L^1$, is the same or different at each instance and are selected from divalent group derived from benzene, biphenyl, terphenyl, fluorene, spirobifluorene, indenofluorene, carbazole, dibenzofuran or dibenzothiophene, each optionally substituted by $R^4$ radicals, or a combination of two or more of these groups; and wherein $L^2$ is the same or different at each instance and selected from a divalent group derived from biphenyl, terphenyl, fluorine, spirobifluorene, indenofluorene, carbazole, dibenzofuran or dibenzothiophene, each optionally substituted by $R^4$ radicals, or a combination of two or more of these groups.

20. The compound according to claim 1, wherein $L^2$ is selected from a divalent group derived from carbazole, dibenzofuran or dibenzothiophene, each optionally substituted by $R^4$ radicals.

21. The compound according to claim 19, wherein $L^2$ is selected from a divalent group derived from carbazole, dibenzofuran or dibenzothiophene, each optionally substituted by $R^4$ radicals.

* * * * *